(12) United States Patent
Vendeville et al.

(10) Patent No.: US 8,921,355 B2
(45) Date of Patent: Dec. 30, 2014

(54) MACROCYCLIC INDOLE DERIVATIVES USEFUL AS HEPATITIS C VIRUS INHIBITORS

(75) Inventors: Sandrine Marie Helene Vendeville, Mechelen (BE); Pierre Jean-Marie Bernard Raboisson, Mechelen (BE); Tse-I Lin, Mechelen (BE); Abdellah Tahri, Anderlecht (BE); Katie Ingrid Eduard Amssoms, Hove (BE)

(73) Assignee: Janssen R & D Ireland, Eastgate Village, Eastgate Little Island, Co Cork (IE)

( * ) Notice: Subject to any disclaimer, the term of this patent is extended or adjusted under 35 U.S.C. 154(b) by 543 days.

(21) Appl. No.: 13/000,583

(22) PCT Filed: Jul. 8, 2009

(86) PCT No.: PCT/EP2009/004942
§ 371 (c)(1),
(2), (4) Date: Dec. 21, 2010

(87) PCT Pub. No.: WO2010/003658
PCT Pub. Date: Jan. 14, 2010

(65) Prior Publication Data
US 2011/0105473 A1     May 5, 2011

(30) Foreign Application Priority Data

Jul. 8, 2008 (EP) .................................... 08159965
Jul. 11, 2008 (EP) .................................... 08160254
Aug. 4, 2008 (EP) .................................... 08161743

(51) Int. Cl.
| | | |
|---|---|---|
| A61K 31/55 | (2006.01) | |
| C07D 513/12 | (2006.01) | |
| C07D 513/18 | (2006.01) | |
| C07D 515/12 | (2006.01) | |
| C07D 515/18 | (2006.01) | |
| C07D 513/14 | (2006.01) | |
| A61K 45/06 | (2006.01) | |
| C07D 513/22 | (2006.01) | |

(52) U.S. Cl.
CPC .............. $A61K\ 31/55$ (2013.01); $C07D\ 513/14$ (2013.01); $C07D\ 513/18$ (2013.01); $C07D\ 515/18$ (2013.01); $A61K\ 45/06$ (2013.01); $C07D\ 513/22$ (2013.01)
USPC .................. 514/214.02; 514/214.03; 540/478

(58) Field of Classification Search
None
See application file for complete search history.

(56) References Cited

U.S. PATENT DOCUMENTS

| | | |
|---|---|---|
| 5,807,876 A | 9/1998 | Armistead et al. |
| 6,054,472 A | 4/2000 | Armistead et al. |
| 6,344,465 B1 | 2/2002 | Armistead et al. |
| 6,498,178 B2 | 12/2002 | Stamos et al. |
| 2007/0270405 A1 | 11/2007 | Bender et al. |
| 2007/0270406 A1 | 11/2007 | Gentles et al. |
| 2008/0146537 A1 | 6/2008 | Bender et al. |

FOREIGN PATENT DOCUMENTS

| | | |
|---|---|---|
| WO | 9740028 A1 | 10/1997 |
| WO | 9840381 A1 | 9/1998 |
| WO | 0056331 A1 | 9/2000 |
| WO | 0219369 A2 | 3/2002 |
| WO | 2006/020082 A1 | 2/2006 |
| WO | 2007/033032 A1 | 3/2007 |
| WO | 2007026024 A2 | 3/2007 |
| WO | 2007054741 A1 | 5/2007 |
| WO | 2007092000 A1 | 8/2007 |
| WO | 2007140200 A2 | 12/2007 |
| WO | 2008075103 A1 | 6/2008 |
| WO | 2009/010783 A1 | 1/2009 |

OTHER PUBLICATIONS

U.S. Appl. No. 13/836,168, filed Mar. 2013, Vendeville et al.*
Dierynck, et al., Binding Kinetics of Darunavir to Human Immunodeficiency Virus Type 1 Protease Explain the Potent Antiviral Activity and High Genetic Barrier, Journal of Virology, Dec. 15, 2007, pp. 13845-13851, vol. 81, No. 24.
Kingsbury et al, A Recyclable Ru-Based Metathesis Catalyst, The Journal of the American Chemical Society, 1999, p. 791-799, vol. 121.
Jinkun Huang, Olefin Metathesis-Active Ruthenium Complexes Bearing a Nucleophilic Carbene Ligand, The Journal of the American Chemical Society, 1999, p. 2674-2678, vol. 121.
Kim et al, The Burden of Hepatitis C in the United States, Hepatology, 2002, S30-S34, vol. 36, No. 5, s1.

(Continued)

*Primary Examiner* — Noble Jarrell
(74) *Attorney, Agent, or Firm* — Andrea Jo Kamage

(57) ABSTRACT

Inhibitors of HCV replication of formula (I) including stereochemically isomeric forms, and salts, hydrates, solvates thereof, wherein $R^1$, $R^2$, $R^4$, $R^5$, $R^6$ and $R^7$ have the meaning defined in the claims. The present invention also relates to processes for preparing said compounds, pharmaceutical compositions containing them and their use in HCV therapy.

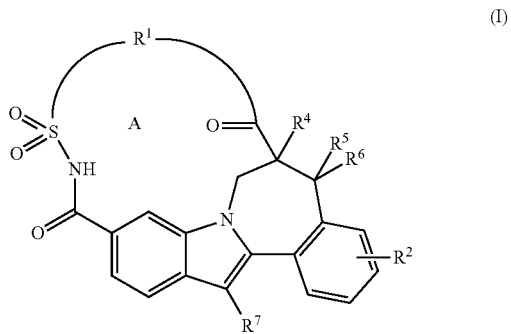

18 Claims, No Drawings

(56) References Cited

OTHER PUBLICATIONS

Krieger, et al, Enhancement of Hepatitis C Virus RNA Replication by Cell Culture, Journal of Virology, May 1, 2001, 4614-1624, 75-10, DE.

Lohmann, et al., Replication of Subgenomic Hepatitis C Virus RNAs in a Hepatoma Cell Line, Science, 1999, pp. 110-113, vol. 285.

Pauwels, et al., Binding-Site Identification and Genotypic Profiling of Hepatitis C Virus Polymerase Inhibitors, Journal of Virology, 2007, pp. 6909-6919, vol. 81, No. 13.

Miller et al, Application of Ring-Closing Metathesis to the Synthesis of Rigidified Amino Acids and Peptides, The Journal of the American Chemical Society, 1996, p. 9606-9614, vol. 118.

Consensus Development Panel, National Institutes of Health Consensus Development Conference Statement: Management of Hepatitis C: 2002, Hepatology, Jun. 2002, S3-S20, vol. 36, No. 5.

Kazutaka et al., Journal of Med. Chemistry, vol. 49, pp. 6950-6953.

* cited by examiner

MACROCYCLIC INDOLE DERIVATIVES USEFUL AS HEPATITIS C VIRUS INHIBITORS

This application is a national stage application of PCT/EP2009/004942, filed Jul. 8, 2009, which claims priority benefit of Application No. EP08159965.6 filed Jul. 8, 2008, Application No. EP08160254.2 filed Jul. 11, 2008 and Application No. EP08161743.3 filed Aug. 4, 2008. The complete disclosures of the aforementioned related patent applications are hereby incorporated herein by reference for all purposes.

FIELD OF THE INVENTION

The present invention is concerned with macrocyclic indole derivatives having inhibitory activity on the replication of the hepatitis C virus (HCV). It further concerns compositions comprising these compounds as active ingredients as well as processes for preparing these compounds and compositions.

BACKGROUND OF THE INVENTION

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhoea virus (BVDV). HCV is a positive-sense, single-stranded RNA virus, with a genome of around 9,600 bases. The genome comprises both 5' and 3' untranslated regions that adopt RNA secondary structures, and a central open reading frame that encodes a single polyprotein of around 3,010-3,030 amino acids. The polyprotein encodes ten gene products, which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV). Following the initial acute infection, a majority of infected individuals develops chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology*, 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. *Hepatology*, 36, 5 Suppl. S30-S34, 2002).

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective. Thus, the treatment of this chronic disease is an unmet clinical need, since current therapy is only partially effective and limited by undesirable side effects.

One area of particular focus has been the search for inhibitors of the NS5b RNA-dependent RNA polymerase (RdRp). Close structural homologs of this polymerase do not exist within the uninfected host cell and the finding of inhibitors of said polymerase would provide a more specific mode of action. Inhibitors that are currently under investigation can be classified as either nucleoside inhibitors (NIs) or non-nucleoside inhibitors (NNIs). NIs directly compete with nucleotide substrates for binding to highly conserved active sites. Greater specificity may be achieved by NNIs, which may interact outside of the highly conserved active site at a unique allosteric site common only to structurally related polymerases.

Indole derivatives have been described for HCV inhibitory activity. WO 2007/092000 discloses tetracyclic indole derivatives as HCV NS5B inhibitors for the treatment and/or prevention of HCV virus infection. US 2008/0146537 discloses cyclopropyl fused indolobenzazepine HCV NS5B inhibitors. WO 2008/075103 discloses macrocyclic indole derivatives useful for the treatment or prevention of infection by hepatitis C virus.

To date, preliminary clinical trials have resulted in a high failure rate, thereby highlighting the need to pursue the search for novel NS5b inhibitors. There is a high medical need for safe and effective anti-HCV treatment. Such HCV inhibitors may overcome the disadvantages of current HCV therapy such as side effects, limited efficacy, the emergence of resistance, and compliance failures, as well as improve the sustained viral response. In particular wherein the therapeutic compounds have good bioavailability and a favorable pharmacokinetic and metabolic profile.

SUMMARY OF THE INVENTION

It has been found that certain macrocyclic indole derivatives exhibit antiviral activity in subjects infected with HCV with useful properties regarding one or more of the following parameters: antiviral efficacy, favorable mutant prophile, lack of toxicity, favorable pharmacokinetic and metabolic profile, and ease of formulation and administration. These compounds are therefore useful in treating or combating HCV infections.

The present invention concerns inhibitors of HCV replication, which can be represented by formula (I),

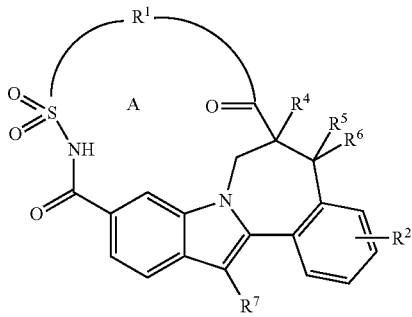

(I)

including stereochemically isomeric forms, and N-oxides, salts, hydrates, and solvates thereof, wherein:

$R^1$ is a bivalent chain selected from

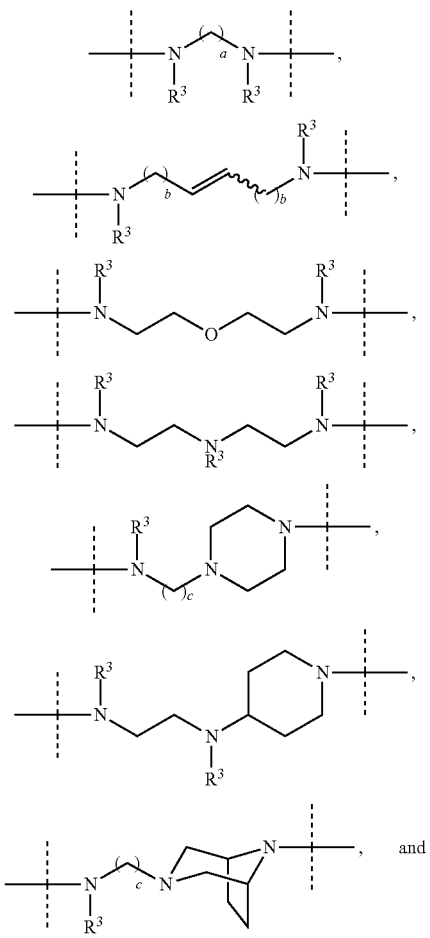

and

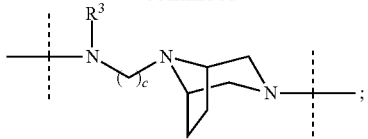

each $R^3$ is independently selected from the group comprising hydrogen, $C_{1-4}$alkyl and $C_{3-5}$cycloalkyl;
a is 3, 4, 5 or 6;
each b is independently 1 or 2;
c is 1 or 2;
macrocycle A has 14 to 18 member atoms;
each $R^2$ is independently hydrogen, halo or $C_{1-4}$alkoxy;
$R^4$ and $R^5$ are hydrogen or $R^4$ and $R^5$ together form a double bond or a methylene group to form a fused cyclopropyl;
$R^6$ is hydrogen or methyl; and
$R^7$ is a $C_{3-7}$cycloalkyl optionally substituted with halo.

The invention further relates to methods for the preparation of the compounds of formula (I), including stereochemically isomeric forms, and N-oxides, quaternary amines, metal complexes, salts, hydrates or solvates thereof, their intermediates, and the use of the intermediates in the preparation of the compounds of formula (I).

The invention relates to the compounds of formula (I) per se, including stereochemically isomeric forms, and N-oxides, quaternary amines, metal complexes, salts, hydrates or solvates thereof, for use as a medicament. The invention relates to the compounds of formula (I) per se, including stereochemically isomeric forms, and N-oxides, quaternary amines, metal complexes, salts, hydrates or solvates thereof, for treating hepatitis C. The invention further relates to pharmaceutical compositions comprising a carrier and an antivirally effective amount of a compound of formula (I) as specified herein. The pharmaceutical compositions may comprise combinations of the aforementioned compounds with other anti-HCV agents. The pharmaceutical compositions may comprise combinations of the aforementioned compounds with anti-HIV agents. The invention further relates to the aforementioned pharmaceutical compositions for administration to a subject suffering from HCV infection.

The invention also relates to the use of a compound of formula (I), including stereochemically isomeric forms, or N-oxides, quaternary amines, metal complexes, salts, hydrates or solvates thereof, for the manufacture of a medicament for inhibiting HCV replication. The invention also relates to the use of a compound of formula (I), including stereochemically isomeric forms, or N-oxides, quaternary amines, metal complexes, salts, hydrates or solvates thereof, for the manufacture of a medicament for preventing or treating conditions associated with HCV. The invention also relates to a method of inhibiting HCV replication in a warm-blooded animal said method comprising the administration of an effective amount of a compound of formula (I), including stereochemically isomeric forms, or N-oxides, quaternary amines, metal complexes, salts, hydrates or solvates thereof. The invention also relates to a method for preventing or treating conditions associated with HCV in a warm-blooded animal said method comprising the administration of an effective amount of a compound of formula (I), including stereochemically isomeric forms, or N-oxides, quaternary amines, metal complexes, salts, hydrates or solvates thereof.

DETAILED DESCRIPTION

The present invention will now be further described. In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous to formulate a particular embodiment.

As used in the foregoing and hereinafter, the following definitions apply unless otherwise noted.

For the purpose of the present invention, the terms "subject" or "infected subject" or "patient" refers to an individual infected with HCV, in need of treatment.

The term "halo" or "halogen" is generic to fluoro, chloro, bromo and iodo.

As used herein "$C_{1-4}$alkyl" as a group or part of a group defines straight or branched chain saturated hydrocarbon radicals having from 1 to 4 carbon atoms such as for example methyl, ethyl, prop-1-yl, prop-2-yl, but-1-yl, but-2-yl, isobutyl, 2-methylprop-1-yl; "$C_{1-3}$alkyl" as a group or part of a group defines straight or branched chain saturated hydrocarbon radicals having from 1 to 3 carbon atoms such as for example methyl, ethyl, prop-1-yl, prop-2-yl.

The term "$C_{1-6}$alkylene" as a group or part of a group refers to $C_{1-6}$alkyl groups that are divalent, i.e., with two single bonds for attachment to two other groups. Non-limiting examples of alkylene groups includes methylene, ethylene, methylmethylene, propylene, ethylethylene, 1-methylethylene and 1,2-dimethylethylene.

"$C_{3-7}$cycloalkyl" is generic to cyclopropyl, cyclobutyl, cyclopentyl, cyclohexyl and cycloheptyl. The term "$C_{3-5}$cycloalkyl" is meant to comprise cyclopropyl, cyclobutyl and cyclopentyl.

The term "$C_{1-4}$alkoxy" or "$C_{1-4}$alkyloxy" as a group or part of a group refers to a radical having the Formula —OR$^a$ wherein R$^a$ is $C_{1-4}$alkyl as defined above. Non-limiting examples of suitable $C_{1-4}$alkoxy include methoxy, ethoxy, propoxy, isopropoxy, butoxy, isobutoxy, sec-butoxy and tert-butoxy.

It should be noted that the radical positions on any molecular moiety used in the definitions may be anywhere on such moiety as long as it is chemically stable.

Radicals used in the definitions of the variables include all possible isomers unless otherwise indicated. For instance, piperidinyl includes piperidin-1-yl, piperidin-2-yl, piperidin-3-yl, and piperidin-4-yl; pentyl includes pent-1-yl, pent-2-yl and pent-3-yl.

When any variable occurs more than one time in any constituent, each definition is independent.

Whenever used hereinafter, the term "compounds of formula (I)", or "the present compounds" or similar terms, it is meant to include the compounds of formula (I), including stereochemically isomeric forms, and their N-oxides, quaternary amines, metal complexes, salts, hydrates or solvates thereof. One embodiment comprises the compounds of formula (I) or any subgroup thereof specified herein, including the possible stereochemically isomeric forms, as well as the N-oxides, salts, hydrates, and solvates thereof. Another embodiment comprises the compounds of formula (I) or any subgroups thereof specified herein, including the possible stereochemically isomeric forms, as well as the N-oxides, salts, hydrates, and solvates thereof.

Whenever used hereinafter, the term "optionally substituted" is meant to include unsubstituted as well as substituted with at least one of the specified substituting radicals. For the purpose of example, "$C_{1-4}$alkyl optionally substituted with chloro" is meant to include unsubstituted $C_{1-4}$alkyl as well as $C_{1-4}$alkyl substituted with chloro.

The compounds of formula (I) may have one or more centers of chirality and may exist as stereochemically isomeric forms. The term "stereochemically isomeric forms" as used herein defines all the possible compounds made up of the same atoms bonded by the same sequence of bonds but having different three-dimensional structures, which the compounds of formula (I) may possess.

With reference to the instances where (R) or (S) is used to designate the absolute configuration of a chiral atom within a substituent, the designation is done taking into consideration the whole compound and not the substituent in isolation.

In one aspect, the present invention provides compounds of formula (I)

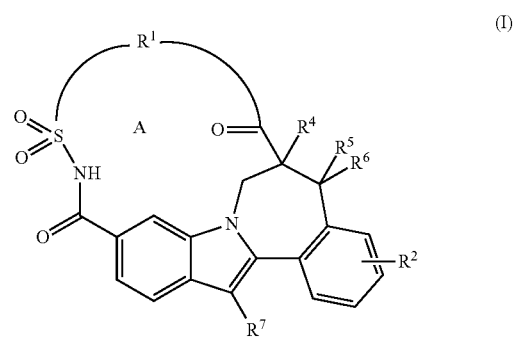

including stereochemically isomeric forms, and N-oxides, salts, hydrates, and solvates thereof, wherein $R^1$, $R^2$, $R^4$, $R^5$, $R^6$, $R^7$ and A have the same meaning as defined herein. Embodiments of the present inventions concerns compounds of formula (I), or any subgroup thereof as defined herein, wherein one or more of the definitions for $R^1$, $R^2$, $R^4$, $R^5$, $R^6$, and $R^7$ as specified in the embodiments herein-under apply:

Particular subgroups of the compounds of formula (I) are compounds of formula (II), (III) or (IV)

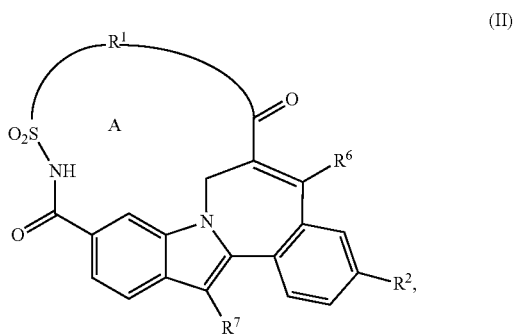

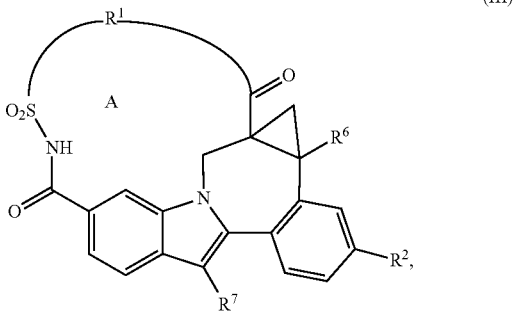

-continued

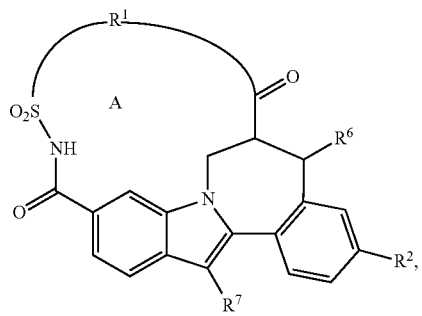

wherein R¹, R², R⁴, R⁵, R⁶, R⁷ and A have the same meaning as defined herein.

In one embodiment, R¹ is a bivalent chain selected from

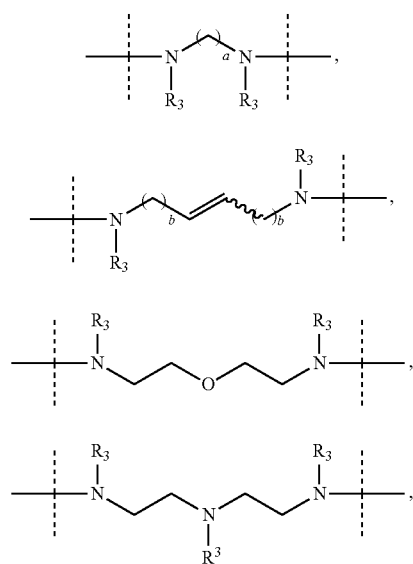

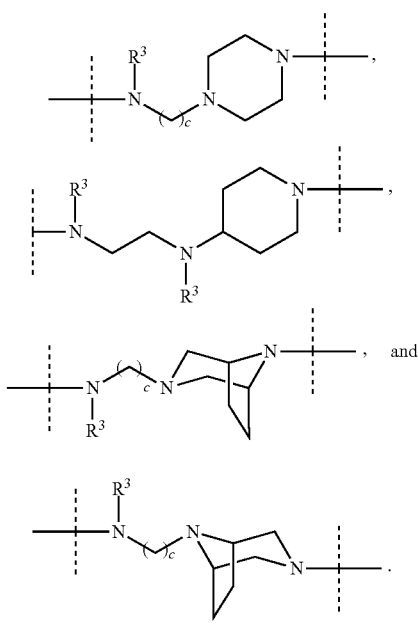

In a particular embodiment, R¹ is selected from

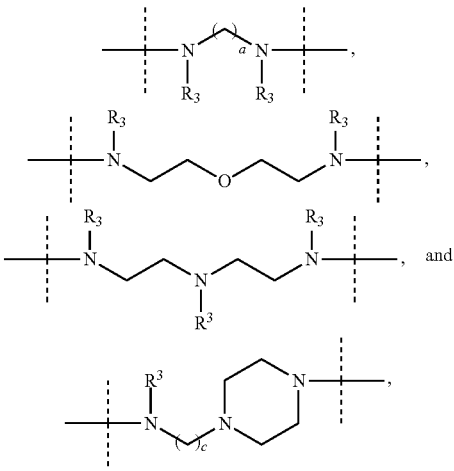

wherein a and c are as defined herein above, or wherein a is 4 or 5 and c is 1 or 2. In another particular embodiment R¹ is selected from —N(R³)—(CH$_2$)$_4$—N(R³)—,

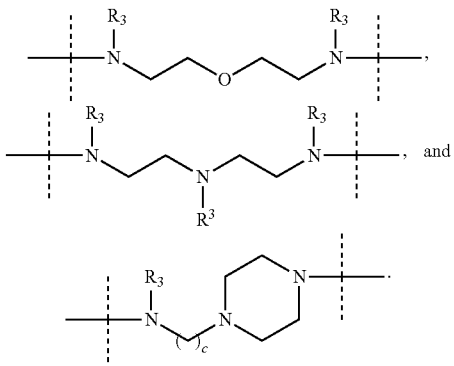

When R¹ is

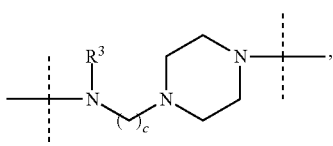

it is understood R¹ may be oriented in two directions, i.e. the piperazinyl moiety may be connected to the sulfonamide group while the aliphatic amine is connected to the carbonyl group, or, the piperazinyl moiety is connected to the carbonyl group and the aliphatic amine is connected to the sulfonamide group.

Preferably, when R¹ is

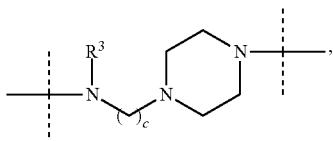

the piperazinyl moiety is connected to the carbonyl group and the aliphatic amine is connected to the sulfonamide group.

In a more particular embodiment, $R^1$ is selected from

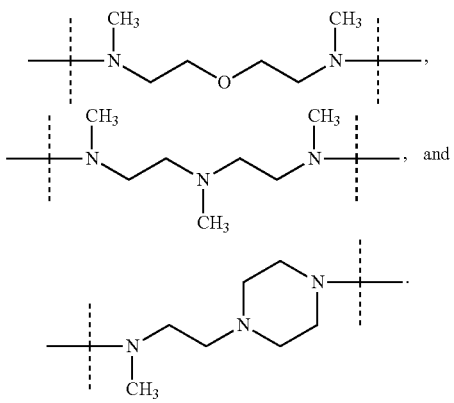

Alternatively, $R^1$ is selected from

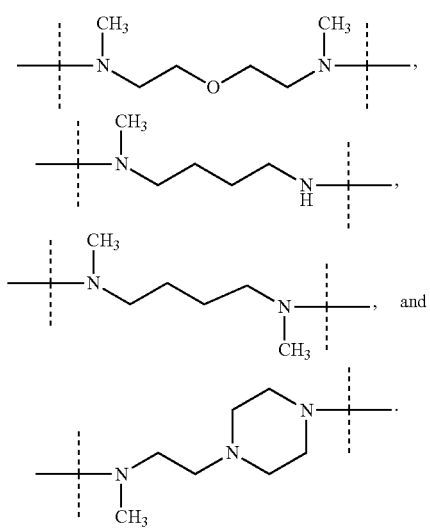

In a preferred embodiment, $R^1$ is

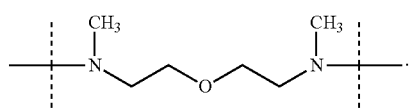

In another embodiment, $R^1$ is

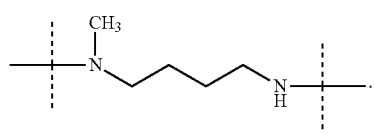

In another embodiment $R^1$ is

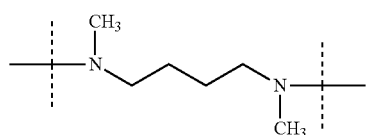

In another preferred embodiment, $R^1$ is

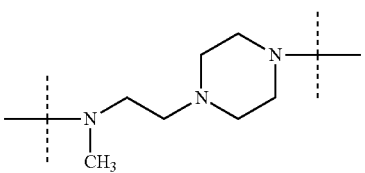

Each $R^3$ is independently selected from the group comprising hydrogen, $C_{1-4}$alkyl and $C_{3-5}$cycloalkyl. In a particular embodiment, $R^3$ is independently selected from the group consisting of hydrogen, methyl, ethyl, isopropyl and cyclopropyl. In a more particular embodiment, each $R^3$ is independently selected from the group consisting of hydrogen and methyl; or, $R^3$ is methyl.

Macrocycle A has 14 to 18 member atoms. In a particular embodiment, macrocycle A has 16, 17 or 18 member atoms. In a more particular embodiment, A has 17 member atoms.

$R^2$ is selected from the group comprising hydrogen, halo or $C_{1-4}$alkoxy. In a particular embodiment, $R^2$ is selected from the group comprising hydrogen, chloro, fluoro or methoxy. In a more particular embodiment, $R^2$ is hydrogen or methoxy or chloro; or, alternatively, $R^2$ is fluoro or methoxy; or, in a preferred embodiment, $R^2$ is methoxy. In another embodiment, $R^2$ is positioned on the benzene ring in meta or para with respect to the bond linking the benzene to the indole group. In a preferred embodiment, $R^2$ is positioned on the benzene ring in para with respect to the bond linking this benzene to the indole group.

$R^4$ and $R^5$ are hydrogen or $R^4$ and $R^5$ together form a double bond or a methylene group to form a fused cyclopropyl. In a particular embodiment, $R^4$ and $R^5$ are hydrogen or $R^4$ and $R^5$ together form a methylene group to form a fused cyclopropyl.

In another particular embodiment, $R^4$ and $R^5$ together form a double bond.

In another embodiment, $R^6$ is selected from hydrogen and methyl. In a particular embodiment, $R^6$ is hydrogen when the compound of formula (I) is a compound of formula (III) or (IV). In another particular embodiment, $R^6$ is methyl when the compound of formula (I) is a compound of formula (II).

$R^7$ is a $C_{3-7}$cycloalkyl optionally substituted with halo. In a particular embodiment, $R^7$ is selected from cyclopentyl, cyclohexyl, and fluorocyclohexyl (in particular, 2-fluorocyclohexyl). In a preferred embodiment, $R^7$ is cyclohexyl.

A particular subgroup of compounds of formula (I) are compounds of formula (I) wherein $R^4$ and $R^5$ together form a double bond, and wherein one or more of the definitions for $R^1$, $R^2$, $R^6$, and $R^7$ as specified in the embodiments herein apply. A more particular subgroup of compounds of formula (I) are compounds of formula (II), wherein $R^1$, $R^2$, $R^4$, $R^5$, $R^6$, and $R^7$ and A have the same meaning as defined herein. More particular are those compound represented by the following structural formulae (II-1), (II-2), and (II-3) wherein $R^2$, $R^6$ and $R^7$ have the same meaning as defined herein for compounds of formula (I) or subgroups thereof.

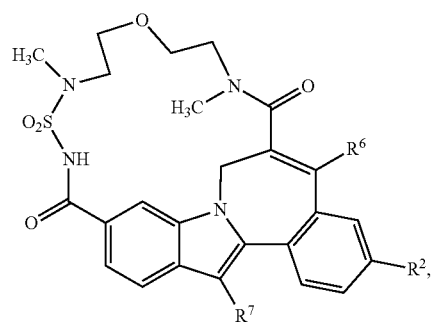
(II-1)

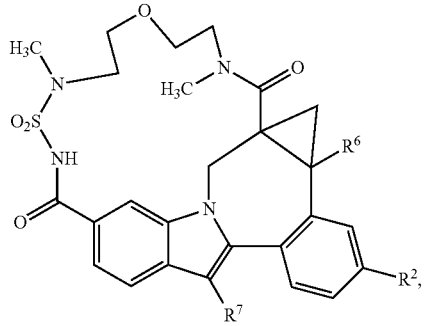
(III-1)

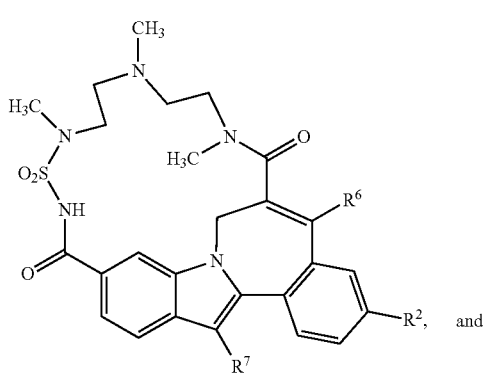
(II-2)

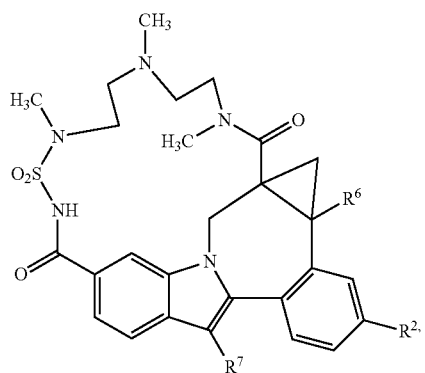
(III-2)

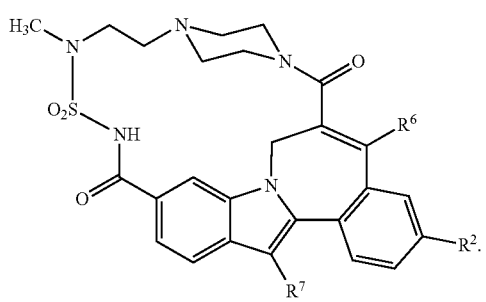
(II-3)

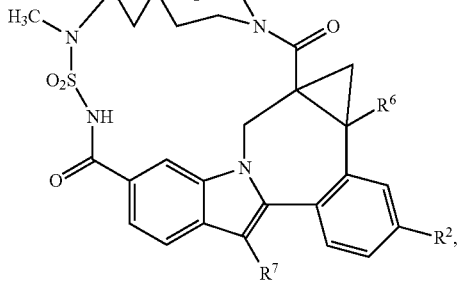
(III-3)

(III-4)

In a particular embodiment, the invention provides compounds of, independently, formula (II), (II-1), (II-2) and (II-3) wherein $R^6$ is hydrogen or methyl, more in particular, wherein $R^6$ is a methyl.

In another embodiment, the invention provides compounds of formula (II) or subgroups thereof wherein $R^7$ is cyclohexyl or 2-fluorocyclohexyl.

In another embodiment, the invention provides compounds of formula (II) or subgroups thereof wherein $R^2$ is hydrogen, methoxy or chloro. Alternatively, the invention provides compounds of formula (II) or subgroups thereof wherein $R^2$ is fluoro or methoxy.

A particular subgroup of compounds of formula (I) are compounds of formula (III), wherein $R^1$, $R^2$, $R^4$, $R^5$, $R^6$, $R^7$ and A have the same meaning as defined herein. More particular are those compounds represented by the following structural formulae (III-1), (III-2), (III-3) and (III-4) wherein $R^2$, $R^6$ and $R^7$ have the same meaning as defined herein for compounds of formula (I).

In particular, the invention provides compounds of, independently, formula (III), (III-1), (III-2), (III-3) and (III-4) wherein $R^6$ is hydrogen.

In another embodiment, the invention provides compounds of formula (III) or subgroups thereof wherein $R^7$ is cyclohexyl or 2-fluorocyclohexyl.

In another embodiment, the invention provides compounds of formula (III) or subgroups thereof wherein $R^2$ is hydrogen, methoxy or chloro.

A particular subgroup of compounds of formula (I) are compounds of formula (IV), wherein $R^1$, $R^2$, $R^4$, $R^5$, $R^6$, $R^7$ and A have the same meaning as defined herein. More particular are those compound represented by the following structural formulae (IV-1), (IV-2), and (IV-3) wherein $R^2$, $R^6$ and $R^7$ have the same meaning as defined herein for compounds of formula (I).

(IV-1)

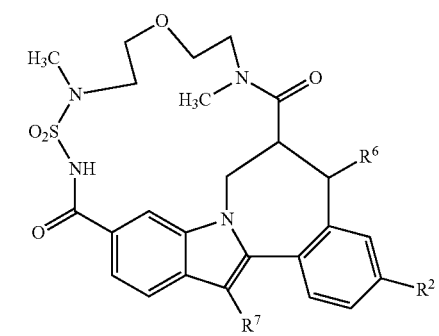

(IV-2)

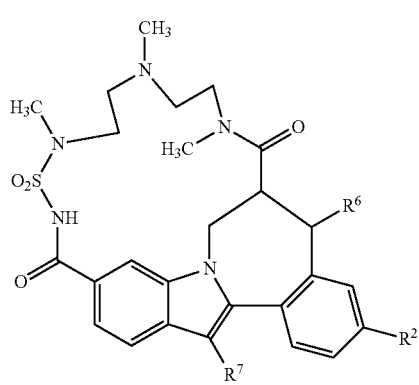

(IV-3)

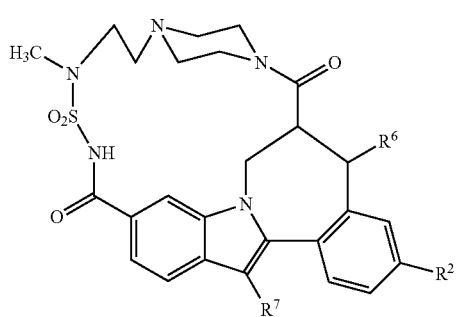

In another embodiment, the invention provides compounds of formula (IV) or subgroups thereof wherein $R^7$ is cyclohexyl or 2-fluorocyclohexyl.

In another embodiment, the invention provides compounds of formula (IV) or subgroups thereof wherein $R^2$ is hydrogen, methoxy or chloro.

In a particular embodiment, the present invention concerns compounds of formula (II-1), (III-1), and (IV-1). Another embodiment of the present invention concerns compounds of formula (II-2), (III-2) and (IV-2). Another embodiment of the present invention concerns compounds of formula (II-3), (III-3) and (IV-3).

In a particular embodiment, the invention provides compounds of formula (I) selected from the group comprising

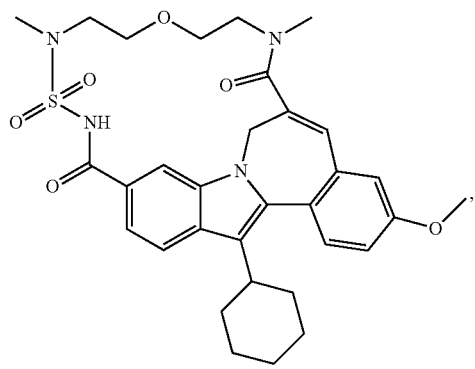

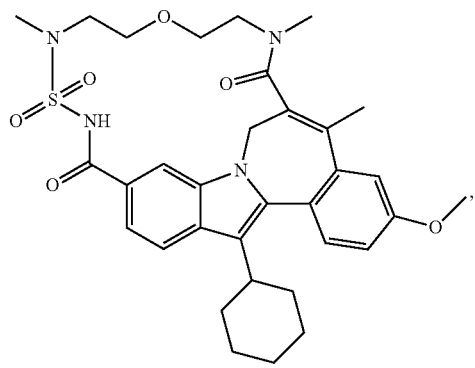

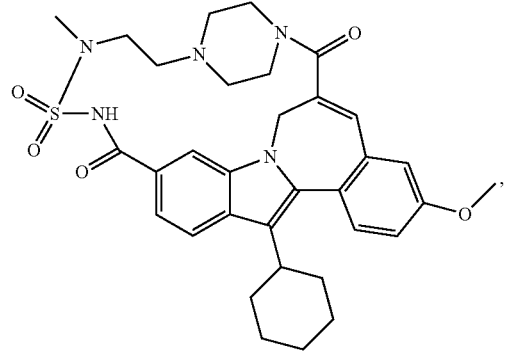

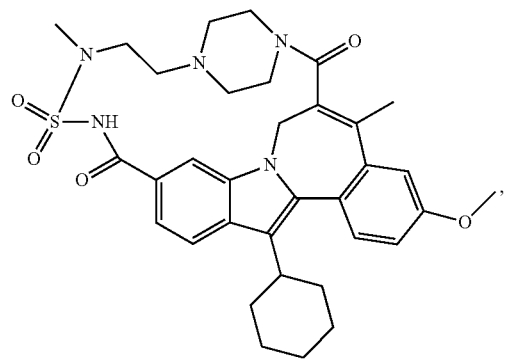

15
-continued
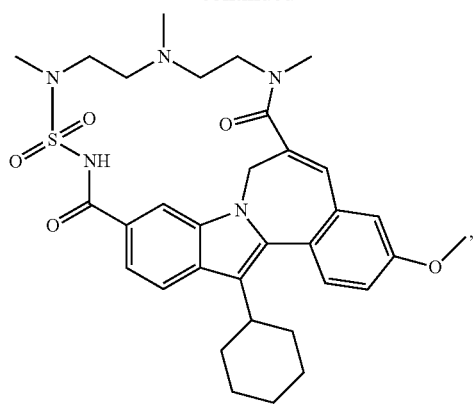
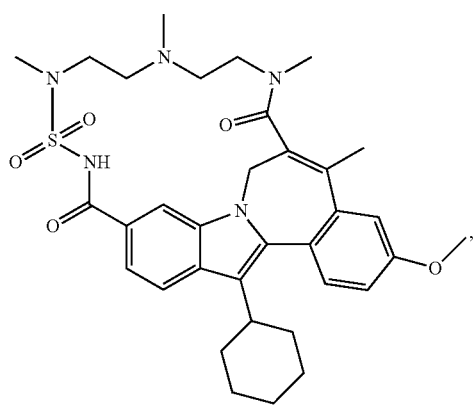
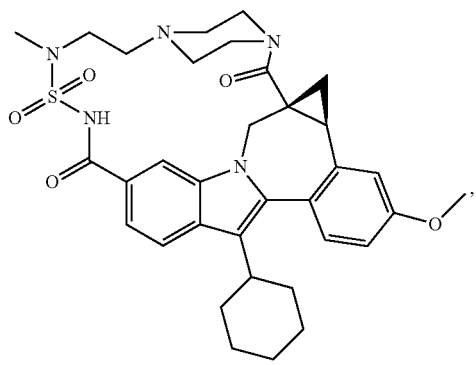
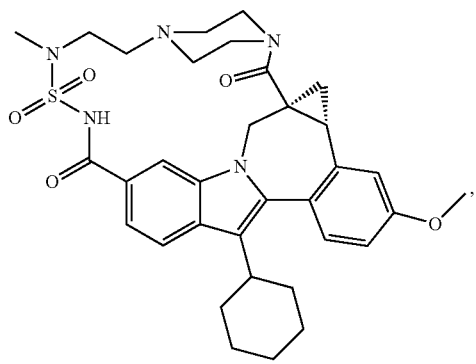
16
-continued
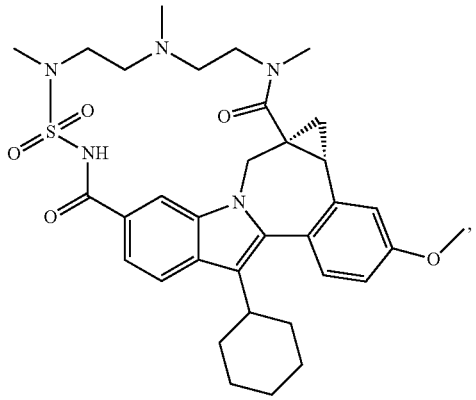
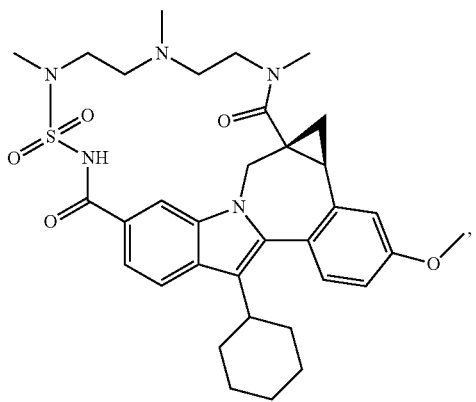
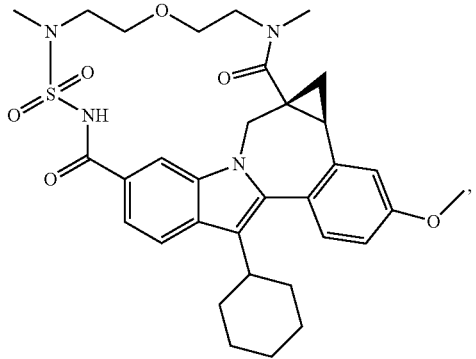
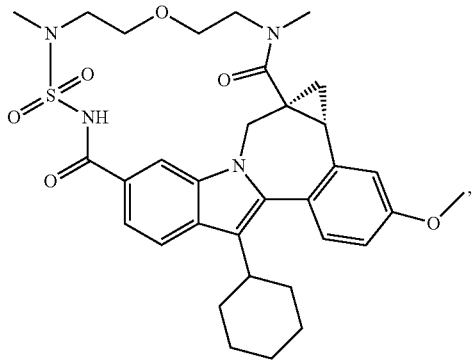

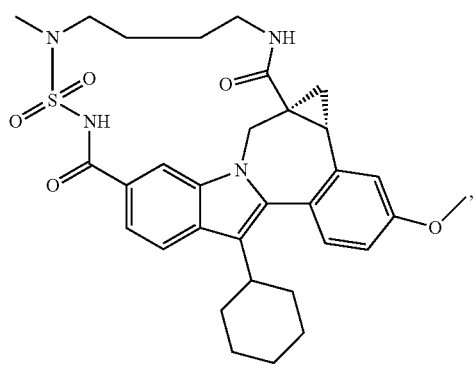
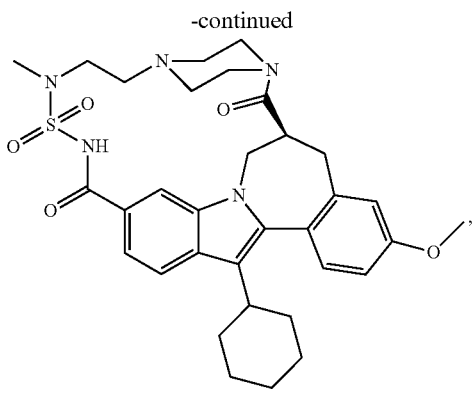
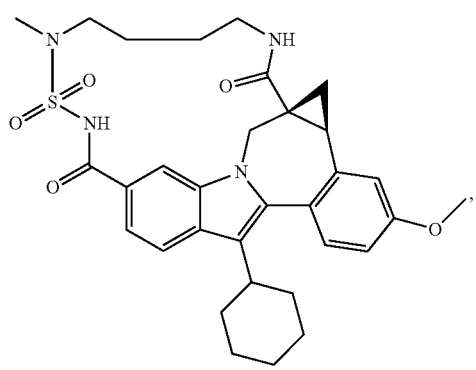
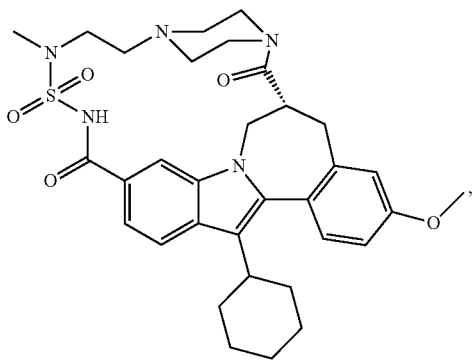
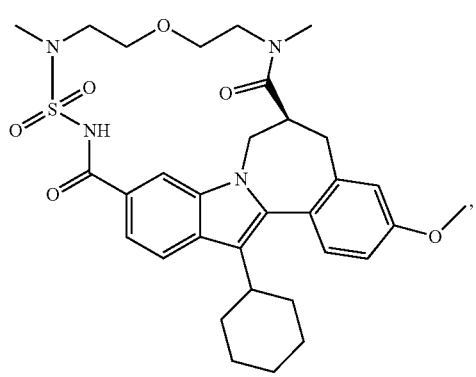
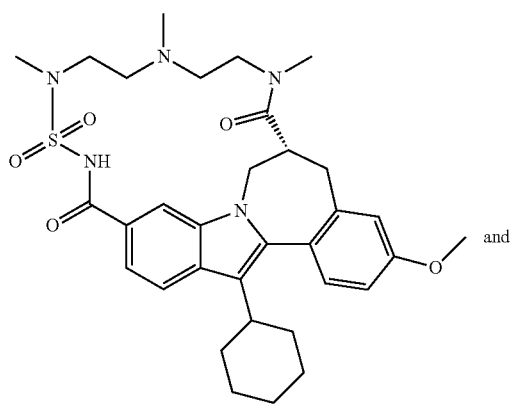
and
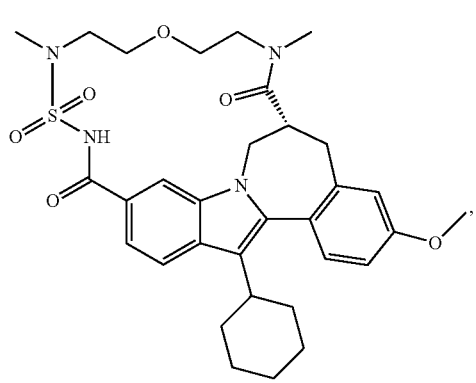
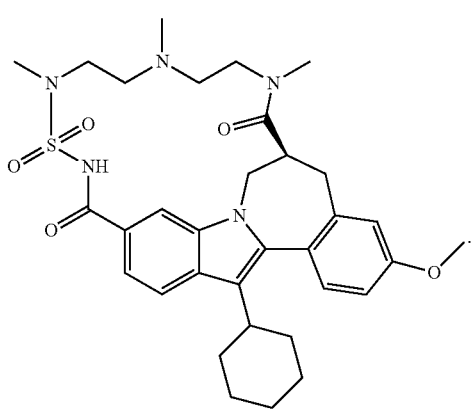
More in particular, the present invention provides compounds of formula (I) selected from

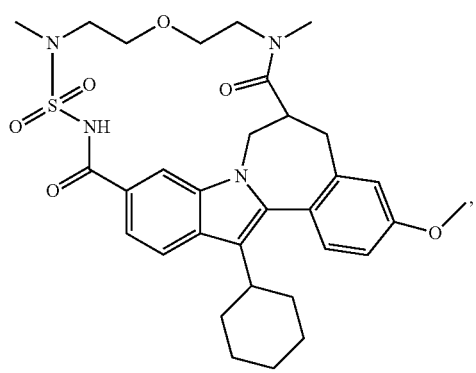
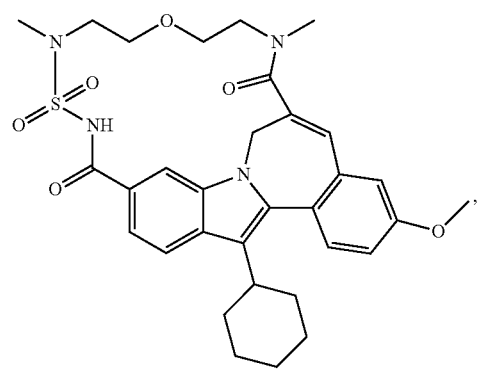
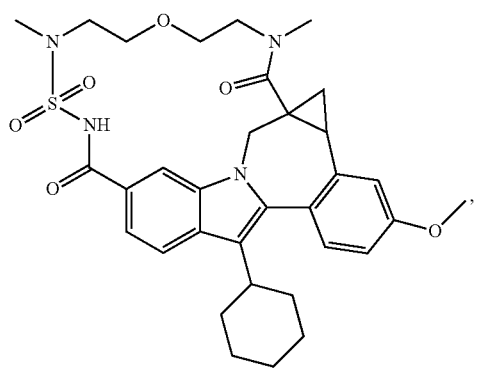
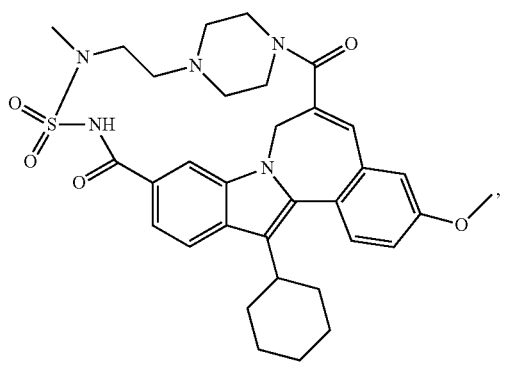
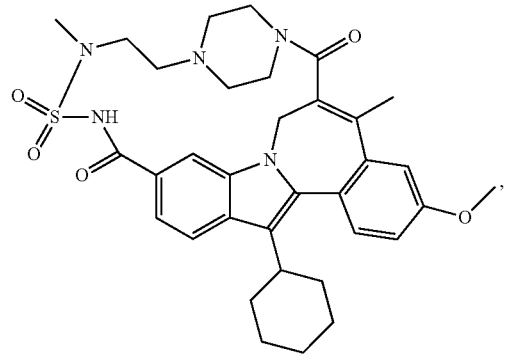
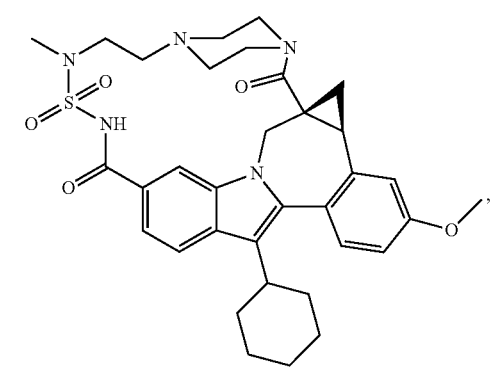
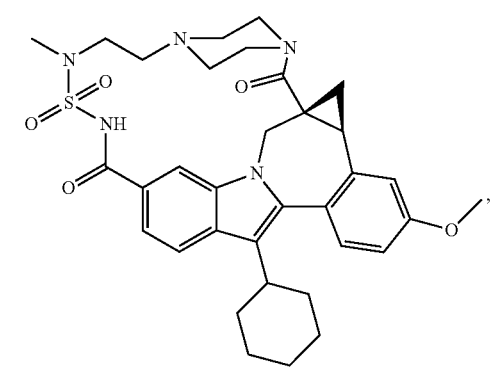
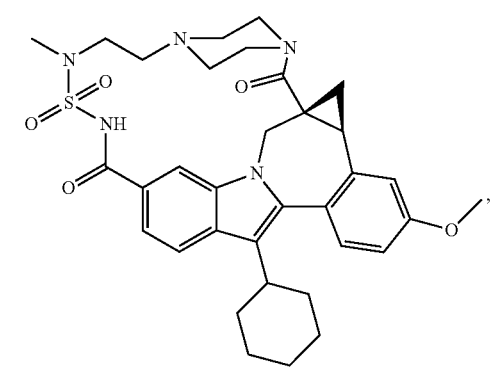
and

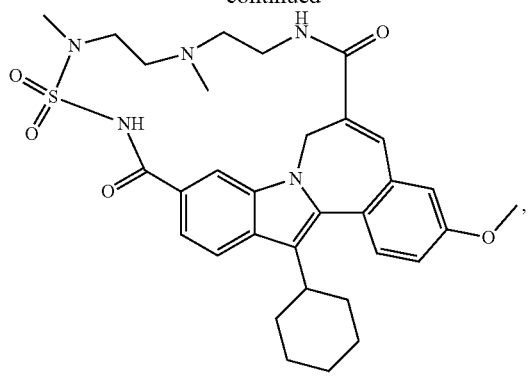
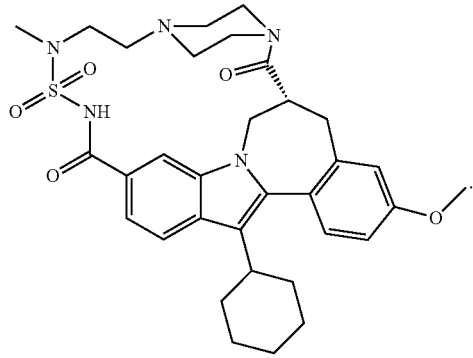 [SMILES: COc1ccc2c(c1)C[C@@H]1Cn3c-2c(C2CCCCC2)c2ccc(cc23)C(=O)NS(=O)(=O)N(C)CCN2CCN(CC2)C1=O]
Alternatively, the present invention provides compounds of formula (I) selected from
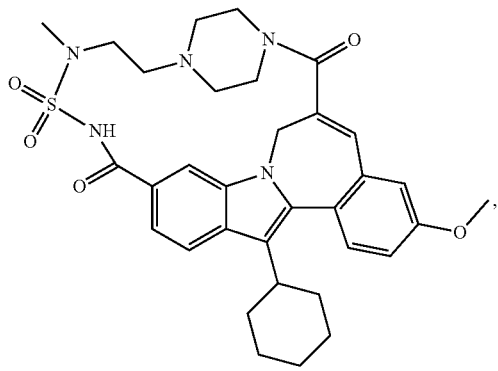
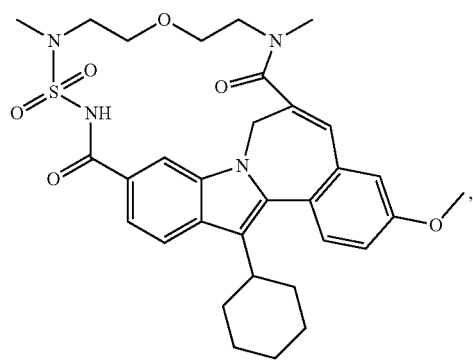
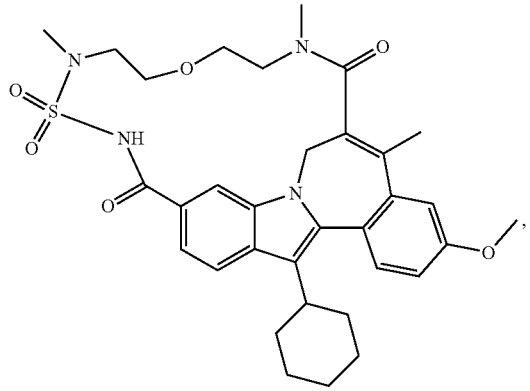
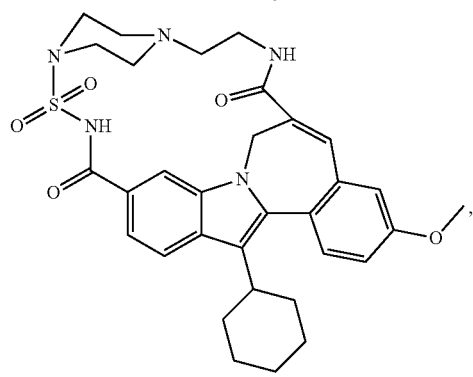
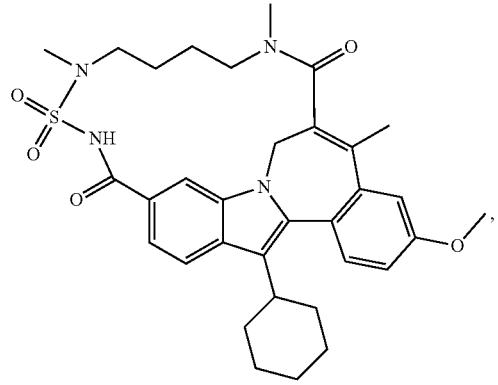
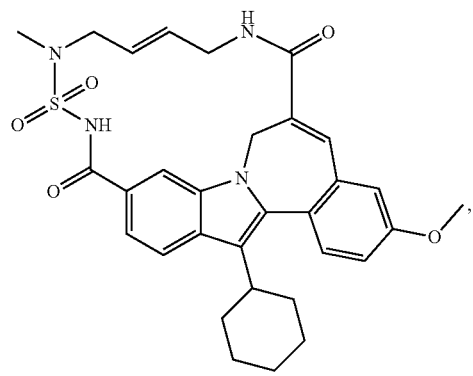

23
-continued
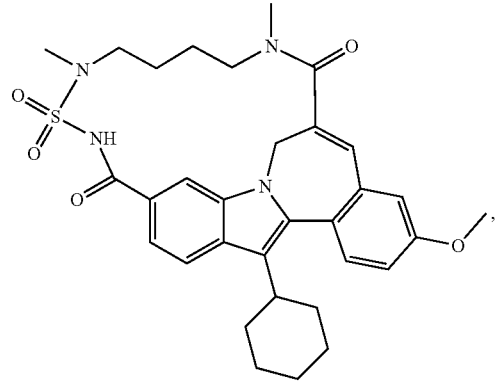
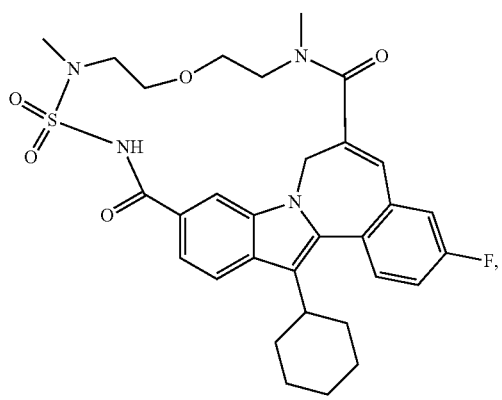
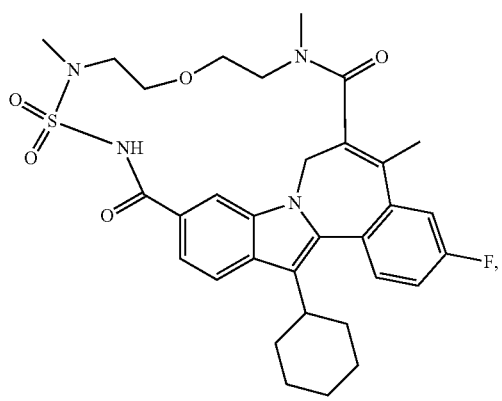
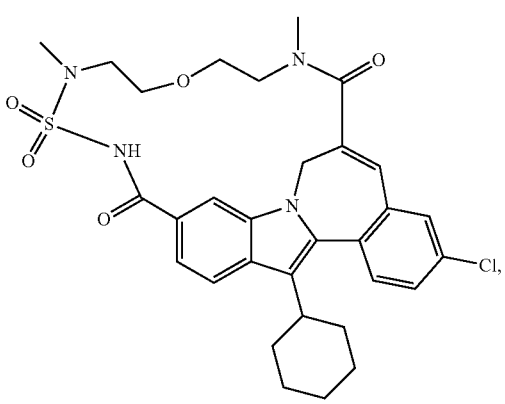
24
-continued
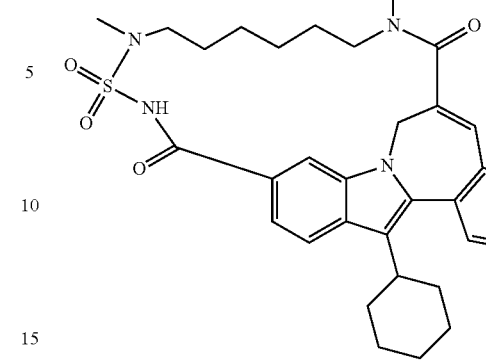
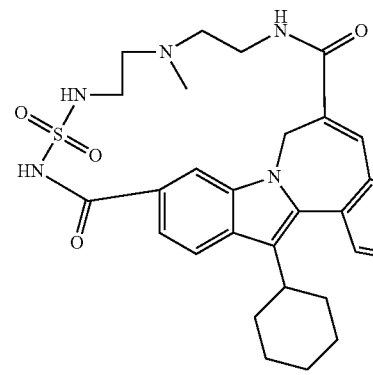
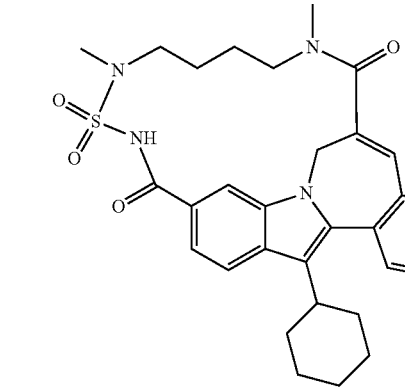
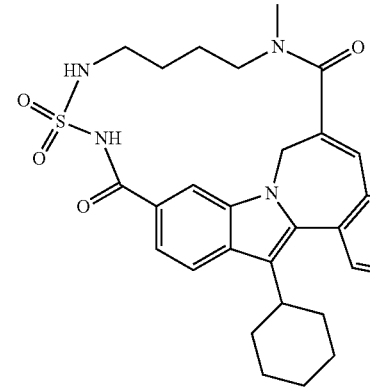

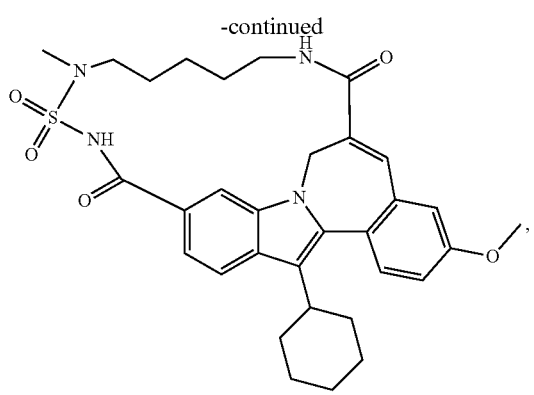

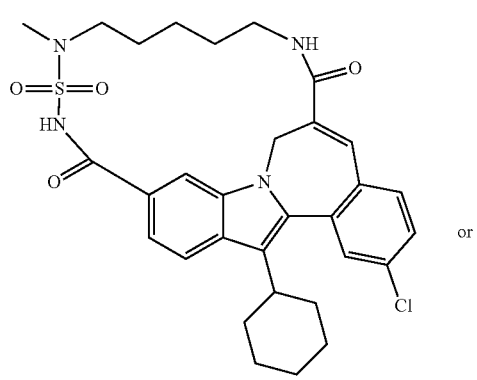

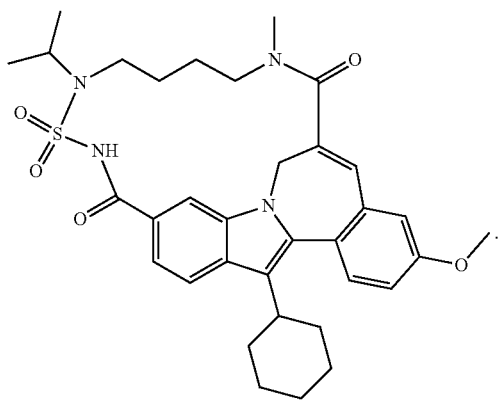

More in particular, the present invention provides compounds of formula (I) selected from

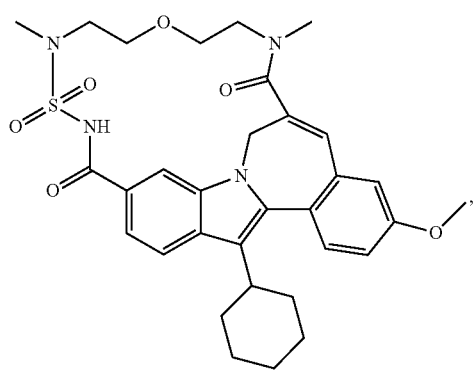

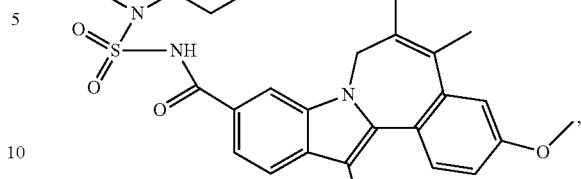

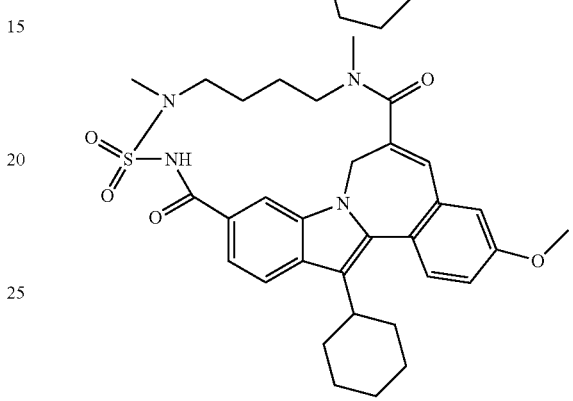

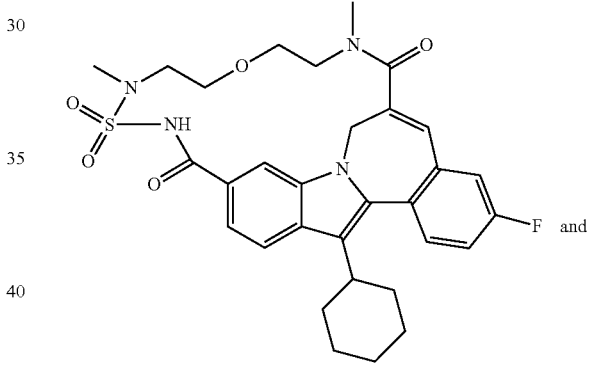

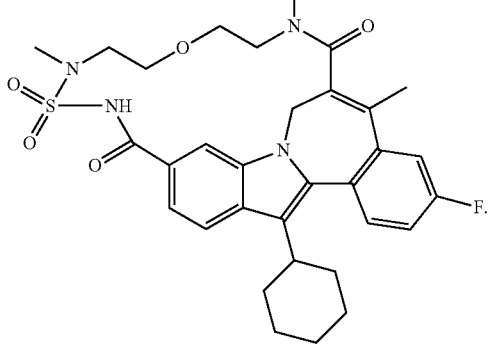

Unless otherwise mentioned or indicated, the chemical designation of a compound encompasses the mixture of some or all possible stereochemically isomeric forms, which said compound might possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula (I) or any subgroup thereof, can be obtained separately by conventional methods. Appropriate physical separation methods that may advantageously be employed are, for example, selective crystallization and chromatography, e.g. column chromatography.

For some of the compounds of formula (I), their N-oxides, salts, hydrates, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

In an embodiment, the present invention concerns compounds of formula (IIIA), (IIIB), (IVA) and (IVB),

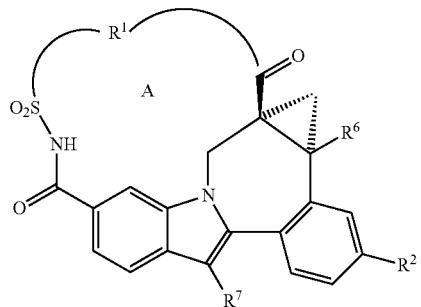

(IIIA)

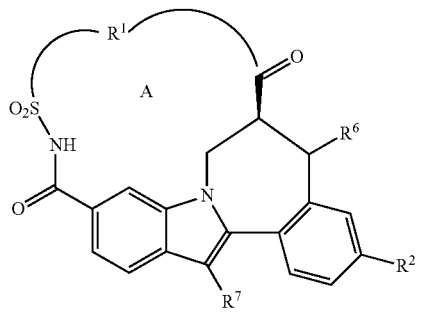

(IIIB)

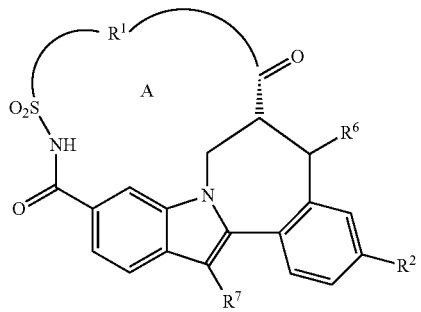

(IVA)

(IVB)

wherein $R^1$, $R^2$, $R^6$, $R^7$ and A have the same meaning as that defined herein.

In a more particular embodiment, the present invention concerns compounds of Formula (IIIA-1), (IIIA-2), (IIIA-3), (IIIA-4), (IIIB-1), (IIIB-2), (IIIB-3), (IIIB-4), (IVA-1), (IVA-2), (IVA-3), (IVB-1), (IVB-2) and (IVB-3)

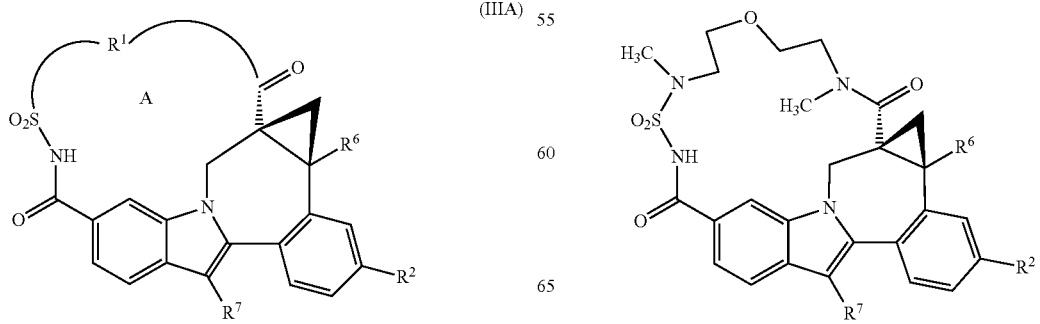

(IIIA-1)

(IIIA-2)
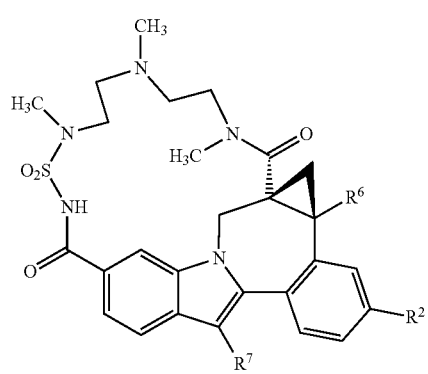
(IIIA-3)
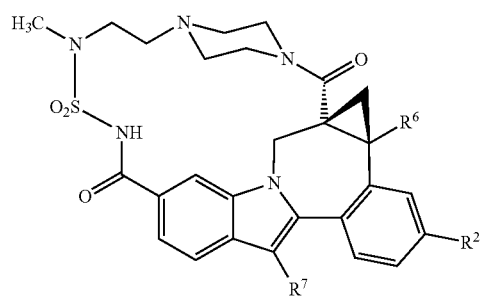
(IIIA-4)
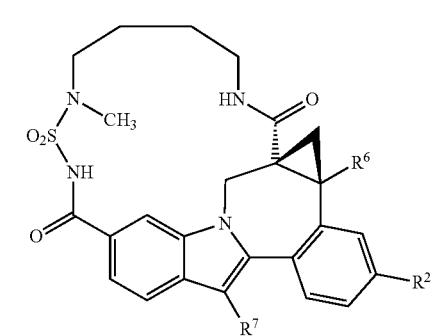
(IIIB-1)
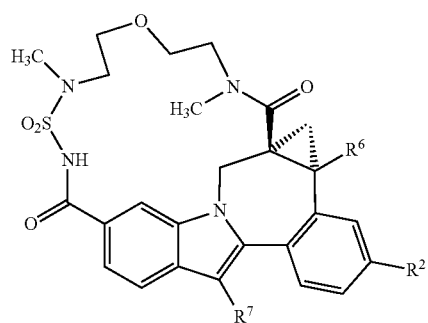
(IIIB-2)
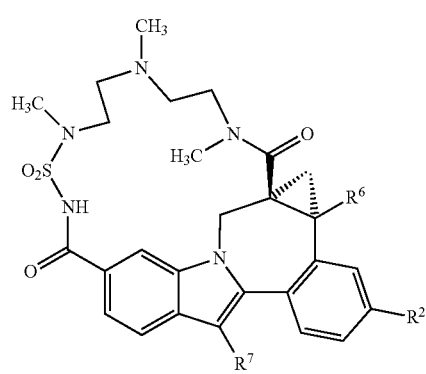
(IIIB-3)
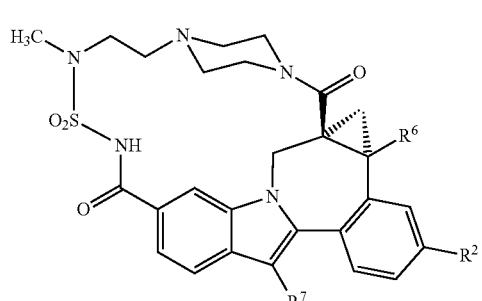
(IIIB-4)
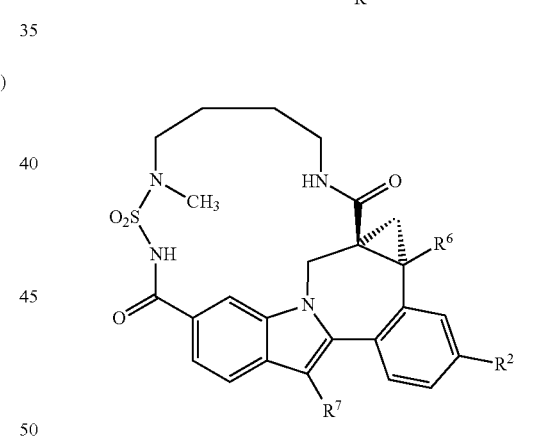
(IVA-1)
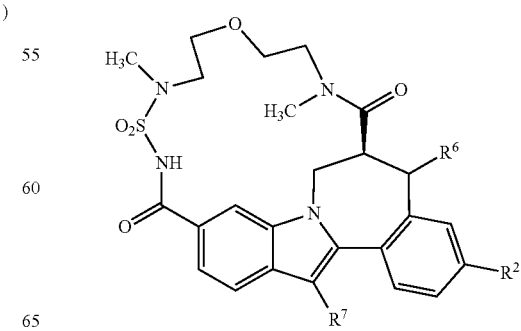

(IVA-2)
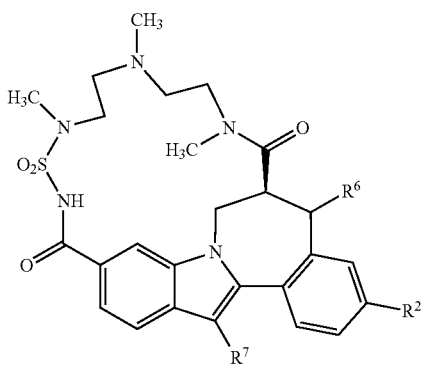

(IVA-3)
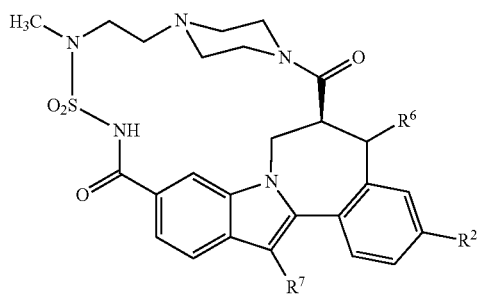

(IVB-1)
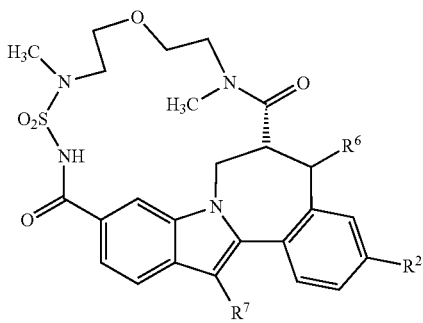

(IVB-2)
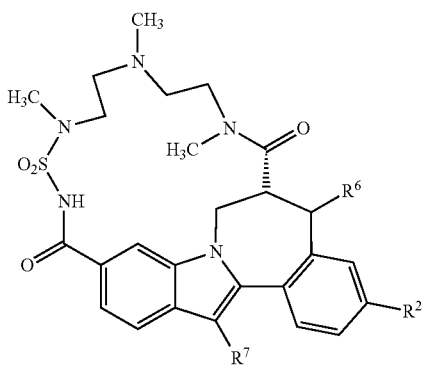

(IVB-3)
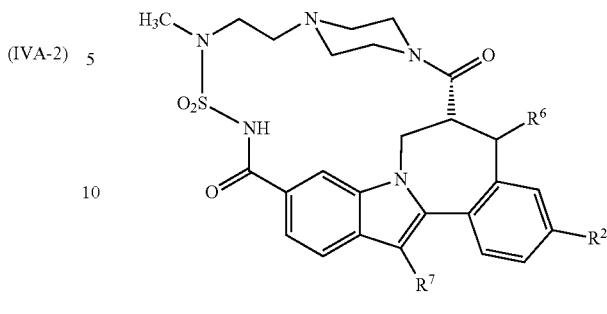

wherein $R^2$, $R^6$ and $R^7$ have the same meaning as that defined herein.

In another embodiment, where applicable, compounds of formula (I) or subgroups thereof have the stereochemical configuration as illustrated by formula (IA).

(IA)
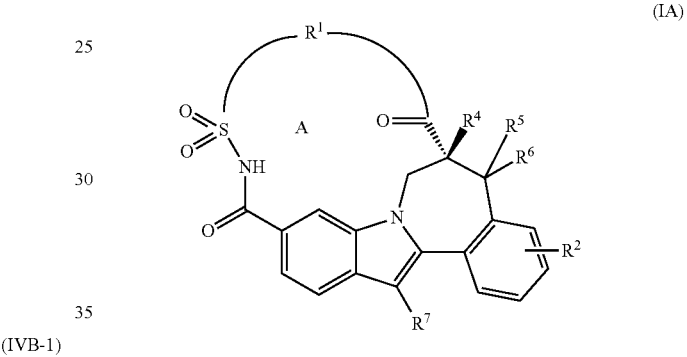

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter-ion is pharmaceutically acceptable. However, salts of acids and bases, which are non-pharmaceutically acceptable, may also find use, for example, in the preparation or purification of a pharmaceutically acceptable compound. All salts, whether pharmaceutically acceptable or not are included within the ambit of the present invention.

The pharmaceutically acceptable acid and base salts as mentioned hereinabove are meant to comprise the therapeutically active non-toxic acid and base addition salt forms that the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-amino-salicylic, pamoic and the like acids.

Conversely, said salt forms can be converted by treatment with an appropriate base into the free base form.

The compounds of formula (I) or any subgroup thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "quaternary amine" as used hereinbefore defines the quaternary ammonium salts which the compounds of formula (I) or any subgroup thereof are able to form by reaction between a basic nitrogen of a compound of formula (I) or any subgroup thereof and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) or any subgroup thereof wherein one or several nitrogen atoms are oxidized to the so-called N-oxide.

It will be appreciated that the compounds of formula (I) or any subgroup thereof may have metal binding, chelating, complex forming properties and therefore may exist as metal complexes or metal chelates. Such metalated derivatives of the compounds of formula (I) or any subgroup thereof are intended to be included within the scope of the present invention.

Some of the compounds of formula (I) or any subgroup thereof and intermediates may also exist in one or more tautomeric form. Such forms although not explicitly indicated in the above formula are intended to be included within the scope of the present invention. Accordingly, the compounds and intermediates may be present as a mixture of tautomers or as an individual tautomer.

In the invention, particular preference is given to compounds of Formula I or any subgroup thereof, that in the inhibition assays described below have an inhibition value of less than 100 µM, preferably less than 50 µM, more preferably less than 10 µM, preferably less than 5 µM, even more preferably less than 1 µM preferably less than 100 nM, and in particular less than 10 nM, as determined by a suitable assay, such as the assays used in the Examples below.

It is to be understood that the above defined subgroups of compounds of formula (I) as well as any other subgroup defined herein, are meant to include stereochemically isomeric forms, and any N-oxides, salts, quaternary amines, hydrates, solvates and metal complexes of such compounds.

Preparation of the Compounds of Formula (I)

General Synthetic Schemes

Compounds of formula (I) may be prepared following the different methods A, B, C, D, E, F and G described below, from indole derivatives A-1

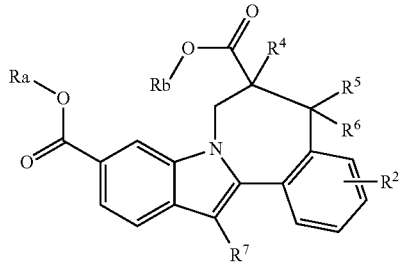

(A-1)

wherein $R^2$, $R^4$, $R^5$, $R^6$ and $R^7$ are as defined for compounds of formula (I) or subgroups thereof, and Ra is selected from methyl and tert-butyl and Rb is selected from methyl. The compounds of formula (A-1) are either known in the art or may be obtained as described in US20070270406A1, WO2007/054741 and WO2007/092000.

Method A

A schematic overview for the synthesis of the compounds of formula (I) is given in scheme 1. The method starts from a compound of formula A-1.

Compounds of formula A-2 may be prepared by the regioselective hydrolysis of the ester bearing the Rb group, under basic conditions, using a hydroxide such as LiOH or NaOH, in polar solvents such as water, an alcohol such as methanol or ethanol, tetrahydrofurane (THF), or a mixture thereof. This method may be used when Rb is a methyl group and Ra is a tert-butyl group, or Ra is a methyl group.

A monoprotected bifunctional $R^1$ derived reagent of formula PG-$R^1$—H wherein $R^1$ is as defined for formula (I) or subgroups thereof; may then be coupled to the carboxylic acid of compounds A-2 to form an amide bond, leading to compounds A-3. "PG", as used herein, is a suitable amine protecting group, chosen from the ones known in the art. Preferably PG is a tert-butyloxycarbonyl (Boc) protecting group or a 4-nitrobenzenesulfonyl (nosyl) group.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Scheme 1

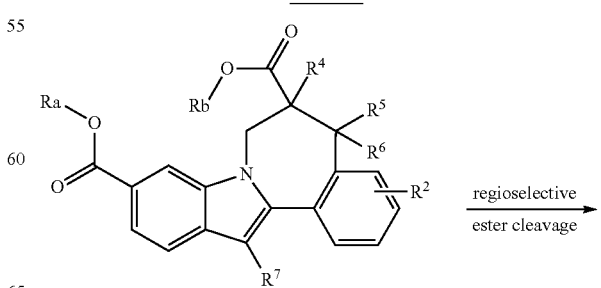

A-1

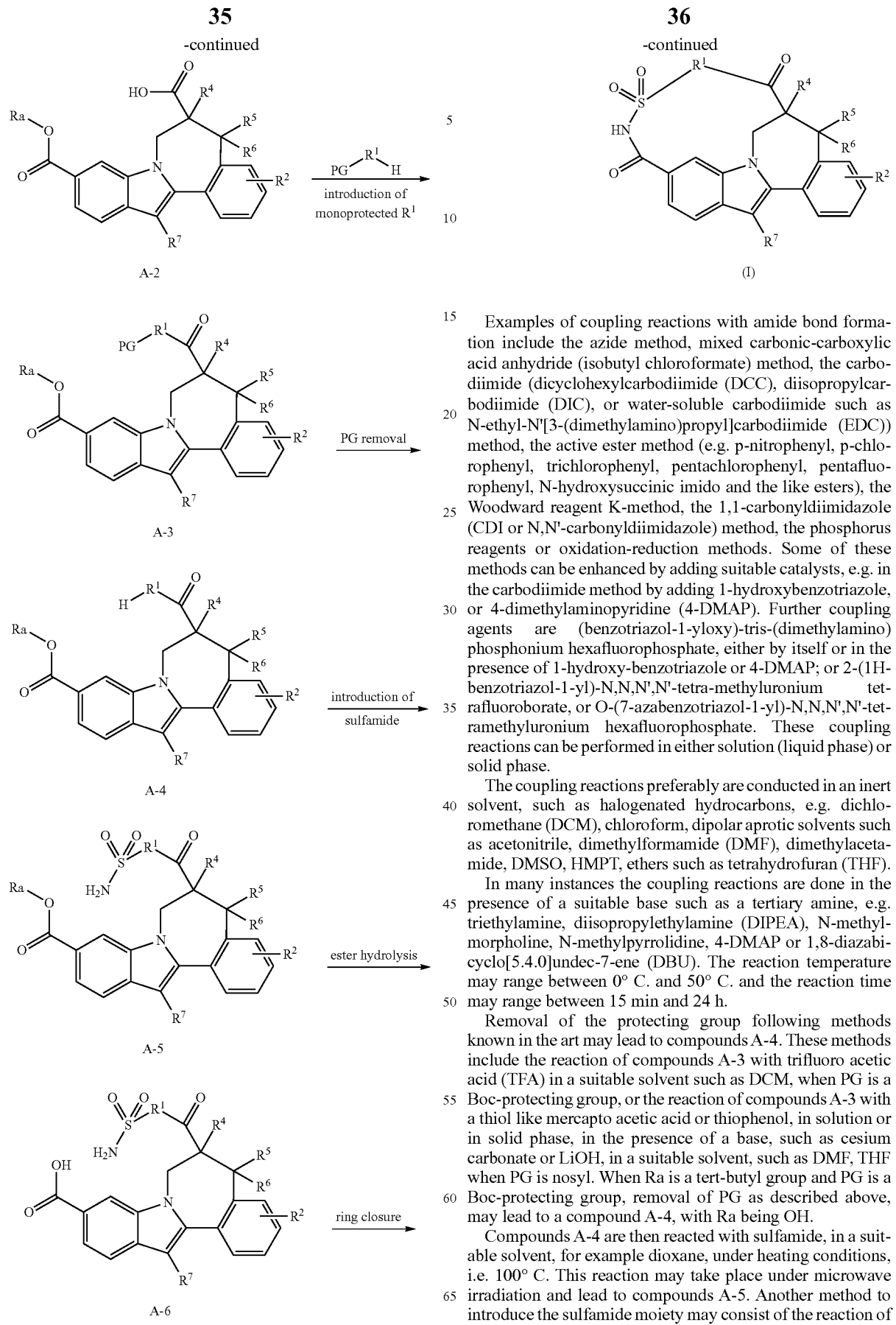

Examples of coupling reactions with amide bond formation include the azide method, mixed carbonic-carboxylic acid anhydride (isobutyl chloroformate) method, the carbodiimide (dicyclohexylcarbodiimide (DCC), diisopropylcarbodiimide (DIC), or water-soluble carbodiimide such as N-ethyl-N'[3-(dimethylamino)propyl]carbodiimide (EDC)) method, the active ester method (e.g. p-nitrophenyl, p-chlorophenyl, trichlorophenyl, pentachlorophenyl, pentafluorophenyl, N-hydroxysuccinic imido and the like esters), the Woodward reagent K-method, the 1,1-carbonyldiimidazole (CDI or N,N'-carbonyldiimidazole) method, the phosphorus reagents or oxidation-reduction methods. Some of these methods can be enhanced by adding suitable catalysts, e.g. in the carbodiimide method by adding 1-hydroxybenzotriazole, or 4-dimethylaminopyridine (4-DMAP). Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

The coupling reactions preferably are conducted in an inert solvent, such as halogenated hydrocarbons, e.g. dichloromethane (DCM), chloroform, dipolar aprotic solvents such as acetonitrile, dimethylformamide (DMF), dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

Removal of the protecting group following methods known in the art may lead to compounds A-4. These methods include the reaction of compounds A-3 with trifluoro acetic acid (TFA) in a suitable solvent such as DCM, when PG is a Boc-protecting group, or the reaction of compounds A-3 with a thiol like mercapto acetic acid or thiophenol, in solution or in solid phase, in the presence of a base, such as cesium carbonate or LiOH, in a suitable solvent, such as DMF, THF when PG is nosyl. When Ra is a tert-butyl group and PG is a Boc-protecting group, removal of PG as described above, may lead to a compound A-4, with Ra being OH.

Compounds A-4 are then reacted with sulfamide, in a suitable solvent, for example dioxane, under heating conditions, i.e. 100° C. This reaction may take place under microwave irradiation and lead to compounds A-5. Another method to introduce the sulfamide moiety may consist of the reaction of compound A-4 with aminosulfonyl-chloride, in the presence of a suitable base, such as triethylamine, DIPEA, or pyridine, in a suitable solvent, such as a chlorinated solvent like DCM, or DMF, THF.

The ester function of compounds A-5, i.e. —CO—O—Ra, may then be hydrolyzed, using conditions known in the art, and including the saponification in basic media as described above, leading to compounds A-6. Heating may be required to complete this reaction. Acidic conditions may also be used to hydrolyze the ester function of compounds A-5, for example TFA in a suitable solvent like DCM, when Ra is a tert-butyl group.

Compounds (I) may be obtained by macrocyclisation by forming the intramolecular acylsulfamide bond, in the presence of coupling agents, such as CDI which converts the carboxylic acid group to a reactive species acylimidazole, under heating. This acylimidazole may then be purified before adding a suitable base such as DBU, in order to perform the ring closure, which may take place under heating conditions. Solvents used for these reactions may include acetonitrile or THF. Other coupling agents, such as those known in the art, may also be used to achieve the ring closure.

Method B

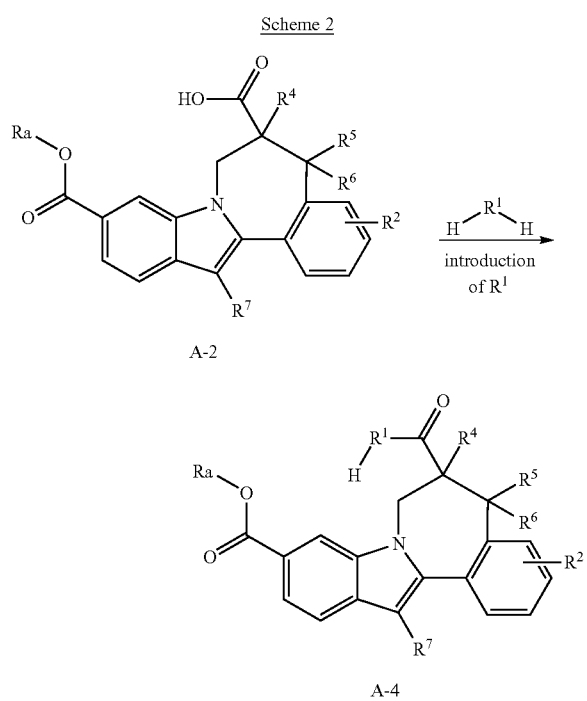

Scheme 2

A-2

A-4

An alternate method leading to compounds A-4 as illustrated in scheme 2, may be the formation of an amide bond between compounds A-2 and a symmetrical bivalent chain R1, used in excess compared to compounds A-2. This amide bond may be synthesized as described above, in particular using a coupling agent such as [dimethylamino-([1,2,3]triazolo[4,5-b]pyridin-3-yloxy)-methylene]-dimethyl-ammonium hexafluorophosphate (HATU), in the presence of a base such as DIPEA and in a suitable solvent like DCM, DMF, or more preferably THF. Compounds A-4 may then be reacted as described above in method A in order to prepare compounds (I).

Method C

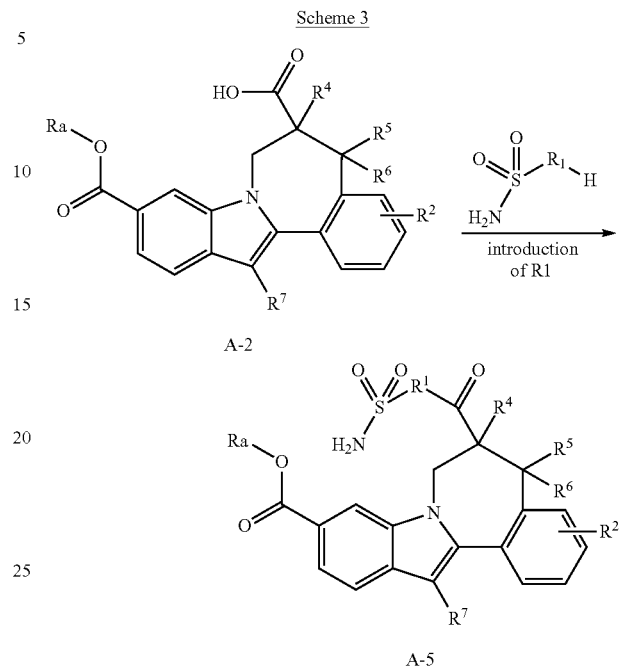

Scheme 3

A-2

A-5

Compounds may be prepared directly from compounds A-2, in a similar way as described above for the synthesis of compounds A-3, but using a bivalent chain $R^1$ bearing one sulfamide moiety instead of a protecting group. Such a sulfamide chain $R^1$ may be introduced on H—$R^1$—H by heating a reagent of formula H—$R^1$—H, which can either be monoprotected by a suitable protecting group (i.e. PG-$R^1$—H), or not if it is symmetrical, with sulfamide in a suitable solvent, such as dioxane, under microwave irradiation. The protecting group may then be removed by methods known in the art, for example by reaction with TFA in dichloromethane when the protecting group is a Boc-protecting group, leading to the monosulfamide derivatized $R^1$ chain.

Method D

Compounds of formula A-3 or A-4 may undergo functional group manipulation, such as alkylation or reductive amination, before PG removal of compounds A-3 and/or reaction leading to the sulfamide A-4.

Method E

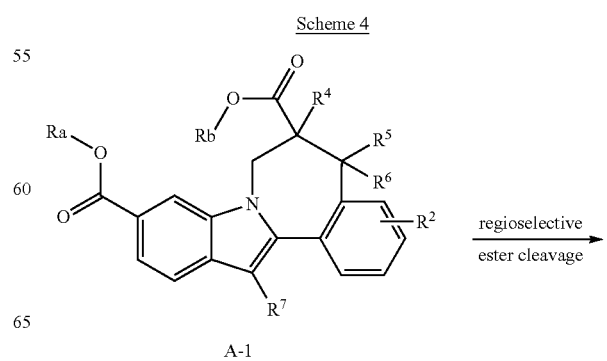

Scheme 4

A-1

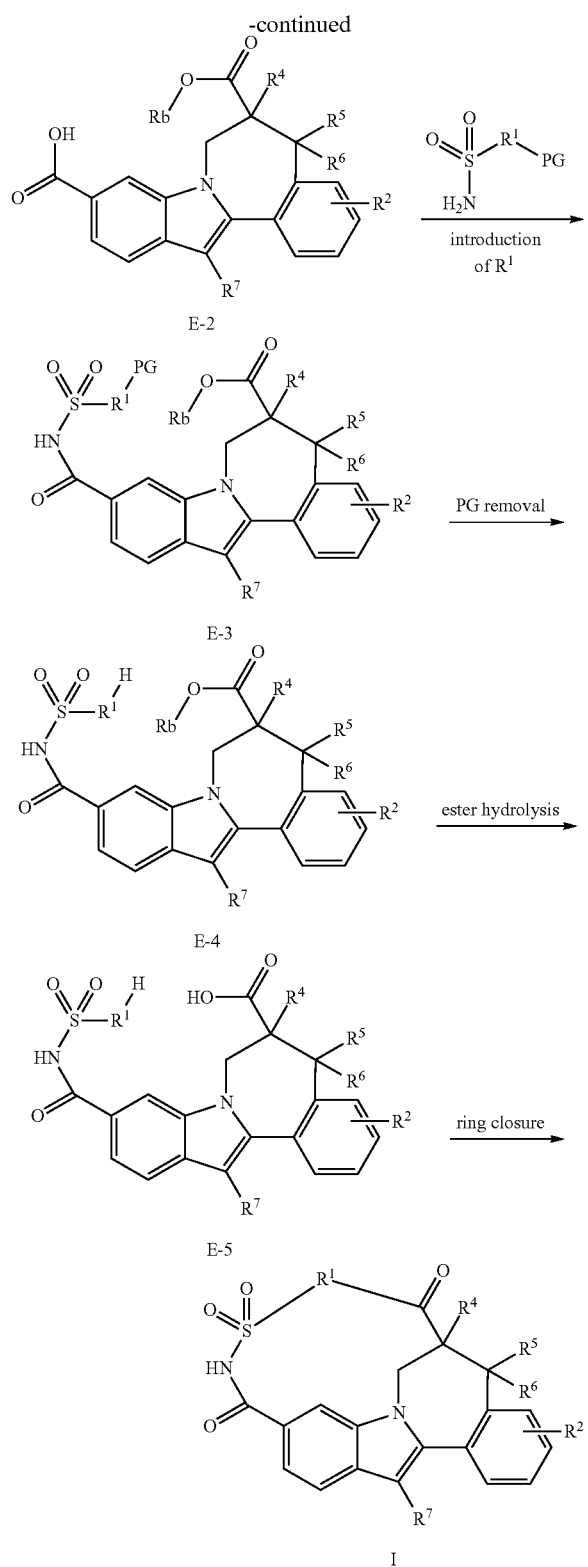

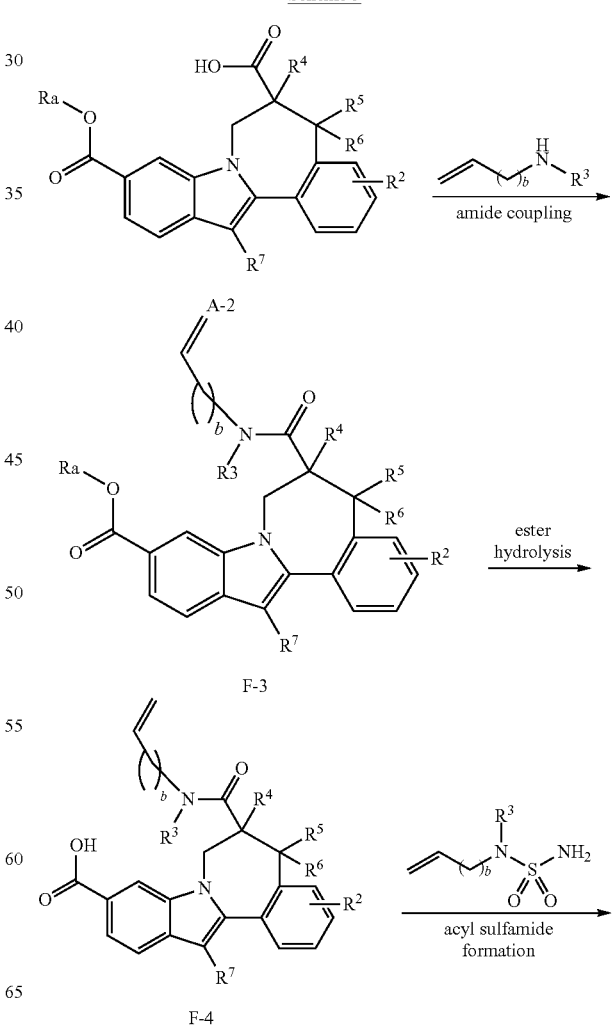

described for the last step of method A. Preferably the coupling agent used to activate the carboxylic acid group may be CDI, in a suitable solvent like acetonitrile or THF, under heating conditions. Addition of the sulfamide chain in the presence of a base such as DBU may subsequently lead to compounds E-3. PG is a suitable amine protecting group, chosen from the ones known in the art. Preferably, within method E, PG is a Boc-protecting group.

Removal of the protecting group PG of compounds E-3 following methods known in the art may lead to compounds E-4. These methods include the reaction of compounds E-3 with TFA in a suitable solvent such as DCM, when PG is a Boc-protecting group.

The ester function of compounds E-4 (Rb is a methyl group) may then be hydrolyzed, using conditions known in the art, and including the saponification in basic media as described above, leading to compounds E-5.

Alternatively, compounds E-3 may undergo the saponification reaction in basic media to hydrolyze the ester bearing Rb, prior to the removal of the amine protecting group using the conditions described above, and leading to compounds E-5.

Compounds (I) may be obtained by macrocyclisation of compounds E-5 by forming the intramolecular amide bond, in the presence of coupling agents, as described in method A. Preferably this amide formation step may be performed under high dilution conditions.

Method F

Scheme 5

The ester bearing the Ra group of compounds A-1 (Ra being for example a tert-butyl group and Rb a methyl group) may be hydrolyzed as described above, in acidic conditions, using for instance TFA in a suitable solvent like DCM, to yield the carboxylic acid derivative E-2.

Reaction of compounds E-2 with the sulfamide moiety introduced on a mono-protected bivalent chain R1, may lead to the acyl sulfamide compounds E-3, using the conditions

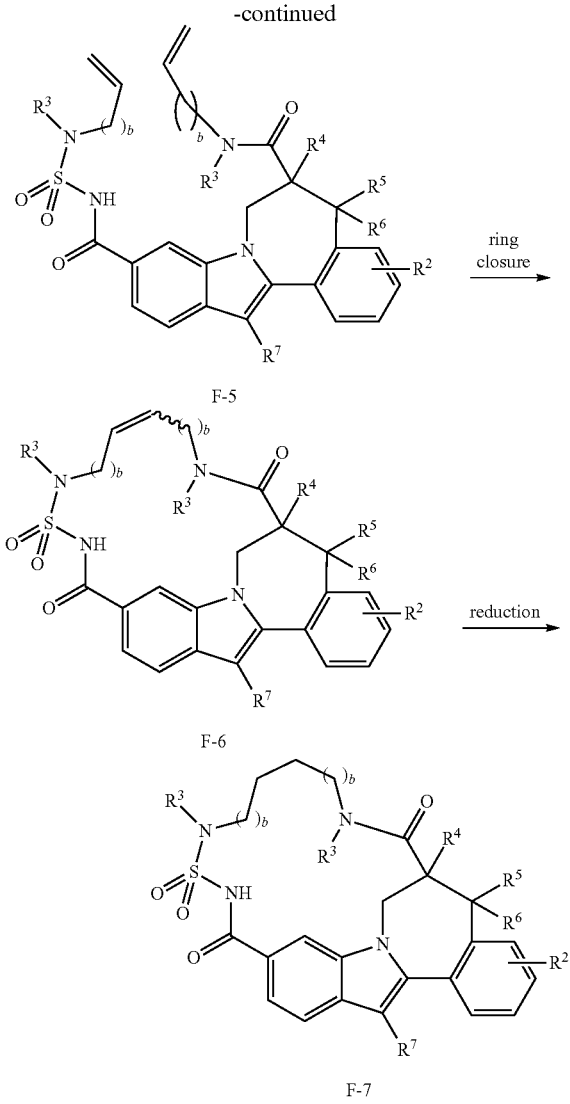

F-5

F-6

F-7 ring closure reduction

Compounds F-3 may be obtained by an amide forming reaction, starting from compounds A-2 and an alkenylamine, as described for the second step of method A. Subsequent ester hydrolysis under basic or acidic conditions as described previously may lead to compounds F-4. The acylsulfamide bond may then be formed using the method described for the last step of method A, using an alkenyl sulfamide compound and leading to compounds F-5.

Alternatively, the acylsulfamide group may be introduced on a compound of formula E-2, prior to the hydrolysis of the ester bearing the Rb group and coupling of the obtained carboxylic acid with an alkenamine as described above, leading to compound F-5.

Formation of the macrocycle, i.e. compound of formula F-6, which is a compound of formula (I) bearing the following bivalent chain as $R^1$:

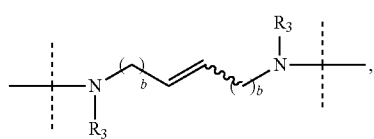

can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. benzylidene-bis(tricyclo-hexylphosphine)dichlororuthenium and (1,3-bis-(2,4,6-trimethylphenyl)-2-imidazolidinylidene)dichloro(phenylmethylene)(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene) dichloro-(o-isopropoxyphenylmethylene)ruthenium respectively. Also, other catalysts containing other transition metals such as Mo can be used for this reaction.

The metathesis reactions may be conducted in a suitable solvent such as for example ethers, e.g. THF, dioxane; halogenated hydrocarbons, e.g. dichloromethane, $CHCl_3$, 1,2-dichloroethane and the like, hydrocarbons, e.g. toluene. These reactions are conducted at increased temperatures under nitrogen atmosphere.

Compounds of formula (I) or any subgroup thereof or any subgroups thereof may be converted into each other following art-known functional group transformation reactions. For example, amino groups may be N-alkylated, nitro groups reduced to amino groups, a halo atom may be exchanged for another halo.

Compounds of formula F-6 may be submitted to catalytic hydrogenation, using for example Pd/C as a catalyst, in a suitable solvent such as methanol, ethanol, THF, acetic acid or a mixture thereof, to yield compounds of formula F-7, where the alkene of the bivalent chain R1 is reduced to the corresponding alkane. Compounds of formula F-6 belonging to the group of compounds of formula (II) may lead to compounds F-7 having the structure of compounds of formula (IV) after this hydrogenation step.

More generally, a compound of formula (II) may be transformed to a compound of formula (IV) by catalytic hydrogenation as shown below.

Scheme 6

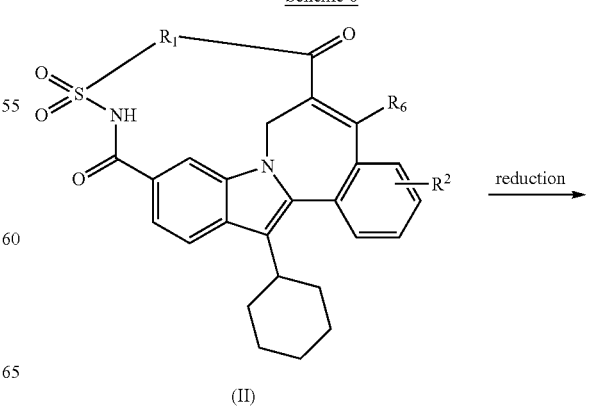

(II)

reduction

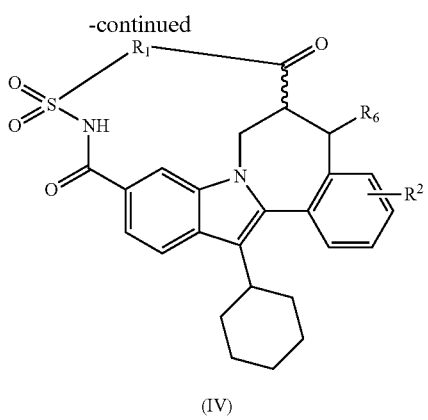

(IV)

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

Method G describes the synthesis of enantiomerically pure starting materials A-2, belonging to the groups of compounds (III) and (IV).

Method G

Scheme 7

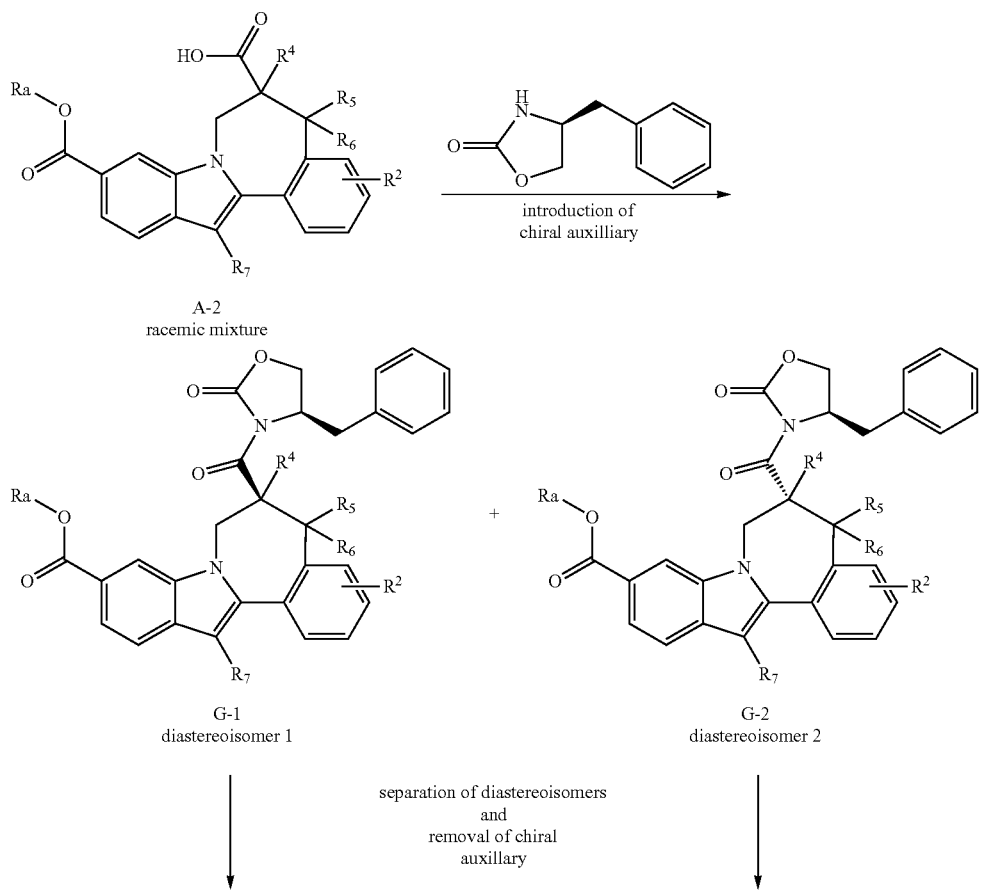

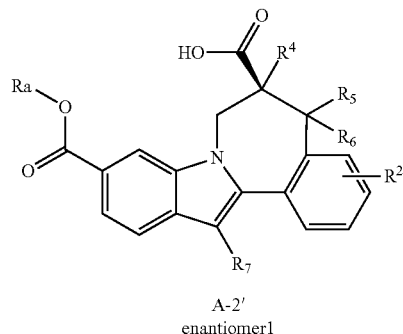

A-2'
enantiomer1

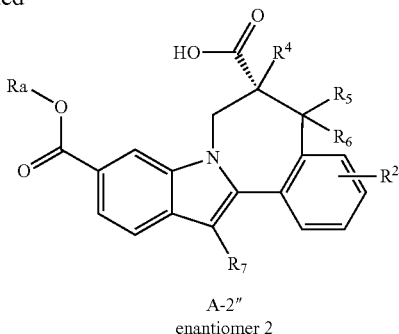

A-2''
enantiomer 2

A racemic mixture A-2 may be reacted with a chiral auxiliary, such as (S)-4-benzyl-2-oxazolidinone, after having being transformed to its acylchloride using methods known in the art, such as reaction of A-2 with oxalyl chloride in a suitable solvent like THF, in the presence of a catalytic amount of DMF. The acid chloride may then be reacted with the anion of (S)-4-benzyl-2-oxazolidinone formed by the reaction with a strong base, such as butyl lithium, in a suitable solvent such as THF, at low temperatures, typically −78° C., and under an inert atmosphere, leading to the diastereoisomers G1 and G2, which can be isolated by methods known in the art, such as chromatography on silica gel.

Removal of the chiral auxiliary from each of the diastereoisomers G1 and G2 may then be performed with a base such as NaOH in a suitable solvent, such as methanol, water, THF, leading to the enantiomerically pure compounds A-2' and A-2''. Using these enantiomerically pure starting materials may lead to enantiomerically pure compounds of formula (I) bearing one stereocenter, such as compounds of formula (IIIA), (IIIB).

Pure stereochemically isomeric forms of the compounds of formula (I) or any subgroups thereof may be obtained by the application of art-known procedures. Diastereomers may be separated by physical methods such as selective crystallization and chromatographic techniques, e.g., counter-current distribution, liquid chromatography and the like.

The compounds of formula (I) or any subgroups thereof may be obtained as racemic mixtures of enantiomers, which can be separated from one another following art-known resolution procedures. The racemic compounds of formula (I) or any subgroups thereof, which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) or any subgroups thereof involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) or any subgroups thereof, as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I) or any subgroups thereof, as specified herein.

Therefore, according to an embodiment of the present invention, the compounds of formula (I) or any subgroup thereof may be formulated into various pharmaceutical forms for administration purposes. It is understood that all compositions usually employed for systemically administering drugs are included as appropriate compositions. To prepare the pharmaceutical compositions of this invention, an effective amount of the particular compound, optionally in salt form or a metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) or any subgroups thereof and a pharmaceutically acceptable carrier.

Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) and any subgroup thereof show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis.

However, compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

Due to their antiviral properties, particularly their anti-HCV properties, the compounds of formula (I) or any subgroup thereof, including stereochemically isomeric forms, and their N-oxides, quaternary amines, metal complexes, salts, hydrates and solvates, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to virally infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), or any subgroups thereof, as specified herein.

The present invention also concerns combinations of a compound of formula (I) or any subgroup thereof, as specified herein with other anti-HCV agents. In an embodiment, the invention concerns combination of a compound of Formula (I) or any subgroup thereof with at least one anti-HCV agent. In a particular embodiment, the invention concerns combination of a compound of Formula (I) or any subgroup thereof with at least two anti-HCV agents. In a particular embodiment, the invention concerns combination of a compound of Formula (I) or any subgroup thereof with at least three anti-HCV agents. In a particular embodiment, the invention concerns combination of a compound of Formula (I) or any subgroup thereof with at least four anti-HCV agents.

The combination of previously known anti-HCV compound, such as interferon-$\alpha$ (IFN-$\alpha$), pegylated interferon-$\alpha$, ribavirin or a combination thereof, and, a compound of formula (I) or any subgroup thereof can be used as a medicine in a combination therapy. In an embodiment, the term "combination therapy" relates to a product containing mandatory (a) a compound of formula (I), and (b) at least one other anti-HCV compound, as a combined preparation for simultaneous, separate or sequential use in treatment of HCV infections, in particular, in the treatment of infections with HCV.

Anti-HCV compounds encompass agents selected from HCV polymerase inhibitors, R-7128, MK-0608, VCH759, PF-868554, GS9190, NM283, valopicitabine, PSI-6130, XTL-2125, NM-107, R7128 (R4048), GSK625433, R803, R-1626, BILB-1941, HCV-796, JTK-109 and JTK-003, ANA-598, IDX-184, MK-3281, MK-1220, benzimidazole derivatives, benzo-1,2,4-thiadiazine derivatives, phenylalanine derivatives, A-831 and A-689; HCV proteases (NS2-NS3 and NS3-NS4A) inhibitors, the compounds of WO02/18369 (see, e.g., page 273, lines 9-22 and page 274, line 4 to page 276, line 11), BI-1335, TMC435350, MK7009, ITMN-191, BILN-2061, VX-950, BILN-2065, BMS-605339, VX-500, SCH 503034; inhibitors of other targets in the HCV life cycle, including helicase, and metalloprotease inhibitors, ISIS-14803; immunomodulatory agents such as, $\alpha$-, $\beta$-, and $\gamma$-interferons such as rIFN-$\alpha$ 2b, rIFN-$\alpha$ 2ba, consensus IFN-$\alpha$ (infergen), feron, reaferon, intermax $\alpha$, rIFN-$\beta$, infergen+actimmune, IFN-omega with DUROS, albuferon, locteron, Rebif, Oral IFN-$\alpha$, IFN-$\alpha$ 2b XL, AVI-005, pegylated-infergen, pegylated derivatized interferon-$\alpha$ compounds such as pegylated rIFN-$\alpha$ 2b, pegylated rIFN-$\alpha$ 2a, pegylated IFN-$\beta$, compounds that stimulate the synthesis of interferon in cells, interleukins, Toll like receptor (TLR) agonists, compounds that enhance the development of type 1 helper T cell response, and thymosin; other antiviral agents such as ribavirin, ribavirin analogs such as rebetol, copegus and viramidine (taribavirin), amantadine, and telbivudine, inhibitors of internal ribosome entry, alpha-glucosidase 1 inhibitors such as MX-3253 (celgosivir) and UT-231B, hepatoprotectants such as IDN-6556, ME-3738, LB-84451 and MitoQ, broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No.

6,054,472, WO97/40028, WO98/40381, WO00/56331, mycophenolic acid and derivatives thereof, and including, but not, limited to VX-497, VX-148, and/or VX-944); and other drugs for treating HCV such as zadaxin, nitazoxanide, BIVN-401 (virostat), PYN-17 (altirex), KPE02003002, actilon (CPG-10101), KRN-7000, civacir, GI-5005, ANA-975, XTL-6865, ANA-971, NOV-205, tarvacin, EHC-18, NIM811, DEBIO-025, VGX-410C, EMZ-702, AVI 4065, Bavituximab, and Oglufanide; or combinations of any of the above.

Thus, to combat or treat HCV infections, the compounds of formula (I) or any subgroups thereof may be co-administered in combination with for instance, interferon-α (IFN-α), pegylated interferon-α, ribavirin or a combination thereof, as well as therapeutics based on antibodies targeted against HCV epitopes, small interfering RNA (si RNA), ribozymes, DNAzymes, antisense RNA, small molecule antagonists of for instance NS3 protease, NS3 helicase and NS5B polymerase.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and at least one other HCV inhibitory compound, e.g. IFN-α, pegylated IFN-α, ribavirin or a combination thereof.

Furthermore, it is known that a large percentage of patients infected with human immunodeficiency virus 1 (HIV) are also infected with HCV, i.e. they are HCV/HIV co-infected. HIV infection appears to adversely affect all stages of HCV infection, leading to increased viral persistence and accelerated progression of HCV-related liver disease. In turn, HCV infection may affect the management of HIV infection, increasing the incidence of liver toxicity caused by antiviral medications.

The present invention therefore also concerns combinations of a compound of Formula (I) or any subgroup thereof with anti-HIV agents. Also, the combination of one or more additional anti-HIV compounds and a compound of Formula (I) or any subgroups thereof can be used as a medicine. In particular, said combination can be used for inhibition HCV and HIV replication.

The term "combination therapy" also encompasses a product comprising (a) a compound of Formula (I) or any subgroup thereof, and (b) at least one anti-HIV compound, and (c) optionally at least one other anti-HCV compound, as a combined preparation for simultaneous, separate or sequential use in treatment of HCV and HIV infections, in particular, in the treatment of infections with HCV and HIV, or for preventing or treating conditions associated with HCV and HIV.

Thus, the present invention also relates to a product containing (a) at least one compound of Formula (I) or any subgroup thereof, and (b) one or more additional anti-HIV compounds, as a combined preparation for simultaneous, separate or sequential use in anti-HCV and anti-HIV treatment. The different drugs may be combined in a single preparation together with pharmaceutically acceptable carriers. Said anti-HIV compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. NcRTI-1 and the like; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232, 632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors, which comprise fusion inhibitors (e.g. enfuvirtide (T-20)), attachment inhibitors and co-receptor inhibitors, the latter comprise the CCR5 antagonists (e.g. ancriviroc, CCR5 mAb004, maraviroc (UK-427,857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488043, BlockAide/CRT™, FP 21399, hNM01, nonakine, VGV-1; a maturation inhibitor for example is PA-457; inhibitors of the viral integrase e.g. raltegravir (MK-0518), elvitegravir (JTK-303, GS-9137), BMS-538158; ribozymes; immunomodulators; monoclonal antibodies; gene therapy; vaccines; siRNAs; antisense RNAs; microbicides; Zinc-finger inhibitors.

Therefore, HCV infected patients also suffering from conditions associated with HIV or even other pathogenic retroviruses, such as AIDS, AIDS-related complex (ARC), progressive generalized lymphadenopathy (PGL), as well as chronic CNS diseases caused by retroviruses, such as, for example HIV mediated dementia and multiple sclerosis, can conveniently be treated with the present composition.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product that results, directly or indirectly, from the combination of the specified ingredients.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers as well to combinations comprising two or more agents, the "therapeutically effective amount" in the context of combinations is also that amount of the agents taken together so that the combined effect elicits the desired biological or medicinal response. For example, the therapeutically effective amount of a composition comprising (a) the compound of formula (I) and (b) another anti-HCV agent, would be the amount of the compound of formula (I) and the amount of the other anti-HCV agent that when taken together have a combined effect that is therapeutically effective.

In general, it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

In one embodiment of the present invention there is provided an article of manufacture comprising a composition effective to treat an HCV infection or to inhibit the NS5B polymerase of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, in an amount effective for use as a standard or reagent in a test or assay for determining the ability of potential pharmaceuticals to inhibit HCV NS5B polymerase, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto. Unless otherwise indicated, purification of the synthesized compounds by column chromatography or flash chromatography is performed on a silica gel column.

Example 1

Synthesis of Compound 1

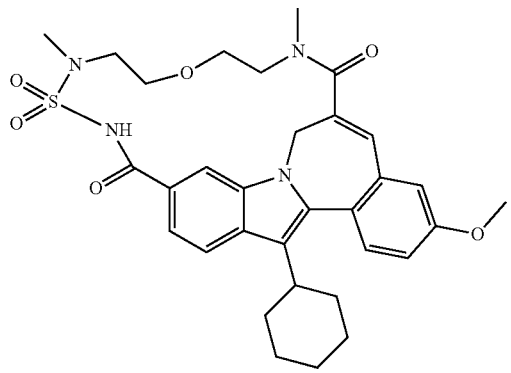

1

Step 1

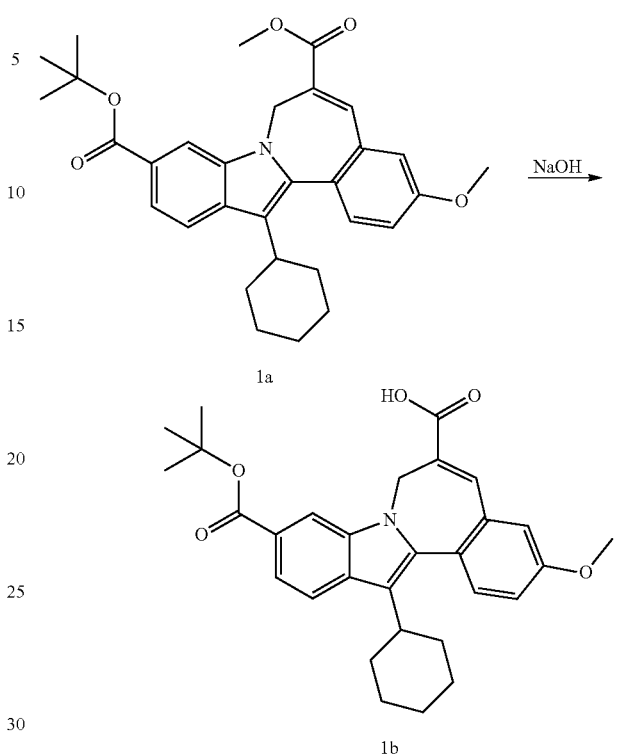

1a

1b

A solution of NaOH (6.38 g) in 25 mL of water was added to a stirred solution of 1a (10-tert-butyl 6-methyl 13-cyclohexyl-3-methoxy-7H-indolo[2,1-a][2]benzazepine-6,10-dicarboxylate, synthesized as described in US 2007270406 A1) in THF (100 mL) and MeOH (150 mL). After 1 hour the reaction was concentrated under reduced pressure, then diluted with ice-cold water (150 mL). The pH of the resulting solution was adjusted to 6 with acetic acid (AcOH). The precipitate was collected by filtration, washed with water and dried under vacuum to give 1.90 g (98%) of 1b as a yellowish powder: m/z=488 (M+H)$^+$ Step 2

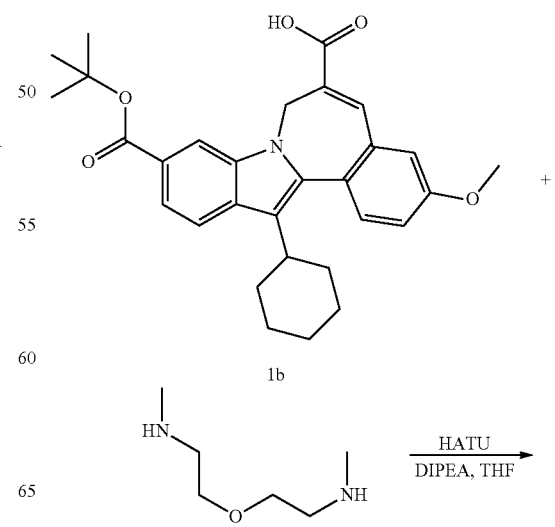

1b

-continued

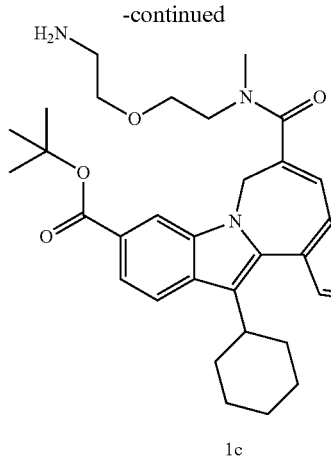

1c

HATU (1.17 g, 3.08 mmol) was added under nitrogen to a stirred solution of 1b (1.00 g, 2.05 mmol), DIPEA (1.07 mL, 6.15 mmol) and 2,2'-oxybis(N-methylethanamine) (1.08 g, 8.20 mmol) in 30 mL of dry THF. After 1 h, the reaction mixture was quenched with water (100 mL) and extracted with ethyl acetate (EtOAc). The organic layer was successively dried (Na$_2$SO$_4$), filtered and evaporated. The residue was triturated in water, filtered and dried to give 1.15 g (93%) the target compound 1c as a yellowish powder: m/z=602 (M+H)$^+$ Step 3

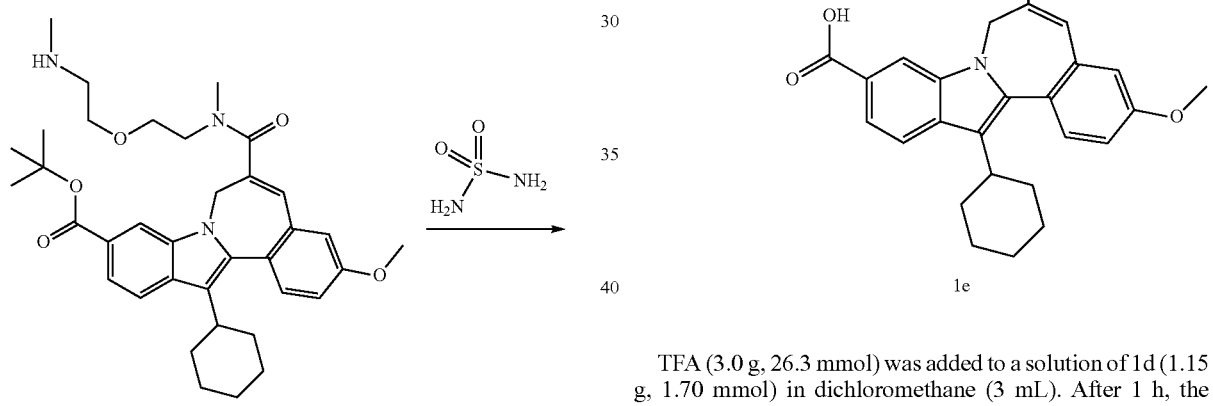

1c

1d

A solution of 1c (1.15 g, 1.91 mmol) and sulfamide (1.84 g, 19.1 mmol) in dioxane (10 mL) was heated at 100° C. in a microwave oven for 20 minutes. The reaction mixture was cooled down to room temperature, then evaporated under vacuum. The residue was triturated in water, filtered and washed with water. The powder was reconstituted in EtOAc, dried (Na$_2$SO$_4$) and evaporated to give 1.15 g (88%) of the desired product 1d as a yellowish powder: m/z=681 (M+H)$^+$ Step 4

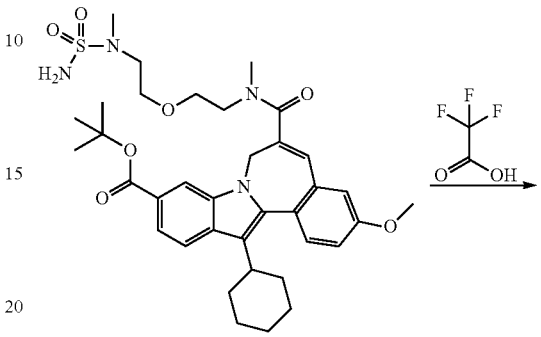

1d

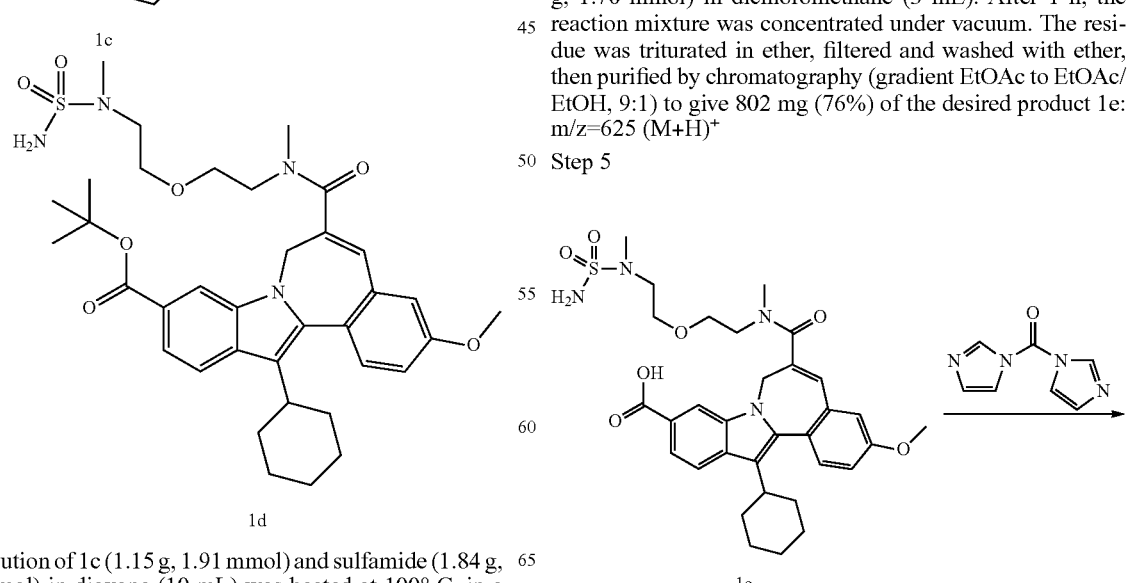

1e

TFA (3.0 g, 26.3 mmol) was added to a solution of 1d (1.15 g, 1.70 mmol) in dichloromethane (3 mL). After 1 h, the reaction mixture was concentrated under vacuum. The residue was triturated in ether, filtered and washed with ether, then purified by chromatography (gradient EtOAc to EtOAc/ EtOH, 9:1) to give 802 mg (76%) of the desired product 1e: m/z=625 (M+H)$^+$ Step 5

-continued

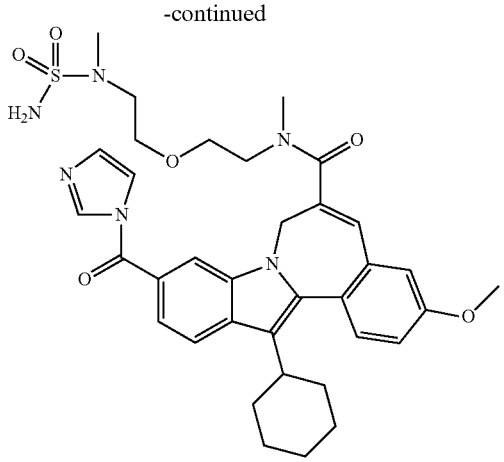

1f

Carbonyldiimidazole (389 mg, 2.40 mmol) was added to a stirred solution of 1e (500 mg, 0.80 mmol) in dry THF (3 mL). The reaction mixture was stirred at room temperature for 1 h: complete conversion to intermediate 1f was observed. The resulting solution was evaporated, then the residue was purified by flash chromatography (gradient EtOAc to CH$_3$CN 1:0 to 0:1) to give 550 mg of the target product 1f which was used as such in the next step: m/z=675 (M+H)$^+$ Step 6

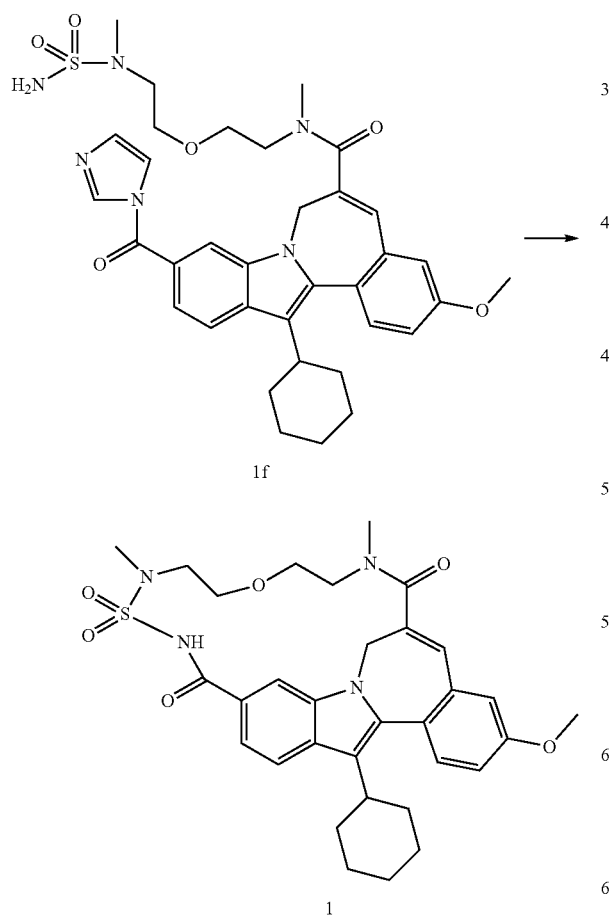

DBU (244 mg, 0.32 mmol) was added to a solution of 1f (550 mg) in acetonitrile (25 mL). The reaction mixture was stirred overnight at room temperature, then concentrated under reduced pressure. The residue was dissolved in water (30 mL) and the pH of the resulting solution was adjusted to 5. The precipitate was collected by filtration, washed with water and dried. Recrystallization from ethanol followed by a purification by column chromatography (gradient EtOAc to EtOAc/EtOH 9:1) provided 380 mg (78%) of the title product 1 as a white powder: m/z=607 (M+H)+, $^1$H NMR (DMSO-d$_6$) δ 1.15 (m, 1H), 1.40 (m, 3H), 1.71 (m, 2H), 1.88 (m, 1H), 2.01 (m, 3H), 2.56 (m, 3H), 2.77 (m, 1H), 2.99 (s, 3H), 3.26 (m, 2H), 3.50-3.71 (m, 6H), 3.87 (s, 3H), 4.44 (d, J=14.1 Hz, 1H), 5.09 (d, J=15.0 Hz, 1H), 6.95 (s, 1H), 7.13 (s, 1H), 7.19 (d, J=8.6 Hz, 1H), 7.47 (d, J=8.0 Hz, 1H), 7.54 (d, J=8.3 Hz, 1H), 7.88 (d, J=7.8 Hz, 1H), 8.33 (s, 1H), 11.40 (s, 1H).

Example 2

Synthesis of Compound 2

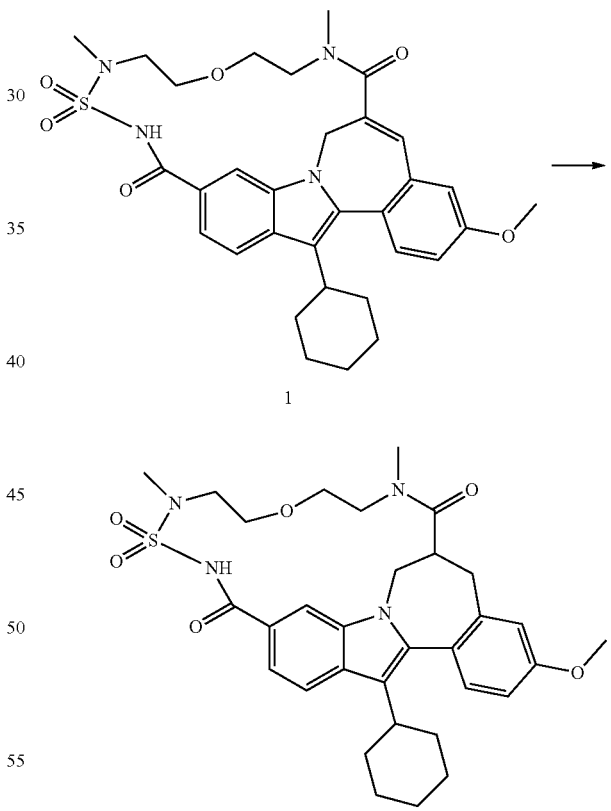

A solution of 1 (56 mg, 0.092 mmol) in MeOH (15 mL) and THF (5 mL) was hydrogenated in an H-cube apparatus using a 10% Pd on Carbon cartridge. Then, solvent was evaporated and the residue was purified by column chromatography (CH$_2$Cl$_2$/CH$_3$CN, 9:1) to give 23 mg (41%) of the desired product 2 as a white powder: m/z=609 (M+H)$^+$.

Examples 3 and 4

Synthesis of Compounds 3 and 4

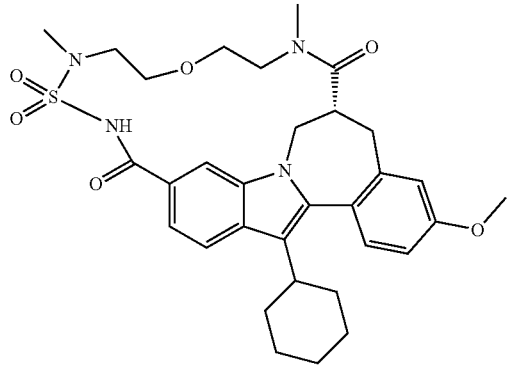

3

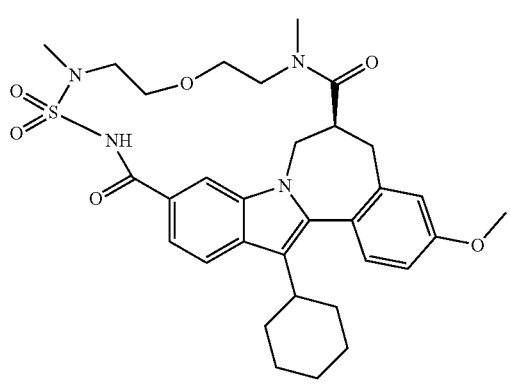

4

The racemic mixture 2 was purified by SFC, using a 6.5 minutes run on a chiral CHIRALCEL OD-H column (250×10 mm, coated on 5 μm silica gel) and 55% methanol/45% $CO_2$ as mobile phase, at a flow rate of 10 mL/min and lead to the two pure enantiomers 3 and 4. Retention times under these conditions were observed at 4.25 min and 5.54 min.

Example 5

Synthesis of Compound 5

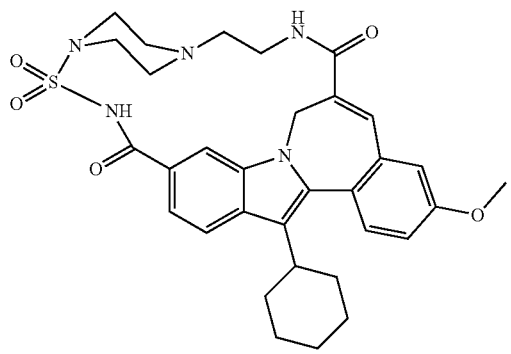

5

Step 1

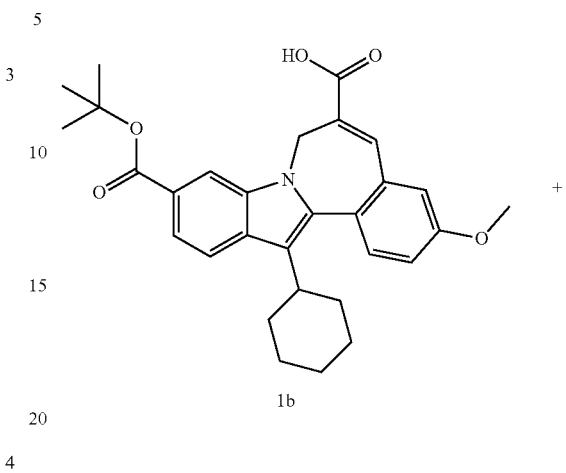

1b

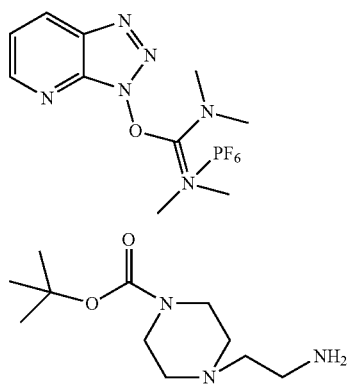

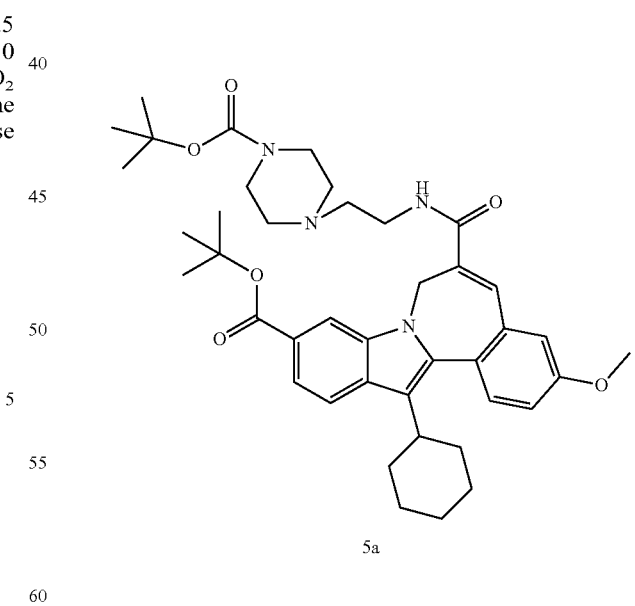

5a

The compound 5a was synthesized in 96% yield from intermediate 1b and 2-[4-(tert-butyloxycarbonyl)piperazin-1-yl]ethylamine following the procedure reported for the synthesis of intermediate 1c: m/z=699 (M+H)$^+$.

Step 2

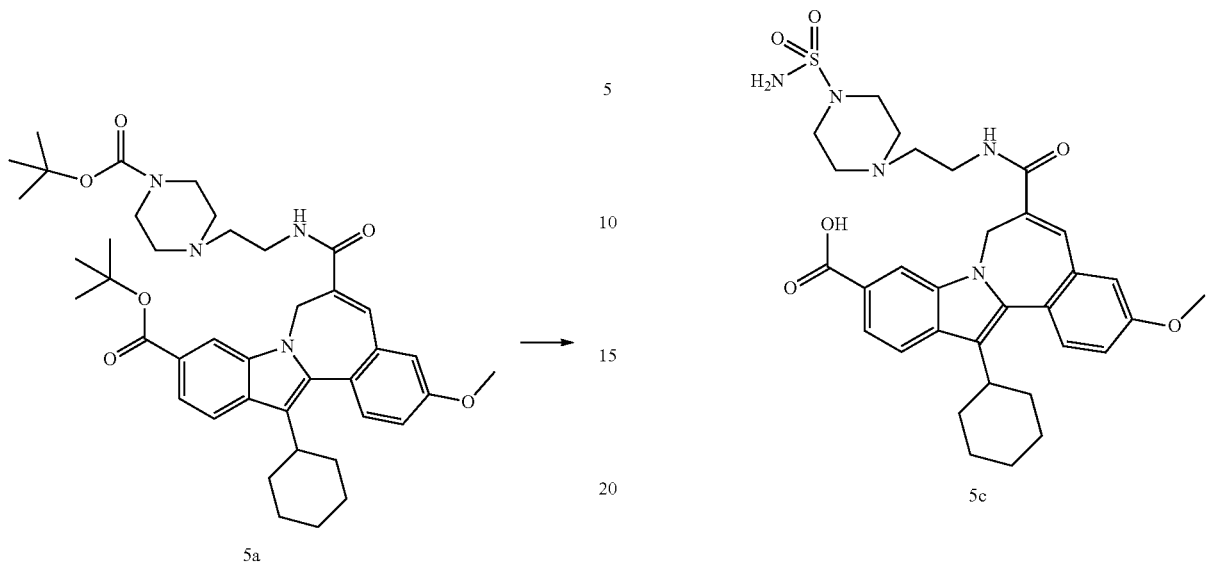

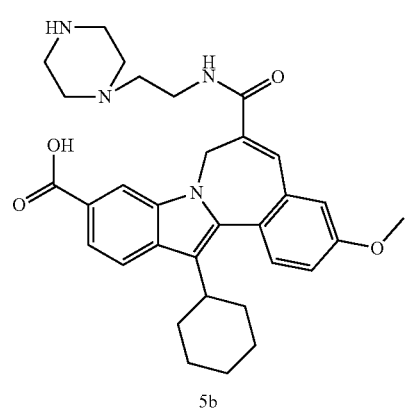

Trifluoroacetic acid (5.00 g, 43.9 mmol) was added to 740 mg of intermediate 5a. After 1 hour at room temperature, the solvent was evaporated. The residue was triturated in EtOH/Et₂O, filtered and dried under high vacuum to give 380 mg (64%) of the desired product 5b as a yellowish powder: m/z=543 (M+H)⁺.

Step 3

A solution of 5b (380 mg, 0.700 mmol) and sulfamide (673 mg, 7.00 mmol) in dioxane (10 mL) was heated at 100° C. in a microwave oven for 15 minutes. Then, the reaction mixture was successively cooled down at room temperature, concentrated under vacuum, triturated in water and filtered. Purification by column chromatography (gradient EtOAc/CH₂Cl₂ 1:1 to 1:0) gave 210 mg (46%) of the desired product 5c: m/z=622 (M+H)⁺.

Step 4

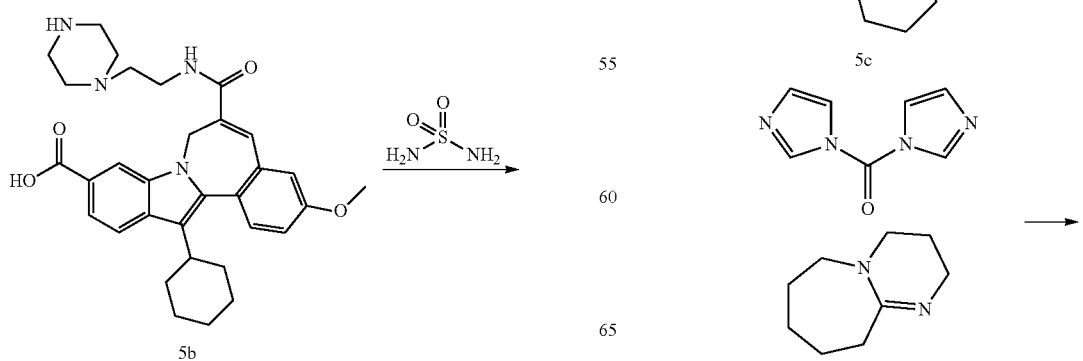

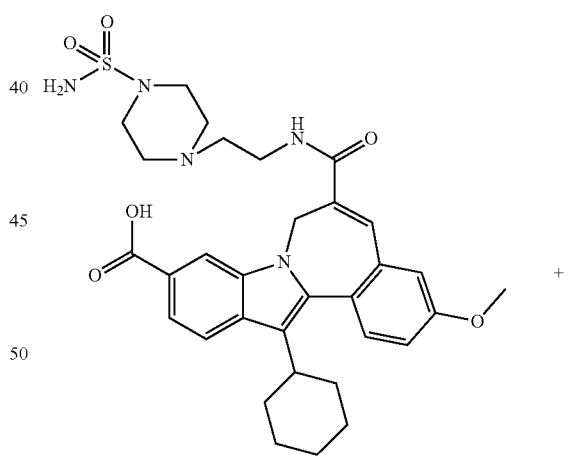

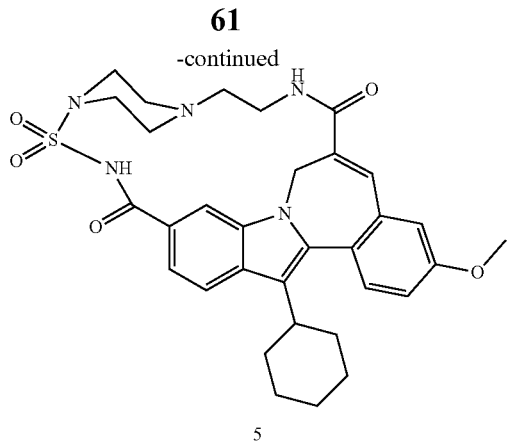

The title product 5d was synthesized in 11% yield following the procedure (steps 5 and 6) reported for the synthesis of compound 1, followed by a recrystallization from ethanol, affording the desired product as white powder, m/z=604 (M+H)$^+$.

Example 6

Synthesis of Compound 6

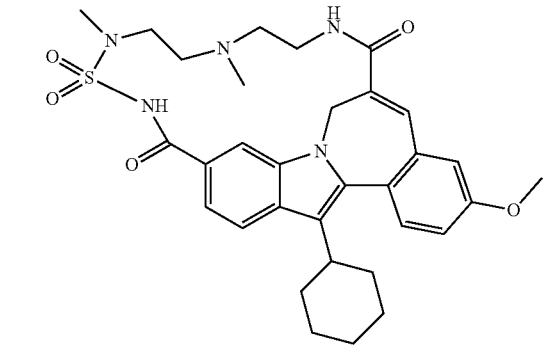

Step 1

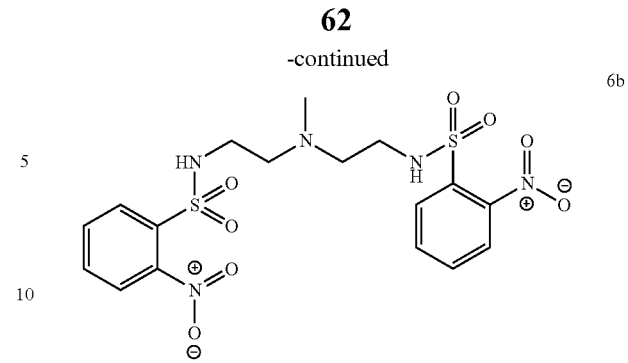

To a solution of $N_1$-(2-aminoethyl)-$N_1$-methylethane-1,2-diamine (10.58 g, 90 mmoles) in DCM (350 mL) was added slowly a solution of 2-nitrobenzene-1-sulfonyl chloride dissolved in DCM (50 mL). After 2 h at RT, the reaction mixture (RM) was washed with water, dried over MgSO$_4$, filtered and concentrated. The residue was purified by flash chromatography on silica gel with a gradient of methanol in DCM (0 to 10%), yielding to 6.9 g of N-(2-((2-aminoethyl)(methyl)amino)ethyl)-2-nitrobenzenesulfonamide 6a and 3.9 g of N,N'-(2,2'-(methylazanediyl)-bis(ethane-2,1-diyl))bis(2-nitrobenzenesulfonamide) 6b; m/z (6a)=303 (M+H)$^+$, m/z (6b)=488 (M+H)$^+$.

Step 2

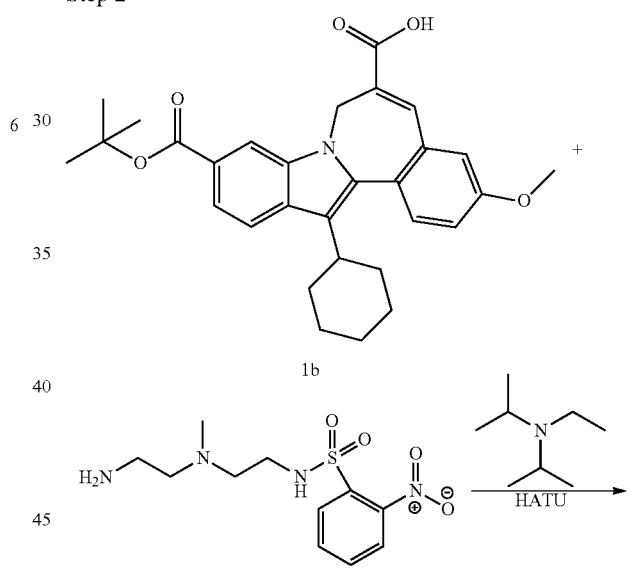

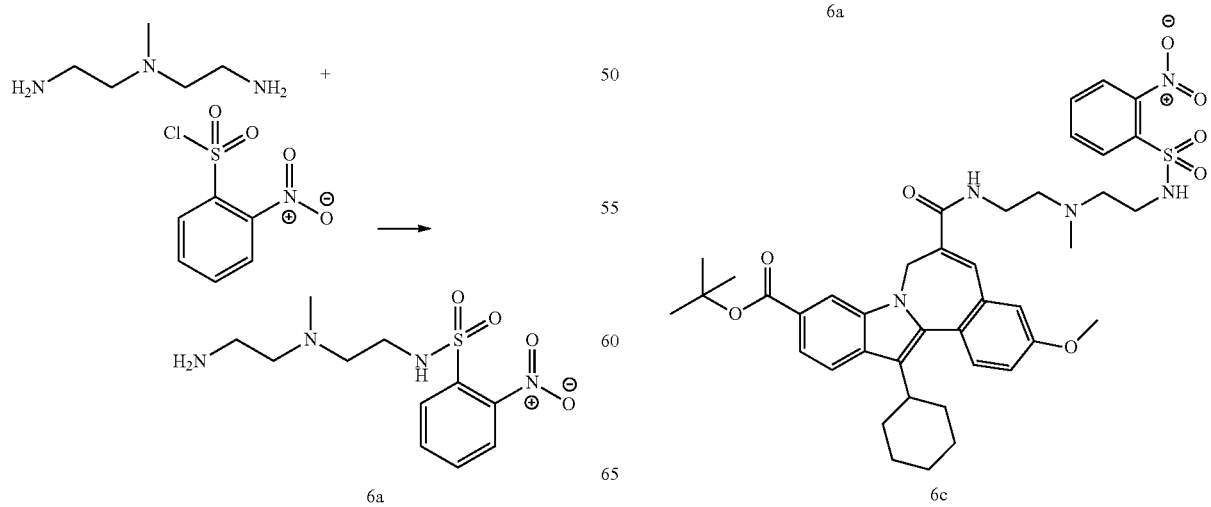

To a solution of carboxylic acid 1b (500 mg, 1.025 mmole), HATU (585 mg, 1.5 eq) and diisopropylethylamine (212 mg, 1.6 eq) in dry DMF (10 mL) was added N-(2-((2-aminoethyl)(methyl)amino)ethyl)-2-nitrobenzenesulfonamide 6a (341 mg, 1.1 eq). After 30 minutes at RT, the RM was diluted with water. The yellow precipitate was filtered off and washed with water. It was then reconstituted in EtOAc, dried over MgSO$_4$, filtered, concentrated and dried under vacuum to give 800 mg of the desired product 13-Cyclohexyl-3-methoxy-6-(2-{methyl-[2-(2-nitro-benzenesulfonylamino)-ethyl]-amino}-ethylcarbamoyl)-7H-benzo[3,4]azepino[1,2-a]indole-10-carboxylic acid tert-butyl ester 6c as a yellow powder; m/z=772 (M+H)$^+$.

Step 3

To a solution of 13-cyclohexyl-3-methoxy-6-(2-{methyl-[2-(2-nitro-benzenesulfonyl-amino)-ethyl]-amino}-ethylcarbamoyl)-7H-benzo[3,4]azepino[1,2-a]indole-10-carboxylic acid tert-butyl ester 6c (650 mg, 0.842 mmole) and cesium carbonate (1.646-g, 6 eq) in dry DMF (10 mL) was added slowly a solution of methyl iodide (122 mg, 1.02 mmole) in dry DMF (2 mL). After stirring for 1 h at RT, the RM was diluted with water and extracted with EtOAc. The organic layer was then washed with water, dried over MgSO$_4$, filtered and concentrated. The residue was purified by flash chromatography on silica gel, using a gradient of EtOAc in DCM (0 to 100%), yielding to 550 mg (83% yield) of the desired product 13-Cyclohexyl-3-methoxy-6-[2-(methyl-{2-[methyl-(2-nitro-benzenesulfonyl)-amino]-ethyl}-amino)-ethylcarbamoyl]-7H-benzo[3,4]azepino[1,2-a]indole-10-carboxylic acid tert-butyl ester 6d as a yellow solid; m/z=786 (M+H)$^+$.

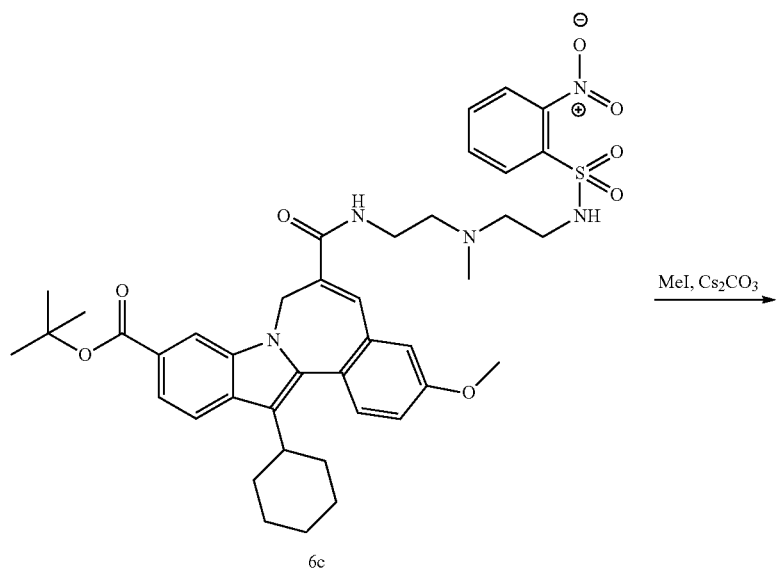

6c

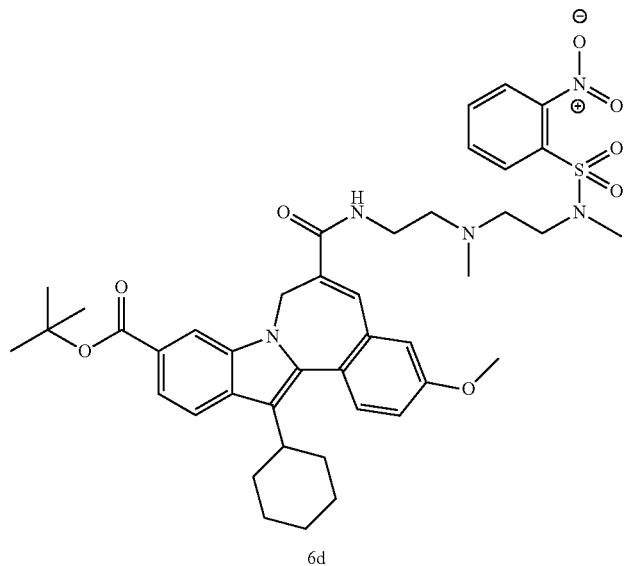

6d

Step 4

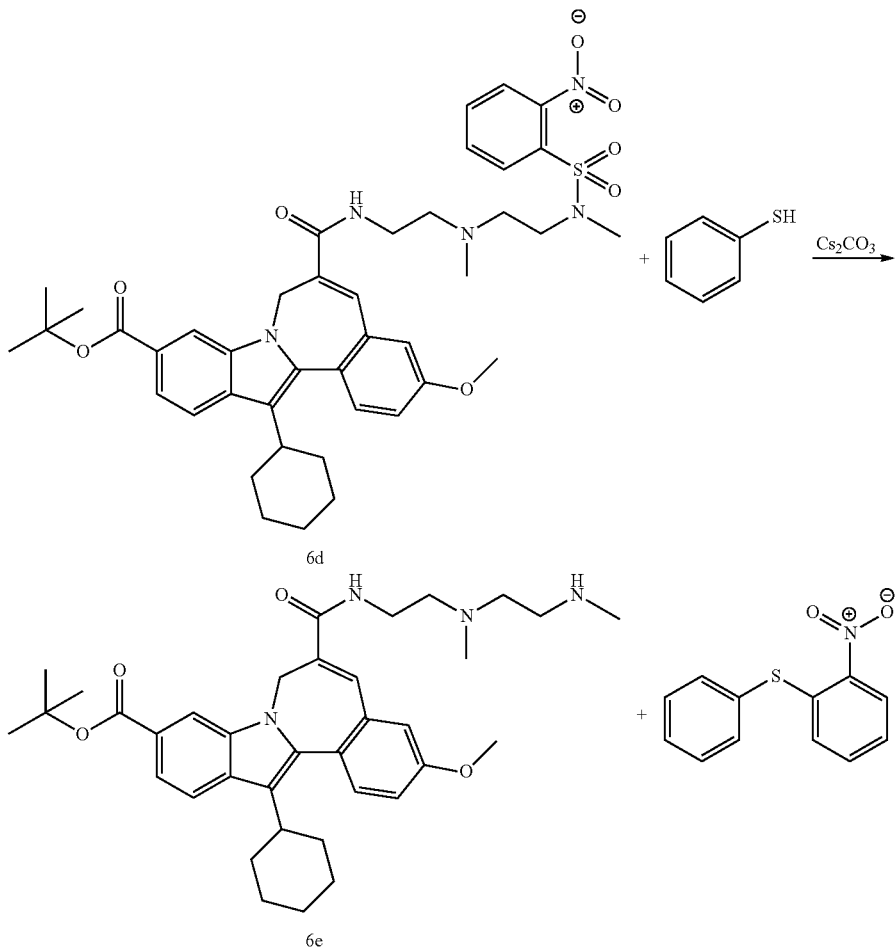

A mixture of 13-cyclohexyl-3-methoxy-6-[2-(methyl-{2-[methyl-(2-nitro-benzene-sulfonyl)amino]-ethyl}-amino)-ethylcarbamoyl]-7H-benzo[3,4]azepino[1,2-a]indole-10-carboxylic acid tert-butyl ester 6d (380 mg, 0.483 mmole), cesium carbonate (315 mg, 2 eq) and thiophenol (107 mg, 2 eq) in DMF (5 mL) was stirred at RT overnight. Cesium carbonate (315 mg, 2 eq) and thiophenol (107 mg, 2 eq) were then added to the RM and the RM was stirred for 1 h. Upon completion of the reaction, the RM was filtered and loaded on a cartridge containing a SCX-resin, pre-washed with DCM. After rinsing the cartridge with DCM (several times, until a colorless fraction was obtained) the product was eluted with $NH_3$ in MeOH, yielding to 240 mg of the desired product 13-cyclohexyl-3-methoxy-6-{2-[methyl-(2-methylamino-ethyl)-amino]-ethylcarbamoyl}-7H-benzo[3,4]azepino[1,2-a]indole-10-carboxylic acid tert-butyl ester 6e, which was further purified by preparative HPLC; m/z=601 (M+H)$^+$.

Step 5

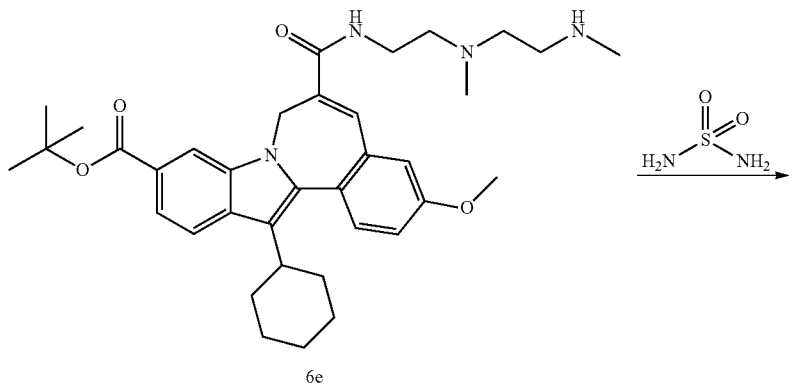

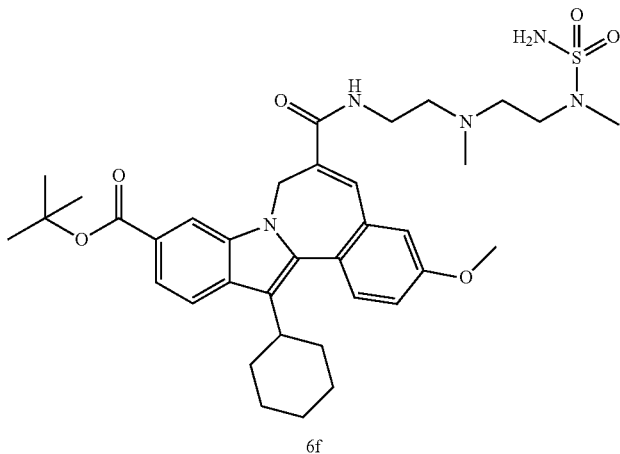

6f

The synthesis of product 6f was performed using the procedure described for the synthesis of compound 1d, using intermediate 6e instead of intermediate 1c, yielding 200 mg (50%) of the target product; m/z=680 (M+H)$^+$.

Step 6

Step 7

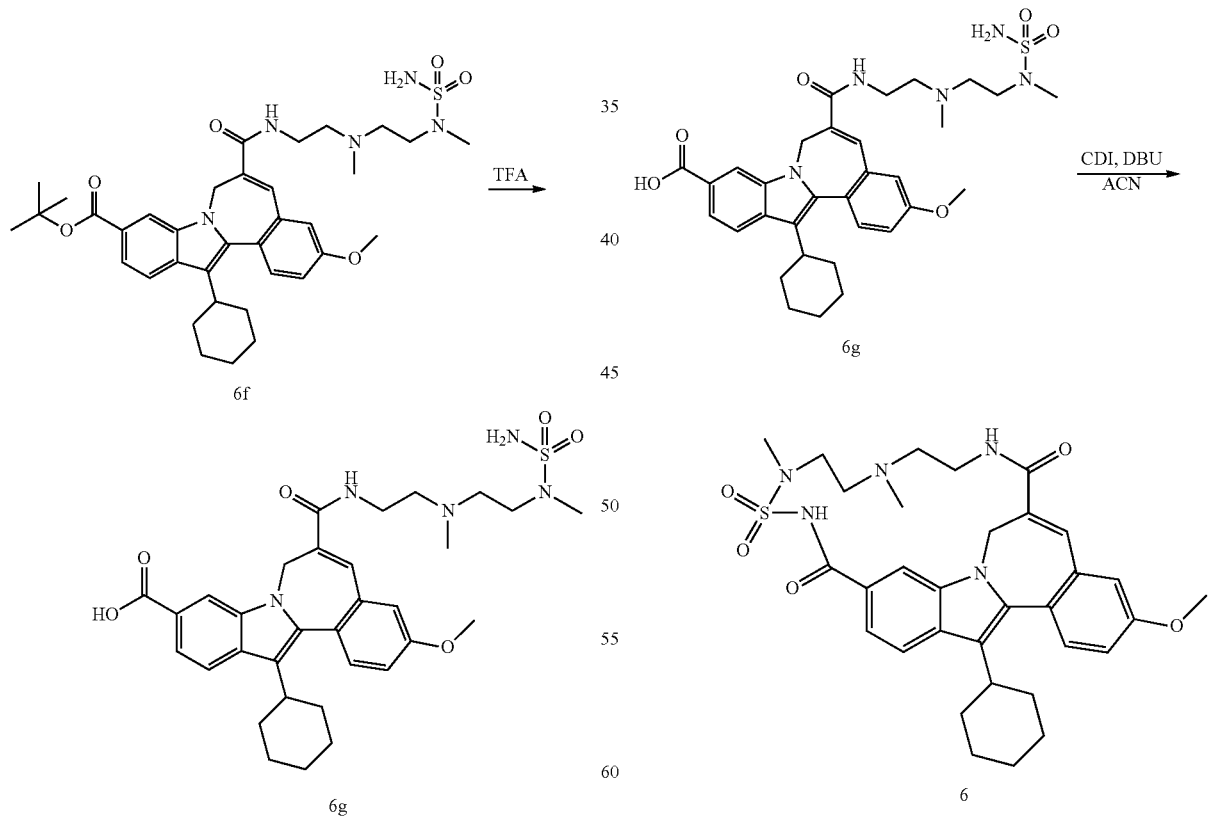

The synthesis of product 6g was performed using the procedure described for the synthesis of compound 1e, using intermediate 6f instead of intermediate 1d, yielding 187 mg (quantitative yield) of the target product; m/z=624 (M+H)$^+$.

The synthesis of product 6 was performed using the procedure described for the synthesis of compound 1, using intermediate 6g instead of intermediate 1e, yielding 43 mg (22% yield) of the target product; m/z=606 (M+H)$^+$.

Example 7

Synthesis of Compound 7

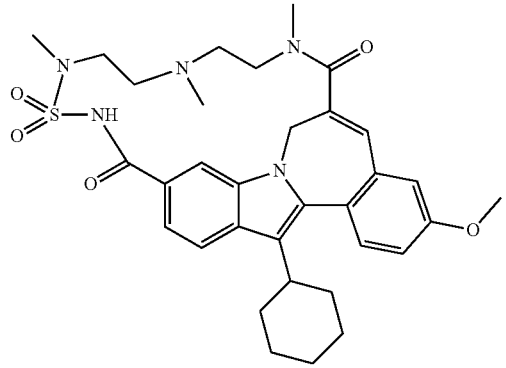

Step 1

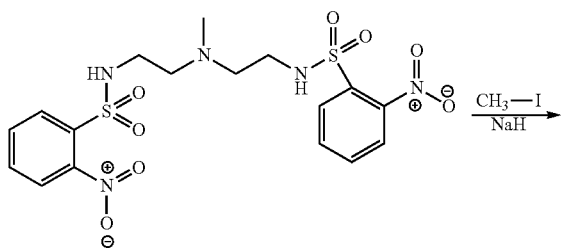

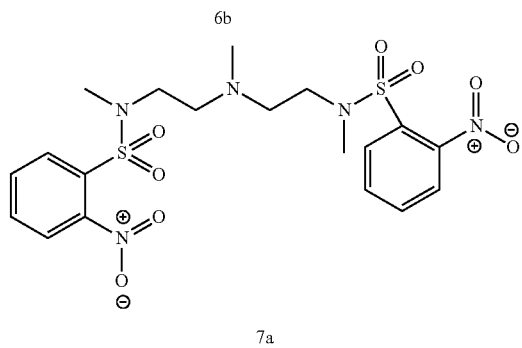

To a solution of N,N'-(2,2'-(methylazanediyl)bis(ethane-2,1-diyl))bis(2-nitrobenzene-sulfonamide) 6b (3 g, 6.15 mmoles) in dry DMF (50 mL) was added portion wise sodium hydride (738 mg, 3 eq, 60% in mineral oil) at 0° C. After 20 minutes, a solution of methyl iodide dissolved in dry DMF (5 mL) was added slowly to the RM. After stirring for 1 h at RT, the RM was quenched with water and extracted with EtOAc. The organic layer was washed with water, dried over MgSO$_4$, filtered and concentrated. Purification by flash chromatography with a gradient of EtOAc in DCM (20 to 80%) afforded 1.94 g (61%) of the desired product N,N'-(2,2'-(methylazanediyl)bis(ethane-2,1-diyl))bis(N-methyl-2-nitrobenzene-sulfonamide) 7a; m/z=516 (M+H)$^+$.

Step 2

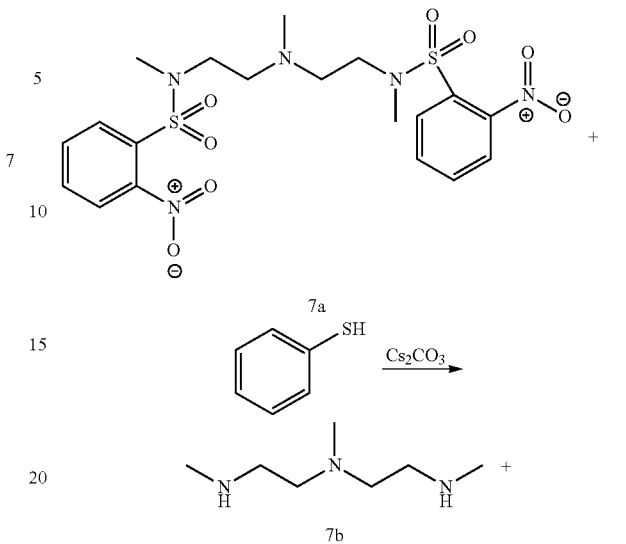

A mixture of N,N'-(2,2'-(methylazanediyl)bis(ethane-2,1-diyl))bis(N-methyl-2-nitro-benzenesulfonamide) 7a (1.24 g, 2.405 mmoles), cesium carbonate (2.35 g, 3 eq) and thiophenol (795 mg, 3 eq) in DMF (25 mL) was stirred at RT during 1 h. Upon completion of the reaction, the RM was filtered and loaded on a MP-TsOH cartridge, prewashed with DCM. After rinsing the cartridge with DCM (several times, until a colorless fraction was obtained) the product was eluted with NH$_3$ in MeOH, yielding to 220 mg (63%) of N$_1$,N$_2$-dimethyl-N$_1$-(2-(methylamino)ethyl)ethane-1,2-diamine 7b, which was used directly in the next step; m/z=146 (M+H)$^+$.

Step 3

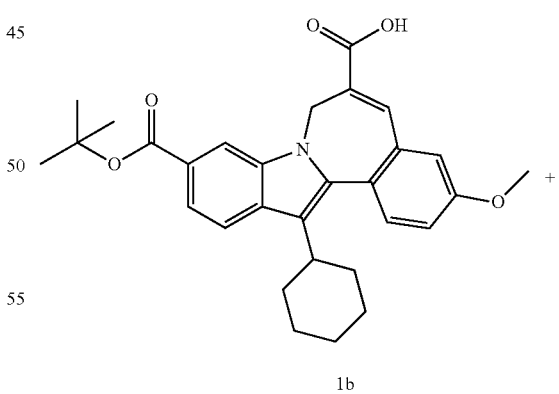

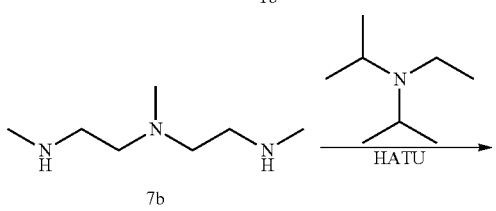

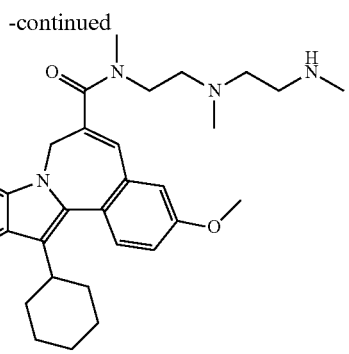

7c

The synthesis of 13-cyclohexyl-3-methoxy-6-(methyl-{2-[methyl-(2-methylamino-ethyl)-amino]-ethyl}-carbamoyl)-7H-benzo[3,4]azepino[1,2-a]indole-10-carboxylic acid tert-butyl ester 7c was performed following the procedure reported for the synthesis of compound 1c, using $N_1,N_2$-dimethyl-$N_1$-(2-(methylamino)ethyl)ethane-1,2-diamine 7b instead of Methyl-[2-(2-methylamino-ethoxy)-ethyl]-amine. After purification by flash chromatography with a gradient of ammonia in methanol 7M in EtOAc (5 to 15%), 100 mg of the desired product 7c were obtained as a yellow oil; m/z=615 (M+H)⁺.

Step 4

The synthesis of 7d was performed following the procedure reported for the synthesis of compound 1d, using 13-cyclohexyl-3-methoxy-6-(methyl-{2-[methyl-(2-methyl-amino-ethyl)-amino]-ethyl}-carbamoyl)-7H-benzo[3,4]azepino[1,2-a]indole-10-carboxylic acid tert-butyl ester 7c instead of 13-cyclohexyl-3-methoxy-6-{methyl-[2-(2-methylamino-ethoxy)-ethyl]-carbamoyl}-7H-benzo[3,4]azepino[1,2-a]indole-10-carboxylic acid tert-butyl ester 1c. After purification by flash chromatography with a gradient of methanol in EtOAc (0 to 10%), 50 mg of the desired product 7d were obtained; m/z=694 (M+H)⁺.

Step 5

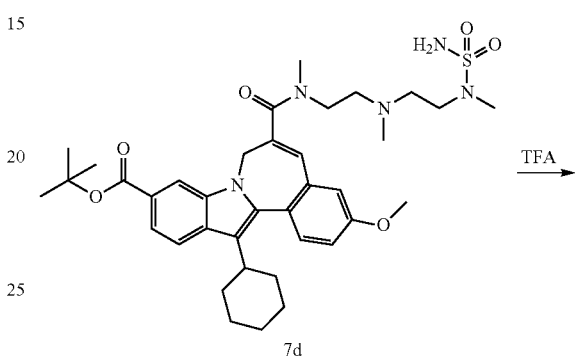

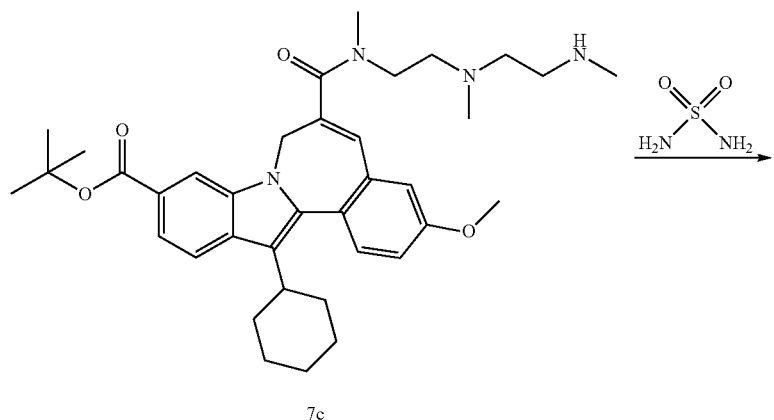

7c

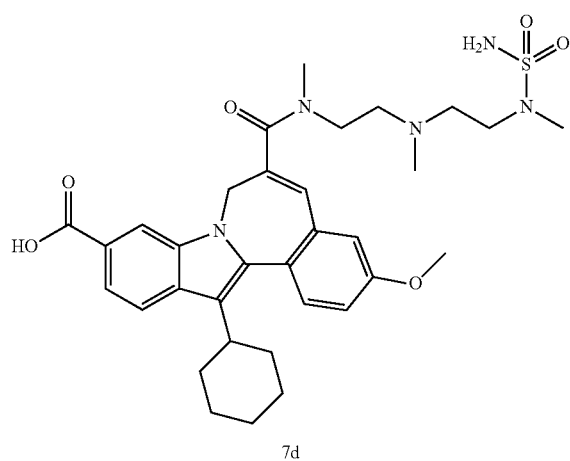

7d

73
-continued

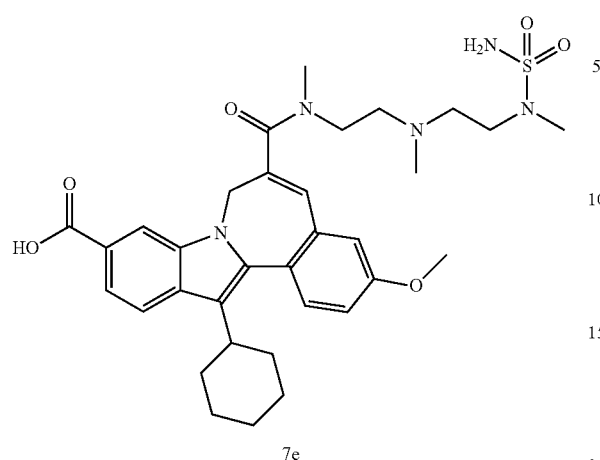

7e

The synthesis of 7e was performed following the procedure reported for the synthesis of compound 1e, using intermediate 7d instead of intermediate 1d; m/z=638 (M+H)⁺.

Step 6

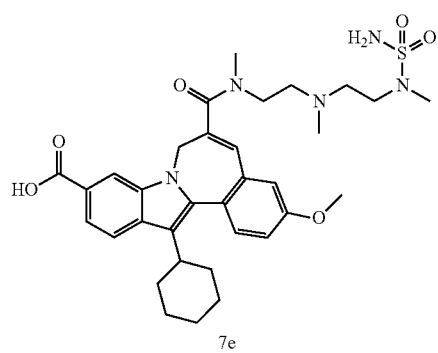

7e

CDI, DBU
ACN

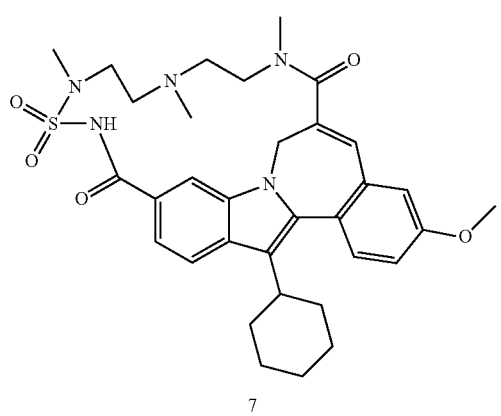

7

The synthesis of product 7 is being performed using the procedure described for the synthesis of compound 1, using intermediate 7e instead of intermediate 1e.

74
Example 8
Synthesis of Compound 8

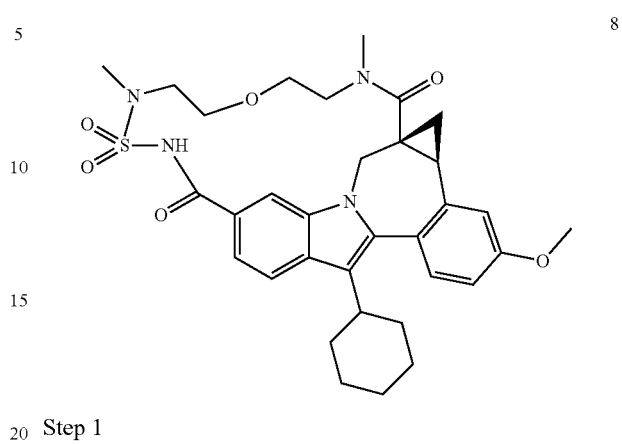

8

Step 1

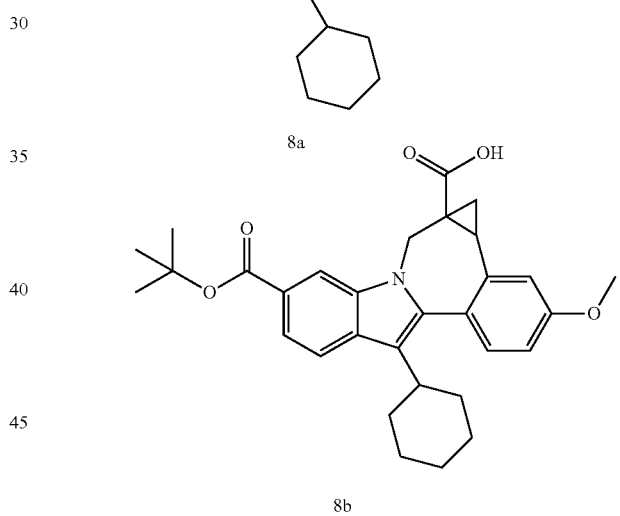

8a

8b

The synthesis of 8b was performed following the procedure reported for the synthesis of compound 1b, using methyl ester 8a instead of 1a. The desired product 8b was obtained in 95% yield as a light yellow solid; m/z=502 (M+H)⁺.

Step 2

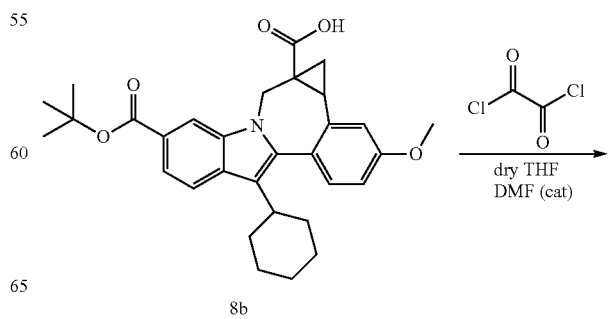

8b dry THF
DMF (cat)

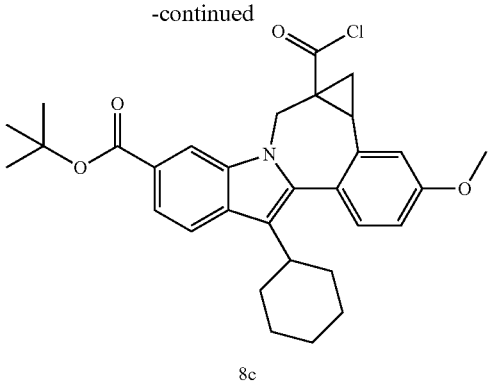

8c

At 0° C. and under protective atmosphere, oxalyl chloride (4.07 ml, 47.4 mmol) was added to a solution of carboxylic acid 8b (19.83 g, 39.5 mmol) and DMF (5-drops) in tetrahydrofuran (dry) (100 mL). Upon addition of oxalyl chloride immediate formation of gas was observed. The reaction was stirred at 0° C. for 1.5 hour. Then, an extra amount of 0.5 eq of oxalyl chloride was added and the reaction was stirred for 1 more hour (repeated once until full conversion was obtained). The reaction was then evaporated to dryness in vacuo to afford 20.5 g (97%) of the acid chloride 8c as a white solid; m/z (methyl ester formed by addition of methanol prior to analysis)=516 (M+H)$^+$.

Step 3

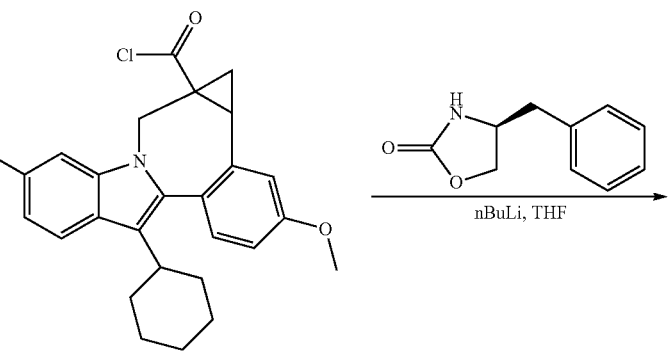

8c

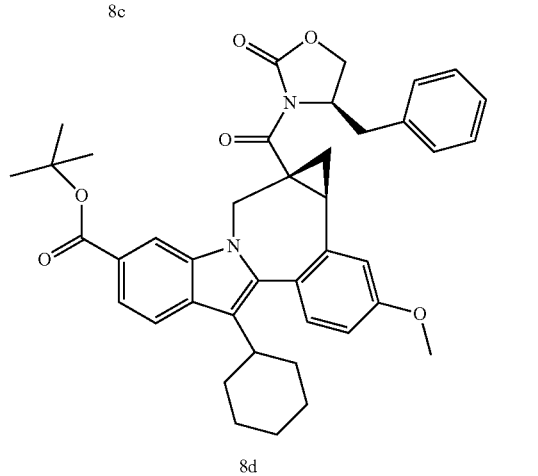

8d

+

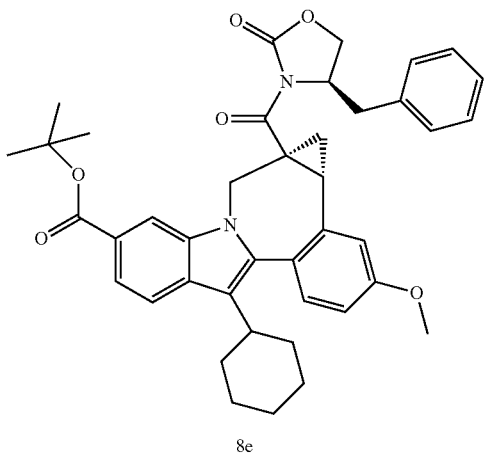

8e

To a solution of (S)-4-benzyl-2-oxazolidinone (7.50 g, 42.3 mmol) in tetrahydrofuran (dry) (60 ml) under nitrogen atmosphere n-butyllithium (26.4 ml, 42.3 mmol) was added slowly at −78° C. The reaction mixture was stirred for 40 minutes at −78° C. After 40 minutes, the anion solution was added via a canula to a solution of the acid chloride 8c (20 g, 38.5 mmol) in 60 mL THF at −78° C. The reaction mixture was stirred for 1.5 hours at −78° C. When the reaction was finished, it was quenched with an ammonia chloride solution at −70° C. The reaction mixture was then warmed up to room temperature and extracted with EtOAc, washed with brine and dried over $Na_2SO_4$. The organic layer was filtered and concentrated to afford 26.34 g of a yellow solid. The two enantiomers 8d and 8e were separated by flash column chromatography using 5:1 Heptane/EtOAc and were obtained as light yellow solids; m/z=661 (M+H)$^+$.

Step 4

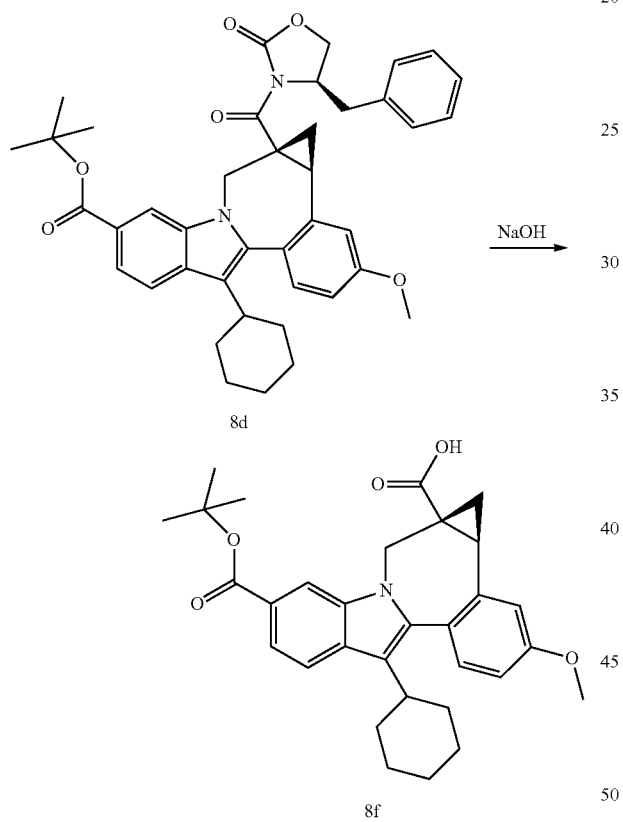

Diastereoisomer 8d (11.17 g, 16.90 mmol) was first dissolved in THF (130 ml) then methanol (130 ml) was added. 1N NaOH solution (101 mL, 101 mmol) was added slowly so that the temperature was kept below 30° C. The reaction mixture was stirred at room temperature for 2 hours. When the reaction was finished 1N HCl solution was added until the pH reached 2. 500 mL $H_2O$ was then added and the reaction mixture was extracted with EtOAc, washed with brine and concentrated. Purification by flash column chromatography using 1:1 Heptane/EtOAc afforded 5.24 g (60%) of the desired enantiomer (4bR,5aS)-9-(tert-butoxycarbonyl)-12-cyclohexyl-3-methoxy-4b,5,5a,6-tetrahydrobenzo[3,4]cyclopropa[5,6]azepino[1,2-a]indole-5a-carboxylic acid 8f with an ee of 97%; m/z=502 (M+H)$^+$.

Step 5

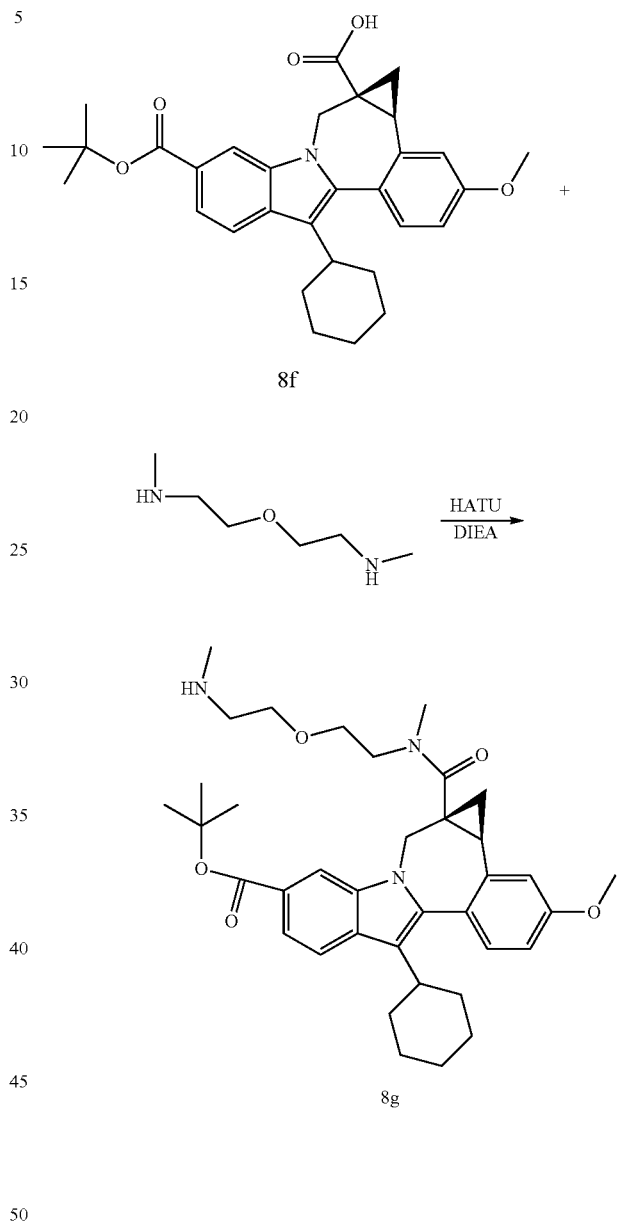

To a stirred solution of intermediate 8f (2 g, 3.99 mmol) in dry DMF (50 mL) at 0° C., were added di-isopropyl ethylamine (DIEA, 1.54 g, 11.9 mmol), HATU (2.27 g, 5.98 mmol) and 2,2'-oxybis(N-methylethanamine) (2.1 g, 15.95 mmol). The resulting mixture was stirred at 0° C. for 1 hour then kept at room temperature for 12 hours. The reaction mixture was then successively poured into an iced water solution, extracted with dichloromethane, dried over $MgSO_4$ then concentrated. The residue was purified by column chromatography using a gradient of methanol in dichloromethane (0 to 10%) to yield 0.94 g (38% yield) of the desired product tert-butyl(1aR,12bS)-8-cyclohexyl-11-methoxy-1a-(methyl{2-[2-(methylamino)ethoxy]ethyl}carbamoyl)-1,1a,2,12b-tetrahydrocyclopropa[d]indolo[2,1-a][2]benzazepine-5-carboxylate 8g as a white solid; m/z 616 (M+H)$^+$.

Step 6

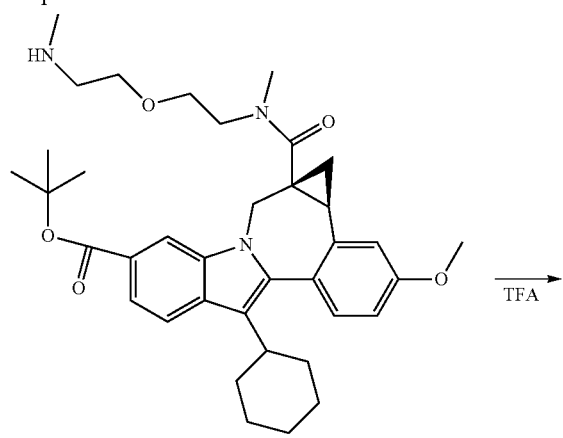

8g

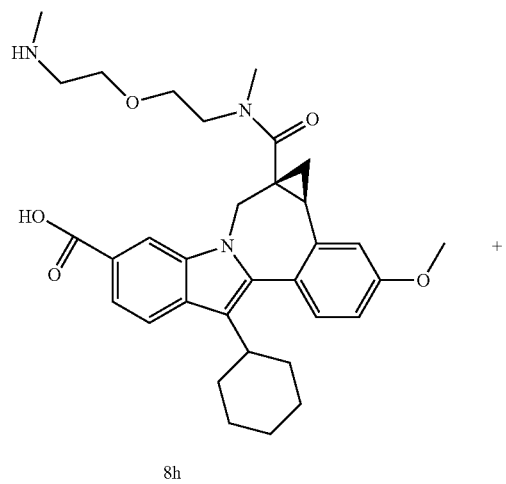

8h

The synthesis of (1aR,12bS)-8-cyclohexyl-11-methoxy-1a-(methyl{2-[2-(methyl-amino)ethoxy]ethyl}carbamoyl)-1,1a,2,12b-tetrahydrocyclopropa[d]indolo[2,1-a][2]-benzazepine-5-carboxylic acid 8h was performed following the procedure reported for the preparation of compound 1e, using intermediate 8g instead of 1d. The obtained residue was further dissolved in DCM, washed with water, dried over magnesium sulfate, filtered and concentrated to dryness, leading to 0.474 g (56% yield) of title compound 8h; m/z=560 (M+H)$^+$.

Step 7

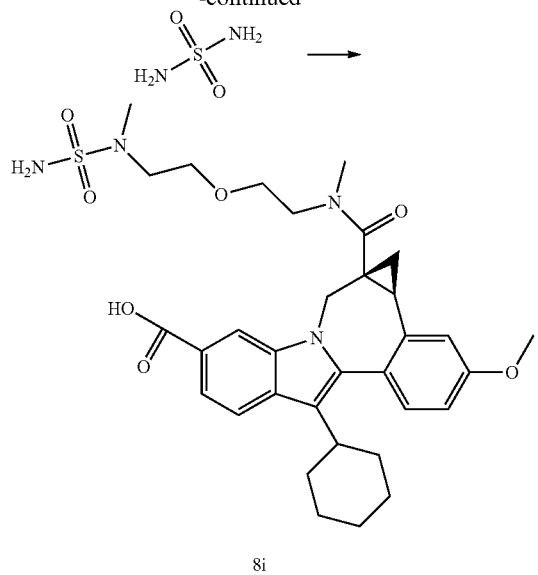

8i

To a solution of intermediate 8h (0.474 g, 0.847 mmol) in dioxane (10 mL) was added sulfamide (0.814 g, 8.47 mmol). The resulting mixture was stirred at 100° C. in a microwave oven for 4 hours. The reaction mixture was then cooled down to room temperature and concentrated. The residue was purified by column chromatography using a gradient of methanol in dichloromethane (0 to 10%) to give 143 mg (26%) of the title product (1aR,12bS)-1a-[(2-{2-[(aminosulfonyl)(methyl)amino]ethoxy}ethyl) (methyl)carbamoyl]-8-cyclohexyl-11-methoxy-1,1a,2,12b-tetrahydrocyclopropa[d]indolo[2,1-a][2]benzazepine-5-carboxylic acid 8i; m/z=639 (M+H)$^+$.

Step 8

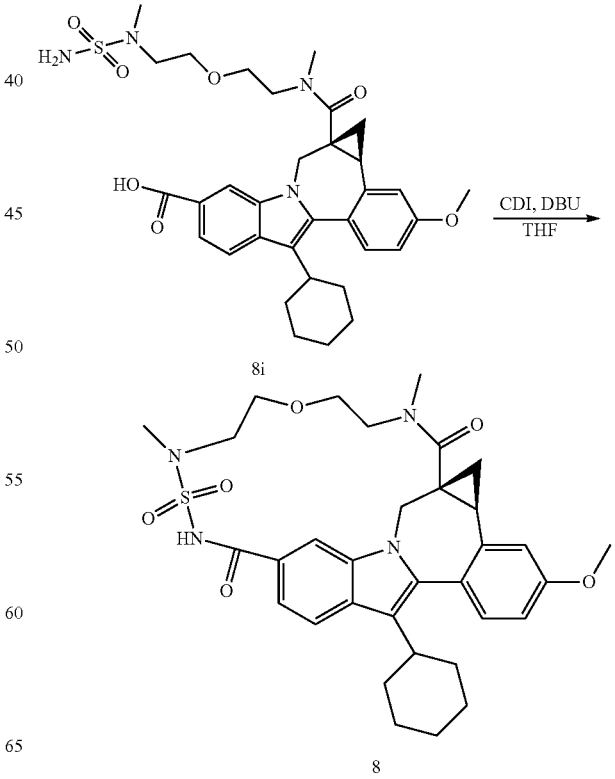

The synthesis of (1aR,12bS)-8-cyclohexyl-11-methoxy-16,22-dimethyl-1,12b-dihydro-5,1a-(methanoiminothioiminoethanooxyethanoiminomethano)cyclopropa[d]-indolo[2,1-a][2]benzazepine-13,23(2H)-dione 15,15-dioxide 8 was performed following the 2-step procedure reported for the synthesis of compound 1, using intermediate 8i instead of 1e, yielding to 90 mg (52% yield) of a white solid; m/z=621 (M+H)$^+$. 1H NMR (400 MHz, CHLOROFORM-d) δ ppm 1.3-1.5 (m, 3H) 1.75-1.8 (m, 5H) 1.85-2.05 (m, 6H) 2.5-3 (m, 3H) 3.2 (s, 3H) 3.22 (s, 3H) 3.4-3.7 (m, 6H) 3.87 (s, 3H) 3.75-3.9 (m, 1H) 4.9-5.1 (m, 1H) 6.95-7.16 (d, J=8.39 Hz, 1H) 7.28 (s, 1H) 7.44-7.55 (m, 2H) 7.80 (d, J=8.39 Hz, 1H) 9.4 (br. s., 1H).

Example 9

Synthesis of Compound 9

Step 1 propa[5,6]azepino[1,2-a]indole-5a-carboxylic acid 9a was obtained in 27% yield, and 96% ee, following the procedure reported for the synthesis of compound 8f, starting from the diastereoisomer 8e instead of 8d; m/z=502 (M+H)$^+$.

Step 2 tert-butyl(1aS,12bR)-8-cyclohexyl-11-methoxy-1a-(methyl {2-[2-(methylamino)ethoxy]ethyl}carbamoyl)-1,1a,2,12b-tetrahydrocyclopropa[d]indolo[2,1-a][2]benzazepine-5-carboxylate 9b was prepared in 60% yield from 9a and 2,2'-oxybis(N-methyl-ethanamine) following the procedure used for the preparation of compound 1c; m/z=616 (M+H)$^+$.

Step 3

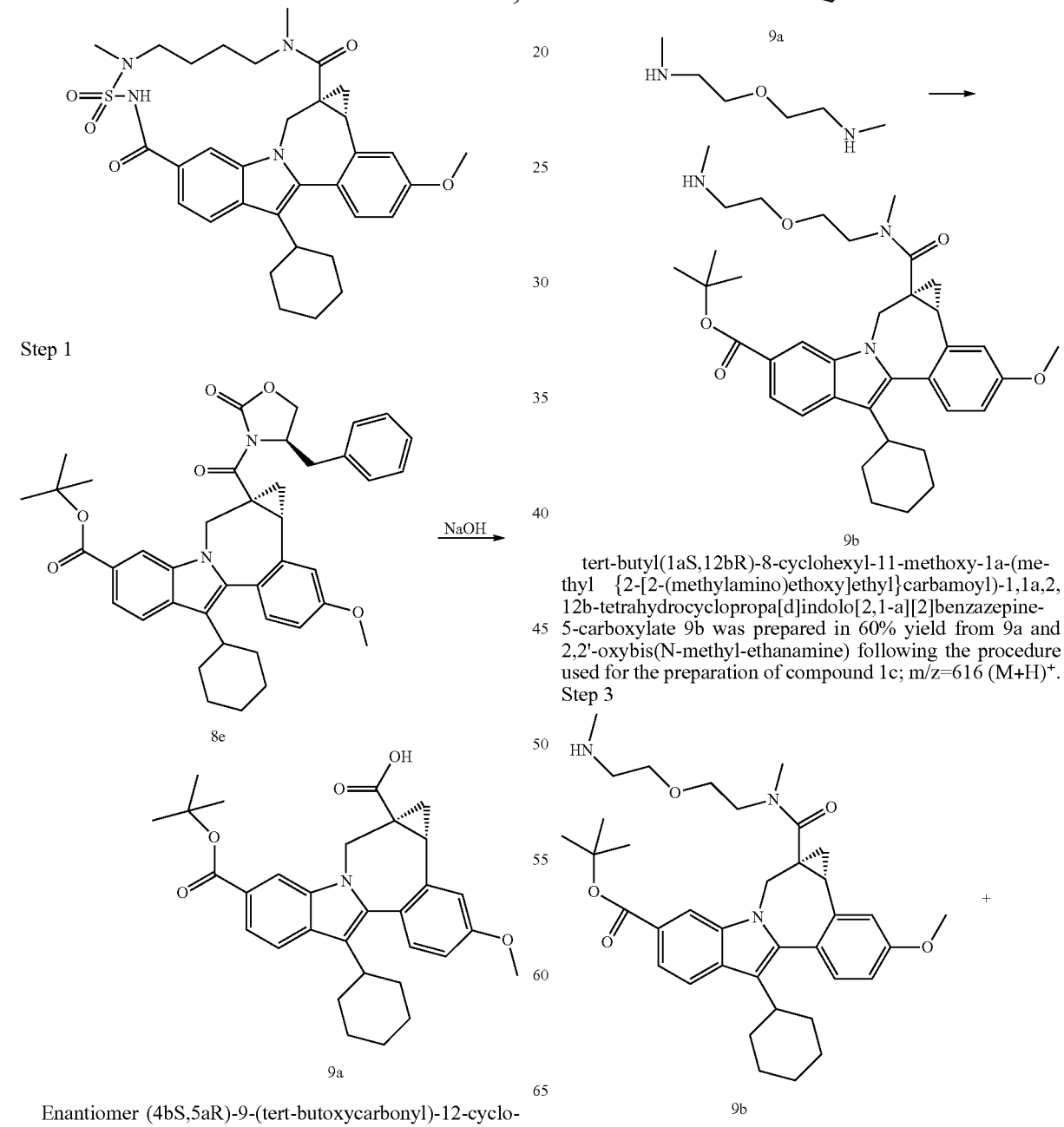

Enantiomer (4bS,5aR)-9-(tert-butoxycarbonyl)-12-cyclohexyl-3-methoxy-4b,5,5a,6-tetrahydrobenzo[3,4]cyclo- -continued

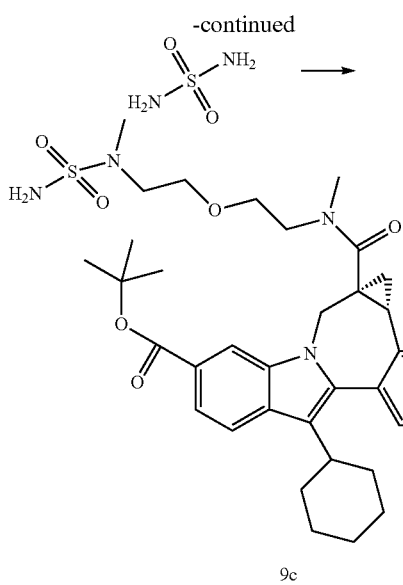

9c

To a solution of intermediate 9b (0.73 g, 1.185 mmol) in dioxane (10 mL) was added sulfamide (1.14 g, 11.85 mmol). The resulting mixture was stirred at 100° C. in a microwave oven for 3 hours. The reaction mixture was cooled down to room temperature then concentrated. The residue was purified by column chromatography using a gradient of methanol in dichloromethane (0 to 10%) to yield 743 mg (80%) of the title product tert-butyl(1aS,12bR)-1a-[(2-{2-[(aminosulfonyl)(methyl)amino]-ethoxy}ethyl)(methyl)carbamoyl]-8-cyclohexyl-11-methoxy-1,1a,2,12b-tetrahydro-cyclopropa[d]indolo[2,1-a][2]benzazepine-5-carboxylate 9c.

Step 4

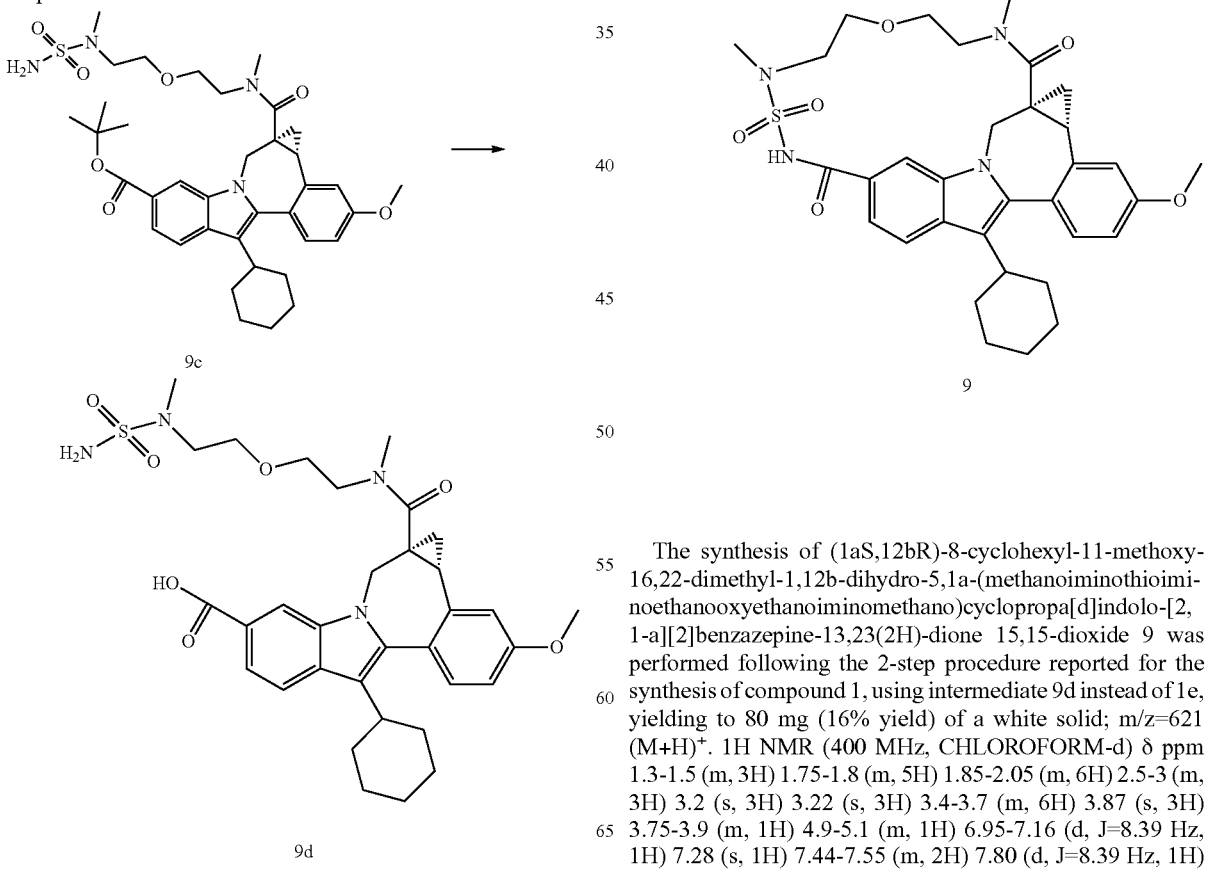

The synthesis of (1aS,12bR)-1a-[(2-{2-[(aminosulfonyl)(methy)amino]ethoxy}ethyl)(methyl)carbamoyl]-8-cyclohexyl-11-methoxy-1,1a,2,12b-tetrahydrocyclopropa[d]indolo[2,1-a][2]benzazepine-5-carboxylic acid 9d was performed following the procedure reported for the preparation of compound 1e, using intermediate 9c instead of 1d, yielding 517 mg (79% yield) of a brownish foam; m/z=639 (M+H)⁺.

Step 5

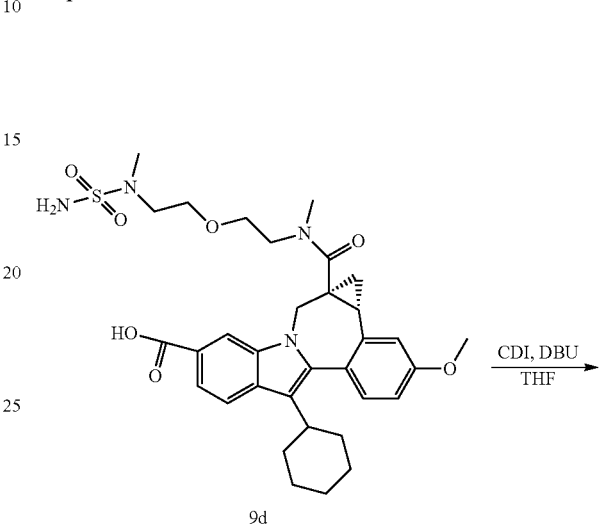

The synthesis of (1aS,12bR)-8-cyclohexyl-11-methoxy-16,22-dimethyl-1,12b-dihydro-5,1a-(methanoiminothioiminoethanooxyethanoiminomethano)cyclopropa[d]indolo-[2,1-a][2]benzazepine-13,23(2H)-dione 15,15-dioxide 9 was performed following the 2-step procedure reported for the synthesis of compound 1, using intermediate 9d instead of 1e, yielding to 80 mg (16% yield) of a white solid; m/z=621 (M+H)⁺. 1H NMR (400 MHz, CHLOROFORM-d) δ ppm 1.3-1.5 (m, 3H) 1.75-1.8 (m, 5H) 1.85-2.05 (m, 6H) 2.5-3 (m, 3H) 3.2 (s, 3H) 3.22 (s, 3H) 3.4-3.7 (m, 6H) 3.87 (s, 3H) 3.75-3.9 (m, 1H) 4.9-5.1 (m, 1H) 6.95-7.16 (d, J=8.39 Hz, 1H) 7.28 (s, 1H) 7.44-7.55 (m, 2H) 7.80 (d, J=8.39 Hz, 1H) 9.4 (br. s., 1H).

Example 10

Synthesis of Compound 10

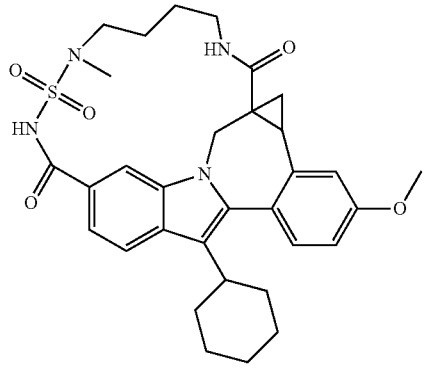

Step 1

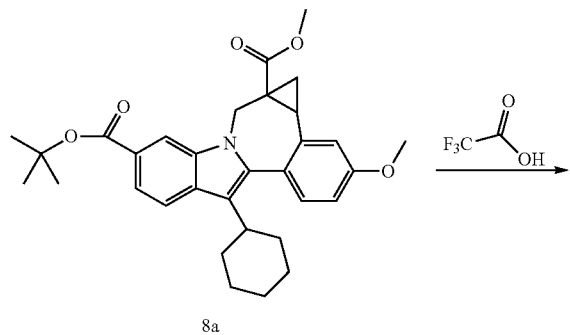

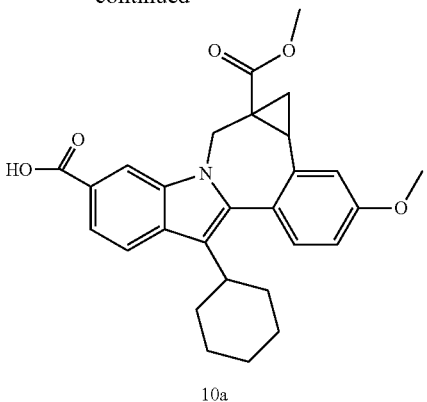

To a solution of 5-tert-butyl 1a-methyl 8-cyclohexyl-11-methoxy-1,12b-dihydrocyclo-propa[d]indolo[2,1-a][2]benzazepine-1a,5(2H)-dicarboxylate 8a (2 g, 3.88 mmol) in dichloromethane (25 mL) was added TFA (22.34 g, 194 mmol). The resulting mixture was stirred at room temperature for 6 hours then concentrated to dryness. The residue was successively dissolved in dichloromethane, washed with water, dried under MgSO$_4$, filtered and concentrated. The residue was then purified by column chromatography using dichloromethane and ethyl acetate as eluent to yield 1.7 g (95%) of the title product 8-cyclohexyl-11-methoxy-1a-(methoxycarbonyl)-1,1a,2,12b-tetrahydrocyclopropa[d]indolo[2,1-a][2]benzazepine-5-carboxylic acid 10a as a white powder; m/z 460 (M+H)$^+$.

Step 2

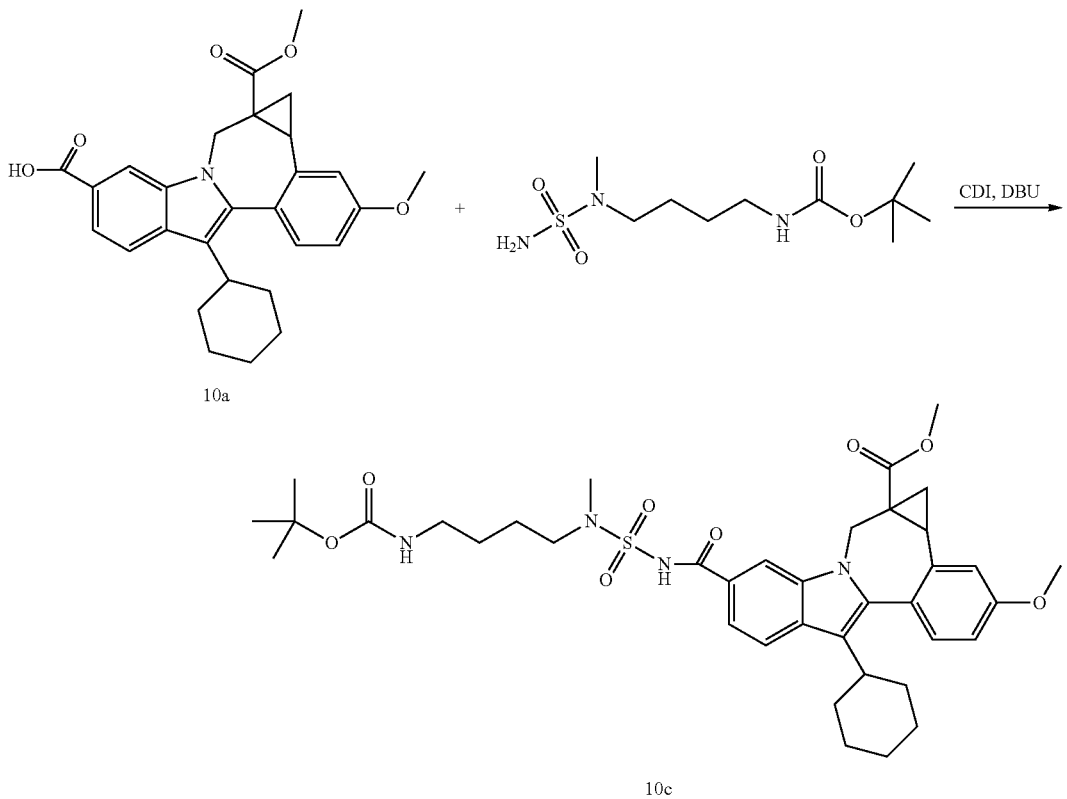

1,1'-Carbonyldiimidazole (0.847 g, 5.22 mmol) was added to a stirred solution of 8-cyclohexyl-11-methoxy-1a-(methoxycarbonyl)-1,1a,2,12b-tetrahydrocyclopropa[d]-indolo[2,1-a][2]benzazepine-5-carboxylic acid 10a (0.8 g, 1.74 mmol) in THF (15 mL) at 25° C. The evolution of $CO_2$ was instantaneous and when it slowed the solution was heated at 50° C. for 2 hours and then cooled to room temperature. Tert-butyl{4-[(amino-sulfonyl)(methyl)amino]butyl}carbamate 10b (0.735 g, 2.61 mmol) was added followed by the addition of DBU (0.53 g, 3.48 mmol). Stirring was continued for 12 hours at 50° C. The mixture was cooled to room temperature then partitioned between dichloromethane and water. The water was extracted with dichloromethane. The organic layers were dried over $MgSO_4$ then concentrated to dryness. The residue was purified by column chromatography using dichloromethane and ethyl acetate to yield 0.66 g (53%) of the title product methyl 5-({[{4-[(tert-butoxycarbonyl)amino]butyl}(methyl)amino]sulfonyl}carbamoyl)-8-cyclohexyl-11-methoxy-1,12b-dihydrocyclopropa[d]indolo[2,1-a][2]benzazepine-1a(2H)-carboxylate 10c as a white foam; m/z 723 $(M+H)^+$ Step 3

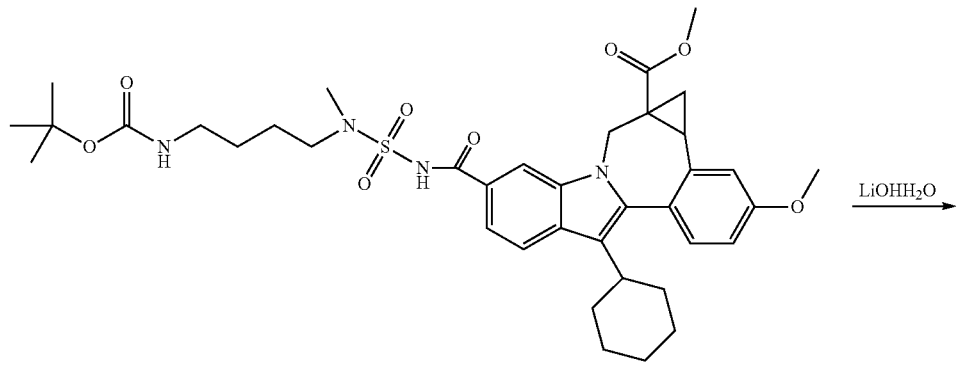

10c

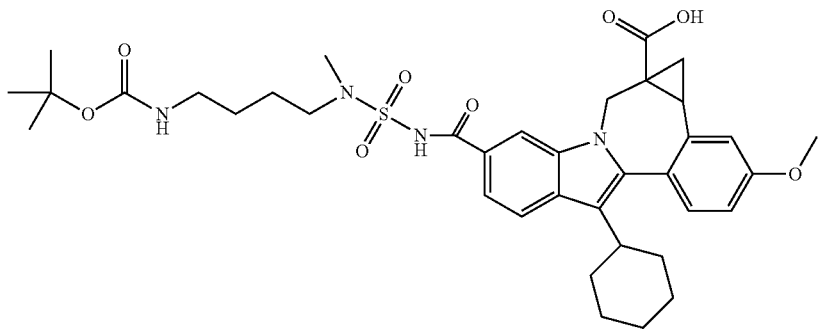

10d

To a solution of intermediate 10c (0.65 g, 0.899 mmol) in THF (20 mL) was added lithium hydroxide (0.75 g, 1.8 mmol) dissolved in water (5 mL). The resulting mixture was stirred at room temperature overnight then diluted with water and neutralized with a 2M HCl aqueous solution. The resulting mixture was extracted with dichloromethane, dried over MgSO$_4$ then concentrated. The residue was purified by column chromatography using a gradient of methanol in CH$_2$Cl$_2$ to yield 0.55 g (86%) of the title product 5-({[{4-[(tert-butoxycarbonyl)amino]butyl}(methyl)amino]sulfonyl}-carbamoyl)-8-cyclohexyl-11-methoxy-1,12b-dihydrocyclo-propa[d]indolo[2,1-a][2]benzazepine-1a(2H)-carboxylic acid 10d as a white solid; m/z 709 (M+H)$^+$
Step 4

TFA (2.5 g, 22 mmol) was added to a solution of intermediate 10d (0.52 g, 0.734 mmol) in DCM (10 mL). The resulting mixture was stirred at RT for approximately 10 hours. The reaction was then evaporated to dryness and the residue was purified by column chromatography using a gradient of methanol in DCM to afford 0.3 g (68%) of the title compound 5-({[(4-aminobutyl)(methyl)amino]sulfonyl}carbamoyl)-8-cyclohexyl-11-methoxy-1,12b-dihydrocyclo-propa[d]indolo[2,1-a][2]benzazepine-1a(2H)-carboxylic acid 10e as a TFA salt; m/z 609 (M+H)$^+$

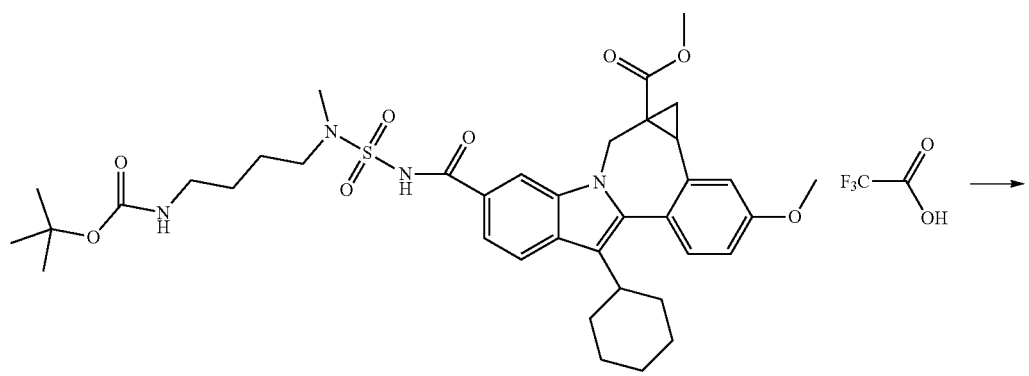

10d

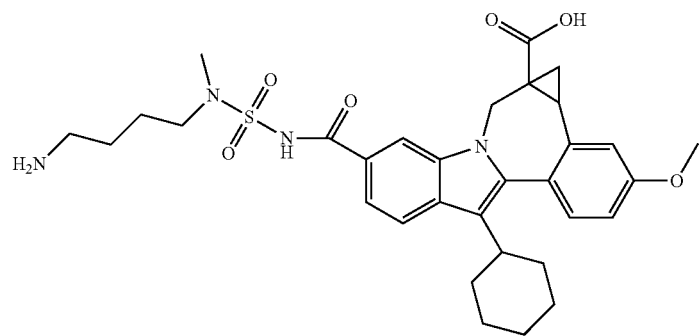

10e

Step 5

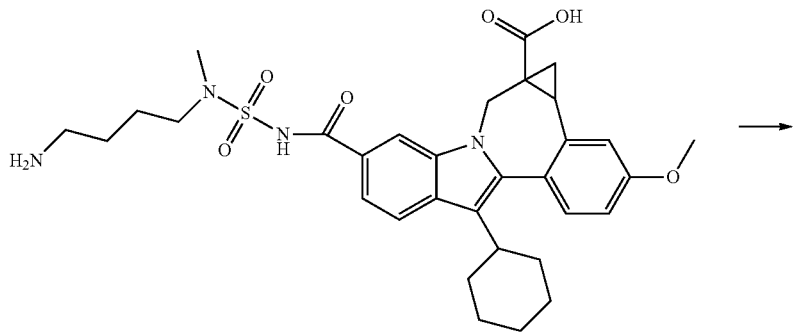

10e

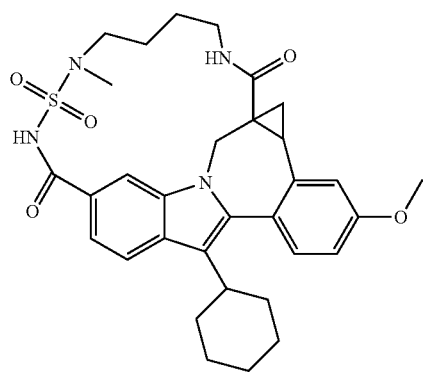

10

To a stirred solution of intermediate 10e (0.22 g, 0.36 mmol) in dry DMF (100 mL), at 0° C., were added DIPEA (0.14 g, 1.08 mmol) and HATU (0.206 g, 0.542 mmol). The resulting mixture was stirred at 0° C. for 1 hour then kept at room temperature for 12 hours. The reaction mixture was then successively poured into an iced watered solution, extracted with dichloromethane, dried over MgSO$_4$ and then concentrated. The residue was purified by column chromatography to yield 0.188 g (88%) of the title product 8-cyclohexyl-11-methoxy-16-methyl-1,12b-dihydro-5,1a-(methanoiminothioiminobutanoimino)cyclopropa[d]indolo[2,1-a][2]benzazepine-13,22(2H)-dione 15,15-dioxide 10 as a white solid. $^1$H NMR (DMSO-d$_6$): 11.5 (s, 1H), 8.4 (s, 1H), 8.3 (s, 1H), 7.8 (d, J=8.2 Hz, 1H), 7.3 (d, J=8.2 Hz, 1H), 7.25 (d, J=8.4 Hz, 1H), 7.15 (s, 1H), 7 (d, J=8.4 Hz, 1H), 5.6 (d, J=16 Hz, 1H), 3.85 (s, 3H), 3.55 (d, J=16 Hz, 1H), 3-3.2 (m, 2H), 3 (s, 3H), 2.7-2.9 (m, 4H), 1.8-2.1 (m, 5H), 1.6-1.7 (m, 2H), 1.3-1.6 (m, 6H), 1-0.7 (m, 3H); m/z 609 (M+H)$^+$ Example 11

Synthesis of Compound 11

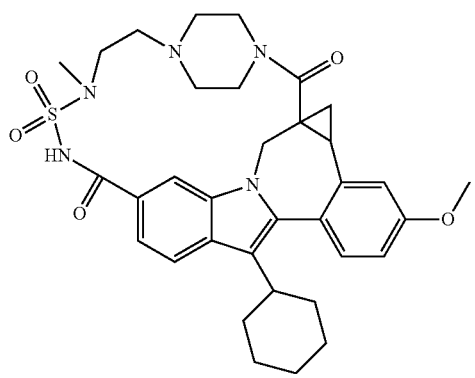

11

Step 1

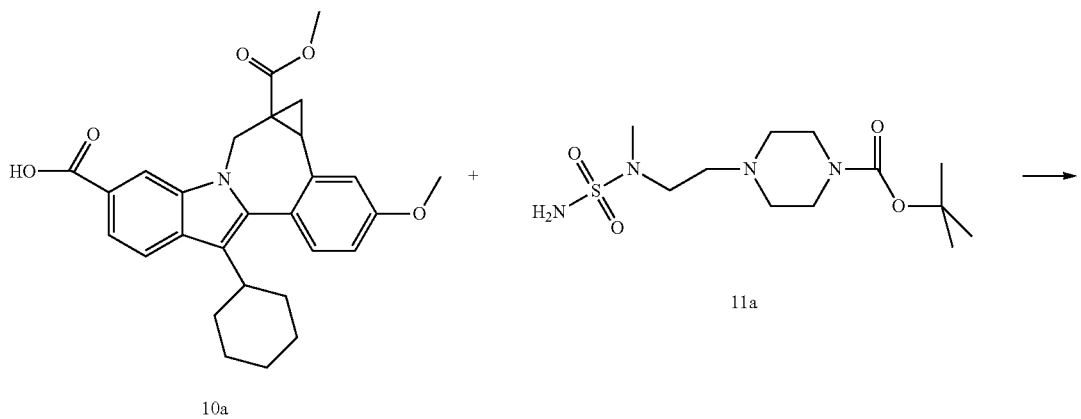

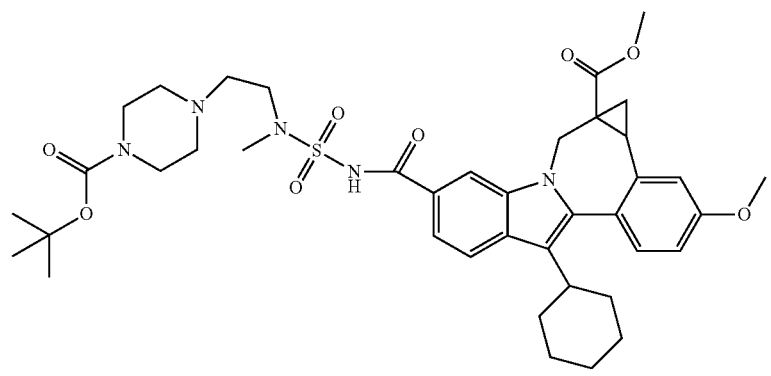

1,1′-carbonyldiimidazole (0.522 g, 3.22 mmol) was added to a stirred solution of 8-cyclohexyl-11-methoxy-1a-(methoxycarbonyl)-1,1a,2,12b-tetrahydrocyclopropa-[d]indolo[2,1-a][2]benzazepine-5-carboxylic acid 10a (0.74 g, 1.61 mmol) in THF (15 mL) at 25° C. The evolution of $CO_2$ was instantaneous and when it slowed the solution was heated at 50° C. for 2 hours and then cooled to room temperature. Tert-butyl 4-{2-[(aminosulfonyl)(methyl)amino] ethyl}piperazine-1-carboxylate 11a (1.038 g, 3.22 mmol) was added followed by the addition of DBU (0.49 g, 3.22 mmol). Stirring was continued for 12 hours at 50° C. The mixture was cooled to room temperature then partitioned between dichloromethane and water. The water was extracted with dichloromethane and the organic layers were dried over $MgSO_4$ then concentrated to dryness. The residue was purified by column chromatography using dichloromethane and ethyl acetate to yield 0.83 g (68%) of the title compound methyl 5-({[{2-[4-(tert-butoxycarbonyl)piperazin-1-yl] ethyl}(methyl)amino]sulfonyl}carbamoyl)-8-cyclohexyl-11-methoxy-1,12b-dihydrocyclopropa[d]indolo[2,1-a][2] benzazepine-1a(2H)-carboxylate 11b as a white foam; m/z 764 (M+H)$^+$ Step 2

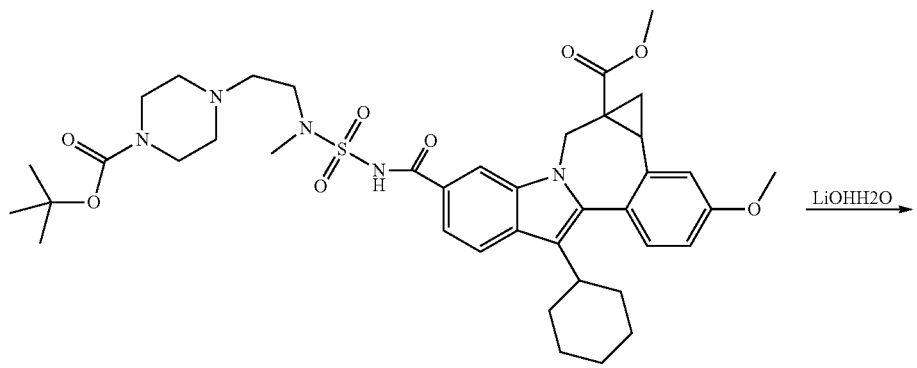

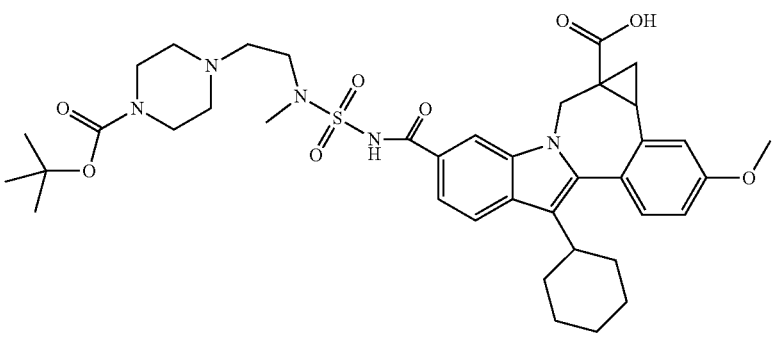

11c

To a solution of intermediate 11b (0.6 g, 0.785 mmol) in THF (20 mL) was added LiOH (0.82 g, 1.96 mmol) in water (5 mL). The resulting mixture was stirred at room temperature overnight then diluted with water and neutralized with a 2M HCl aqueous solution. The resulting mixture was extracted with dichloromethane, dried over MgSO$_4$ then concentrated. The resulting residue was purified by column chromatography using CH$_2$Cl$_2$ and methanol to yield 0.4 g (68%) of the title compound 5-({[{2-[4-(tert-butoxycarbonyl)piperazin-1-yl]ethyl}(methyl)amino]sulfonyl}carbamoyl)-8-cyclohexyl-11-methoxy-1,12b-dihydrocyclopropa[d]indolo[2,1-a][2]benzazepine-1a(2H)-carboxylic acid 11c as a white solid; m/z 750 (M+H)$^+$ Step 3

TFA (1.44 g, 12.7 mmol) was added to a solution of intermediate 11c (0.38 g, 0.507 mmol) in dichloromethane (10 mL). The resulting mixture was stirred at RT for approximately 10 hours. The reaction was then evaporated to dryness and the residue was purified by column chromatography using dichloromethane and methanol to afford the title compound 8-cyclohexyl-11-methoxy-5-({[methyl(2-piperazin-1-yl-ethyl)amino]sulfonyl}carbamoyl)-1,12b-dihydrocyclopropa[d]indolo[2,1-a][2]-benzazepine-1a(2H)-carboxylic acid 11d (0.24 g, 73%); m/z 650 (M+H)$^+$

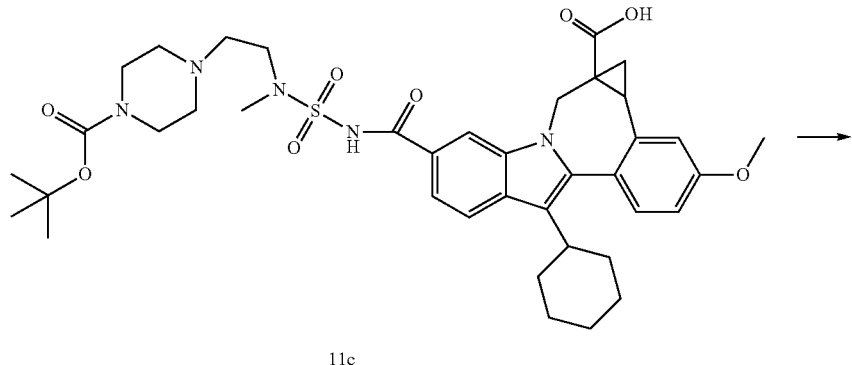

11c

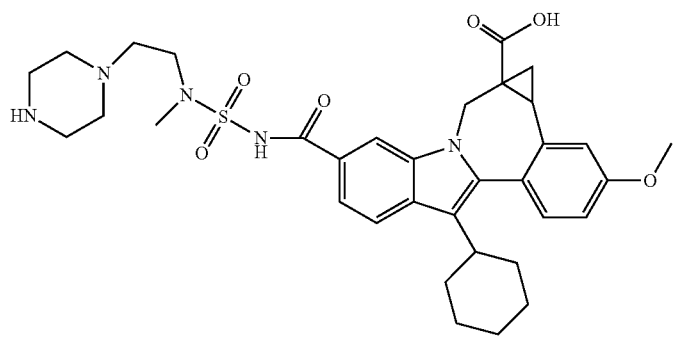

11d

Step 4

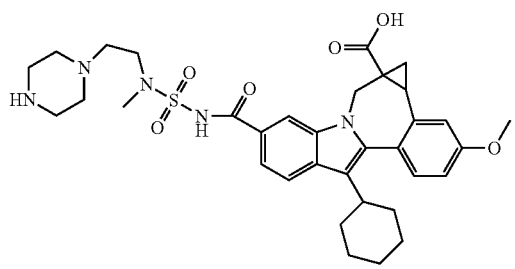

11d

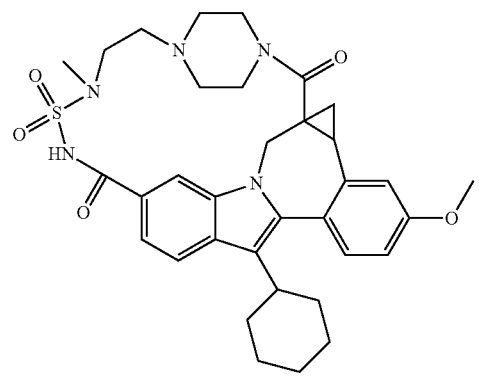

11

To a stirred solution of intermediate 11d (0.24 g, 0.37 mmol) in dry DMF (100 mL), at 0° C., were added di-isopropyl ethylamine (0.143 g, 1.1 mmol) and HATU (0.211 g, 0.554 mmol). The resulting mixture was stirred at 0° C. for 1 hour then kept at room temperature for 12 hours. The reaction mixture was then successively poured into an iced watered solution, extracted with dichloromethane, dried over MgSO$_4$ and concentrated. The residue was purified by column chromatography using dichloro-methane/methanol to yield 0.018 g (18%) of the title compound 31-cyclohexyl-8-methoxy-22-methyl-21-thia-1,13,20,22,25-pentaazaheptacyclo-[23.2.2.1$^{3,13}$.1$^{12,15}$.1$^{14,18}$.0$^{3,5}$.0$^{6,11}$]dotriaconta-6,8,10,12 (31),14(30),15,17-heptaene-2,19-dione 21,21-dioxide 11 as a white solid; m/z 632 (M+H)$^+$ Example 12

Synthesis of Compound 12

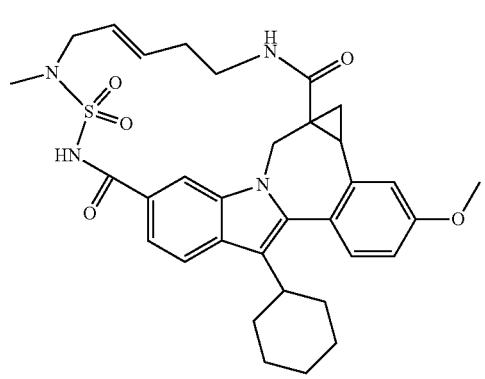

12

Step 1

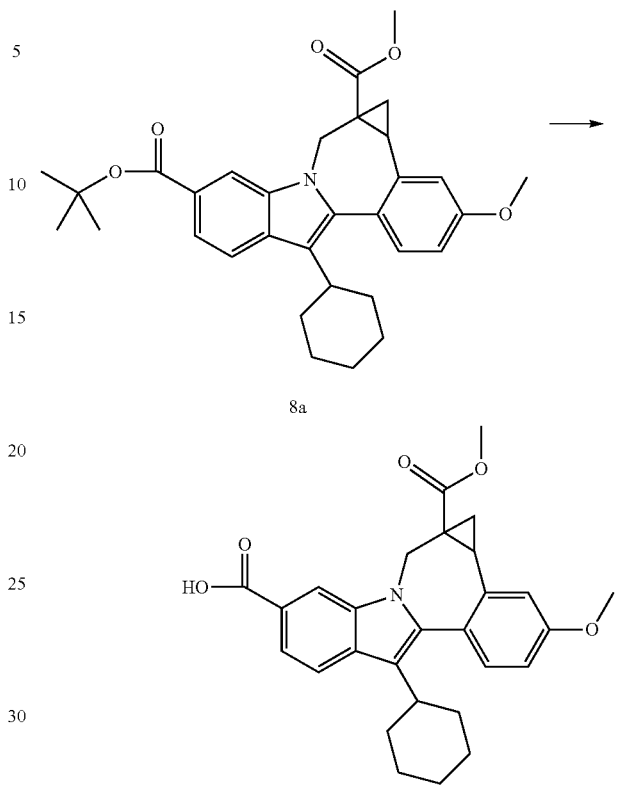

To a solution of 5-tert-butyl-1a-methyl-8-cyclohexyl-11-methoxy-1,12b-dihydrocyclo-propa[d]indolo[2,1-a][2]benzazepine-1a,5(2H)-dicarboxylate 8a (2 g, 3.88 mmol) in dichloromethane (25 mL) was added trifluoroacetic acid (22.34 g, 194 mmol). The resulting mixture was stirred at room temperature for 6 hours then concentrated to dryness. The residue was successively dissolved in dichloromethane, washed with water, dried under MgSO$_4$, filtered and concentrated. The residue was purified by column chromatography using dichloromethane and ethyl acetate as eluent to yield 1.7 g (95%) of the title product 8-cyclohexyl-11-methoxy-1a-(methoxycarbonyl)-1,1a,2,12b-tetrahydrocyclopropa[d]indolo[2,1-a][2]benzazepine-5-carboxylic acid 12a as a white powder; m/z 460 (M+H)$^+$ Step 2

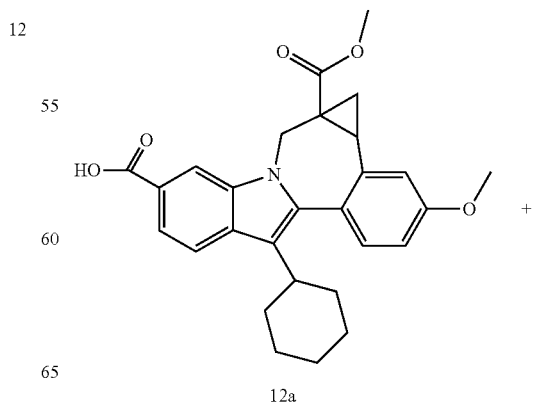

12a

+

-continued

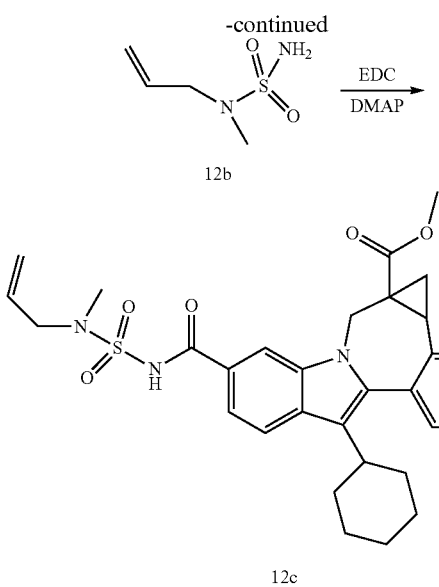
12b

To a solution of intermediate 12a (1.73 g, 3.76 mmol) in THF (25 mL) at 0° C. were added successively 4-dimethylaminopyridine (DMAP) (1.38 g, 3.76 mmol), N1-((ethylimino)methylene)-N3,N3-dimethylpropane-1,3-diamine hydrochloride (EDC) (2.16 g, 11.29 mmol) and allyl(methyl)aminosulfonamide 12b (1.3 g, 8.66 mmol). The resulting mixture was stirred at 0° C. for 2 h then at room temperature for 8 h. Water was then added and the reaction mixture was filtered. The resulting solid was purified by column chromatography using dichloromethane and ethyl acetate to yield 500 mg (23%) of the title product methyl 5-({[allyl(methyl)amino]sulfonyl}-carbamoyl)-8-cyclohexyl-11-methoxy-1,12b-dihydrocyclopropa[d]indolo[2,1-a][2]-benzazepine-1a(2H)-carboxylate 12c; m/z 592 (M+H)+
Step 3

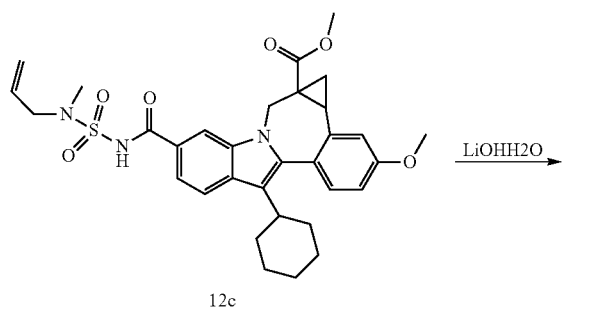

To a solution of intermediate 12c (0.5 g, 0.845 mmol) in THF (20 mL) was added lithium hydroxide (0.73 g, 1.69 mmol) in water (5 mL). The resulting mixture was stirred at room temperature overnight then diluted with water and neutralized with a 2M HCl aqueous solution. The resulting mixture was extracted with dichloromethane, dried over MgSO4 then concentrated. The resulting residue was purified by column chromatography using CH2Cl2 and methanol to yield 0.4 g (75%) of the title product 5-({[allyl(methyl)amino]sulfonyl}carbamoyl)-8-cyclohexyl-11-methoxy-1,12b-dihydrocyclopropa[d]indolo[2,1-a][2]benzazepine-1a(2H)-carboxylic acid 12d as a white solid; m/z 578 (M+H)+
Step 4

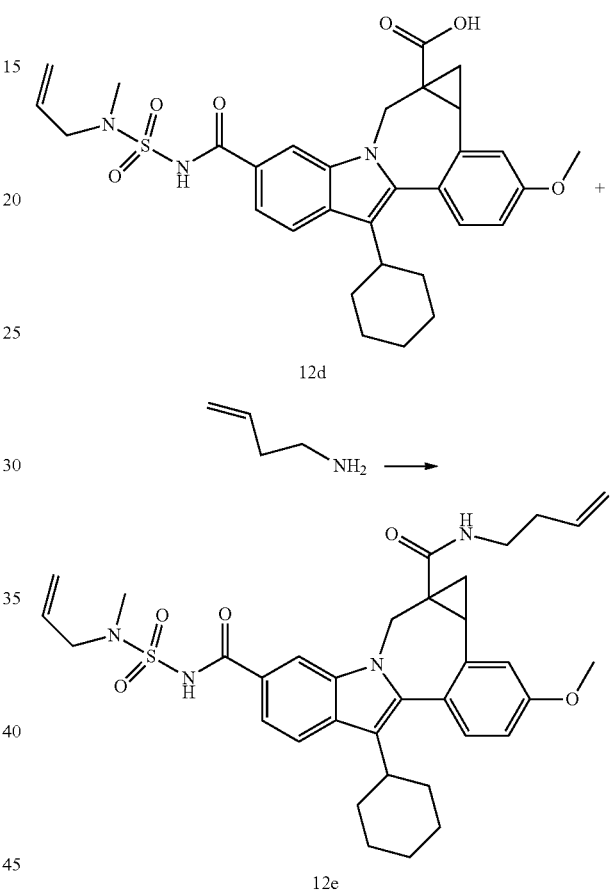

To a solution of intermediate 12d (0.2 g, 0.346 mmol) in THF (15 mL), at 0° C., were added successively 4-dimethylaminopyridine (DMAP) (0.127 g, 1.04 mmol), N1-((ethylimino)methylene)-N3,N3-dimethylpropane-1,3-diamine hydrochloride (EDC) (0.199 g, 1.04 mmol) and but-3-en-1-amine (0.062 g, 0.866 mmol). The resulting mixture was stirred at 0° C. for 2 h then at room temperature for 8 h. Water was then added and the resulting mixture was filtered. The solid was washed with dichloromethane then the filtrate was successively extracted with dichloromethane, dried over MgSO4, filtered and concentrated. The resulting residue was purified by column chromatography with dichloromethane and ethyl acetate to yield 70 mg (32%) of the title product $N^5$-{[allyl(methyl)amino]sulfonyl}-$N^{1a}$-but-3-en-1-yl-8-cyclohexyl-11-methoxy-1,12b-dihydrocyclopropa[d]indolo[2,1-a][2]benzazepine-1a,5(2H)-dicarboxamide 12e; m/z 631 (M+H)+

Step 5

Example 13

Synthesis of Compound 13

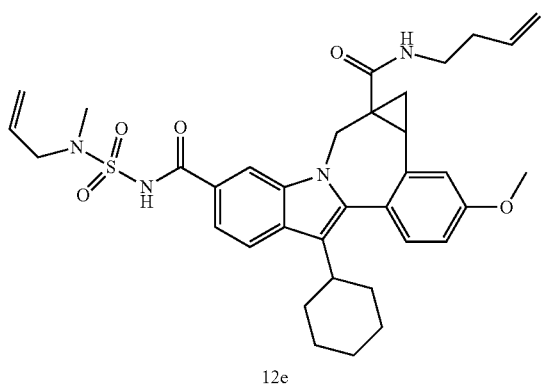

12e

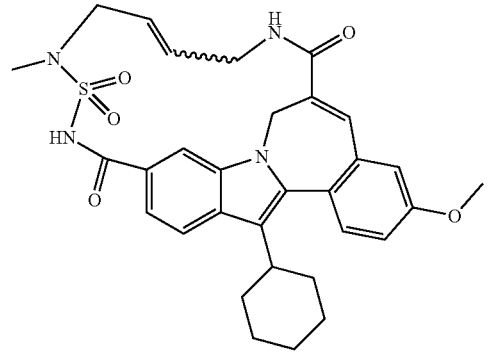

13

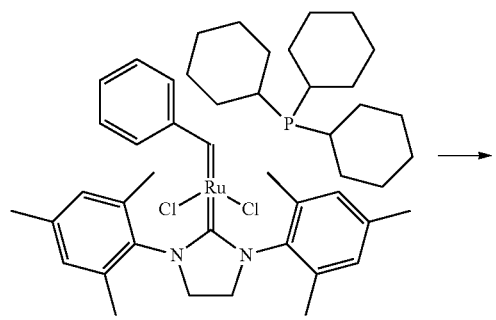

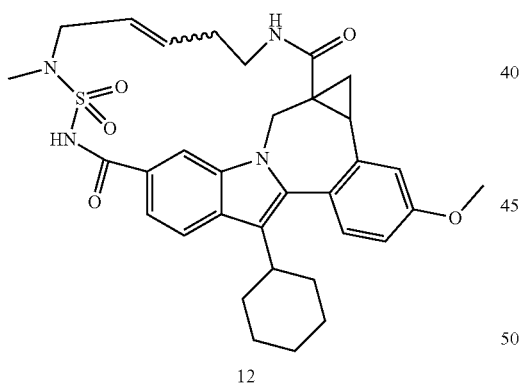

12

Step 1

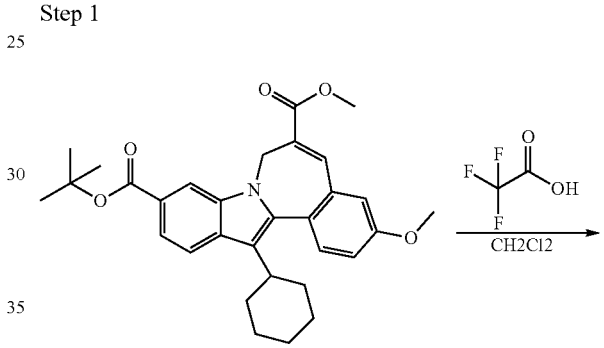

1a

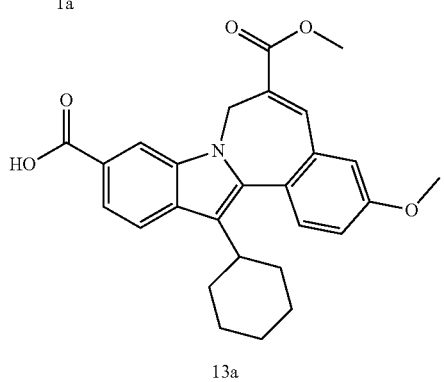

13a

A solution of intermediate 12e (0.1 g, 0.16 mmol) in dichloroethane (50 mL) was degassed with argon for 10 minutes then Hoveyda-Grubbs 1$^{st}$ generation catalyst (0.03 mg, 0.032 mmol) was added. The resulting mixture was warmed to 70° C. and kept under argon overnight. The mixture was then cooled down to room temperature and the solvent was removed under vacuum. The resulting dark residue was purified by column chromatography using DCM and ethyl acetate to give 15 mg (16%) of the title product 8-cyclohexyl-11-methoxy-16-methyl-1,12b-dihydro-5,1a-(methaniminothio-iminopent[2]enoiminomethano)cyclopropa[d]indolo[2,1-a][2]benzazepine-13,23(2H)-dione 15,15-dioxide 12 as a white solid; m/z 603 (M+H)$^+$ 13-Cyclohexyl-3-methoxy-7H-benzo[3,4]azepino[1,2-a] indole-6,10-dicarboxylic acid 10-tert-butyl ester 6-methyl ester 1a (1 g, 1 eq) was dissolved in dry dichloromethane under N$_2$, followed by the addition of trifluoroacetic acid (TFA) (8.88 ml, 60 eq). The solution was stirred at RT for 24 h. The solvent was then removed under reduced pressure. The crude product was triturated with diethyl ether. The crystals were filtered off and dried under vacuum overnight to afford the title product 13-Cyclohexyl-3-methoxy-7H-benzo[3,4] azepino[1,2-a]indole-6,10-dicarboxylic acid 6-methyl ester 13a (89%, 0.86 g); LC-MS: Rt. 3.19 min., m/z 446 [M+H]$^+$.

Step 2

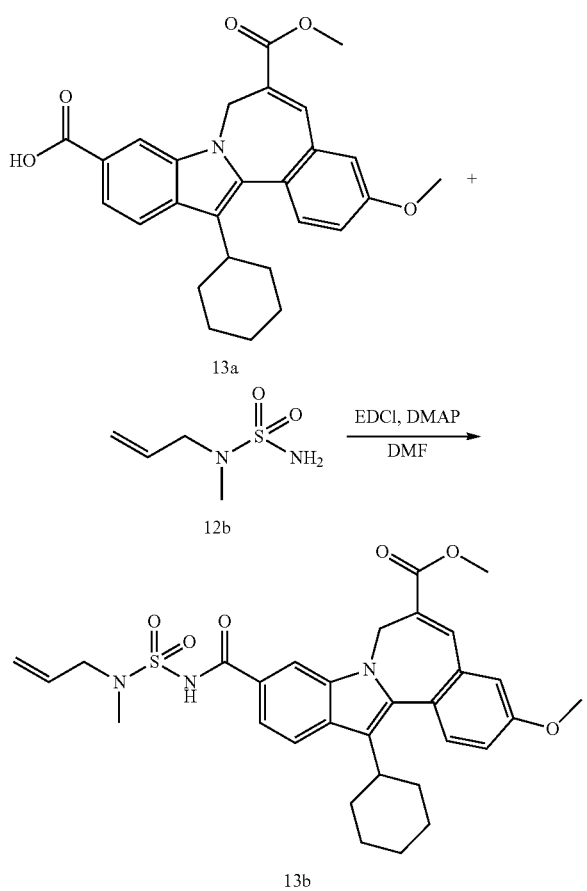

13-Cyclohexyl-3-hydroxy-7H-benzo[3,4]azepino[1,2-a]indole-6,10-dicarboxylic acid 6-methyl ester 13a (0.86 g, 1 eq), N-methyl-N-allyl-sulfuric diamide 12b (0.67 g, 2.03 eq), $N^1$-((ethylimino)methylene)-$N^3$,$N^3$-dimethylpropane-1,3-diamine hydrochloride (EDCI) (1.14 g, 3.06 eq) and dimethyl-pyridin-4-yl-amine (DMAP) (0.67 g, 3.04 eq) were dissolved in dry dimethylformamide (20 ml) under $N_2$. The solution was stirred at RT for 3 days. This solution was slowly added into ice water. The water layer was extracted with ethyl acetate (3×50 ml) and washed with tetrahydrofurane (3×50 ml). The combined organic layers were dried over magnesium sulfate, filtered and evaporated under reduced pressure. The crude product was purified by preparative HPLC to give 0.63 g (55%) of the title product 13b; LC-MS: Rt. 6.16 min., m/z 578 [M+H]$^+$. $^1$H-NMR (DMSO) δ (ppm) 1.13-1.20 (m, 1H, $CH_2$), 1.30-1.47 (m, 3H, $CH_2$(2×)), 1.62-1.78 (m, 2H, $CH_2$), 1.81-1.93 (m, 1H, $CH_2$), 1.93-2.12 (m, 3H, $CH_2$ (2×)), 2.70-2.82 (m, 1H, CH), 2.86 (s, 3H, $CH_3N$), 3.79 (s, 3H, $CH_3O$), 3.88 (s, 3H, $CH_3O$), 3.90-3.98 (m, 2H, $CH_2$), 4.21 (d, 1H, J=12.97 Hz, $CH_2$), 5.21 (d, 1H, J=10.15 Hz, $CH_2$), 5.31 (d, 1H, J=17.13 Hz, $CH_2$), 5.61 (d, 1H, J=13.12 Hz, $CH_2$), 5.78-5.90 (m, 1H, $CH_{arom}$), 7.25 (dd, 1H, J=2.50 and J=8.60 Hz, $CH_{arom}$), 7.32-7.35 (m, 1H, $CH_{arom}$), 7.54 (d, 1H, J=8.60 Hz, $CH_{arom}$), 7.61 (d, 1H, J=8.45 Hz, $CH_{arom}$), 7.88 (d, 1H, J=9.01 Hz, $CH_{arom}$), 7.91 (s, 1H, CH), 8.31-8.34 (brs, 1H, $NHSO_2$).

Step 3

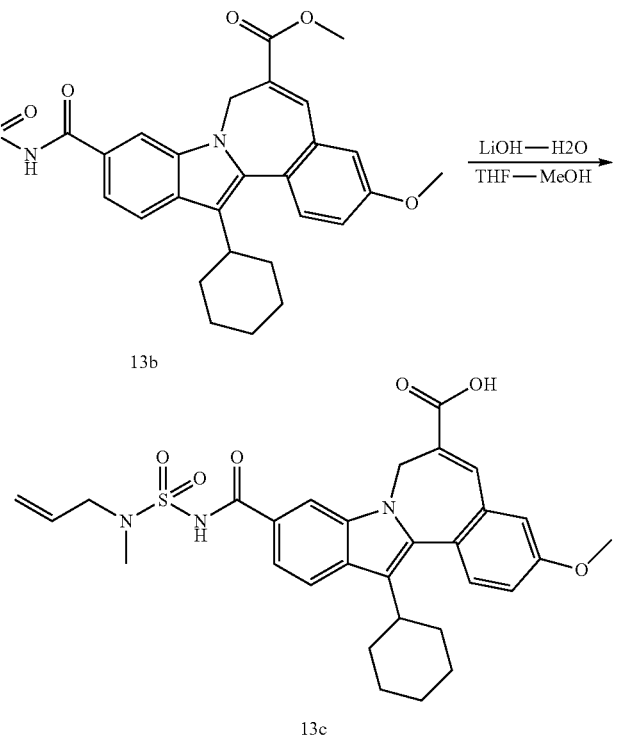

Compound 13b (0.60 g, 1 eq) was dissolved in a mixture of tetrahydrofurane:methanol (1:1) (20 ml), followed by the addition of a LiOH solution in water (0.09 g, 2 eq). The solution was stirred overnight at RT for several days. The solvents were then evaporated under reduced pressure and the water layer was acidified with a 3 N HCl solution until pH 2. The resulting crystals were filtered off, washed with water and isopropyl ether and dried under vacuum overnight to afford 0.44 g (74%) of the title product 13c; LC-MS: Rt. 5.84 min., m/z 562 [M−H]⁻.

Step 4

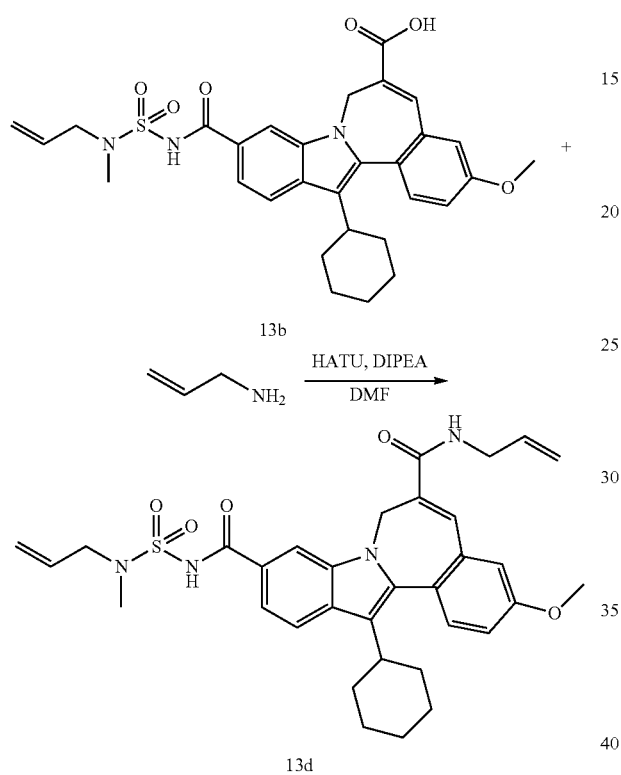

Compound 13c (0.44 g, 1 eq) and HATU (0.47 g, 1.6 eq) were dissolved in dimethylformamide under N$_2$, followed by the addition of DIPEA (0.15 g, 0.20 ml, 1.5 eq) and allylamine (0.07 ml, 1.2 eq). The solution was stirred at RT for 3 days. The dimethylformamide solution was then slowly poured into ice water. The resulting crystals were filtered off, washed with water and dried under vacuum overnight to afford 0.47 g (100%) of the title product 13d; LC-MS: Rt. 3.01 min., m/z 603 [M+H]⁺.

Step 5

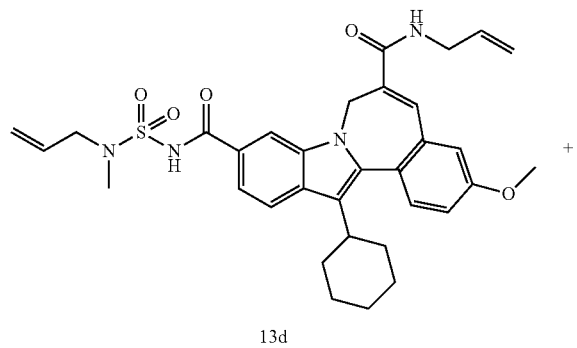

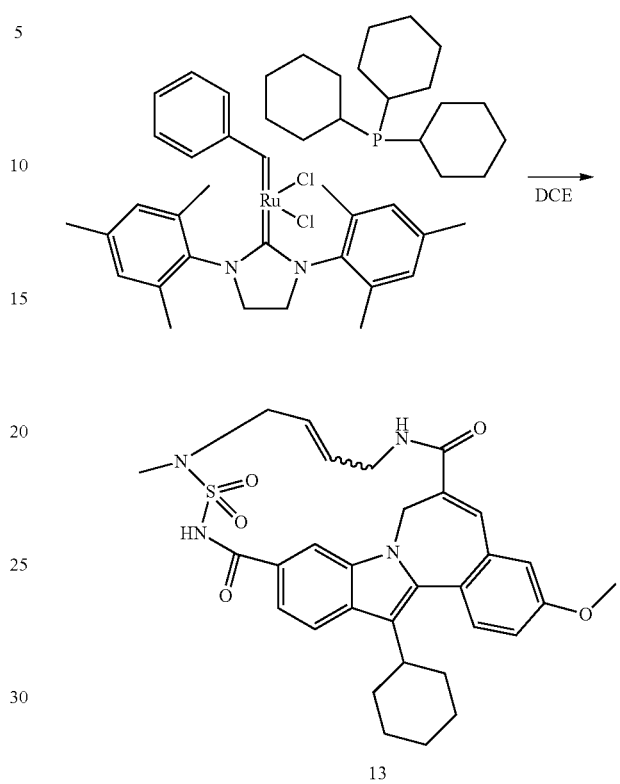

N$_2$ was bubbled through a solution of compound 13d (0.47 g, 1 eq) in 50 ml of dichloroethane for 1 h. Then Grubbs 2$^{nd}$ generation catalyst (0.13 g, 0.2 eq) was added and the reaction mixture was heated at 80° C. overnight. The solution was cooled down to RT and some extra amount of catalyst was added (65 mg). The solution was heated at 80° C. under N$_2$ for several hours. The solution was then evaporated under reduced pressure. The product was purified by flash chromatography on elution of dichloromethane:methanol (100 to 95:5), and was subsequently recrystallized from methanol. Finally the product was purified by preparative HPLC chromatography to afford 30 mg (5.86%) of the title product 13; LC-MS: Rt. 5.33 min., m/z 575 [M+H]⁺. ¹H-NMR (DMSO) δ (ppm) 1.05-1.21 (m, 1H, CH$_2$), 1.30-1.48 (m, 3H, CH$_2$ (2×)), 1.62-1.78 (m, 2H, CH$_2$), 1.82-1.93 (m, 1H, CH$_2$), 1.93-2.12 (m, 3H, CH$_2$ (2×)), 2.65-2.90 (m, 4H, CH and CH$_3$N), 3.56 (d, 2H, J=18.10 Hz, CH$_2$), 3.80-3.97 (brs, 5H, CH$_2$ and CH$_3$O), 4.21 (d, 1H, J=15.12 Hz, CH$_2$), 4.28-4.46 (m, 1H, CH), 5.72 (d, 1H, J=14.15 Hz, CH$_2$), 5.78-5.88 (m, 1H, CH), 6.53 (s, 1H, CH$_2$), 7.18-7.28 (m, 2H, CH$_{arom}$ (2×)), 7.39-7.49 (m, 1H, CH$_{arom}$), 7.55 (d, 1H, J=8.38 Hz, CH$_{arom}$), 7.62 (s, 1H, CH$_{arom}$), 7.72-7.84 (m, 1H, NH), 8.29 (s, 1H, CH), 8.51-8.62 (brs, 1H, NH).

Example 14

Synthesis of Compound 14

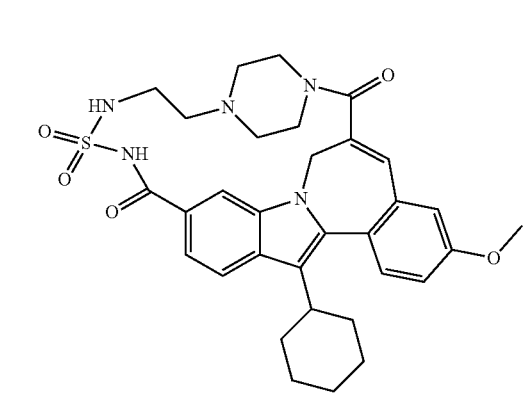

14

Step 1

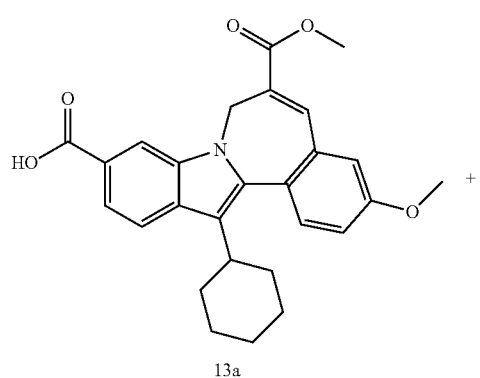

13a

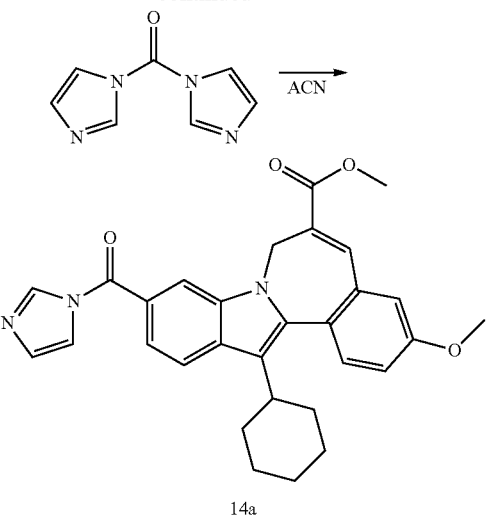

14a

13-Cyclohexyl-3-methoxy-7H-benzo[3,4]azepino[1,2-a]indole-6,10-dicarboxylic acid 6-methyl ester 13a (0.60 g, 1 eq) was dissolved in dry acetonitrile (50 ml) under $N_2$, followed by the addition of di-imidazol-1-yl-methanone (CDI) (0.66 g, 3 eq). The solution was stirred overnight at 50° C. The solvent was then evaporated under reduced pressure and the crude product was purified by flash chromatography on elution with heptane:acetonitrile and finally ethyl acetate. The product was recrystallized from ethyl acetate to give 0.50 g (75%) of the title product 14a.

Step 2

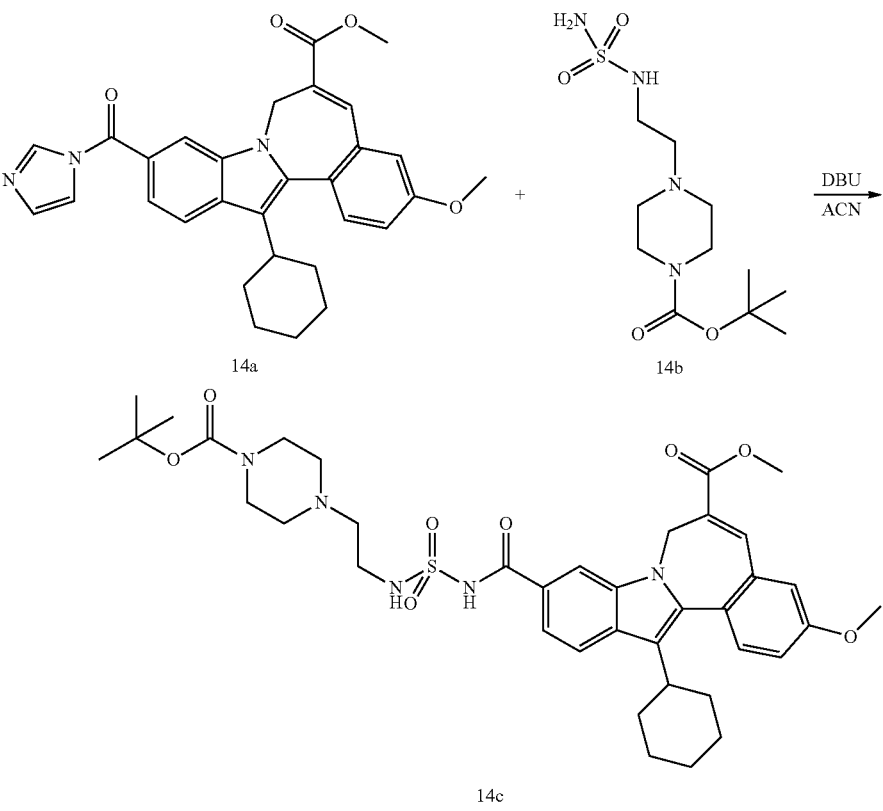

Compound 14a (0.50 g, 1 eq) was dissolved in dry acetonitrile (50 ml), followed by the addition of tert-butyl 4-(2-(sulfamoylamino)ethyl)piperazine-1-carboxylate 14b (0.47 g, 1.50 eq) and 2,3,4,6,7,8,9,10-octahydro-pyrimido[1,2-a]azepine (DBU) (0.31 g, 2 eq). The solution was heated at 50° C. overnight, then evaporated under reduced pressure. The resulting residue was stirred in a 0.1N citric acid water solution. The crystals were filtered off and dried under vacuum overnight. The product was purified by column chromatography on elution with dichloromethane to remove the first impurity. The other obtained fractions were added together. This product was further purified by flash chromatography on elution with dichloromethane:methanol (100 to 99:1) to oafford 0.41 g (55%) of the title product 14c; LC-MS: Rt. 5.59 min., m/z 736 [M+H]$^+$. $^1$H-NMR (CDCl$_3$) δ (ppm) 1.18-1.34 (m, 1H, CH$_2$), 1.35-1.50 (brs, 10H, CH$_2$ and C(CH$_3$)$_3$), 1.70-1.85 (m, 3H, CH$_2$ (2×)), 1.90-2.12 (m, 5H, CH$_2$ (3×)), 2.30-2.41 (m, 4H, CH$_2$ (2×)), 2.52-2.62 (m, 2H, CH$_2$), 2.77-2.90 (m, 1H, CH), 3.13-3.22 (m, 2H, CH$_2$), 3.43-3.57 (m, 4H, CH$_2$ (2×)), 3.83 (s, 3H, CH$_3$O), 3.92 (s, 3H, CH$_3$O), 4.16-4.23 (m, 1H, CH$_2$), 5.58-5.69 (m, 1H, CH$_2$), 7.00 (d, 1H, J=2.54 Hz, CH$_{arom}$), 7.11 (dd, 1H, J=2.67 and J=8.59 Hz, CH$_{arom}$), 7.48 (d, 1H, J=8.44 Hz, CH$_{arom}$), 7.53 (d, 1H, J=8.61 Hz, CH$_{arom}$), 7.83 (s, 1H, CH$_{arom}$), 7.90 (d, 1H, J=8.48 Hz, CH$_{arom}$), 8.09 (s, 1H, CH).

Step 3

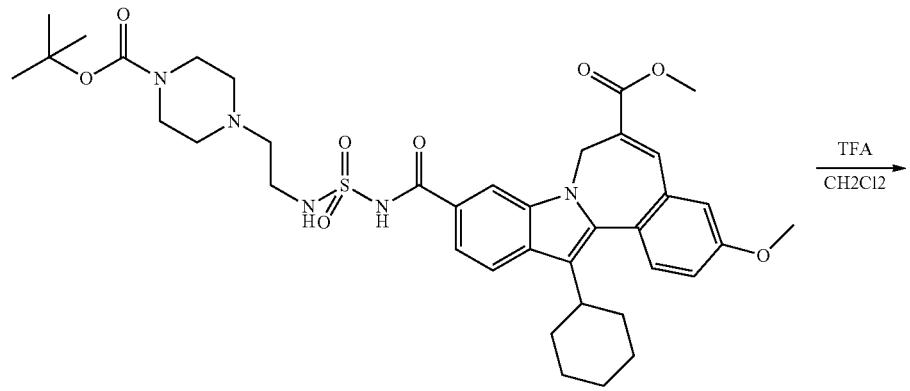

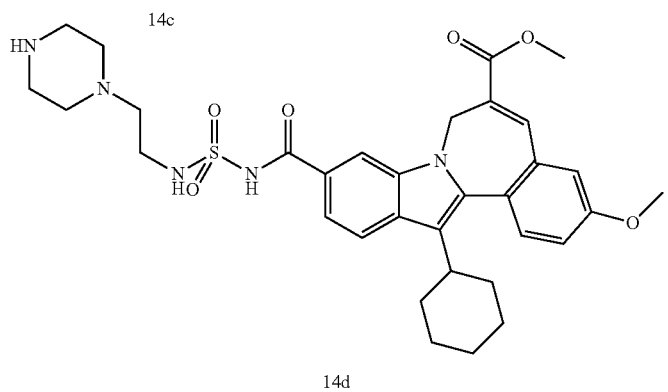

Compound 14c (0.41 g, 1 eq) was dissolved in dry dichloromethane (10 ml) under N$_2$ followed by the addition of trifluoroacetic acid (1.30 ml, 30 eq). The solution was stirred at RT overnight. The solvent was then removed under reduced pressure and the crude product was stirred in diethyl ether. The resulting crystals were filtered off and dried under reduced pressure to afford 0.31 g (87%) of the title product 14d; LC-MS: RT. 3.81 min., m/z 634 [M−H]$^−$.

Step 4

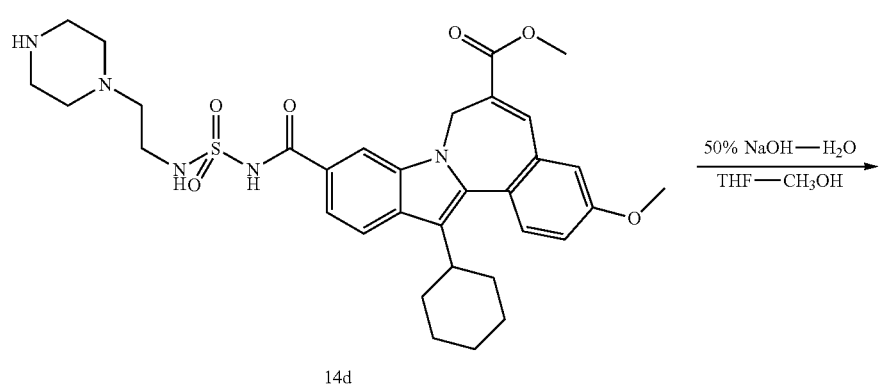

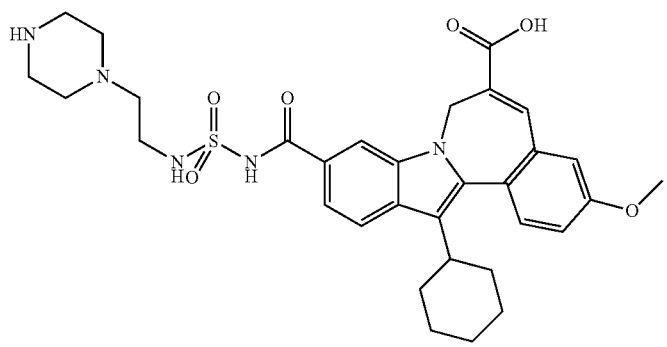

14e

Compound 14d (0.31 g, 1 eq) was dissolved in a mixture of tetrahydrofurane:methanol (1:1), followed by the addition of 50% NaOH-water solution (1 ml). The solution was stirred at RT overnight then evaporated under reduced pressure. The water layer was acidified with acetic acid to pH 4, and extracted with ethyl acetate (7×50 ml). The combined ethyl acetate layers were dried over sodium sulfate, filtered off and evaporated under reduced pressure to obtain the desired compound 14e as a yellow powder (0.30 g, 100%); LC-MS: Rt. 3.64 min., m/z 622 [M+H]$^+$.

Step 5

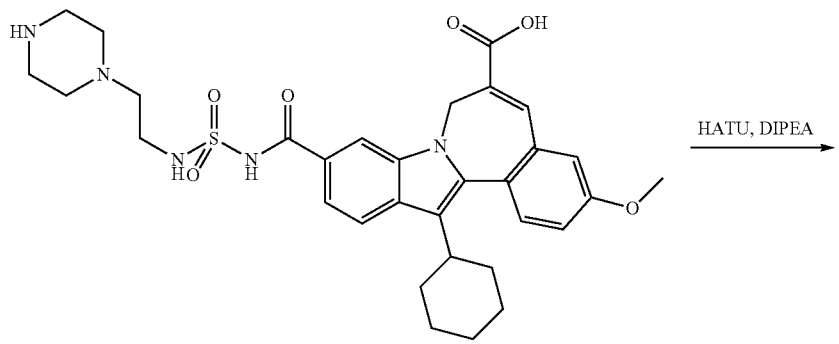

14e

HATU, DIPEA

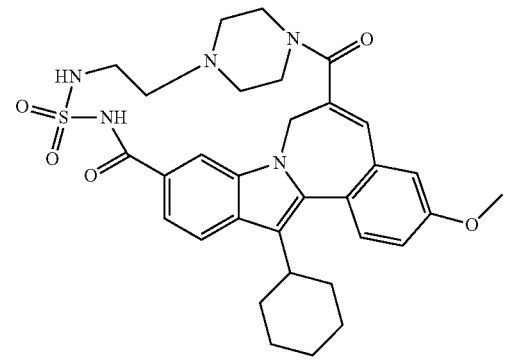

14

The synthesis of the title compound 14 is being performed following the procedure reported for the synthesis of compound 11, using intermediate 14e instead of 11d.

Example 15

Synthesis of Compound 15

15

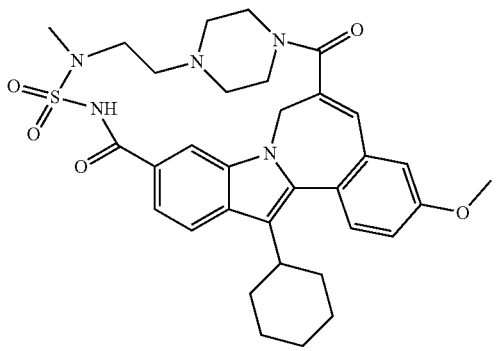

Step 1

Compound 13a (0.20 g, 1 eq) was dissolved in dry acetonitrile under $N_2$, followed by the addition of CDI (0.1 g, 1.3 eq). The solution was stirred at 60° C. for 1 h. According to TLC, the reaction went to completion. DBU (0.10 ml, 1.52 eq) and diaminosulfuric diamide 15a (0.29 g, 2 eq) were then added. The solution was stirred at 60° C. for 3 h, then was evaporated under reduced pressure. A citric acid water solution (0.1N) cooled in ice, was added to the crude product. The residual solution was extracted with ethyl acetate (3×50 ml). The combined organic layers were washed with brine (50 ml), dried over sodium sulfate, filtered off and evaporated under reduced pressure to afford 0.21 g (62%) of the title product 15b; LC-MS: Rt: 5.63 min., m/z 750 [M+H]$^+$.

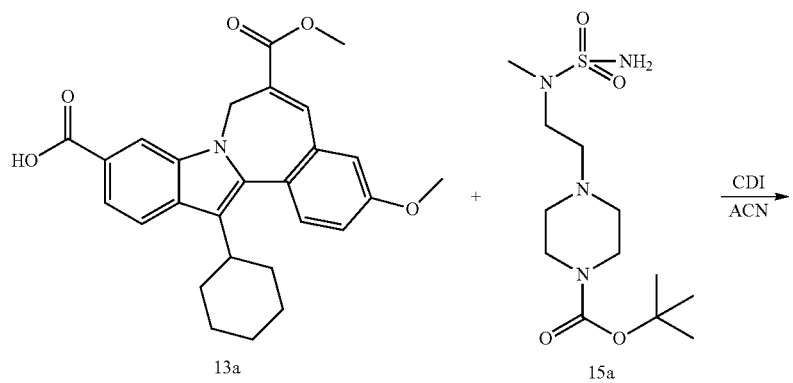

13a 15a

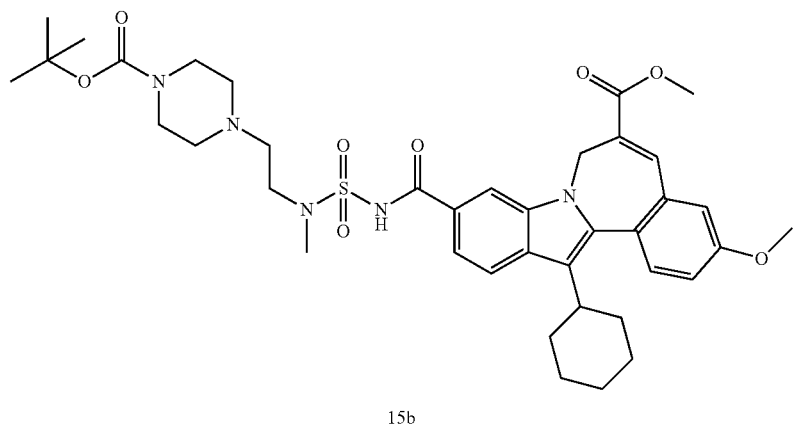

15b

Step 2

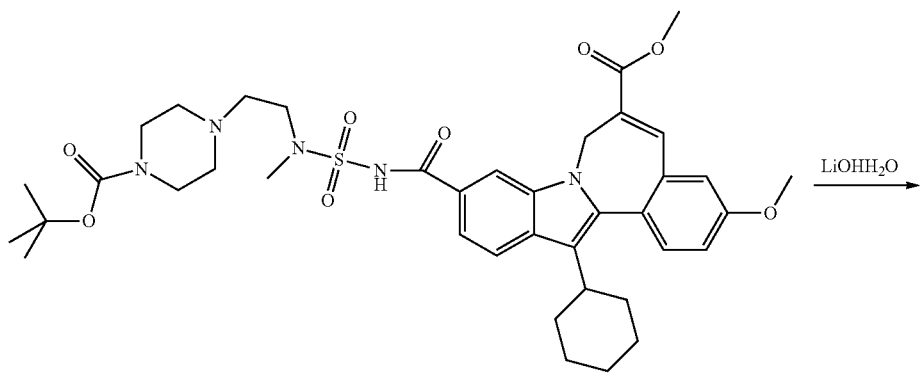

15b

↓ LiOH·H₂O

15c

The synthesis of compound 15c was performed following the procedure reported for the synthesis of compound 5-({[{2-[4-(tert-butoxycarbonyl)piperazin-1-yl]ethyl}(methyl)amino]sulfonyl}carbamoyl)-8-cyclohexyl-11-methoxy-1,12b-dihydrocyclopropa[d]indolo[2,1-a][2]benzazepine-1a(2H)-carboxylic acid (11c), using intermediate 15b instead of methyl 5-({[{2-[4-(tert-butoxycarbonyl)piperazin-1-yl]ethyl}(methyl)amino]sulfonyl}carbamoyl)-8-cyclohexyl-11-methoxy-1,12b-dihydrocyclopropa[d]indolo[2,1-a][2]benzazepine-1a(2H)-carboxylate (11b); m/z 736 [M+H]⁺.

Step 3

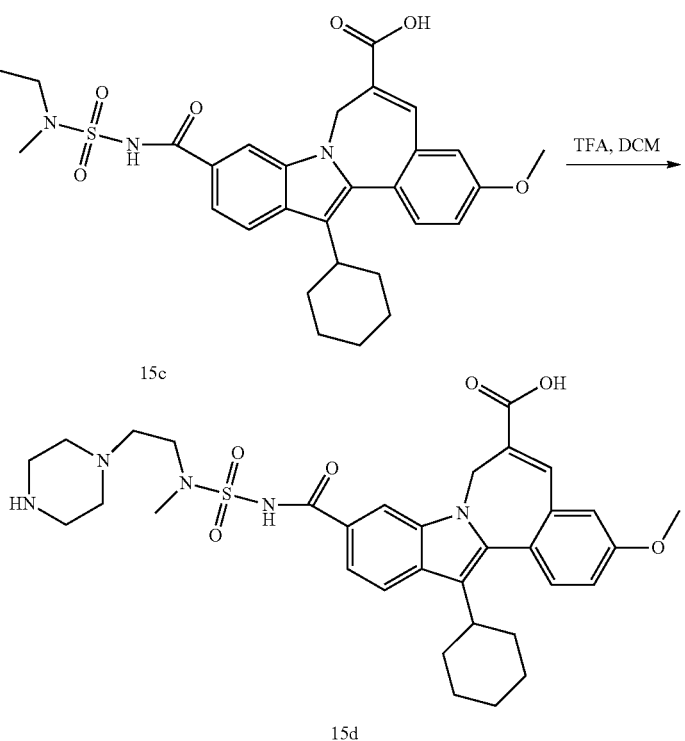

The synthesis of the title compound 15d was performed following the procedure reported for the synthesis of compound 8-cyclohexyl-11-methoxy-5-({[methyl-(2-piperazin-1-ylethyl)amino]sulfonyl}carbamoyl)-1,12b-dihydrocyclopropa[d]-indolo[2,1-a][2]benzazepine-1a(2H)-carboxylic acid (11d), using intermediate 15c instead of 5-({[{2-[4-(tert-butoxycarbonyl)piperazin-1-yl]ethyl}(methyl)amino]-sulfonyl}carbamoyl)-8-cyclohexyl-11-methoxy-1,12b-dihydrocyclopropa[d]indolo-[2,1-a][2]benzazepine-1a(2H)-carboxylic acid (11c), yielding to 448 mg (quantitative yield) of the desired product; m/z 636 [M+H]$^+$.

Step 4

The synthesis of the title compound 15 was performed following the procedure reported for the synthesis of compound 31-cyclohexyl-8-methoxy-22-methyl-21-thia-1,13, 20,22,25-pentaazaheptacyclo[23.2.2.1$^{3,13}$.1$^{12,15}$.1$^{14,18}$.0$^{3,5}$. 0$^{6,11}$]dotriaconta-6,8,10,12(31),14(30),15,17-heptaene-2, 19-dione 21,21-dioxide 11, using intermediate 15d instead of 8-cyclohexyl-11-methoxy-5-({[methyl(2-piperazin-1-ylethyl)amino]-sulfonyl}carbamoyl)-1,12b-dihydrocyclopropa[d]indolo[2,1-a][2]benzazepine-1a(2H)-carboxylic acid 11d, yielding 150 mg (34% yield) of a cream solid; m/z 618 [M+H]$^+$. 1H NMR (400 MHz, DMSO-d6) δ ppm 1.06-1.18 (m, 1H) 1.19-1.31 (m, 2H) 1.31-1.50 (m, 2H) 1.62-1.78 (m, 2H) 1.81-1.93 (m, 1H) 1.93-2.10 (m, 2H) 2.53-3.21 (m, 12H) 3.31-3.67 (m, 4H) 3.86 (s, 3H) 4.33-4.51 (m, 1H) 4.99-5.16 (m, 1H) 7.06-7.14 (m, 2H) 7.17 (d, J=8.02 Hz, 1H) 7.52 (d, J=8.22 Hz, 1H) 7.55-7.68 (m, 1H) 7.77 (m, 1H) 8.39 (m, 1H).

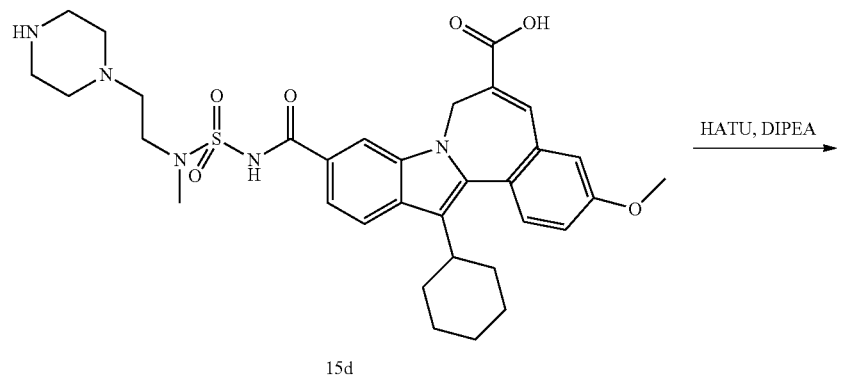

15d

HATU, DIPEA

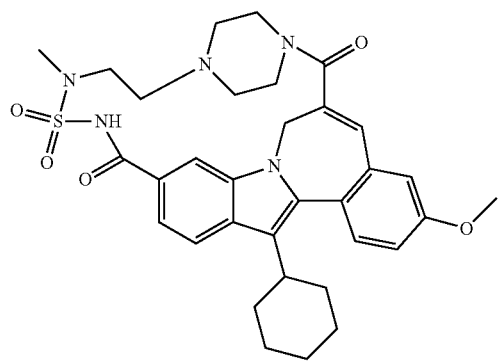

15

Example 16

Synthesis of Compound 16

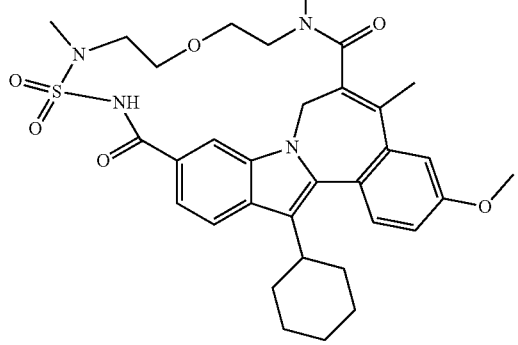

16

Step 1

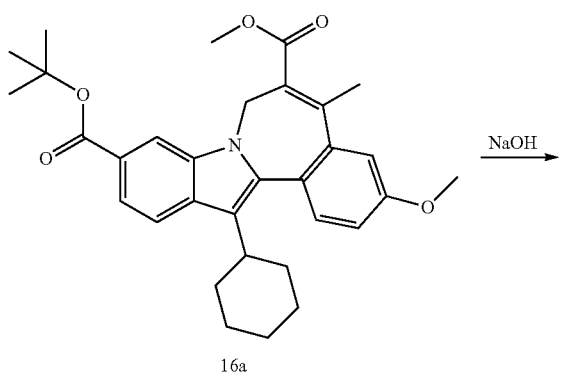

16a

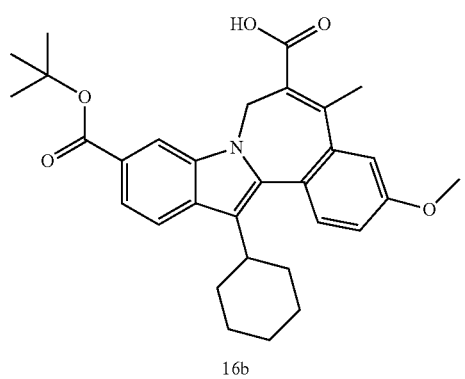

16b

A solution of 50% NaOH w/w in water (9.31 g) was added to a stirred solution of 16a (3.0 g, 5.82 mmoles) in THF (100 mL) and MeOH (150 mL). After 1 hour the reaction mixture was concentrated under reduced pressure, and subsequently diluted with ice-cold water (150 mL). The pH of the resulting solution was adjusted to 6 with diluted HCl. A precipitate was formed, which was collected by filtration, washed with water and dried under vacuum to give 3.17 g (89%) of 16b as a yellowish powder. The product was used without any further purification in the next step; m/z=502 (M+H)$^+$.

Step 2

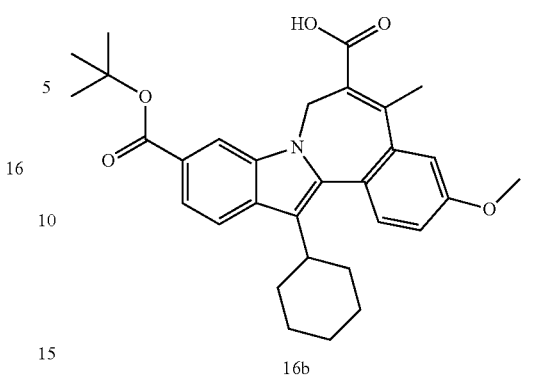

16b

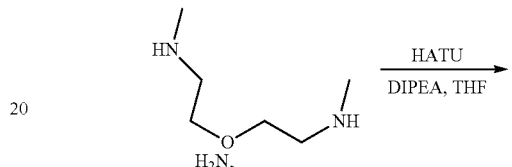

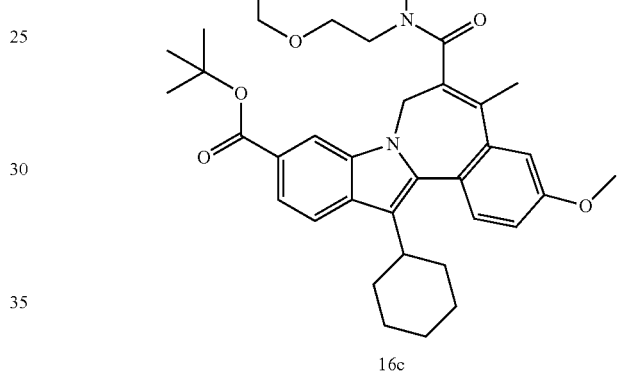

16c

HATU (3.6 g, 9.48 mmol) was added under nitrogen to a stirred solution of 16b (3.17 g, 6.32 mmol), DIPEA (3.3 mL, 3 eq) and 2,2'-oxybis(N-methylethanamine) (3.34 g, 4 eq) in 60 mL of dry THF. After 1 h, the reaction mixture was quenched with water (100 mL) and extracted with ethyl acetate (EtOAc). The organic layer was successively dried (Na$_2$SO$_4$), filtered and evaporated. The residue was triturated in water, filtered and dried to give 4.05 g (quantitative yield) of the target compound 16c, used directly in the next step: m/z=616 (M+H)$^+$

Step 3

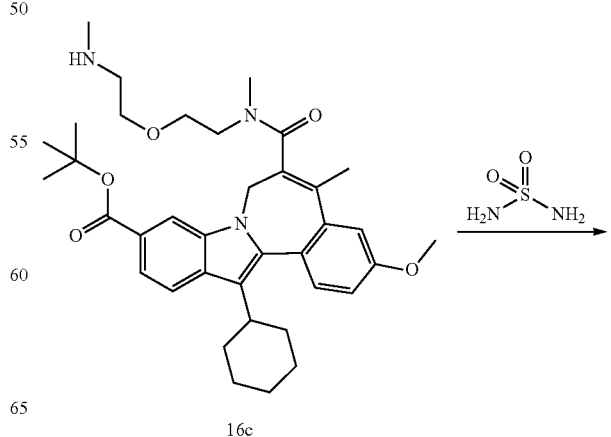

16c

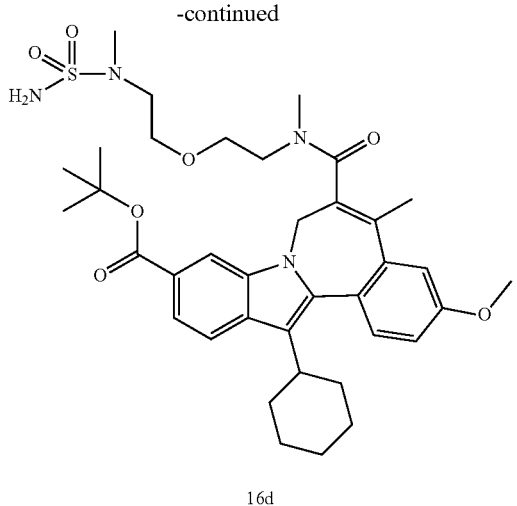

16d

A solution of 16c (3.90 g, 6.33 mmol) and sulfamide (3.04 g, 6 eq) in dioxane (100 mL) was refluxed at 100° C. overnight. The reaction mixture was cooled down to room temperature, then evaporated under vacuum. The residue was redissolved in DCM, washed with water, dried over magnesium sulfate, filtered and concentrated to give 4.48 g (quantitative yield) of the desired product 16d, used directly in the next step: m/z=695 (M+H)$^+$ Step 4

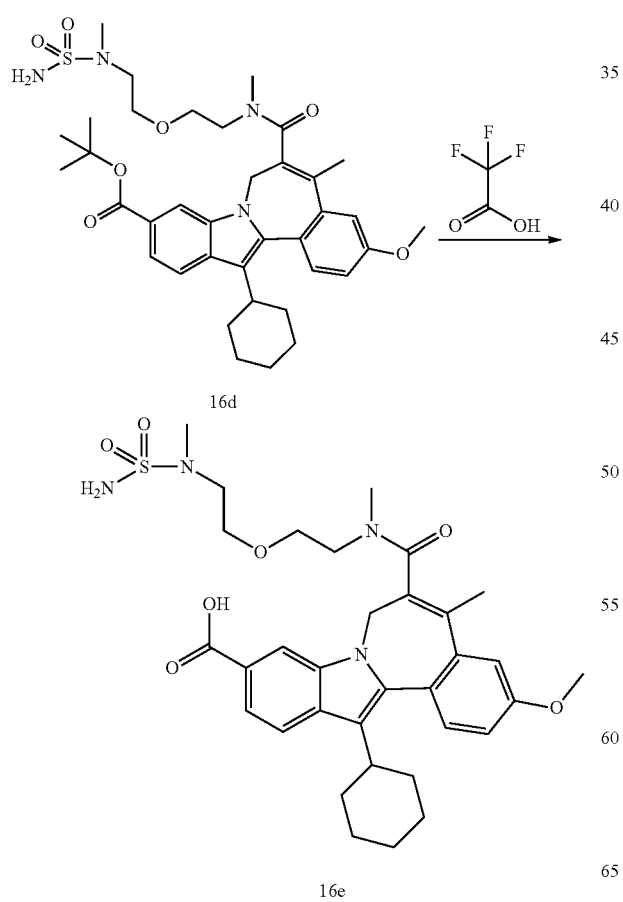

TFA (14.7 g, 129 mmol) was added to a solution of 16d (4.48 g, 6.45 mmol) in dichloromethane (50 mL). After 1 h, the reaction mixture was concentrated under vacuum. The residue was triturated in ether, filtered and washed with ether, then purified by chromatography (gradient EtOAc to EtOAc/EtOH, 9:1) to give 3.05 g (68%) of the desired product 16e: m/z=639 (M+H)$^+$ Step 5

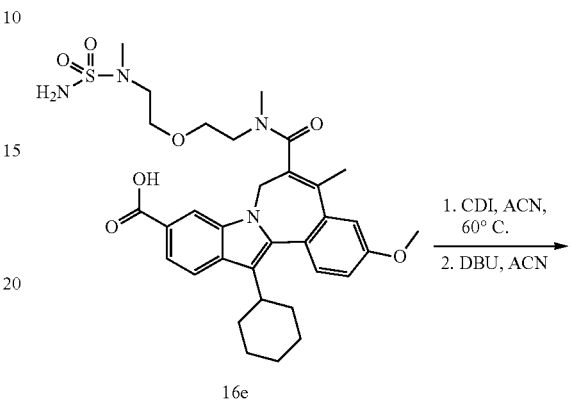

Carbonyldiimidazole (1.07 g, 6.59 mmol) was added to a stirred solution of 16e (3.05 mg, 4.39 mmol) in dry ACN (40 mL). The reaction mixture was stirred at 60° C. for 1 h: complete conversion to the acyl imidazole intermediate was observed. The resulting solution was cooled down to RT, diluted with dry ACN (300 mL) and DBU (1.34 g, 2 eq) was added. The reaction mixture was stirred overnight at room temperature, then concentrated under reduced pressure. The residue was redissolved in DCM, washed with water, dried, filtered and concentrated. Purification by column chromatography (gradient DCM to DCM/MeOH 9:1) provided 930 mg (33%) of the title product 16 as a white powder: m/z=621 (M+H)$^+$, 1H NMR (400 MHz, CHLOROFORM-d) δ ppm 1.15-1.31 (m, 1H) 1.31-1.52 (m, 3H) 1.69-1.81 (m, 2H) 1.84 (s, 3H) 1.88-2.13 (m, 7H) 2.45 (d, J=14.87 Hz, 1H) 2.76-2.92 (m, 1H) 3.14 (s, 3H) 3.40 (d, J=15.65 Hz, 1H) 3.54-3.70 (m, 3H) 3.81-3.90 (m, 1H) 3.93 (s, 3H) 4.03-4.18 (m, 1H) 4.37 (d, J=14.67 Hz, 1H) 4.64-4.80 (m, 2H) 7.06 (d, J=8.80 Hz, 1H) 7.09 (s, 1H) 7.48 (d, J=8.22 Hz, 1H) 7.57 (s, 1H) 7.70 (d, J=8.22 Hz, 1H) 7.89 (d, J=8.41 Hz, 1H) 10.01 (br. s., 1H)

Example 17

Synthesis of Compound 17

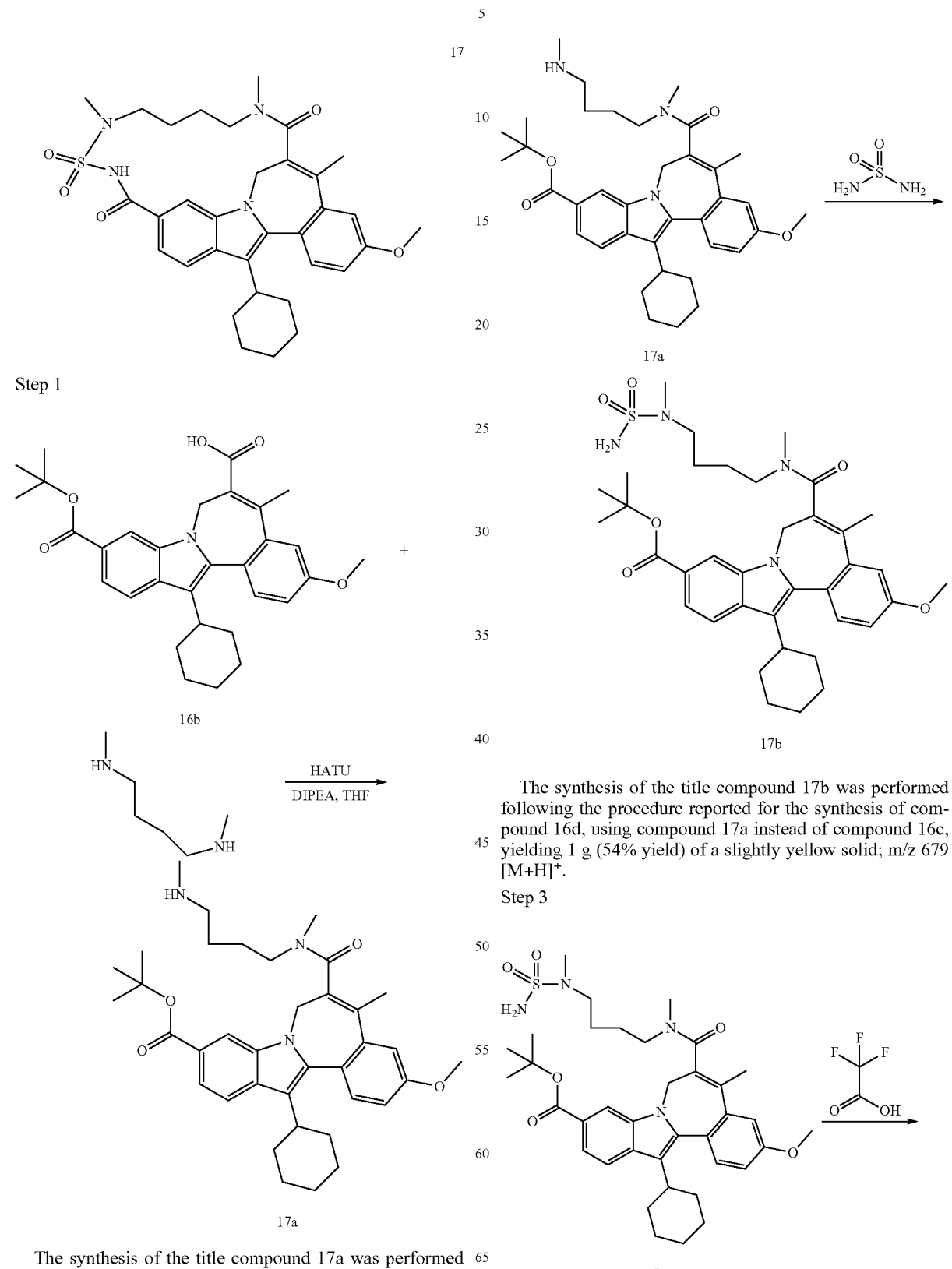

Step 1

Step 1

The synthesis of the title compound 17a was performed following the procedure reported for the synthesis of compound 16c, using $N^1,N^4$-dimethylbutane-1,4-diamine instead of 2,2'-oxybis(N-methylethanamine), yielding 1.25 g (quant. yield) of a white solid; m/z 600 $[M+H]^+$.

Step 2

The synthesis of the title compound 17b was performed following the procedure reported for the synthesis of compound 16d, using compound 17a instead of compound 16c, yielding 1 g (54% yield) of a slightly yellow solid; m/z 679 $[M+H]^+$.

Step 3

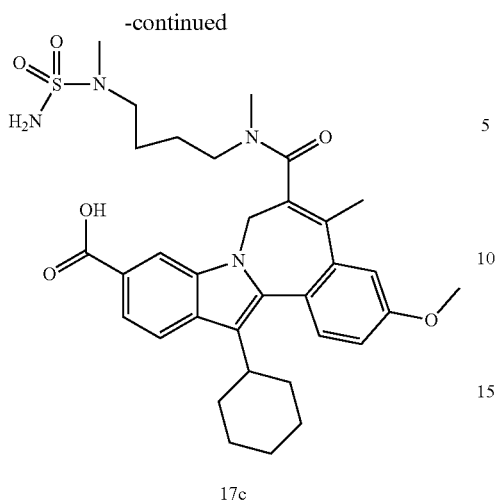

17c

The synthesis of the title compound 17c was performed following the procedure reported for the synthesis of compound 16e, using compound 17b instead of compound 16d, yielding 538 mg (62% yield) of a slightly brown solid; m/z 623 [M+H]⁺.

Step 4

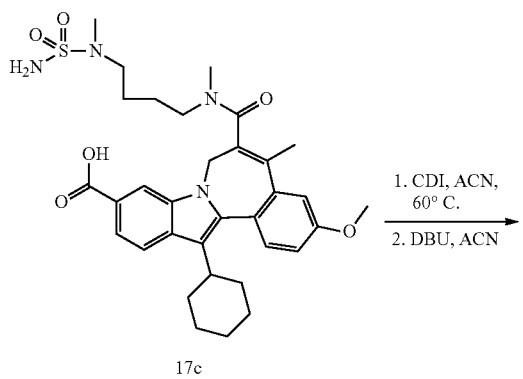

17c

1. CDI, ACN, 60° C.
2. DBU, ACN

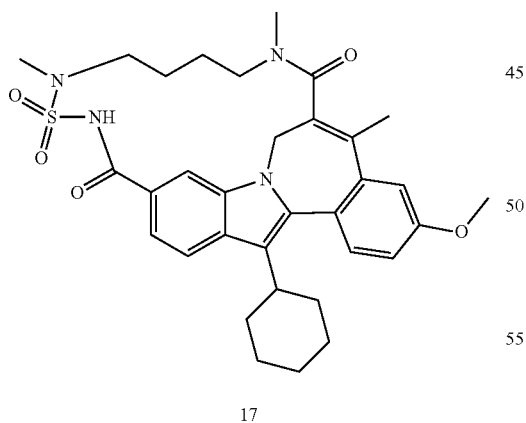

17

The synthesis of the title compound 17 was performed following the procedure reported for the synthesis of compound 16, using compound 17c instead of compound 16e, yielding 70 mg (15% yield) of a white solid; m/z 605 [M+H]⁺. 1H NMR (400 MHz, DMSO-d$_6$) δ ppm 1.08-1.20 (m, 1H) 1.22-1.79 (m, 13H) 1.88 (s, 6H) 2.40-2.47 (m, 1H) 2.69-2.83 (m, 1H) 2.92-3.14 (m, 4H) 3.56-3.72 (m, 3H) 3.89 (s, 3H) 3.92-4.04 (m, 1H) 4.26 (d, J=14.67 Hz, 1H) 4.86 (d, J=14.09 Hz, 1H) 7.18 (dd, J=8.61, 2.15 Hz, 1H) 7.22 (d, J=2.15 Hz, 1H) 7.46-7.57 (m, 2H) 7.80-7.92 (m, 1H) 8.48 (s, 1H) 11.39 (br. s., 1H)

Example 18

Synthesis of Compound 18

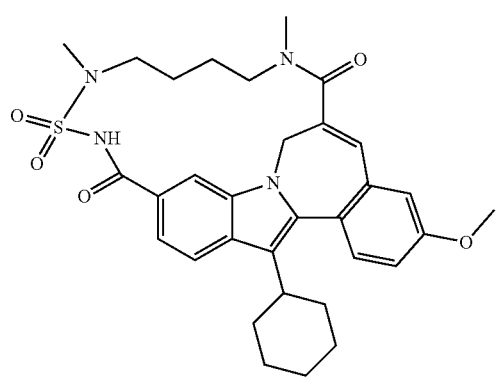

18

The synthesis of the title compound 18 was performed following the 4-step procedure reported for the synthesis of compound 17, starting from intermediate 1b instead of 16b, and yielding 0.5 g of a white solid; m/z 591 [M+H]⁺. 1H NMR (400 MHz, DMSO-d$_6$) δ ppm 1.01-1.19 (m, 1H) 1.18-1.52 (m, 5H) 1.54-1.79 (m, 4H) 1.80-2.08 (m, 4H) 2.42-2.48 (m, 1H) 2.63-2.80 (m, 1H) 2.93 (s, 3H) 2.98-3.14 (m, 1H) 3.43-3.75 (m, 5H) 3.85 (s, 3H) 4.43 (d, J=14.87 Hz, 1H) 5.04 (d, J=14.48 Hz, 1H) 6.84 (br. s., 1H) 7.09 (s, 1H) 7.18 (d, J=8.22 Hz, 1H) 7.45 (d, J=8.22 Hz, 1H) 7.55 (d, J=8.41 Hz, 1H) 7.87 (d, J=8.41 Hz, 1H) 8.35 (br. s., 1H) 11.33 (br. s., 1H)

Example 19

Synthesis of Compound 19

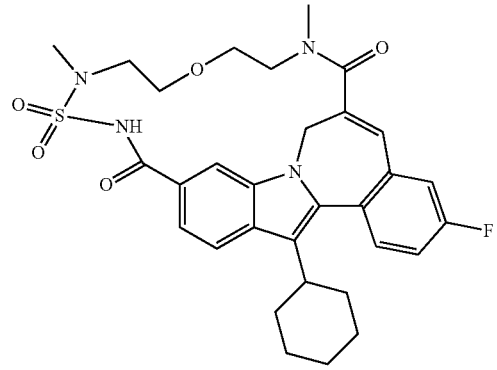

19

The synthesis of the title compound 19 was performed following the 5-step procedure reported for the synthesis of compound 1, starting from intermediate 10-tert-butyl 6-methyl 13-cyclohexyl-3-fluoro-7H-indolo[2,1-a][2]benzazepine-6,10-dicarboxylate 19a instead of 10-tert-butyl 6-methyl 13-cyclohexyl-3-methoxy-7H-indolo[2,1-a][2] benzazepine-6,10-dicarboxylate 1a, and yielded 180 mg of a white solid; m/z 595 [M+H]⁺. 1H NMR (400 MHz, CHLOROFORM-d) δ ppm 1.11-1.29 (m, 1H) 1.29-1.53 (m, 3H)

1.67-1.83 (m, 3H) 1.87-2.11 (m, 4H) 2.30 (br. s., 3H) 2.69-2.82 (m, 1H) 2.81-2.98 (m, 1H) 3.11 (s, 3H) 3.46-3.58 (m, 1H) 3.59-3.79 (m, 3H) 3.90-4.08 (m, 1H) 4.24-4.38 (m, 1H) 4.43 (dd, J=14.73, 1.27 Hz, 1H) 4.97 (d, J=14.63 Hz, 1H) 6.73 (s, 1H) 7.11 (dd, J=9.27, 2.63 Hz, 1H) 7.17-7.30 (m, 1H) 7.57 (dd, J=8.68, 5.76 Hz, 1H) 7.69 (s, 1H) 7.67 (dd, J=8.78, 1.56 Hz, 1H) 7.90 (d, J=8.78 Hz, 1H) 9.84 (br. s., 1H)

Example 20

Synthesis of Compound 20

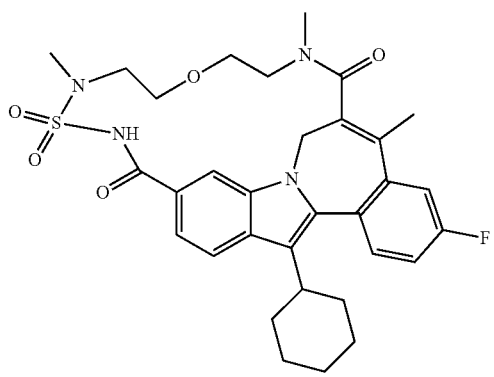

The synthesis of the title compound 20 was performed following the 5-step procedure reported for the synthesis of compound 1, starting from intermediate 10-tert-butyl 6-methyl 13-cyclohexyl-3-fluoro-5-methyl-7H-indolo[2,1-a][2]benzazepine-6,10-dicarboxylate 20a instead of 10-tert-butyl 6-methyl 13-cyclohexyl-3-methoxy-7H-indolo[2,1-a][2]benzazepine-6,10-dicarboxylate 1a, and yielded 130 mg of a white solid; m/z 609 [M+H]$^+$. 1H NMR (400 MHz, CHLOROFORM-d) δ ppm 1.14-1.31 (m, 1H) 1.32-1.46 (m, 3H) 1.64-1.81 (m, 3H) 1.84 (s, 3H) 1.87-1.99 (m, 3H) 2.01 (s, 3H) 2.47 (d, J=14.63 Hz, 1H) 2.73-2.87 (m, 1H) 3.14 (s, 3H) 3.43 (d, J=15.02 Hz, 1H) 3.56-3.64 (m, 2H) 3.65 (d, J=3.12 Hz, 1H) 3.74-3.88 (m, 1H) 4.00-4.12 (m, 1H) 4.35 (d, J=14.83 Hz, 1H) 4.64-4.75 (m, 1H) 4.81 (d, J=14.63 Hz, 1H) 7.16-7.32 (m, 2H) 7.53 (dd, J=8.39, 6.05 Hz, 1H) 7.64 (s, 1H) 7.70 (d, J=8.39 Hz, 1H) 7.91 (d, J=8.39 Hz, 1H) 10.09 (br. s., 1H)

Example 21

Synthesis of Compound 21

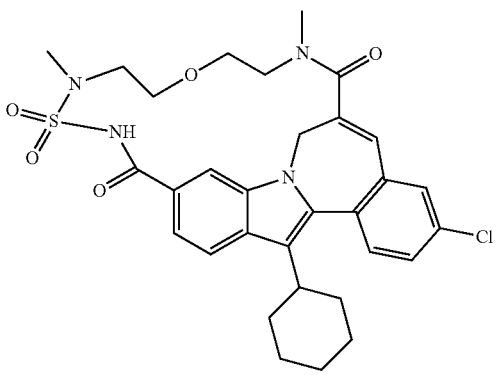

The synthesis of the title compound 21 was performed following the 5-step procedure reported for the synthesis of compound 1, starting from intermediate 10-tert-butyl 6-methyl 3-chloro-13-cyclohexyl-7H-indolo[2,1-a][2]benzazepine-6,10-dicarboxylate 21a instead of 10-tert-butyl 6-methyl 13-cyclohexyl-3-methoxy-7H-indolo[2,1-a][2]benzazepine-6,10-dicarboxylate 1a, and yielding 270 mg of a white solid; m/z 611 [M+H]$^+$. 1H NMR (400 MHz, DMSO-d6) δ ppm 1.08-1.22 (m, 1H) 1.31-1.52 (m, 3H) 1.63-1.78 (m, 2H) 1.81-2.09 (m, 4H) 2.50 (s, 3H) 2.69-2.80 (m, 1H) 3.00 (s, 3H) 3.08-3.19 (m, 1H) 3.19-3.28 (m, 1H) 3.46-3.88 (m, 6H) 4.52 (d, J=14.87 Hz, 1H) 5.12 (d, J=13.11 Hz, 1H) 6.97 (s, 1H) 7.49 (d, J=7.83 Hz, 1H) 7.58-7.70 (m, 3H) 7.94 (d, J=8.61 Hz, 1H) 8.36 (s, 1H) 11.39 (br. s., 1H)

Example 22

Synthesis of Compound 22

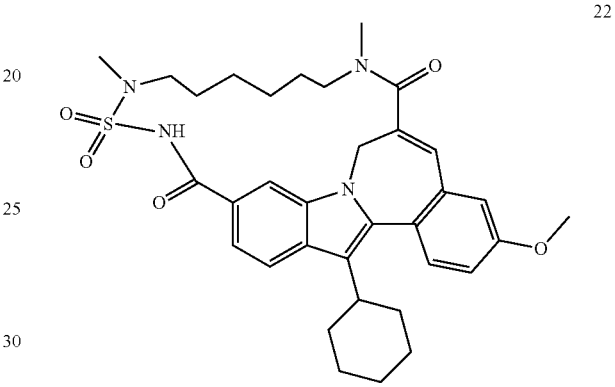

The synthesis of the title compound 22 was performed following the 5-step procedure reported for the synthesis of compound 1, using N$^1$,N$^6$-dimethylhexane-1,6-diamine instead of 2,2'-oxybis(N-methylethanamine) in step 2, and yielded 50 mg of a white solid; m/z 619 [M+H]$^+$. 1H NMR (400 MHz, CHLOROFORM-d) δ ppm 1.00-1.64 (m, 11H) 1.66-1.87 (m, 3H) 1.87-2.15 (m, 4H) 2.47 (s, 3H) 2.66-2.91 (m, 2H) 3.23 (s, 3H) 3.25-3.33 (m, 1H) 3.33-3.45 (m, 1H) 3.90 (s, 3H) 4.09-4.25 (m, 1H) 4.39 (d, J=14.28 Hz, 1H) 5.14 (d, J=14.48 Hz, 1H) 6.81 (s, 1H) 6.90 (s, 1H) 7.06 (dd, J=8.61, 2.15 Hz, 1H) 7.45 (d, J=8.22 Hz, 1H) 7.50 (d, J=8.61 Hz, 1H) 7.81-7.96 (m, 2H) 8.94 (br. s., 1H)

Example 23

Synthesis of Compound 23

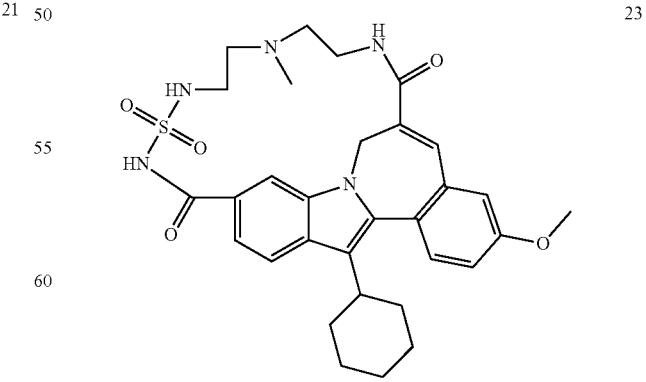

The synthesis of the title compound 23 was performed following the 5-step procedure reported for the synthesis of compound 1, using N$^1$,N$^2$-dimethyl-N$^1$-(2-(methylamino)

ethyl)ethane-1,2-diamine instead of 2,2'-oxybis(N-methyl-ethanamine) in step 2, and yielded 20 mg of a white solid; m/z 592 [M+H]+. 1H NMR (400 MHz, DMSO-d6) δ ppm 1.04 (d, J=5.87 Hz, 1H) 1.06-1.22 (m, 1H) 1.27-1.51 (m, 3H) 1.60-1.78 (m, 2H) 1.80-1.92 (m, 1H) 1.92-2.07 (m, 3H) 2.12 (s, 3H) 2.27-2.41 (m, 1H) 2.69-2.83 (m, 2H) 2.83-2.97 (m, 2H) 3.01-3.15 (m, 2H) 3.17-3.28 (m, 2H) 3.86 (s, 3H) 4.21 (d, J=15.65 Hz, 1H) 5.54 (d, J=15.65 Hz, 1H) 7.11-7.25 (m, 2H) 7.35 (s, 1H) 7.47 (d, J=8.22 Hz, 1H) 7.53 (d, J=9.00 Hz, 1H) 7.70-7.83 (m, 1H) 8.32 (br. s., 1H) 8.37-8.50 (m, 1H)

Example 24

Synthesis of Compound 24

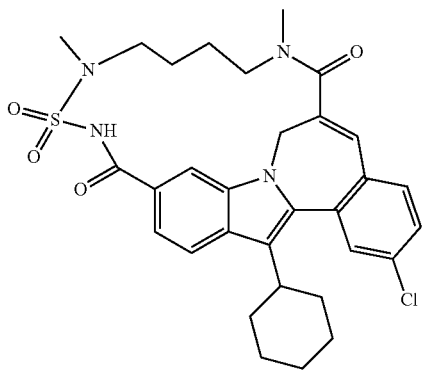

The synthesis of the title compound 24 was performed following the 4-step procedure reported for the synthesis of compound 17, starting from intermediate 10-(tert-butoxycarbonyl)-2-chloro-13-cyclohexyl-7H-indolo[2,1-a][2]benzazepine-6-carboxylic acid 24b instead of 10-(tert-butoxycarbonyl)-13-cyclohexyl-3-methoxy-5-methyl-7H-indolo[2,1-a][2]benzazepine-6-carboxylic acid 16b, and yielded 0.25 g of a white solid; m/z 595 [M+H]+. 1H NMR (400 MHz, Chloroform-d) δ ppm 1.25-1.5 (m, 4H) 1.5-1.8 (m, 4H) 1.9-2.1 (m, 4H) 1.8 (s., 3H) 2.8-2.13 (m, 3H) 2.5-2.6 (m, 2H) 3.2 (s, 3H) 3.6 (br. s., 1H) 4.1 (br. s., 1H) 4.45 (d, J=15 Hz, 1H) 5 (d, J=15 Hz, 1H) 6.6 (s, 1H) 7.25 (d, J=8.4 Hz, 1H) 7.4 (dd, J=8.5, J=2.5 Hz, 1H) 7.5-7.6 (m, 2H) 7.69 (s, 1H) 7.9 (d, J=8.4 Hz, 1H) 9.1 (br. s., 1H)

Example 25

Synthesis of Compound 25

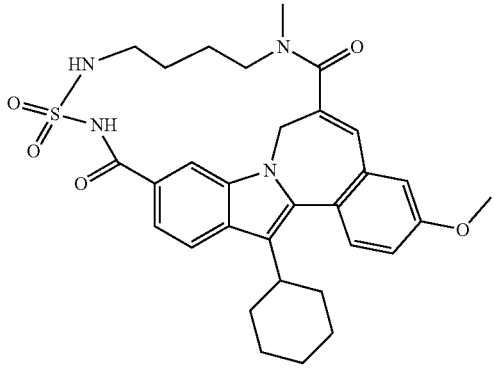

The synthesis of the title compound 25 was performed following the 5-step procedure reported for the synthesis of compound 10, starting from intermediate 10-tert-butyl 6-methyl 13-cyclohexyl-3-methoxy-7H-indolo[2,1-a][2]benzazepine-6,10-dicarboxylate 1a instead of 5-tert-butyl 1a-methyl 8-cyclohexyl-11-methoxy-1,12b-dihydrocyclopropa[d]indolo[2,1-a][2]benzazepine-1a,5(2H)-dicarboxylate 8a, and yielded 45 mg of a white solid; m/z 577 [M+H]+. 1H NMR (400 MHz, DMSO-d6) δ ppm 1.03-1.19 (m, 1H) 1.25-1.49 (m, 4H) 1.49-2.29 (m, 10H) 2.67-2.82 (m, 1H) 2.84-3.04 (m, 1H) 3.05-3.24 (m, 1H) 3.48-3.72 (m, 5H) 3.86 (s, 3H) 4.42 (d, J=14.67 Hz, 1H) 5.00 (d, J=14.28 Hz, 1H) 6.84 (br. s., 1H) 7.09 (s, 1H) 7.18 (d, J=8.41 Hz, 1H) 7.47 (d, J=7.83 Hz, 1H) 7.55 (d, J=8.41 Hz, 1H) 7.75-7.92 (m, 1H) 8.19-8.41 (m, 1H) 11.27 (br. s., 1H)

Example 26

Synthesis of Compound 26

Step 1

-continued

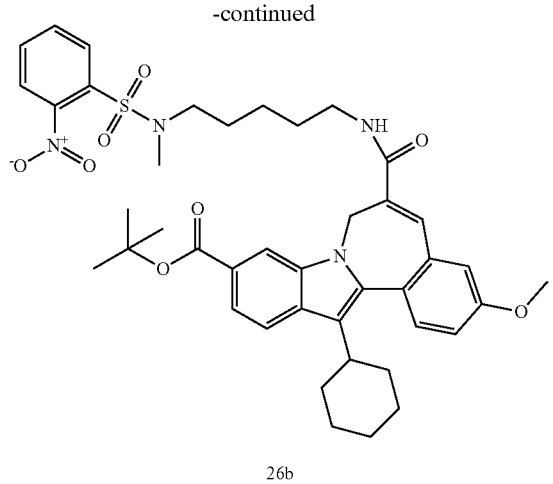

26b

A solution of 606 mg (1.24 mmole) of 1b, 410 mg (1.1 eq) of 26a, 710 mg (1.5 eq) of HATU and 0.65 mL (3 eq) of diisopropylethyl amine in dry DMF (10 mL) was stirred at RT during 1 h. The RM was then diluted with water and the resulting yellow precipitate was filtered off, washed with water, and purified by flash chromatography (eluant DCM to DCM/MeOH 0.5%) to give a quantitative yield of the desired product 26b as a yellow powder; m/z 771 [M+H]⁺.

Step 2

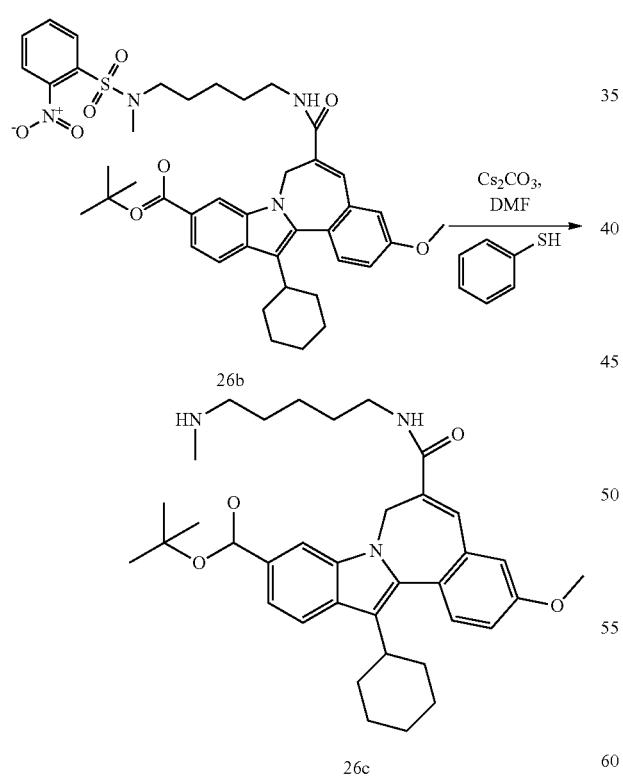

26b

26c

To a solution of 1.1 g (1.44 mmole) of 26b and thiophenol (0.32 g, 2 eq) in dry DMF (15 mL) was added cesium carbonate (0.94 g, 2 eq) at RT. After 2 h, the RM was diluted with water and extracted with EtOAc. The organic layer was washed with brine, dried over magnesium sulfate, filtered and concentrated. The resulting residue was further purified by flash chromatography (eluant: DCM to DCM/NH3 in MeOH 85/15) to give 0.77 g (90% yield) of 26c as a yellow powder; m/z 586 [M+H]⁺.

Step 3

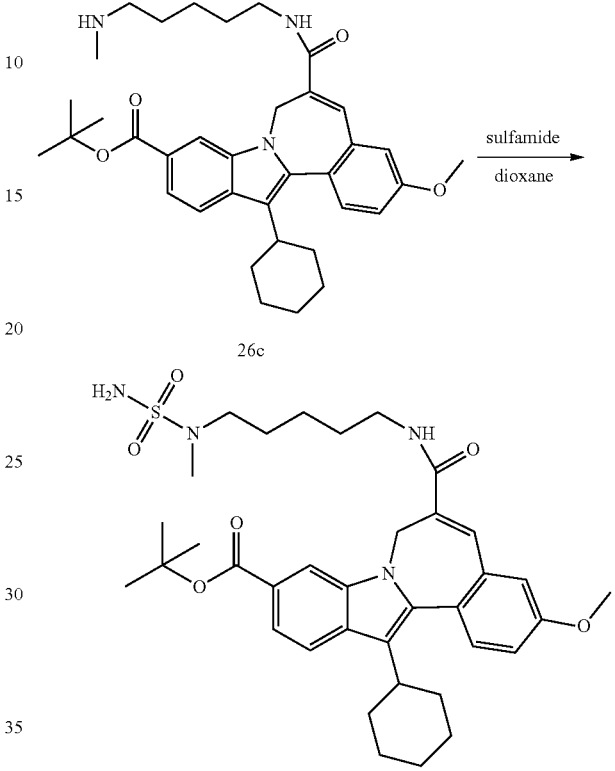

26c

26d

A mixture of 26c (0.72 g, 1.23 mmole) and sulfamide (0.35 g, 3 eq) in dioxane (15 mL) was refluxed until completion (~7 h). The RM was then concentrated under vacuo and the residue was triturated in DCM. The resulting precipitate of sulfamide in excess was filtered off. The organic layer was concentrated and purified by flash chromatography (eluant: DCM to DCM/MeOH 1%) to give 776 mg (95% yield) of the desired product 26d as a light yellow powder; m/z 665 [M+H]⁺.

Step 4

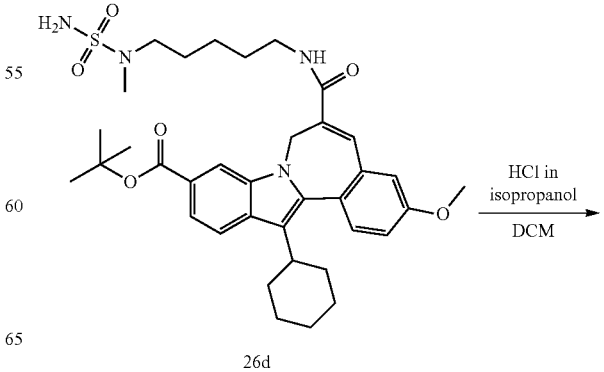

26d

-continued

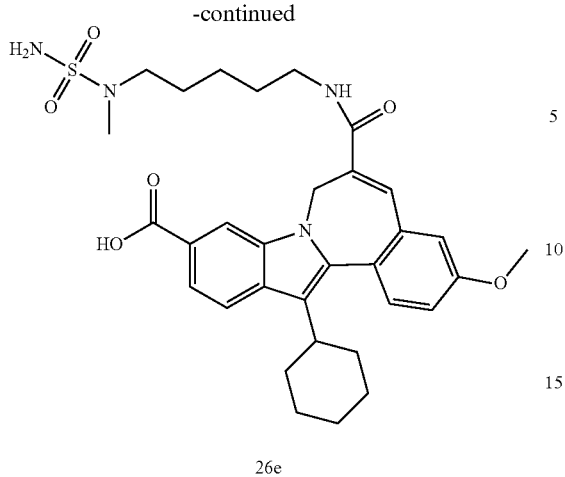

26e

A solution of 26d (0.72 g, 1.086 mmole) in 10 mL of HCl in isopropanol and 5 mL of DCM was stirred at RT for 3 h. The RM was then concentrated under vacuo, and the residue was triturated in diethyl ether. The resulting precipitate was filtered off, washed with ether and dried in a vacuum oven overnight to give 661 mg (97% yield) of the desired product 26e as a light yellow powder; m/z 609 [M+H]$^+$.

Step 5

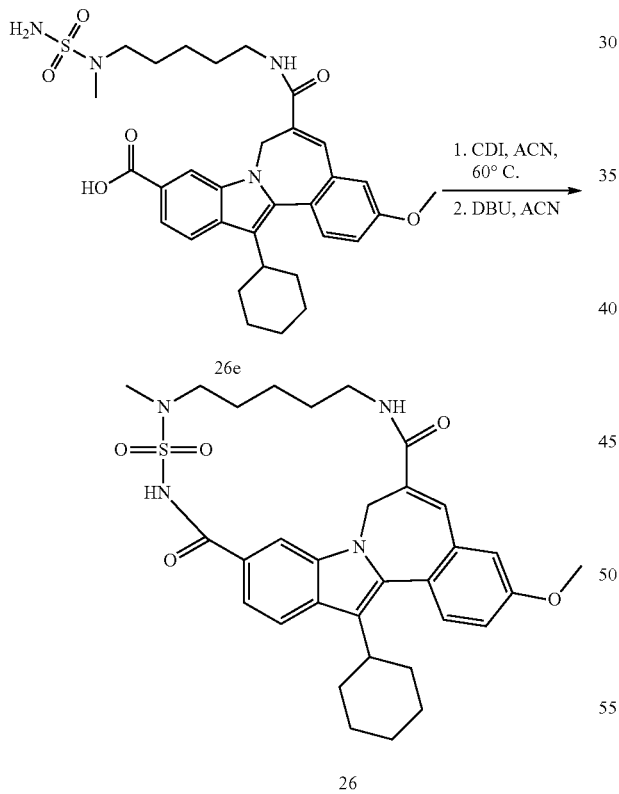

26

A solution of 26e (0.6 g, 0.971 mmole) and CDI (0.205 g, 1.3 eq) in acetonitrile (10 mL) was heated at 60° C. until complete formation of the acyl imidazole intermediate (~1 h). The RM was then diluted with 20 mL of acetonitrile and DBU (0.296 g, 2 eq) was added at RT. The RM was stirred at RT until completion, then was concentrated. The residue was redissolved in water and acetic acid was then added until pH 2. The resulting precipitate was filtered off, washed with water, and purified by flash chromatography (eluant: DCM to DCM/MeOH 5%) to give 0.315 g (55% yield) of the desired product 26 as a slightly yellow powder; m/z 591 [M+H]$^+$. 1H NMR (400 MHz, DMSO-d$_6$) δ ppm 1.07-2.09 (m, 16H) 2.71-2.84 (m, 1H) 2.94 (s, 3H) 3.01-3.18 (m, 2H) 3.19-3.31 (m, 2H) 3.87 (s, 3H) 4.25 (d, J=15.06 Hz, 1H) 5.52 (d, J=15.26 Hz, 1H) 7.16-7.26 (m, 2H) 7.32-7.44 (m, 2H) 7.54 (d, J=9.19 Hz, 1H) 7.86 (d, J=8.61 Hz, 1H) 8.26 (s, 1H) 8.40-8.51 (m, 1H) 11.61 (br. s., 1H)

Example 27

Synthesis of Compound 27

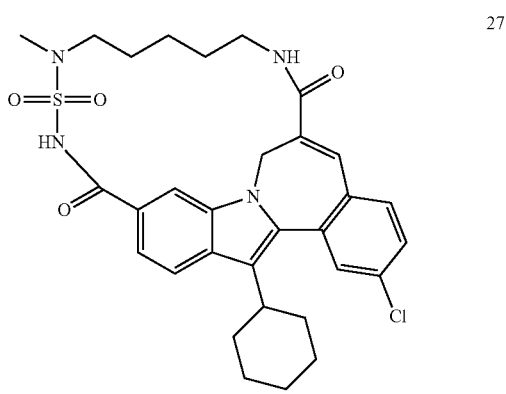 [SMILES: CN1CCCCCNC(=O)C2=Cc3ccc(Cl)cc3-c3c(C4CCCCC4)c4ccc(cc4n3C2)C(=O)NS1(=O)=O]

The synthesis of the title compound 27 was performed following the 5-step procedure reported for the synthesis of compound 26, starting from intermediate 10-(tert-butoxycarbonyl)-2-chloro-13-cyclohexyl-7H-indolo[2,1-a][2]benzazepine-6-carboxylic acid 24b instead of 10-(tert-butoxycarbonyl)-13-cyclohexyl-3-methoxy-7H-indolo[2,1-a][2]benzazepine-6-carboxylic acid 1b, and yielded 85 mg of a yellow solid; m/z 596 [M+H]$^+$. 1H NMR (400 MHz, Chloroform-d) δ ppm 1.21-1.5 (m, 10H) 1.75-1.8 (m, 2H) 1.9-2.1 (m, 4H) 2.75 (br. s., 1H) 3.01 (s, 3H) 3.1-3.2 (m, 2H) 3.5-3.6 (m, 2H) 4.23 (dd, J=15.28, 1.27 Hz, 1H) 5.6 (d, J=15.28 Hz, 1H) 7.4 (s, 1H) 7.5-7.6 (m, 3H) 7.65 (d, J=8.5 Hz, 1H) 7.8 (s, 1H) 7.9 (d, J=8.5 Hz, 1H) 7.69 (s, 1H) 8.64 (br. s., 1H)

Example 28

Synthesis of Compound 28

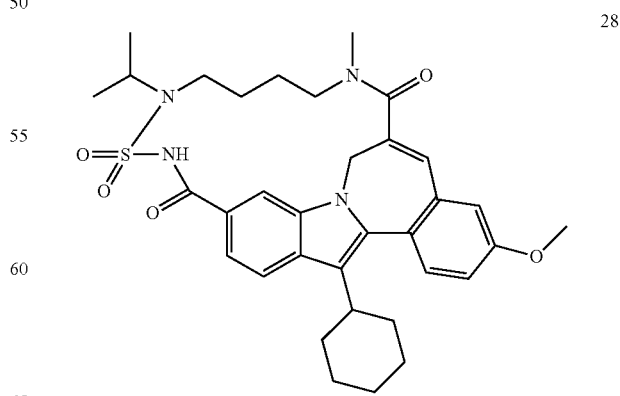

The synthesis of the title compound 28 was performed following the 5-step procedure reported for the synthesis of compound 10, starting from intermediate 10-tert-butyl 6-methyl 13-cyclohexyl-3-methoxy-7H-indolo[2,1-a][2]benzazepine-6,10-dicarboxylate 1a instead of 5-tert-butyl 1a-methyl 8-cyclohexyl-11-methoxy-1,12b-dihydrocyclopropa[d]indolo[2,1-a][2]benzazepine-1a,5(2H)-dicarboxylate 8a, and using N-[4-(methylamino)butyl]-N-(1-methylethyl)sulfamide 28a instead of N-(4-aminobutyl)-N-methylsulfamide 10b, and yielded 50 mg of the desired product 28; m/z 619 [M+H]$^+$. 1H NMR (400 MHz, CHLOROFORM-d) δ ppm 1.05-1.15 (m, 1H) 1.18 (d, J=6.65 Hz, 3H) 1.25 (d, J=6.46 Hz, 3H) 1.28-1.51 (m, 4H) 1.53-2.31 (m, 13H) 2.67-2.85 (m, 1H) 3.01-3.19 (m, 1H) 3.51-3.73 (m, 1H) 3.89 (s, 3H) 3.95-4.15 (m, 1H) 4.42 (d, J=14.48 Hz, 1H) 4.52-4.72 (m, 1H) 5.01 (d, J=14.48 Hz, 1H) 6.68 (s, 1H) 6.87 (s, 1H) 7.05 (d, J=8.41 Hz, 1H) 7.52 (d, J=8.41 Hz, 1H) 7.63 (d, J=8.22 Hz, 1H) 7.77-7.99 (m, 2H) 9.42 (br. s., 1H)

Example 29

Synthesis of Compound 10B

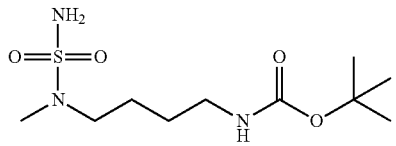

10b

A mixture of tert-butyl 4-(methylamino)butylcarbamate (4 g, 19.77 mmoles) and sulfuric diamide (7.6 g, 4 eq) in dioxane (10 mL) was heated at 100° C. in a microwave oven during 30 minutes. The RM was then concentrated in vacuo, and DCM was added. The resulting white precipitate of sulfuric diamide in excess was filtered off, and the filtrate was successively washed with diluted HCl, then brine, dried over magnesium sulfate, filtered and concentrated. Trituration in diisopropyl ether afforded 3.55 g (64% yield) of tert-butyl 4-(methyl(sulfamoyl)amino)butylcarbamate 10b as a white solid; m/z 282 [M+H]$^+$.

Example 30

Synthesis of Compound 26a

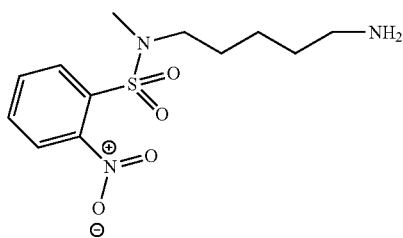

26a

Step 1

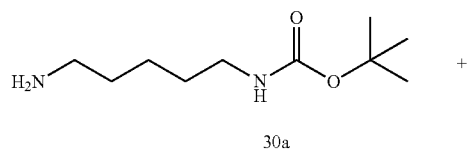

30a

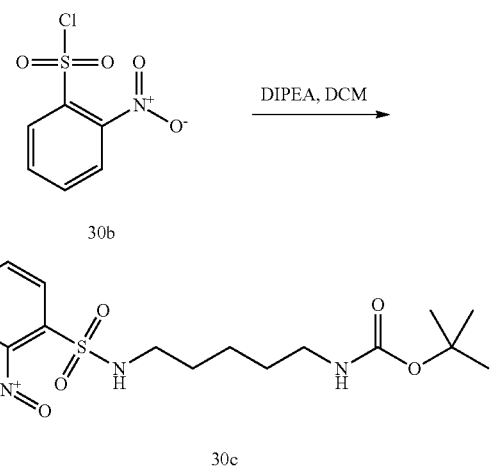

To a solution of tert-butyl 5-aminopentylcarbamate 30a (20 g, 99 mmoles) and 2-nitrobenzene-1-sulfonyl chloride 30b (23 g, 1.05 eq) in DCM (200 mL) was added dropwise diisopropyl ethyl amine (19.2 g, 1.5 eq) at 0° C. After stirring at RT overnight, the RM was successively washed with an aqueous solution of citric acid, then brine, dried over magnesium sulfate, filtered and concentrated. Trituration in diisopropyl ether afforded 32.61 g (85% yield) of tert-butyl 5-(2-nitrophenylsulfonamido)pentylcarbamate 30c as a white solid; m/z 388 [M+H]$^+$.

Step 2

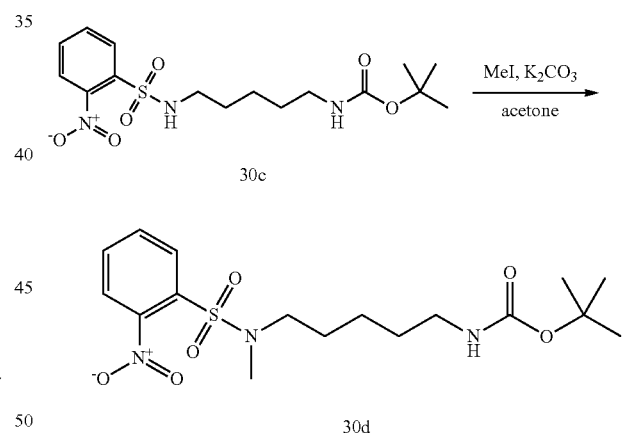

To a mixture of tert-butyl 5-(2-nitrophenylsulfonamido)pentylcarbamate 30c (32.61 g, 84 mmoles) and potassium carbonate (13.96 g, 1.2 eq) in acetone (300 mL) was added methyl iodide (5.5 mL, 1.05 eq). After stirring at RT overnight, more methyl iodide (1 eq) and potassium carbonate (0.6 eq) was added and the RM was stirred at RT until completion. The RM was then diluted with water and extracted with DCM. The organic layer was separated, washed with brine, dried over magnesium sulfate, filtered and concentrated. Trituration in diisopropyl ether afforded 31.59 g (93% yield) of tert-butyl 5-(N-methyl-2-nitrophenylsulfonamido)pentylcarbamate 30d as a white solid; m/z 402 [M+H]$^+$.

Step 3

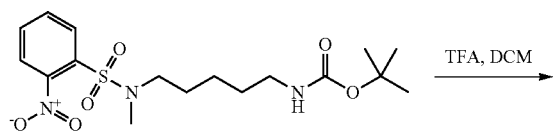

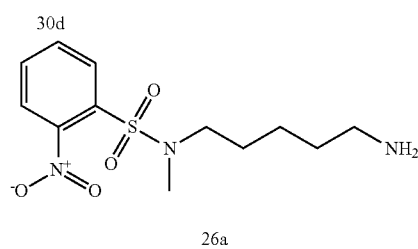

A solution of tert-butyl 5-(N-methyl-2-nitrophenylsulfonamido)pentylcarbamate 30d (31.5 g, 79 mmoles) and trifluoro acetic acid (29.2 mL, 5 eq) in DCM (300 mL) was stirred at RT until completion (~16 h). The RM was then concentrated under vacuo, redissolved in DCM, washed with a saturated sodium bicarbonate aqueous solution (2 times), then brine, dried over magnesium sulfate, filtered and concentrated. Trituration in diisopropyl ether afforded 23.7 g (quantitative yield) of N-(5-aminopentyl)-N-methyl-2-nitrobenzenesulfonamide 26a as a slightly yellow solid; m/z 302 [M+H]$^+$.

Example 31

Synthesis of Compound 28a

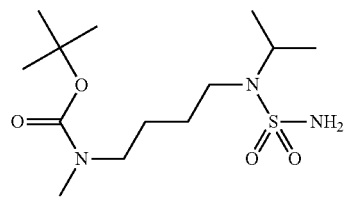

Step 1

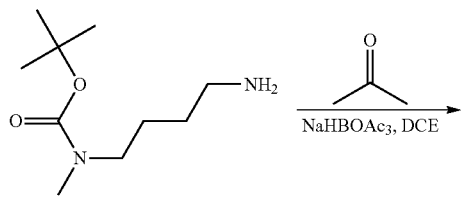

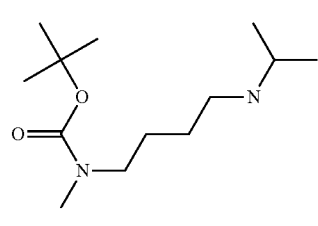

A mixture of tert-butyl 4-aminobutyl(methyl)carbamate 31a (287 mg, 1.42 mmole), acetone (75 mg, 1.29 mmole) and sodium triacetoxyborohydride (383 mg, 1.8 mmole) was stirred under nitrogen at RT until completion. The RM was then concentrated, diluted with a saturated sodium bicarbonate aqueous solution, and extracted with ether (2 times). The organic layers were combined, dried over magnesium sulfate, filtered and concentrated to give 200 mg (63% yield) of the desired product tert-butyl 4-(isopropylamino)butyl(methyl)carbamate 31b, used without further purification in the next step; m/z 245 [M+H]$^+$.

Step 2

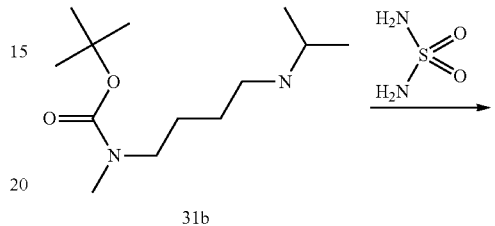

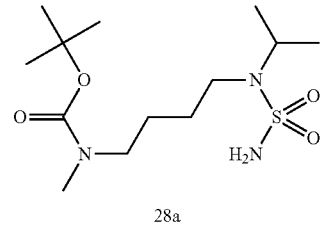

A mixture of tert-butyl 4-(isopropylamino)butyl(methyl)carbamate 31b (3.38 g, 13.8 mmoles) and sulfuric diamide (3.99 g, 3 eq) in dioxane (10 mL) was heated at 110° C. in a microwave oven during 60 minutes. The RM was then concentrated in vacuo, and DCM was added. The resulting white precipitate of sulfuric diamide in excess was filtered off, and the filtrate was concentrated in vacuo. The residue was purified by flash chromatography (eluant: DCM to DCM/MeOH 20%) to give 1.7 g (38% yield) of the desired product tert-butyl 4-(isopropyl(sulfamoyl)amino)butyl(methyl)carbamate 28a; m/z 324 [M+H]$^+$.

Example 32

Synthesis of Compound 19a

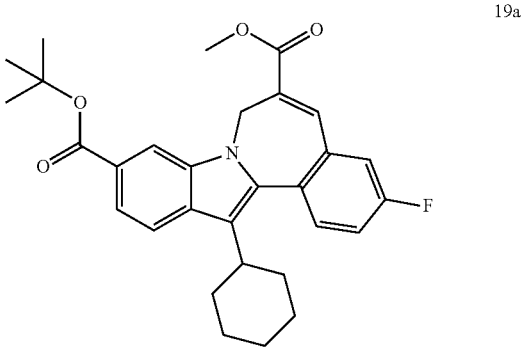 [SMILES: COC(=O)C1=Cc2cc(F)ccc2-c2c(C3CCCCC3)c3ccc(C(=O)OC(C)(C)C)cc3n2C1]

Step 1

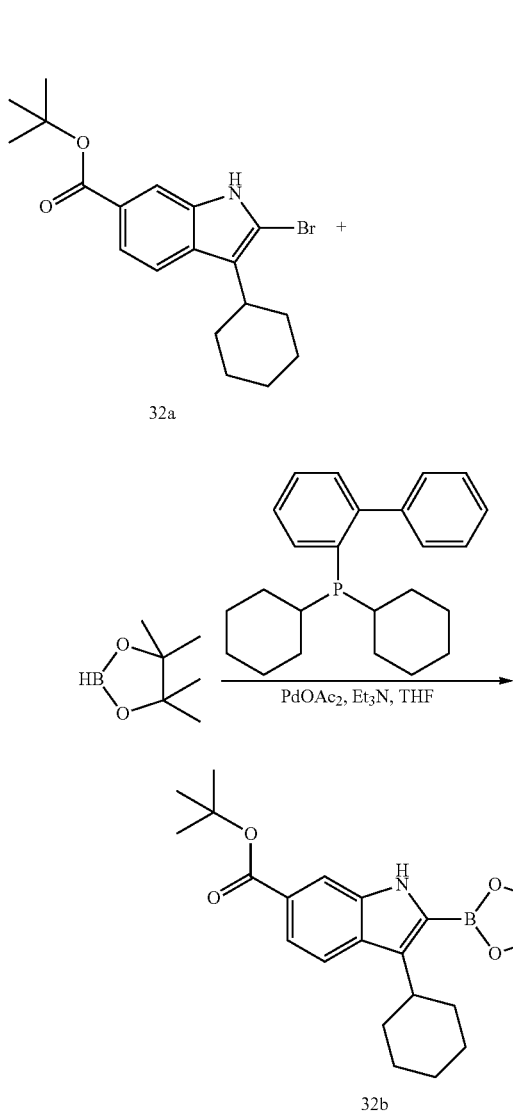

A mixture of tert-butyl 2-bromo-3-cyclohexyl-1H-indole-6-carboxylate 32a (5 g, 13.22 mmoles, synthesized as described in US 2007270406 A1), pinacolborane (5.75 mL, 3 eq) and triethylamine (7.35 mL, 4 eq) in THF (50 mL) was stirred at RT during 3 h. Palladium acetate (90 mg, 0.03 eq) and biphenyl-2-yldicyclohexylphosphine (556 mg, 0.12 eq) were then added and the RM was heated at 80° C. during 2 h. The reaction mixture was then allowed to cool down to RT and poured in a solution of watered NH₄Cl then extracted with ethyl acetate. The organic layers were dried over magnesium sulfate, filtered and concentrated. The residue was purified by column chromatography using a gradient of ethyl acetate in heptane to give 3.5 g (70% yield) of the desired product tert-butyl 3-cyclohexyl-2-(4,4,5,5-tetramethyl-1,3,2-dioxaborolan-2-yl)-1H-indole-6-carboxylate 32b; m/z 426 [M+H]⁺.

Step 2

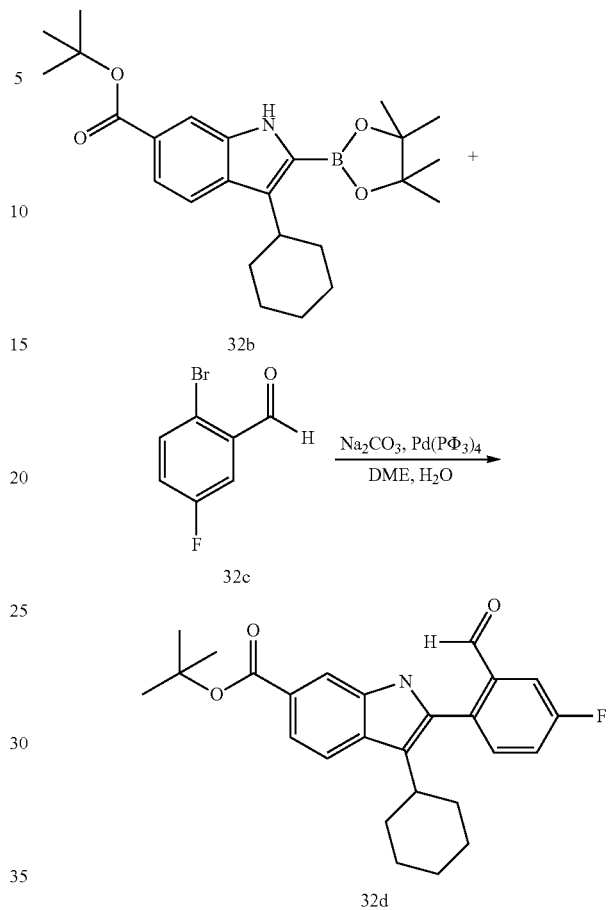

To a mixture of tert-butyl 3-cyclohexyl-2-(4,4,5,5-tetramethyl-1,3,2-dioxaborolan-2-yl)-1H-indole-6-carboxylate 32b (2.77 g, 6.5 mmoles) and 2-bromo-5-fluorobenzaldehyde 32c (1.58 g, 1.2 eq) in DME (40 mL) was added a solution of sodium carbonate (2.07 g, 3 eq) in water (15 mL). The resulting mixture was then flushed with nitrogen at RT during 10 minutes. After the addition of palladium tetrakis triphenylphospine (376 mg, 0.05 eq), the RM was heated at 70° C. during 1 h. The mixture was then allowed to cool down to RT and poured in water, then extracted with ethyl acetate (3 times). The organic layers were combined, dried over MgSO₄, filtered and concentrated. The residue was recrystalized from di-isopropyl ether/heptane to give 2 g (73% yield) of the desired product tert-butyl 3-cyclohexyl-2-(4-fluoro-2-formylphenyl)-1H-indole-6-carboxylate 32d as a white solid; m/z 422 [M+H]⁺.

Step 3

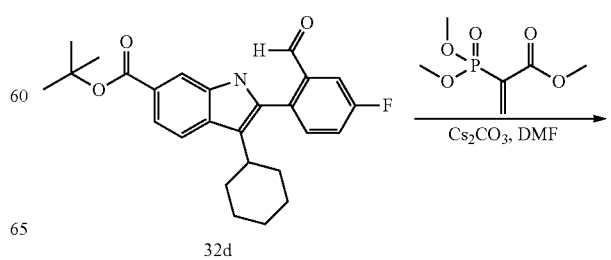

-continued

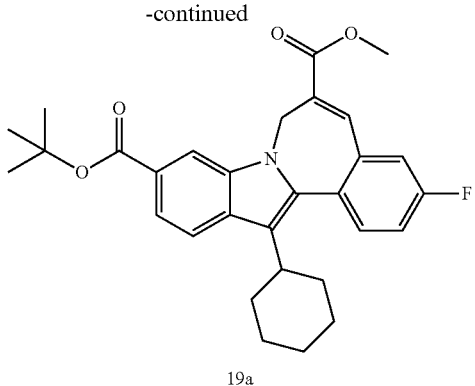

19a

A mixture of tert-butyl 3-cyclohexyl-2-(4-fluoro-2-formylphenyl)-1H-indole-6-carboxylate 32d (2 g, 4.75 mmoles), cesium carbonate (1.85 g, 1.2 eq) and methyl 2-(dimethoxyphosphoryl)acrylate (16.475 mL, 0.36 M solution in toluene, 1.25 eq) in DMF (80 mL) was stirred at 60° C. during 2 h. The reaction mixture was then allowed to cool down to room temperature, poured in water and extracted with ethyl acetate. The organic layer was then dried over MgSO$_4$, filtered and concentrated. The residue was purified by column chromatography using heptanes/dichloromethane to give 2 g (86% yield) of the desired product 10-tert-butyl 6-methyl 13-cyclohexyl-3-fluoro-7H-indolo[2,1-a][2]benzazepine-6,10-dicarboxylate 19a; m/z 490 [M+H]$^+$.

Example 33

Synthesis of Compound 20a

20a

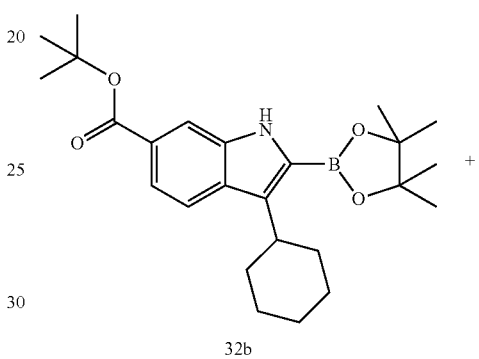

Step 1

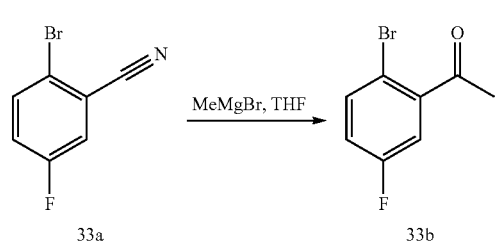

To a solution of 2-bromo-5-fluoro-benzonitrile 33a (10 g, 50 mmol) in dry tetrahydrofuran (100 mL) under nitrogen was added methylmagnesium bromide (3.2 M in ether, 19 mL, 60.0 mmol), and the resulting mixture was heated to reflux for 4 hours.

The RM was then cooled down to RT, poured into a 2 N HCl solution (100 mL) and then diluted with methanol (100 mL). The resulting green solution was concentrated on a steam bath for 1 h at which point the organic solvents had been removed and the crude product had precipitated. The reaction mixture was then extracted with ethyl acetate, dried over MgSO$_4$ and concentrated. The residue was purified by column chromatography using heptane and dichloromethane to give 4.88 g (45% yield) of the desired product 1-(2-bromo-5-fluorophenyl)ethanone 33b as a pink oil; m/z 218 [M+H]$^+$.

Step 2

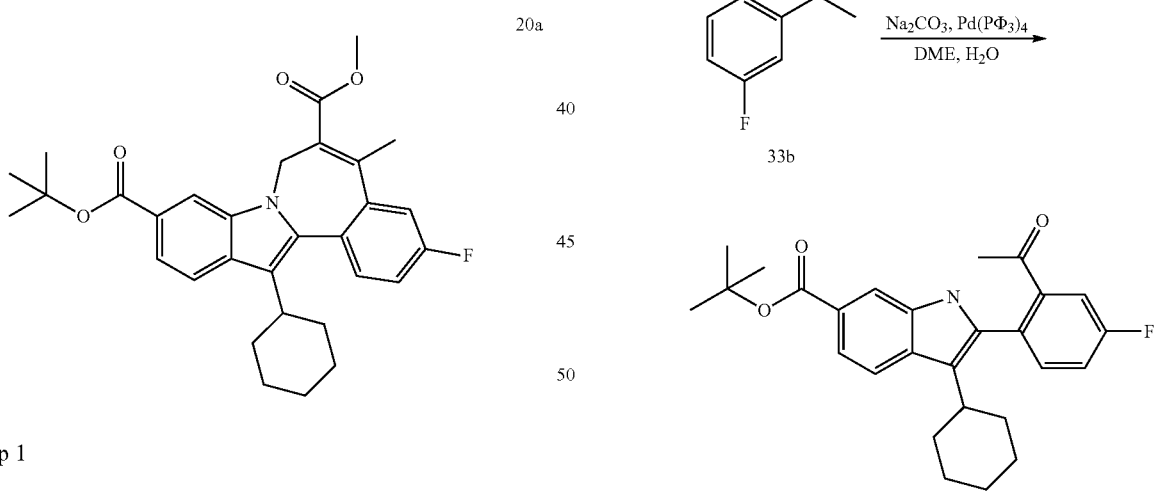

The title product tert-butyl 2-(2-acetyl-4-fluorophenyl)-3-cyclohexyl-1H-indole-6-carboxylate 33c was synthesized following the procedure reported for the synthesis of tert-butyl 3-cyclohexyl-2-(4-fluoro-2-formylphenyl)-1H-indole-6-carboxylate 32d, using 1-(2-bromo-5-fluorophenyl)ethanone 33b instead of 2-bromo-5-fluorobenzaldehyde 32c, and was obtained in 65% yield as a white solid; m/z 436 [M+H]$^+$.

Step 3

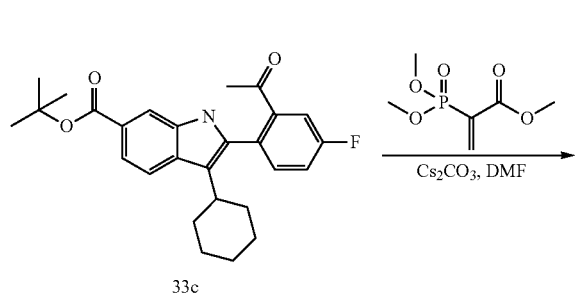

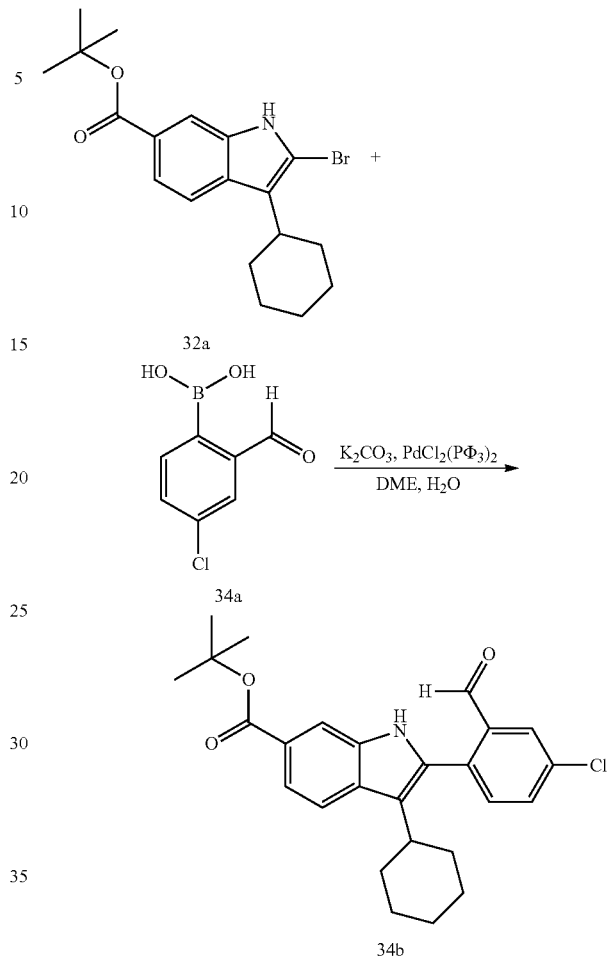

The title product 10-tert-butyl 6-methyl 13-cyclohexyl-3-fluoro-5-methyl-7H-indolo[2,1-a][2]benzazepine-6,10-dicarboxylate 20a was synthesized following the procedure reported for the synthesis of 10-tert-butyl 6-methyl 13-cyclohexyl-3-fluoro-7H-indolo[2,1-a][2]benzazepine-6,10-dicarboxylate 19a, using tert-butyl 2-(2-acetyl-4-fluorophenyl)-3-cyclohexyl-1H-indole-6-carboxylate 33c instead of tert-butyl 3-cyclohexyl-2-(4-fluoro-2-formylphenyl)-1H-indole-6-carboxylate 32d, and was obtained in 11% yield as a white solid; m/z 504 [M+H]⁺.

Example 34

Synthesis of Compound 21a

Step 1

The bromo indole derivative 32a (5 g, 13.22 mmol), 4-chloro-2-formylphenylboronic acid 34a (3.17 g, 17.18 mmol) and potassium carbonate (4.20 g, 30.4 mmol) were dissolved in 100 mL of 1,2-dimethoxyethane (80 ml)/water (20 ml) 4/1 and the obtained solution was flushed thoroughly with argon. Then bis(triphenylphosphine)palladium(II) chloride (0.464 g, 0.661 mmol) was added and the reaction was heated to 63° C. under argon during 3 h. The reaction was then diluted with EtOAc, washed with water and with sat. aq. NaHCO₃, dried (brine, sulfate) and evaporated. The residue was stripped with DIPE and stirred and sonicated in heptane with a few mL DIPE added. The solid was filtered off and dried to afford 4.97 g (86% yield) of the desired product tert-butyl 2-(4-chloro-2-formylphenyl)-3-cyclohexyl-1H-indole-6-carboxylate 34b; m/z 437 [M+H]⁺.

Step 2

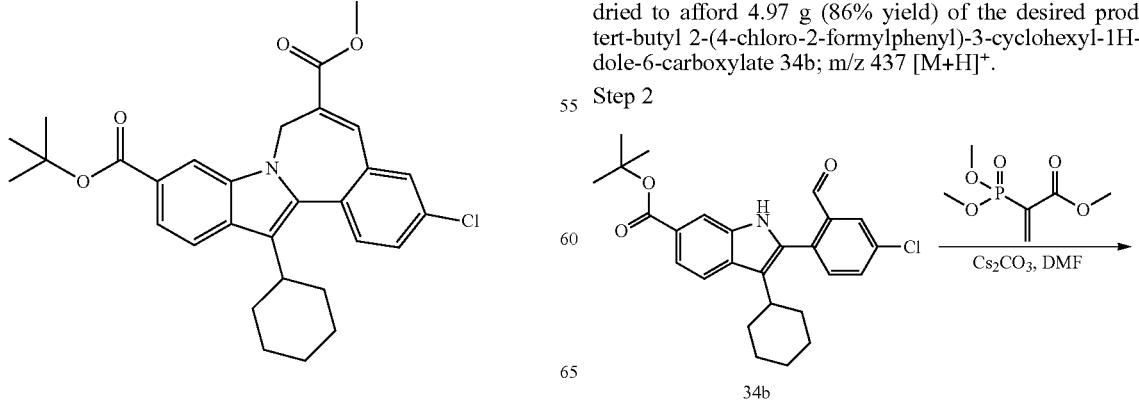

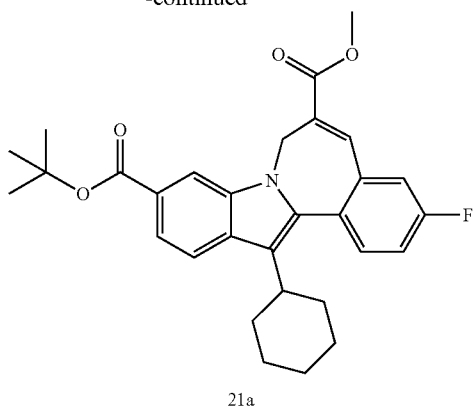

21a

The indole derivative 34b (4.95 g, 11.30 mmol) and cesium carbonate (4.42 g, 13.56 mmol) were dissolved in N,N-dimethylformamide (dry) (50 ml) and methyl 2-(dimethoxyphosphoryl)acrylate (3.23 g, 14.13 mmol) was added. The RM was stirred at 65° C. during 2 h. It was then cooled to rt and dropped onto 300 ml of water vigorously stirred. The resulting yellowish solid was filtered off, washed with water and dried to afford 5.40 g (94% yield) of the desired product 10-tert-butyl 6-methyl 3-chloro-13-cyclohexyl-7H-indolo[2,1-a][2]benzazepine-6,10-dicarboxylate 21a, used without further purification in the next step; m/z 507 [M+H]⁺.

Example 35

Synthesis of Compound 24a

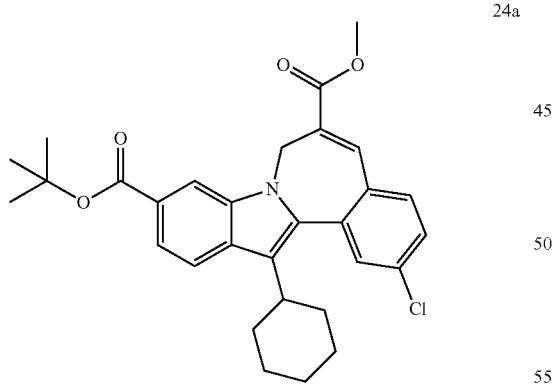

24a

The title compound 24a was synthesized following the 2-step procedure reported for the synthesis of 10-tert-butyl 6-methyl 3-chloro-13-cyclohexyl-7H-indolo[2,1-a][2]benzazepine-6,10-dicarboxylate 21a, using 5-chloro-2-formylphenylboronic acid in the first step, instead of 4-chloro-2-formylphenylboronic acid 34a, and was obtained with an overall yield of 70% as a yellowish solid; m/z 507 [M+H]⁺.

Example 36

Synthesis of Compound 24b

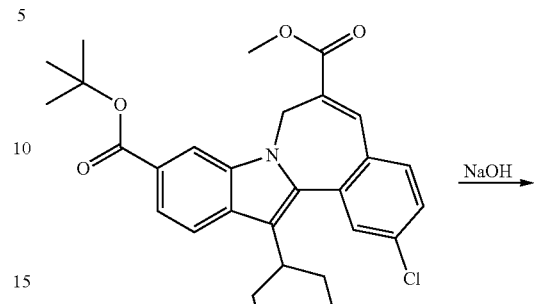

24a

24b

A solution of NaOH (6.38 g) in 25 mL of water was added to a stirred solution of the indole derivative 24a in THF (100 mL) and MeOH (150 mL). After 1 hour the reaction was concentrated under reduced pressure, then diluted with ice-cold water (150 mL). The pH of the resulting solution was adjusted to 6 with HCl then extracted with dichloromethane and dried over MgSO₄. The solvent was removed then the residue was purified by column chromatography using DCM/MeOH as eluant to give 1.7 g (87% yield) of a yellowish solid; m/z 492 [M+H]⁺.

Example 37

Synthesis of Compound 16a

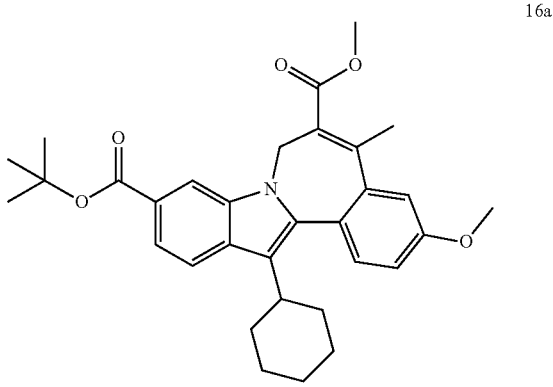 [SMILES: COC(=O)C1=C(C)c2cc(OC)ccc2-c2c(C3CCCCC3)c3ccc(C(=O)OC(C)(C)C)cc3n2C1]

16a

Step 1

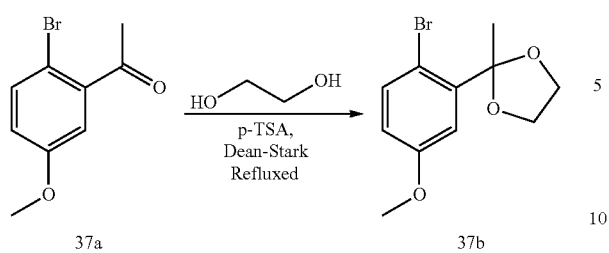

Ethane-1,2-diol (4.06 g) and Tos-OH (0.41 g) were added to a solution of 1-(2-bromo-5-methoxyphenyl)ethanone 37a (5 g) in toluene (950 ml). The solution was heated under reflux with stirring in a 3-neck round-bottomed flask fitted with a Dean-Stark receiver for 3 hours. The reaction mixture was then cooled to room temperature. The mixture was transferred to a separating funnel and a sodium carbonate solution (1M, 50 ml) was added. The mixture was agitated and two phases formed. The organic layer was separated, washed with water (2×50 ml), dried over MgSO₄ and concentrated under vacuum to afford 6.5 g (quantitative yield) of the desired product 2-(2-bromo-5-methoxyphenyl)-2-methyl-1,3-dioxolane 37b as a white solid.

Step 2

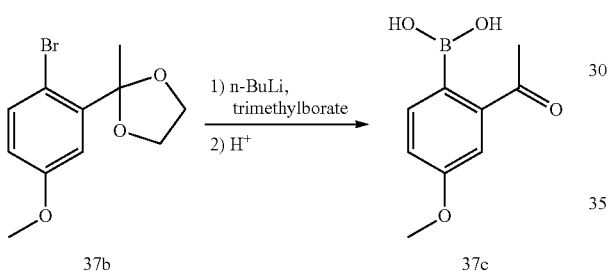

The bromo derivative 37b (6 g) was dissolved in dry THF (60 ml) and the solution was cooled down to −78° C. Then n-BuLi (16.5 ml) was added carefully at such a rate that the temperature did not exceed −60° C. After 1 h, B(O-i-Pr)₃ (6.2 g) was added neatly dropwise at −78° C. After all was added, the cooling bath was removed. The mixture was stirred at 0° C. for 2.5 h, then 2 N HCl (60 ml) was added, and the RM stirred at r.t. for 2 h. The organic solvent was then removed under vacuum and the aqueous layer was saturated with NaCl and extracted with EtOAc. The organic layer was dried over Na₂SO₄ and evaporated under vacuum to give 3 g of the desired product 2-acetyl-4-methoxyphenylboronic acid 37c.

Step 3

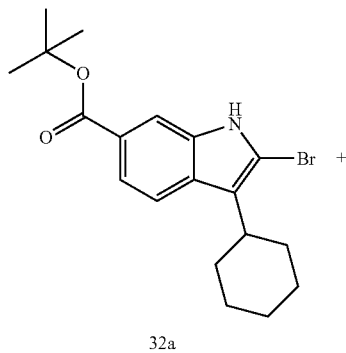

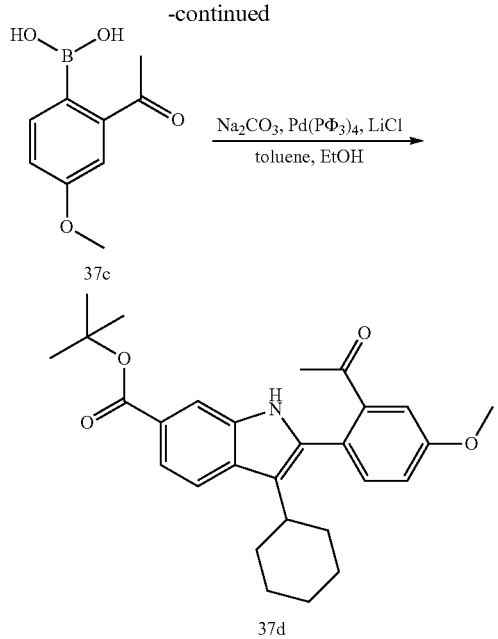

The title product tert-butyl 2-(2-acetyl-4-methoxyphenyl)-3-cyclohexyl-1H-indole-6-carboxylate 37d was synthesized by following a similar procedure to that used for the synthesis of tert-butyl 2-(4-chloro-2-formylphenyl)-3-cyclohexyl-1H-indole-6-carboxylate 34b, using 2-acetyl-4-methoxyphenylboronic acid 37c instead of 4-chloro-2-formylphenylboronic acid 34a.

Step 4

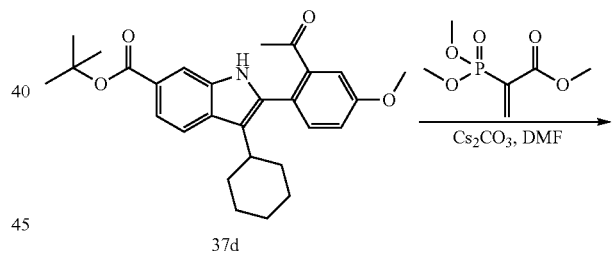

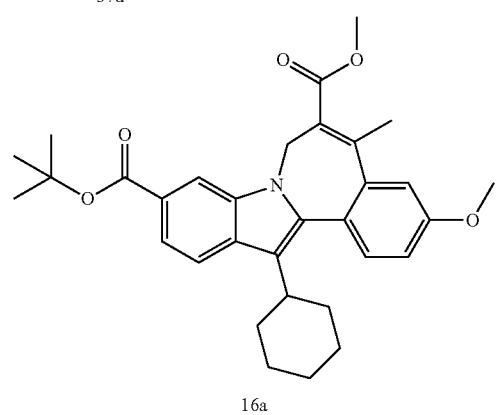

The title product 10-tert-butyl 6-methyl 13-cyclohexyl-3-methoxy-5-methyl-7H-indolo[2,1-a][2]benzazepine-6,10-dicarboxylate 16a was synthesized by following a similar procedure to that used for the synthesis of 10-tert-butyl 6-methyl 13-cyclohexyl-3-fluoro-5-methyl-7H-indolo[2,1-a][2]benzazepine-6,10-dicarboxylate 20a, using tert-butyl 2-(2-acetyl-4-methoxyphenyl)-3-cyclohexyl-1H-indole-6-carboxylate 37d instead of tert-butyl 2-(2-acetyl-4-fluorophenyl)-3-cyclohexyl-1H-indole-6-carboxylate 33c.

Example 38

Synthesis of Compound 38

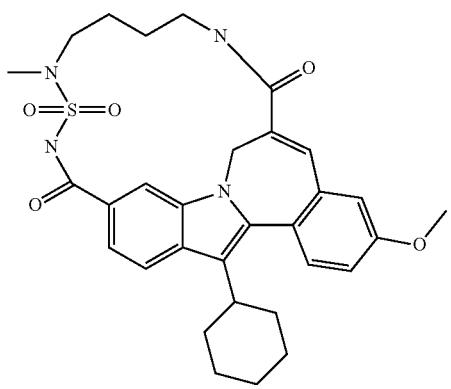

The synthesis of the title compound 38 was performed following the 5-step procedure reported for the synthesis of compound 10, starting from intermediate 13-cyclohexyl-3-methoxy-7H-benzo[3,4]azepino indole-6,10-dicarboxylic acid 10-tert-butyl ester 6-methyl ester 1a instead of 5-tert-butyl 1a-methyl 8-cyclohexyl-11-methoxy-1,12b-dihydrocyclopropa[d] indolo[2,1-a][2]benzazepine-1a,5(2H)-dicarboxylate 8a, and yielded 60 mg of a beige solid; m/z 577 [M+H]$^+$.

Example 39

Activity of Compounds of Formula (I)

Replicon Assay

The compounds of formula (I) were examined for activity in the inhibition of HCV RNA replication in a cellular assay. The assay demonstrated that the compounds of formula (I) inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound was monitored on the Huh-Luc cells, enabling a dose-response curve to be generated for each test compound. EC50 values were then calculated, which value represents the amount of the compound required to decrease by 50% the level of detected luciferase activity, or more specifically, the ability of the genetically linked HCV replicon RNA to replicate.

Enzymatic Assay
1. HCV NS5B 1bJ4
1.a) Protein Purification

The cDNA encoding NS5B amino acid 1-570 (HC-J4, genotype 1b, pCV-J4L6S, genebank accession number AF054247) was subcloned into the Nhe I and Xho I restriction sites of pET-21b. Expression of the subsequent His-tagged C-terminal 21 amino acid deleted NS5B was performed as follows:

The NS5B expression construct was transformed into E. coli BL21(DE3) (Novagen, Madison, Wis.). Five milliliter of LB-medium supplemented with ampicillin (50 μg/mL) was inoculated with one colony. When the pre-culture reached an optical density of 0.6 measured at 600 nm, it was transferred to fresh LB-medium supplemented with ampicillin, at a ratio of 1:200. Cells were grown to an optical density at 600 nm of 0.6, after which the expression cultures were shifted to a growth temperature of 20° C. following induction with isopropyl-1-thio-β-D-galactopyranoside and MgCl$_2$ at a final concentration of 0.4 mM and 10 μM, respectively. After 10 h of induction, cells were harvested by centrifugation and resuspended in 20 mM Tris-HCl, pH 7.5, 300 mM NaCl, 10% glycerol, 0.1% NP40, 4 mM MgCl$_2$, 5 mM DTT supplemented with EDTA-free Complete Protease Inhibitor (Roche, Basel, Switzerland). Cell suspensions were disrupted by sonication and incubated with 10-15 mg/L of DNase I (Roche, Basel, Switzerland) for 30 min. Cell debris was removed through ultracentrifugation at 30,000×g for 1 hour and clarified cell lysate was flash frozen and stored at −80° C. prior to purification.

Clarified cell lysate was thawed and subsequently loaded onto a 5 mL pre-packed HisTrap FF column equilibrated with 25 mM HEPES, pH 7.5, 500 mM NaCl, 10% glycerol and 5 mM DTT. Proteins were eluted with 500 mM imidazole at a flow rate of 1 mL/min. Fractions containing the protein of interest were applied onto a pre-packed 26/10 HiPrep Desalting Column equilibrated with 25 mM HEPES, pH 7.5, 150 mM NaCl, 10% glycerol and 5 mM DTT. The buffer-exchanged NS5B peak was then applied onto a 20 mL Poly-U Sepharose column. Protein was eluted with an increasing salt gradient and fractions collected. Protein purity was assessed on Nu-PAGE pre-cast gels (Invitrogen, Carlsbad, Calif.). Purified NS5B samples were concentrated using Centri-Prep concentrators (Millipore, Billerica, Mass., USA) and protein concentrations were determined by Bradford assay (Pierce, Rockford, Ill., USA).

1.b) Protein Sequence
PDB: 1nb4, Apo Form

The protein sequence is as described in WO 2007/026024. Calc. Mol. Properties: 64941.4 g/mol.

1.c) Inhibition Assay with NS5B 1bJ4

Measurement of HCV NS5B polymerization activity was performed by evaluating the amount of radiolabeled GTP incorporated by the enzyme in a newly synthesized RNA using heteropolymeric RNA template/primer. The RdRp assay was carried out in 384-well plates using 50 nM of purified NS5B enzyme, which was incubated with 300 nM 5'-biotinylated oligo($rG_{13}$)/poly(rC) or oligo (rU15)/poly (rA) primer-template, 600 nM of GTP, and 0.1 μCi of [$^3$H] GTP or [$^3$H]UTP in 25 mM Tris-HCl, pH 7.5, 5 mM $MgCl_2$, 25 mM KCl, 17 mM NaCl and 3 mM of DTT. The 30 μL reaction mixture was incubated at room temperature for 2 h before stopping the reaction by adding 30 μL of streptavidin coated SPA-beads (GE Healthcare, Uppsala, Sweden) in 0.5 M EDTA. The 30 μL reaction was terminated after 2 hours at 25° C. upon addition of 30 μl streptavidin-coated SPA beads (GE Healthcare, Uppsala, Sweden 5 mg/ml in 0.5 M EDTA). After incubation at 25° C. for 30 min, the plate was counted using a Packard TopCount microplate reader (30 sec/well, 1 min count delay) and $IC_{50}$ values were calculated (Table 1: $IC_{50}$ 1bJ4). $IC_{50}$ values represent the concentration of compound required to decrease by 50% the amount of RNA produced which is measured by the detection of incorporated radiolabeled GTP.

2. HCV NS5B con1b 2.a) Cloning, Expression and Purification of NS5B con1b.

The coding sequence for NS5B (genotype 1b consensus strain Con1) lacking 21 C-terminal residues was amplified from plasmid $pFKI_{389}$/ns3-3'_N (Genbank accession no. AJ242654) and subcloned into the pET21b plasmid as described previously (Pauwels et al, 2007, J Virol 81:6909-19). The NS5BΔC21 expression construct was transformed into *E. coli* Rosetta 2 (DE3) (Novagen, Madison, Wis.). One hundred milliliters of LB-medium supplemented with carbenicillin (50 μg/mL) and chloramphenicol (34 μg/mL) was inoculated with one colony, grown overnight, and transferred to fresh LB-medium supplemented with 3% ethanol, carbenicillin and chloramphenicol, at a ratio of 1:200. The remaining of the procedure was as described previously (Pauwels et al, 2007, J Virol 81:6909-19), except that the column used for ion-exchange chromatography was a 6 mL Resource S column (GE Healthcare), and that protein concentrations were determined with the Nanodrop (Nanodrop Technologies, Wilmington, Del., USA).

2.b) RNA-dependent RNA Polymerase Assay.

Fifty-percent inhibitory concentrations (Table 1: $IC_{50}$ con1b) were determined according to the method described previously (Pauwels et al, 2007, J Virol 81:6909-19) using a primer-dependent transcription assay. Following a 10 minute preincubation with the inhibitor, 20 nM of purified Con1b NS5B enzyme was incubated for 10 min. with 150 nM 5'-biotinylated oligo ($rG_{13}$) primer, 15 nM poly (rC) template, 19 mM Tris-HCl, 5 mM $MgCl_2$, 17 mM NaCl, 21 mM KCl, and 2.5 mM DTT. 600 nM GTP and 0.13 μCi of [$^3$H]GTP was then added to initiate the 40-μl reaction mixture, which was then incubated at room temperature for 2 h before the reaction was stopped by addition of 40-μl streptavidin-coated SPA beads.

The following Table 1 lists compounds according to any one of the above examples. The activities of the compounds tested are also depicted in Table 1.

TABLE 1

| Nr. | Structure | $EC_{50}$ (μM) | $IC_{50}$1bJ4 (μM) | $IC_{50}$Con1b (μM) |
|---|---|---|---|---|
| 2 | 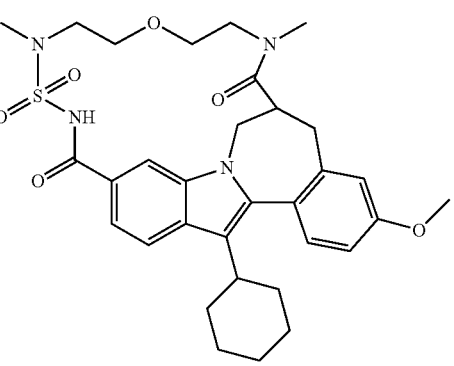 | = 0.09 | = 0.41 | |
| 1 | 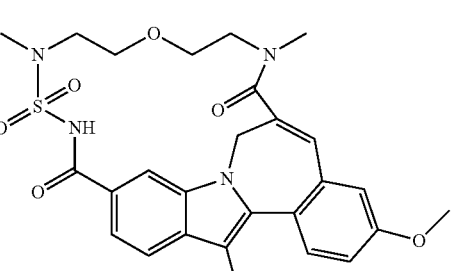 | = 0.07 | = 0.24 | = 0.038 |

TABLE 1-continued

| Nr. | Structure | EC$_{50}$ (µM) | IC$_{50}$1bJ4 (µM) | IC$_{50}$Con1b (µM) |
|---|---|---|---|---|
| 11 | 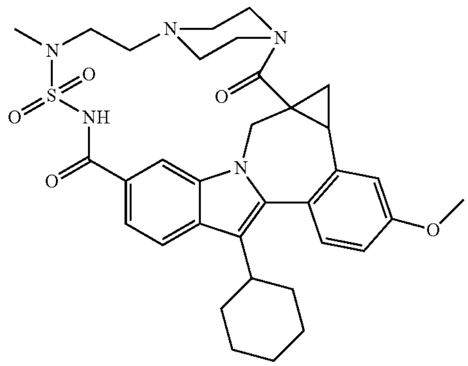 [SMILES: COc1ccc2c(c1)C1CC13Cn1c-2c(C2CCCCC2)c2ccc(cc21)C(=O)NS(=O)(=O)N(C)CCN1CCN(CC1)C3=O] | = 0.055 | = 0.22 | |
| 5 | 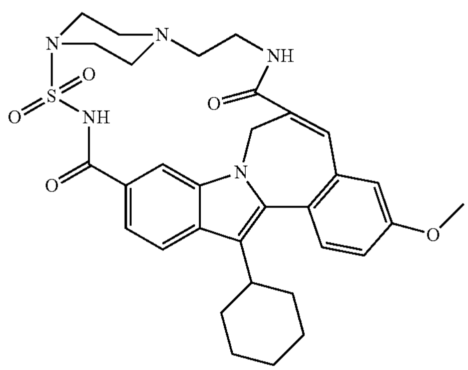 [SMILES: COc1ccc2c(c1)C=C1Cn3c-2c(C2CCCCC2)c2ccc(cc23)C(=O)NS(=O)(=O)N2CCN(CCNC1=O)CC2] | = 0.92 | = 0.29 | |
| 12 | 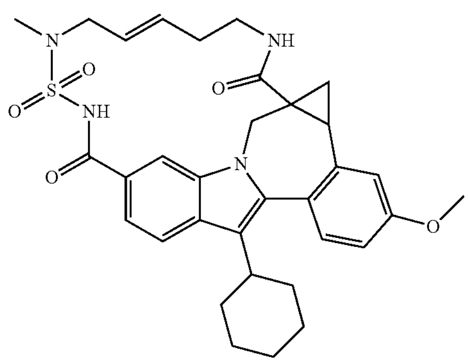 [SMILES: COc1ccc2c(c1)C1CC13Cn1c-2c(C2CCCCC2)c2ccc(cc21)C(=O)NS(=O)(=O)N(C)C/C=C/CCNC3=O] | = 0.29 | = 0.93 | |
| 10 | 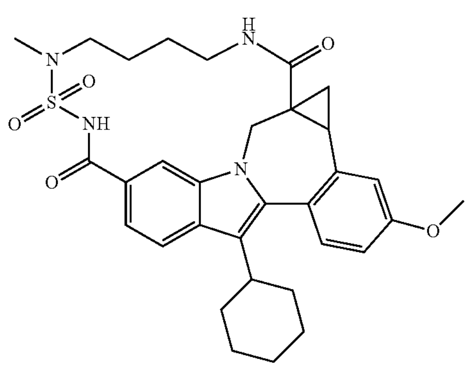 [SMILES: COc1ccc2c(c1)C1CC13Cn1c-2c(C2CCCCC2)c2ccc(cc21)C(=O)NS(=O)(=O)N(C)CCCCNC3=O] | = 0.06 | = 0.28 | |

TABLE 1-continued

| Nr. | Structure | EC$_{50}$ (μM) | IC$_{50}$1bJ4 (μM) | IC$_{50}$Con1b (μM) |
|---|---|---|---|---|
| 13 | 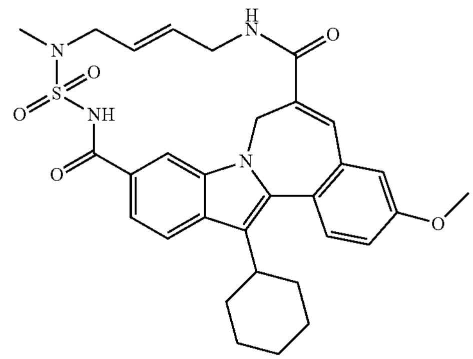 [SMILES: COc1ccc2c(c1)C=C1Cn3c-2c(C2CCCCC2)c2ccc(cc23)C(=O)NS(=O)(=O)N(C)C/C=C/CNC1=O] | = 0.39 | = 0.19 | |
| 3 | 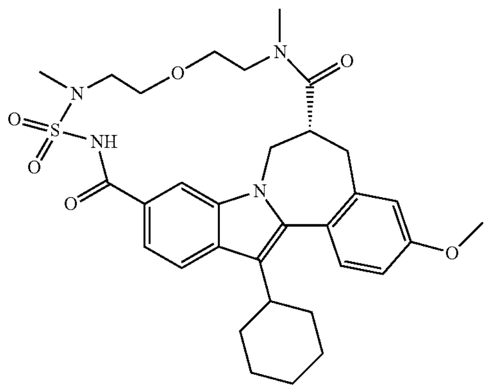 [SMILES: COc1ccc2c(c1)C[C@@H]1Cn3c-2c(C2CCCCC2)c2ccc(cc23)C(=O)NS(=O)(=O)N(C)CCOCCN(C)C1=O] | = 0.079 | | = 0.53 |
| 4 | 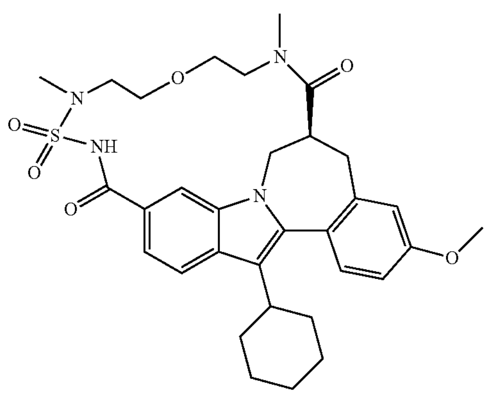 [SMILES: COc1ccc2c(c1)C[C@H]1Cn3c-2c(C2CCCCC2)c2ccc(cc23)C(=O)NS(=O)(=O)N(C)CCOCCN(C)C1=O] | = 3.83 | | = 2.42 |
| 6 | 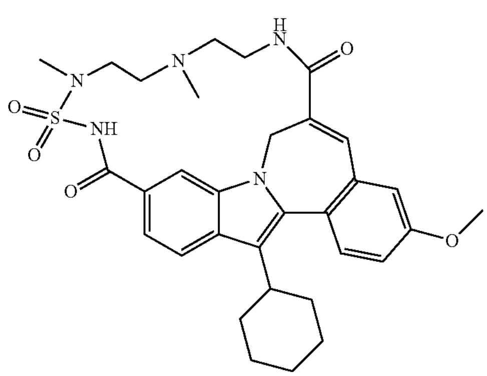 [SMILES: COc1ccc2c(c1)C=C1Cn3c-2c(C2CCCCC2)c2ccc(cc23)C(=O)NS(=O)(=O)N(C)CCN(C)CCNC1=O] | = 0.550 | | |

TABLE 1-continued

| Nr. | Structure | EC$_{50}$ (µM) | IC$_{50}$1bJ4 (µM) | IC$_{50}$Con1b (µM) |
|---|---|---|---|---|
| 8 | 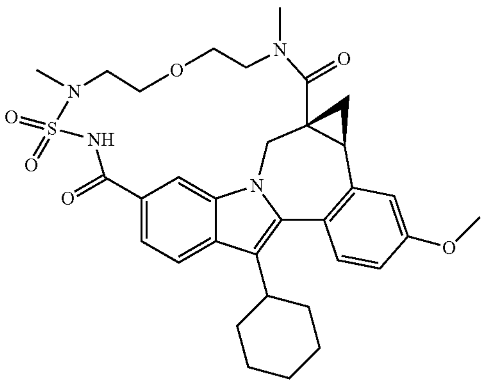 [SMILES: COc1ccc2c(c1)[C@@H]1C[C@]13Cn1c-2c(C2CCCCC2)c2ccc(cc21)C(=O)NS(=O)(=O)N(C)CCOCCN(C)C3=O] | = 0.040 | | |
| 9 | 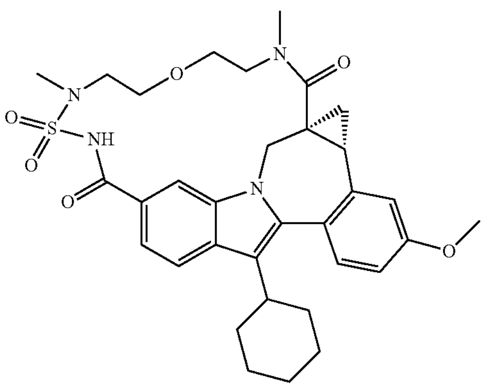 [SMILES: COc1ccc2c(c1)[C@H]1C[C@@]13Cn1c-2c(C2CCCCC2)c2ccc(cc21)C(=O)NS(=O)(=O)N(C)CCOCCN(C)C3=O] | = 0.800 | | |
| 15 | 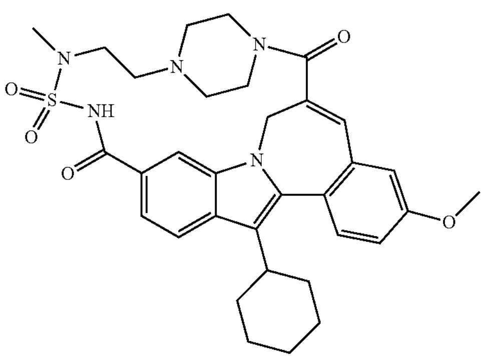 [SMILES: COc1ccc2c(c1)C=C1Cn3c-2c(C2CCCCC2)c2ccc(cc23)C(=O)NS(=O)(=O)N(C)CCN2CCN(CC2)C1=O] | = 0.180 | | |
| 16 | 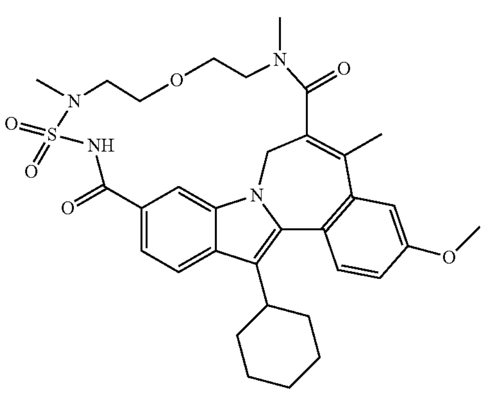 [SMILES: COc1ccc2c(c1)C(C)=C1Cn3c-2c(C2CCCCC2)c2ccc(cc23)C(=O)NS(=O)(=O)N(C)CCOCCN(C)C1=O] | = 0.078 | = 0.040 | |

TABLE 1-continued

| Nr. | Structure | EC$_{50}$ (μM) | IC$_{50}$1bJ4 (μM) | IC$_{50}$Con1b (μM) |
|---|---|---|---|---|
| 17 | 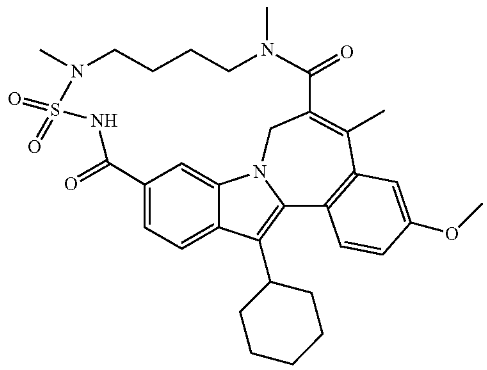 [SMILES: COc1ccc2c(c1)C(C)=C1Cn3c-2c(C2CCCCC2)c2ccc(cc23)C(=O)NS(=O)(=O)N(C)CCCCN(C)C1=O] | = 0.170 | | |
| 18 | 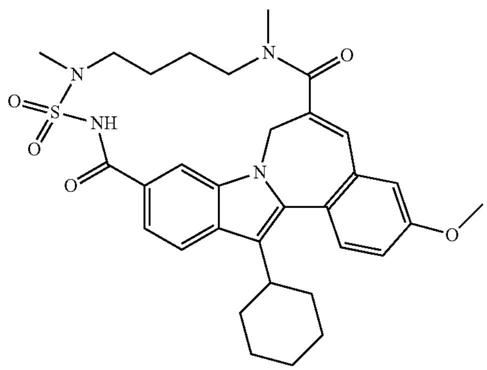 [SMILES: COc1ccc2c(c1)C=C1Cn3c-2c(C2CCCCC2)c2ccc(cc23)C(=O)NS(=O)(=O)N(C)CCCCN(C)C1=O] | = 0.079 | | = 0.026 |
| 19 | 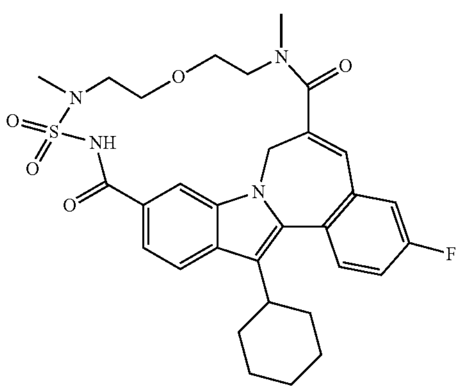 [SMILES: CN1CCOCCN(C)S(=O)(=O)NC(=O)c2ccc3c(C4CCCCC4)c4n(c3c2)CC(=Cc2cc(F)ccc2-4)C1=O] | = 0.072 | | = 0.031 |
| 20 | 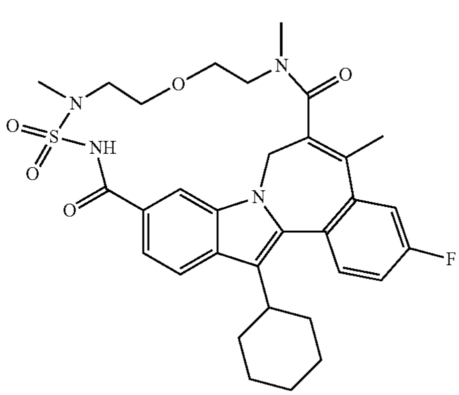 [SMILES: CC1=C2Cn3c(c(C4CCCCC4)c4ccc(cc43)C(=O)NS(=O)(=O)N(C)CCOCCN(C)C2=O)-c2ccc(F)cc21] | = 0.081 | | = 0.038 |

TABLE 1-continued

| Nr. | Structure | EC$_{50}$ (µM) | IC$_{50}$1bJ4 (µM) | IC$_{50}$Con1b (µM) |
|---|---|---|---|---|
| 21 | 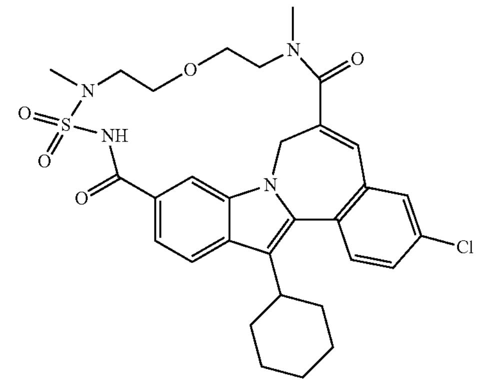 [SMILES: CN1CCOCCN(C)S(=O)(=O)NC(=O)c2ccc3c(C4CCCCC4)c4n(c3c2)CC(=Cc2cc(Cl)ccc2-4)C1=O] | = 0.280 | | |
| 22 | 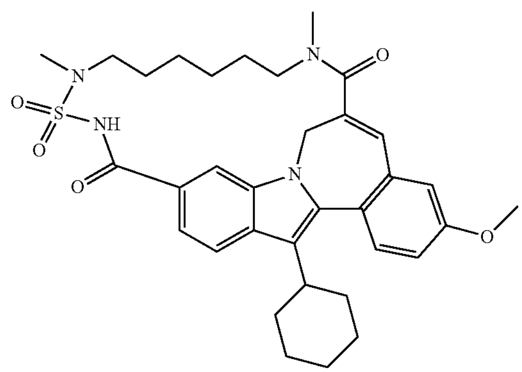 [SMILES: COc1ccc2c(c1)C=C1Cn3c-2c(C2CCCCC2)c2ccc(cc23)C(=O)NS(=O)(=O)N(C)CCCCCCN(C)C1=O] | = 0.160 | | |
| 23 | 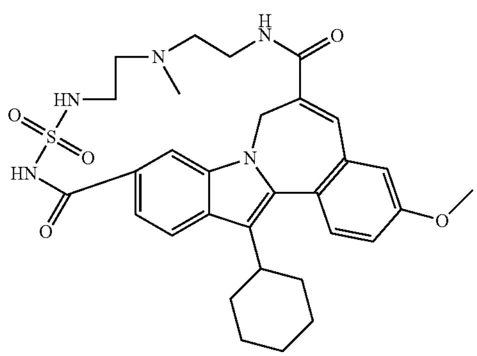 [SMILES: COc1ccc2c(c1)C=C1Cn3c-2c(C2CCCCC2)c2ccc(cc23)C(=O)NS(=O)(=O)NCCN(C)CCNC1=O] | = 0.470 | | |
| 24 | 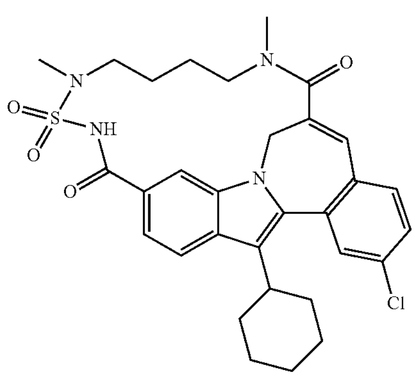 [SMILES: CN1CCCCN(C)S(=O)(=O)NC(=O)c2ccc3c(C4CCCCC4)c4n(c3c2)CC(=Cc2ccc(Cl)cc2-4)C1=O] | = 14.48 | | |

TABLE 1-continued

| Nr. | Structure | EC$_{50}$ (μM) | IC$_{50}$1bJ4 (μM) | IC$_{50}$Con1b (μM) |
|---|---|---|---|---|
| 25 | 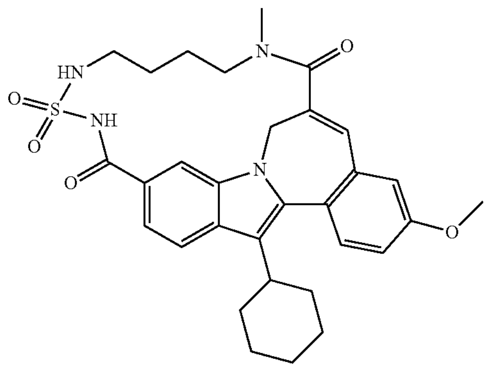 [SMILES: COc1ccc2c(c1)C=C1Cn3c-2c(C2CCCCC2)c2ccc(cc23)C(=O)NS(=O)(=O)NCCCCN(C)C1=O] | = | 0.550 | |
| 26 | 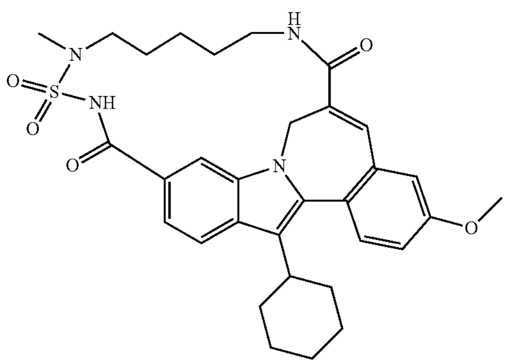 [SMILES: COc1ccc2c(c1)C=C1Cn3c-2c(C2CCCCC2)c2ccc(cc23)C(=O)NS(=O)(=O)N(C)CCCCCNC1=O] | = | 0.130 | |
| 27 | 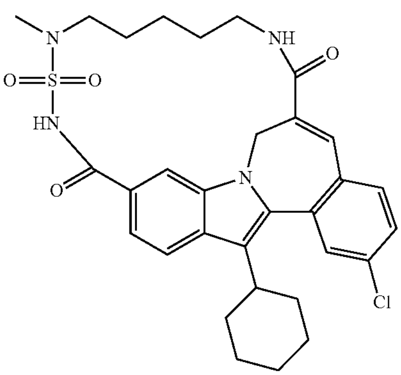 [SMILES: CN1CCCCCNC(=O)C2=Cc3ccc(Cl)cc3-c3c(C4CCCCC4)c4ccc(cc4n3C2)C(=O)NS1(=O)=O] | = | 10.20 | |
| 28 | 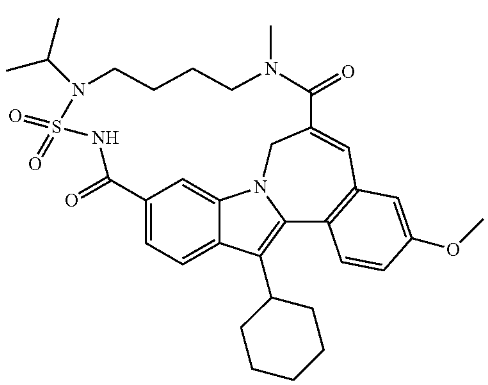 [SMILES: COc1ccc2c(c1)C=C1Cn3c-2c(C2CCCCC2)c2ccc(cc23)C(=O)NS(=O)(=O)N(C(C)C)CCCCN(C)C1=O] | = | 0.330 | |

TABLE 1-continued

| Nr. | Structure | EC$_{50}$ (μM) | IC$_{50}$1bJ4 (μM) | IC$_{50}$Con1b (μM) |
|---|---|---|---|---|
| 38 | 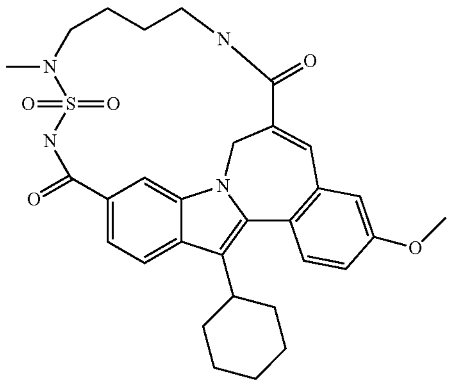 | = 0.912 | | |

Enzyme Binding Affinity

The compounds of formula (I) were examined for their enzymatic binding kinetics using a Surface Plasmon Resonance (SPR)-based method, i.e. Biacore. A slow dissociation of the inhibiting compound from its viral target (low $k_{off}$, low $K_d$) is believed to potentially reduce the development of drug resistance against anti-viral drugs (Dierynck et al. 2007. Journal of Virology, vol. 81, No. 24, 13845-13851). All measurements were performed on a Biacore T100 instrument (GE Healthcare). The purified HIS$_6$-tagged NS5BΔC21 polymerases were immobilized using non-covalent capturing to an NTA sensor chip (GE Healthcare) in immobilization buffer (20 mM MOPS pH 7.4, 500 mM NaCl, 0.005% Tween-P20, 1 mM DTT, 50 μM EDTA). Interaction studies were all performed at 25° C. Inhibitors were serially diluted in running buffer (20 mM Tris-HCl pH 7.4, 150 mM NaCl, 50 μM EDTA, 1 mM DTT, 0.005% Tween-P20) containing 5% dimethyl sulfoxide (DMSO). Single-cycle kinetics were used, in which 5 increasing concentrations of compound were injected for a period of 300 s each in 1 single cycle, and dissociation was monitored for a period of 1200 s. The sensor surface was completely regenerated in between the cycles. Data were analyzed using simultaneous nonlinear regression analysis (global fitting) adapted for single-cycle kinetics with Biacore T100 BiaEval evaluation software 2.0 (GE Healthcare). The individual rate constants $k_{on}$ and $k_{off}$ and a derived affinity constant, $K_d = k_{off}/k_{on}$, were determined by a kinetic evaluation of the sensorgrams. The kinetic models accounted for bulk and limited mass transport effects. Every analysis was performed at least in two independent experiments. The dissociation rate of a kinetic interaction can be translated into a compound residence time (dissociative half-life $t_{1/2} = \ln(2)/k_{off}$) representative for the interaction time between the polymerase and its inhibitor.

The observed association rate constants ($k_{on}$), dissociation rate constants ($k_{off}$), derived affinity constant ($K_d$) and dissociative half-life ($t_{1/2}$) measured for compounds of formula (I) or subgroups thereof on NS5B wild-type enzyme (genotype 1b, Con1b) are given in Table 2.

Table 3 lists binding affinity data for compound nr. 1 on different forms of HCV NS5B polymerase. The different forms studied (NS5B Target) comprise different clinical isolates of different genotypes of the wild type enzyme, and, different mutant NS5B polymerases. The mutant enzymes were obtained by site directed mutagenesis of the 1bJ4 or Con1b NS5B enzyme. Mutations P495L, V494A and L392I are located in the binding pocket of the compounds of the invention to NS5B polymerase.

It was observed that the strong binding of compounds of formula (I) or subgroups thereof is consistent within one genotype, that the compounds of formula (I) or subgroups thereof show affinity for NS5B polymerase of the different genotypes, as well as for NS5B polymerases with mutation in the indole binding pocket, and that binding of the compounds of formula (I) or subgroups thereof is not affected by mutations to other sites in the enzyme.

TABLE 2

| Nr. | $k_{on}$ (1/Ms) | $k_{off}$ (1/s) | $K_d$ (M) | $t_{1/2}$ (min) |
|---|---|---|---|---|
| 16 | 2.2E+04 | 3.6E−05 | 1.6E−09 | 321.5 |
| 18 | 2.0E+04 | 4.8E−05 | 2.4E−09 | 241.0 |
| 1 | 2.0E+04 | 9.0E−05 | 4.4E−09 | 128.4 |
| 28 | 7.3E+03 | 6.6E−05 | 9.0E−09 | 175.5 |
| 25 | 2.9E+04 | 3.1E−04 | 1.1E−08 | 37.8 |
| 17 | 8.7E+03 | 1.6E−04 | 1.8E−08 | 72.0 |
| 27 | 9.5E+03 | 3.8E−03 | 4.0E−07 | 3.1 |
| 24 | 4.8E+03 | 3.7E−03 | 7.6E−07 | 3.1 |
| 38 | 5.3E+03 | 4.1E−05 | 7.7E−09 | 283.8 |

TABLE 3

| NS5B target | $k_{on}$ (1/Ms) | $k_{off}$ (1/s) | $K_d$ (M) | $t_{1/2}$ (min) |
|---|---|---|---|---|
| 1a isolate 1 | 7.4E+04 | 4.8E−04 | 6.5E−09 | 24.2 |
| 1a isolate 2 | 3.9E+04 | 3.7E−04 | 9.4E−09 | 31.3 |
| 1a isolate 3 | 8.1E+04 | 6.0E−04 | 7.4E−09 | 19.2 |
| 1a isolate 4 | 7.4E+04 | 7.7E−04 | 1.1E−08 | 14.9 |
| 1a isolate 5 | 1.1E+05 | 3.1E−04 | 2.8E−09 | 37.2 |
| 1b isolate 1 | 2.6E+04 | 1.0E−04 | 4.0E−09 | 110.2 |
| 1b isolate 2 | 2.9E+04 | 6.7E−05 | 2.3E−09 | 172.1 |
| 1b isolate 3 | 3.7E+04 | 1.2E−04 | 3.3E−09 | 96.4 |
| 1b isolate 4 | 3.5E+04 | 1.7E−04 | 4.9E−09 | 67.5 |
| 2b isolate 1 | 1.8E+04 | 1.4E−02 | 8.2E−07 | 0.8 |
| 2b isolate 2 | 4.3E+04 | 1.2E−02 | 2.7E−07 | 1.0 |
| 2b isolate 3 | 4.4E+03 | 1.7E−02 | 3.8E−06 | 0.7 |
| 3a isolate 1 | 9.5E+04 | 3.7E−04 | 3.9E−09 | 31.1 |
| 3a isolate 2 | 2.5E+04 | 4.7E−04 | 1.9E−08 | 24.6 |
| 3a isolate 3 | 6.0E+04 | 3.6E−04 | 6.1E−09 | 31.7 |
| 4a isolate 1 | 2.0E+05 | 4.3E−04 | 2.1E−09 | 26.7 |
| 4a isolate 2 | 2.8E+05 | 3.8E−04 | 1.4E−09 | 30.1 |
| 4a isolate 3 | 1.8E+05 | 6.0E−04 | 3.4E−09 | 19.1 |
| 5a isolate 4 | 4.3E+04 | 9.7E−04 | 2.2E−08 | 12.0 |
| 6a isolate 5 | 5.0E+04 | 1.6E−03 | 3.2E−08 | 7.3 |
| 1bJ4 | 2.0E+04 | 1.0E−04 | 5.2E−09 | 110.2 |
| Con1b | 2.0E+04 | 9.0E−05 | 4.4E−09 | 128.4 |

TABLE 3-continued

| NS5B target | $k_{on}$ (1/Ms) | $k_{off}$ (1/s) | $K_d$ (M) | $t_{1/2}$ (min) |
|---|---|---|---|---|
| P495L (1bJ4) | 5.9E+03 | 2.2E−02 | 3.8E−06 | 0.5 |
| L392I (Con1b) | 1.8E+04 | 9.7E−04 | 5.5E−08 | 11.9 |
| P495L (Con1b) | 3.4E+03 | 2.2E−02 | 6.4E−06 | 0.5 |
| V494A (Con1b) | 5.5E+04 | 8.4E−04 | 1.5E−08 | 13.8 |
| M414T (1bJ4) | 2.6E+04 | 1.5E−04 | 5.9E−09 | 75.4 |
| M423T (1bJ4) | 2.5E+04 | 1.5E−04 | 6.3E−09 | 75.0 |
| S282T (1bJ4) | 3.4E+04 | 1.3E−04 | 3.9E−09 | 88.9 |
| C316Y (Con1b) | 3.5E+04 | 7.6E−05 | 2.2E−09 | 151.7 |

The invention claimed is:

1. A compound of Formula (I)

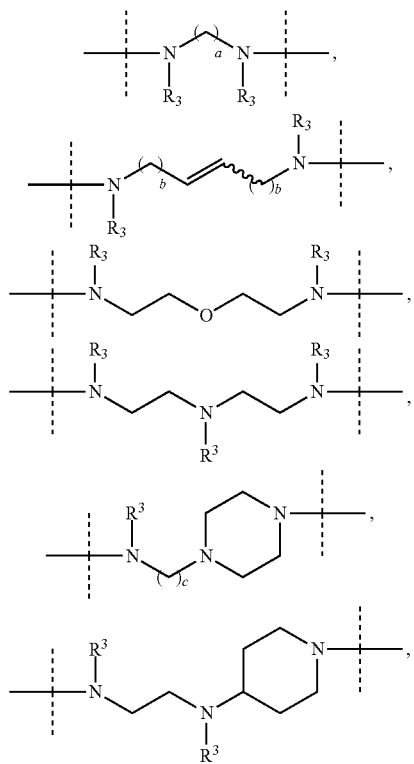

(I)

or a stereochemically isomeric form, N-oxide, salt, hydrate, or solvate thereof, wherein:

$R^1$ is a bivalent chain selected from

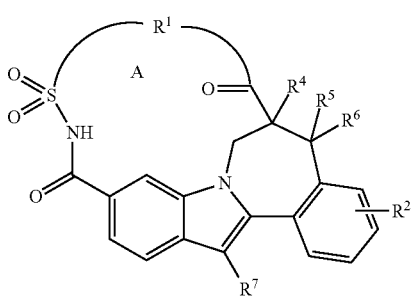

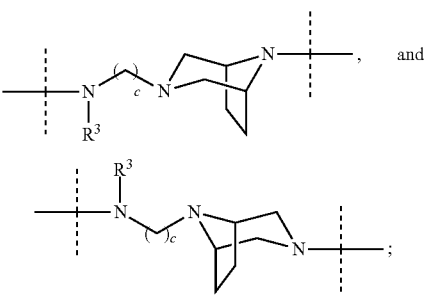

each $R^3$ is independently selected from the group comprising hydrogen, $C_{1-4}$-alkyl and $C_{3-5}$cycloalkyl;

a is 3, 4, 5 or 6;

each b is independently 1 or 2;

c is 1 or 2;

macrocycle A has 14 to 18 member atoms;

each $R^2$ is independently hydrogen, halo or $C_{1-4}$-alkoxy;

$R^4$ and $R^5$ are hydrogen or $R^4$ and $R^5$ together form a double bond or a methylene group to form a fused cyclopropyl;

$R^6$ is hydrogen or methyl; and $R^7$ is a $C_{3-7}$cycloalkyl optionally substituted with halo.

2. The compound of claim 1 wherein,

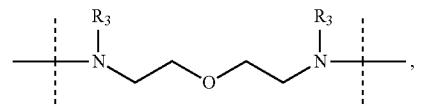

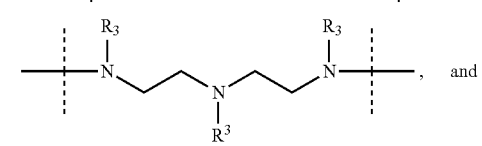

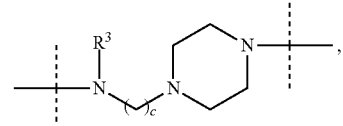

$R^1$ is selected from —N($R^3$)—(CH$_2$)$_4$—N($R^3$)—, and, each $R^3$ is independently selected from hydrogen and methyl.

3. The compound of claim 1 wherein $R^2$ is positioned the benzene group in para with respect to the bond linking this benzene to the indole group.

4. The compound of claim 1 wherein $R^2$ is selected from fluoro and methoxy.

5. The compound of claim 1 wherein $R^7$ is selected from cyclohexyl and 2-fluorocyclohexyl.

6. The compound of claim 1 wherein $R^4$ and $R^5$ together form a double bond.

7. The compound of claim 1 having the stereochemical configuration as illustrated by formula (IA)

(IA)
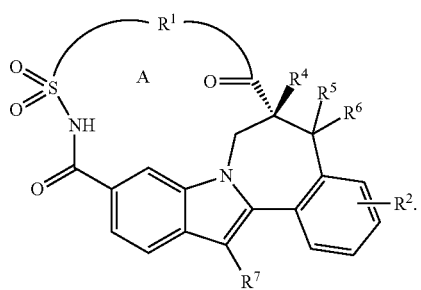
8. The compound of claim 1, selected from the group consisting of:
(II-1)
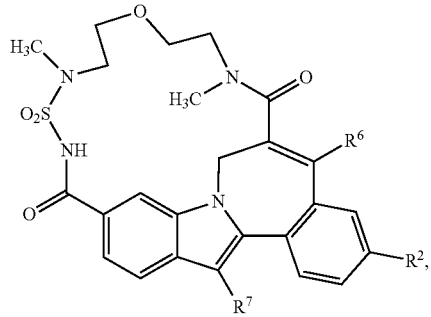
(II-2)
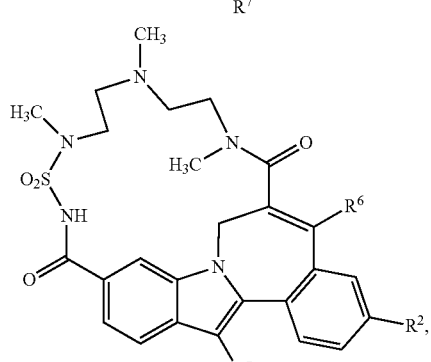
(II-3)
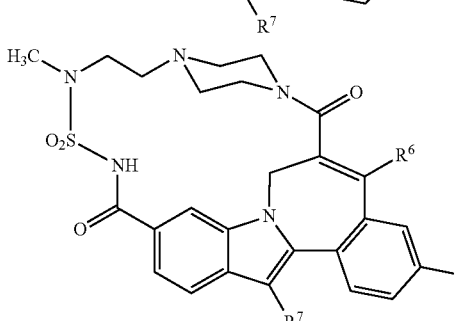
(III-1)
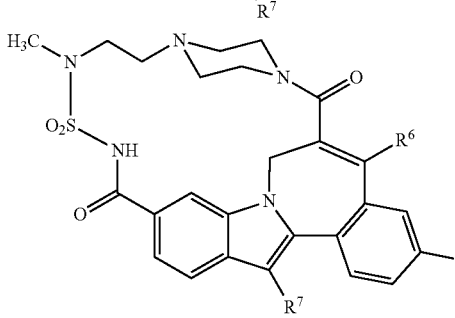
(III-2)
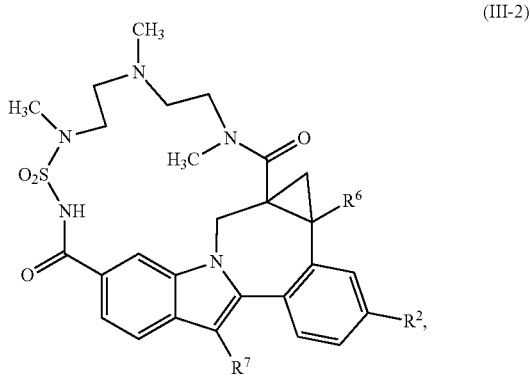
(III-3)
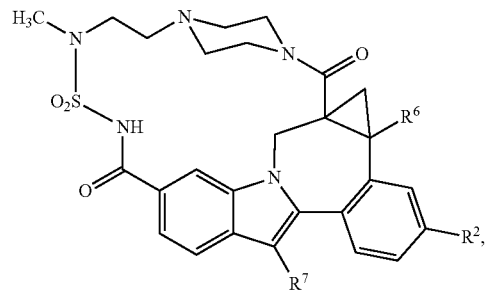
(III-4)
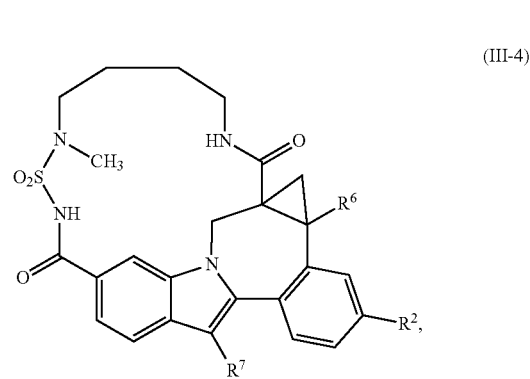
(IV-1)
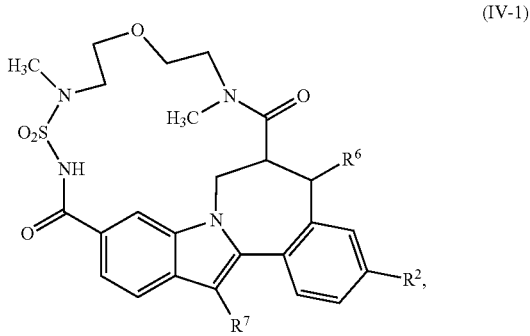

-continued (IV-2)

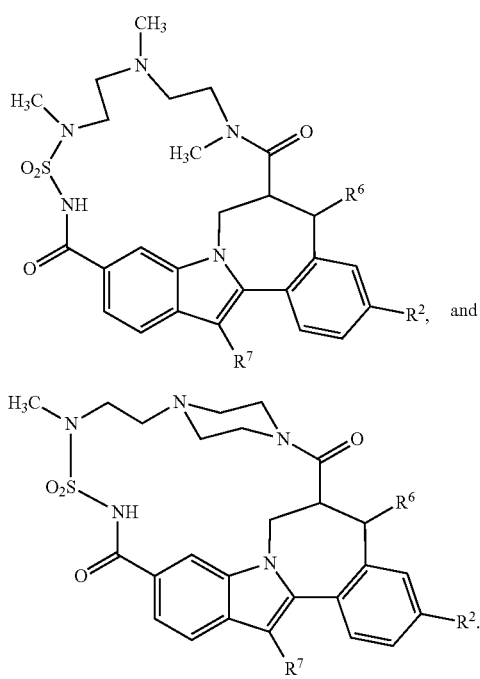

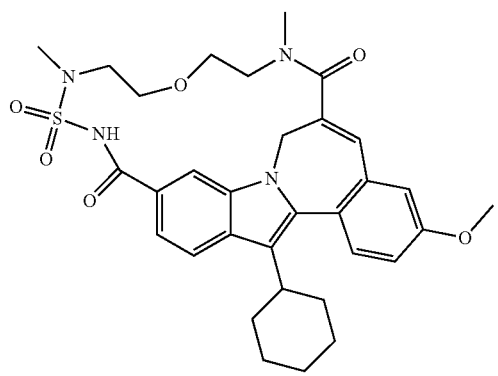 [SMILES: COc1ccc2c(c1)C=C1Cn3c-2c(C2CCCCC2)c2ccc(cc23)C(=O)NS(=O)(=O)N(C)CCOCCN(C)C1=O]

9. A pharmaceutical composition comprising a carrier, and as active ingredient an anti-virally effective amount of the compound of claim 1.

10. The pharmaceutical composition of claim 9, further comprising at least one other anti-HCV compound.

11. The pharmaceutical composition of claim 9, further comprising at least one anti HIV compound.

12. The compound of claim 1, which is or a stereochemically isomeric form, N-oxide, salt, hydrate, or solvate thereof.

13. A pharmaceutical composition comprising a carrier, and as active ingredient an anti-virally effective amount of the compound of claim 12.

14. The pharmaceutical composition of claim 13, further comprising at least one other anti-HCV compound.

15. The pharmaceutical composition of claim 13, further comprising at least one HIV compound.

16. The compound of claim 12, which is

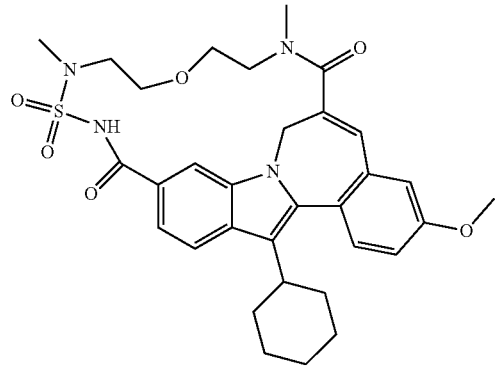 [SMILES: COc1ccc2c(c1)C=C1Cn3c-2c(C2CCCCC2)c2ccc(cc23)C(=O)NS(=O)(=O)N(C)CCOCCN(C)C1=O]

or a salt thereof.

17. The compound of claim 16, which is

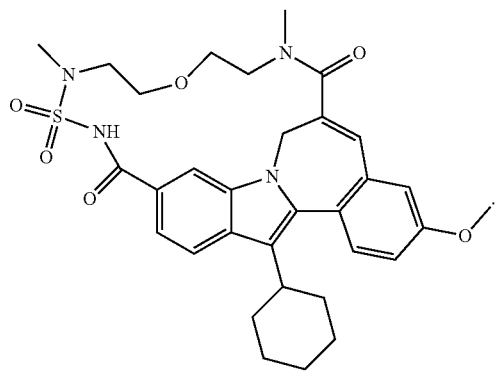

18. The compound of claim 1, wherein macrocycle A has 17 or 18 member atoms.

* * * * *